United States Patent
Mortlock

(10) Patent No.: US 7,407,946 B2
(45) Date of Patent: Aug. 5, 2008

(54) QUINAZOLINE COMPOUNDS

(75) Inventor: Andrew Austen Mortlock, Macclesfield (GB)

(73) Assignee: AstraZeneca AB, Södertälje (SE)

( * ) Notice: Subject to any disclaimer, the term of this patent is extended or adjusted under 35 U.S.C. 154(b) by 240 days.

(21) Appl. No.: 10/539,481

(22) PCT Filed: Dec. 22, 2003

(86) PCT No.: PCT/GB03/05636

§ 371 (c)(1), (2), (4) Date: Jun. 17, 2005

(87) PCT Pub. No.: WO2004/058752

PCT Pub. Date: Jul. 15, 2004

(65) Prior Publication Data

US 2006/0058523 A1    Mar. 16, 2006

(30) Foreign Application Priority Data

Dec. 24, 2002    (EP)    .................................. 02293239

(51) Int. Cl.
*A61K 31/675*    (2006.01)
*C07F 9/6512*    (2006.01)

(52) U.S. Cl. ...................... 514/80; 514/266.3; 544/243; 544/244; 544/284

(58) Field of Classification Search ................... 514/80, 514/266.3; 544/284, 243, 244
See application file for complete search history.

(56) References Cited

U.S. PATENT DOCUMENTS 6,919,338 B2 *    7/2005    Mortlock et al. ......... 514/234.5

2006/0058325 A1 *    3/2006    Mortlock .................. 514/266.2
2006/0116357 A1 *    6/2006    Heron et al. .................. 514/80

FOREIGN PATENT DOCUMENTS

| WO | WO 01/21596 A1 | 3/2001 |
| WO | WO 01/21597 A1 | 3/2001 |
| WO | WO 02/00649 A1 | 1/2002 |
| WO | WO 03/000188 A2 | 1/2003 |

OTHER PUBLICATIONS

Bischoff, J.R. et. al., "A homologue of *Drosophila aurora* kinase . . . ", The EMBO Journal, 1998, vol. 17, No. 11, pp. 3052-3065.*

* cited by examiner

*Primary Examiner*—James O. Wilson
*Assistant Examiner*—Tamthom N Truong

(57) ABSTRACT

Quinazoline derivatives of formula (I) wherein A is 5-membered heteroaryl containing a sulphur atom and optionally containing one or more nitrogen atoms; compositions containing them, processes for their preparation and their use in therapy.

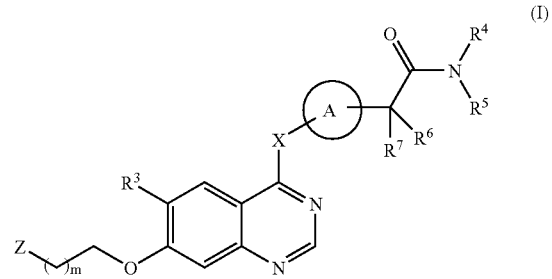

3 Claims, No Drawings

QUINAZOLINE COMPOUNDS

CROSS-REFERENCE TO RELATED APPLICATIONS

This application is a U.S. National Stage under 35 U.S.C § 371 of International Application No. PCT/GB2003/005636 (filed Dec. 22, 2003) which claims priority under 35 U.S.C. § 119(a)-(d) to Application No. EP 02293239.6 filed on Dec. 24, 2002.

The present invention relates to certain quinazoline derivatives for use in the treatment of certain diseases in particular to proliferative disease such as cancer and in the preparation of medicaments for use in the treatment of proliferative disease, to novel quinazoline compounds and to processes for their preparation, as well as pharmaceutical compositions containing them as active ingredient.

Cancer (and other hyperproliferative disease) is characterised by uncontrolled cellular proliferation. This loss of the normal regulation of cell proliferation often appears to occur as the result of genetic damage to cellular pathways that control progress through the cell cycle.

In eukaryotes, an ordered cascade of protein phosphorylation is thought to control the cell cycle. Several families of protein kinases that play critical roles in this cascade have now been identified. The activity of many of these kinases is increased in human tumours when compared to normal tissue. This can occur by either increased levels of expression of the protein (as a result of gene amplification for example), or by changes in expression of co activators or inhibitory proteins.

The first identified, and most widely studied of these cell cycle regulators have been the cyclin dependent kinases (or CDKs). Activity of specific CDKs at specific times is essential for both initiation and coordinated progress through the cell cycle. For example, the CDK4 protein appears to control entry into the cell cycle (the G0-G1-S transition) by phosphorylating the retinoblastoma gene product pRb. This stimulates the release of the transcription factor E2F from pRb, which then acts to increase the transcription of genes necessary for entry into S phase. The catalytic activity of CDK4 is stimulated by binding to a partner protein, Cyclin D. One of the first demonstrations of a direct link between cancer and the cell cycle was made with the observation that the Cyclin D1 gene was amplified and cyclin D protein levels increased (and hence the activity of CDK4 increased) in many human tumours (Reviewed in Sherr, 1996, Science 274: 1672-1677; Pines, 1995, Seminars in Cancer Biology 6: 63-72). Other studies (Loda et al., 1997, Nature Medicine 3(2): 231-234; Gemma et al., 1996, International Journal of Cancer 68(5): 605-11; Elledge et al. 1996, Trends in Cell Biology 6; 388-392) have shown that negative regulators of CDK function are frequently down regulated or deleted in human tumours again leading to inappropriate activation of these kinases.

More recently, protein kinases that are structurally distinct from the CDK family have been identified which play critical roles in regulating the cell cycle and which also appear to be important in oncogenesis. These include the newly identified human homologues of the *Drosophila* aurora and *S. cerevisiae* Ip11 proteins. The three human homologues of these genes Aurora-A, Aurora-B and Aurora-C (also known as aurora2, aurora1 and aurora3 respectively) encode cell cycle regulated serine-threonine protein kinases (summarised in Adams et al., 2001, Trends in Cell Biology. 11(2): 49-54). These show a peak of expression and kinase activity through G2 and mitosis. Several observations implicate the involvement of human aurora proteins in cancer. The Aurora-A gene maps to chromosome 20q13, a region that is frequently amplified in human tumours including both breast and colon tumours. Aurora-A may be the major target gene of this amplicon, since Aurora-A DNA is amplified and mRNA over-expressed in greater than 50% of primary human colorectal cancers. In these tumours Aurora-A protein levels appear greatly elevated compared to adjacent normal tissue. In addition, transfection of rodent fibroblasts with human Aurora-A leads to transformation, conferring the ability to grow in soft agar and form tumours in nude mice (Bischoff et al., 1998, The EMBO Journal. 17(11): 3052-3065). Other work (Zhou et al., 1998, Nature Genetics. 20(2): 189-93) has shown that artificial overexpression of Aurora-A leads to an increase in centrosome number and an increase in aneuploidy, a known event in the development of cancer. Further work has shown an increase in expression of Aurora-B (Adams et al., 2001, Chromsoma. 110(2):65-74) and Aurora-C (Kimura et al., 1999, Journal of Biological Chemistry, 274(11): 7334-40) in tumour cells when compared to normal cells.

Importantly, it has also been demonstrated that abrogation of Aurora-A expression and function by antisense oligonucleotide treatment of human tumour cell lines (WO 97/22702 and WO 99/37788) leads to cell cycle arrest and exerts an antiproliferative effect in these tumour cell lines. Additionally, small molecule inhibitors of Aurora-A and Aurora-B have been demonstrated to have an antiproliferative effect in human tumour cells (Keen et al. 2001, Poster #2455, American Association of Cancer research annual meeting), as has selective abrogation of Aurora-B expression alone by siRNA treatment (Ditchfield et al. 2003. Journal of Cell Biology, 161(2): 267-280). This indicates that inhibition of the function of Aurora-A and/or Aurora-B will have an antiproliferative effect that may be useful in the treatment of human tumours and other hyperproliferative disease. Further, inhibition of Aurora kinases as a therapeutic approach to these diseases may have significant advantages over targeting signalling pathways upstream of the cell cycle (e.g. those activated by growth factor receptor tyrosine kinases such as epidermal growth factor receptor (EGFR) or other receptors). Since the cell cycle is ultimately downstream of all of these diverse signalling events, cell cycle directed therapies such as inhibition of Aurora kinases would be predicted to be active across all proliferating tumour cells, whilst approaches directed at specific signalling molecules (e.g. EGFR) would be predicted to be active only in the subset of tumour cells which express those receptors. It is also believed that significant "cross talk" exists between these signalling pathways meaning that inhibition of one component may be compensated for by another.

A number of quinazoline derivatives have been proposed hitherto for use in the inhibition of various kinases. For example, WO 96/09294, WO 96/15118 and WO 99/06378 describe the use of certain quinazoline compounds as receptor tyrosine kinase inhibitors, which may be useful in the treatment of proliferative disease and WO 00/21955 discloses certain quinazoline derivatives as inhibitors of the effects of VEGF.

Quinazoline derivatives have also been disclosed for use in the inhibition of Aurora-A kinase. WO 02/00649 discloses quinazoline derivative bearing a 5-membered heteroaromatic ring where the ring is, in particular, substituted thiazole or substituted thiophene. However despite the compounds of WO 02/00649 there still exists the need for further compounds having Aurora kinase inhibitory properties.

The applicants have been successful in finding a novel series of compounds which inhibit the effects of the Aurora kinases and in particular Aurora-A and/or Aurora-B kinase and which have certain properties that make them particularly useful in formulating medicaments for the treatment of disease. In particular the compounds are of use in the treatment of proliferative disease such as cancer, occurring as either solid and haematogocial tumours where Aurora kinases are known to be active and especially in diseases such as colorectal, breast, lung, prostate, pancreatic or bladder and renal cancer as well as leukemias and lymphomas.

According to one aspect of the present invention there is provided a compound of formula (I):

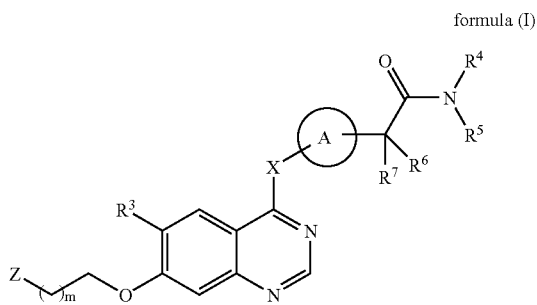

formula (I)

wherein A is 5-membered heteroaryl containing a sulphur atom and optionally containing one or more nitrogen atoms;
X is O, S, S(O), S(O)$_2$ or NR$^{14}$;
m is 0, 1, 2 or 3;
Z is a group selected from —NR$^1$R$^2$, phosphonooxy, C$_{3-6}$cycloalkyl which C$_{3-6}$cycloalkyl is substituted by phosphonooxy or C$_{1-4}$alkyl substituted by phosphonooxy, and a 4- to 7-membered ring linked via a carbon atom, containing a nitrogen atom and optionally containing a further nitrogen atom which ring may be saturated, unsaturated or partially saturated, wherein the ring is substituted on carbon or nitrogen by phosphonooxy or C$_{1-4}$alkyl substituted by phosphonooxy and wherein the ring is optionally further substituted on carbon or nitrogen by 1, 2 or 3 halo or C$_{1-4}$alkyl groups;
R$^1$ is a group selected from —COR$^8$, —CONR$^8$R$^9$ and C$_{1-6}$alkyl which C$_{1-6}$alkyl is substituted by phosphonooxy and optionally further substituted by 1 or 2 halo or methoxy groups;
R$^2$ is a group selected from hydrogen, —COR$^{10}$, —CONR$^{10}$R$^{11}$ and C$_{1-6}$alkyl which C$_{1-6}$alkyl is optionally substituted by 1, 2, or 3 halo or C$_{1-4}$alkoxy groups or —S(O)$_p$R$^{11}$ (where p is 0, 1 or 2) or phosphonooxy, or R$^2$ is a group selected from C$_{2-6}$alkenyl, C$_{2-6}$alkynyl, C$_{3-6}$cycloalkyl and C$_{3-6}$cycloalkylC$_{1-4}$alkyl;
or R$^1$ and R$^2$ together with the nitrogen to which they are attached form a 4- to 7-membered ring optionally containing a further nitrogen atom which ring may be saturated, unsaturated or partially saturated, wherein the ring is substituted on carbon or nitrogen, by a group selected from phosphonooxy and C$_{1-4}$alkyl which C$_{1-4}$alkyl is substituted by phosphonooxy or —NR$^8$R$^9$, and where the ring is optionally further substituted on carbon or nitrogen, by 1, 2 or 3 halo or C$_{1-4}$alkyl groups;
R$^3$ is a group selected from hydrogen, halo, cyano, nitro, C$_{1-6}$alkoxy, C$_{1-6}$alkyl, —OR$^{12}$, —CHR$^{12}$R$^{13}$, —OC(O)R$^{12}$, —C(O)R$^{12}$, —NR$^{12}$C(O)R$^{13}$, C(O)NR$^{12}$R$^{13}$, —NR$^{12}$SO$_2$R$^{13}$ and —NR$^{12}$R$^{13}$;
R$^4$ is hydrogen or a group selected from C$_{1-4}$alkyl, heteroaryl, heteroarylC$_{1-4}$alkyl, aryl and arylC$_{1-4}$alkyl which group is optionally substituted by 1, 2 or 3 substitutents selected from halo, methyl, ethyl, cyclopropyl and ethynyl;

R$^5$ is a group selected from hydrogen, C$_{1-4}$alkyl, C$_{2-4}$alkenyl, C$_{2-4}$alkynyl, C$_{3-6}$cycloalkyl and C$_{3-6}$cycloalkylC$_{1-4}$alkyl;
R$^6$ and R$^7$ are independently selected from hydrogen, halo, C$_{1-4}$alkyl, C$_{3-6}$cycloalkyl, hydroxy and C$_{1-4}$alkoxy;
R$^8$ is C$_{1-4}$alkyl substituted by phosphonooxy and optionally further substituted by 1 or 2 halo or methoxy groups;
R$^9$ is a group selected from hydrogen and C$_{1-4}$alkyl;
R$^{10}$ is a group selected from hydrogen and C$_{1-4}$alkyl which C$_{1-4}$alkyl is optionally substituted by halo, C$_{1-4}$alkoxy, S(O)$_q$ (where q is 0, 1 or 2) or phosphonoxy;
R$^{11}$, R$^{12}$, R$^{13}$ and R$^{14}$ are independently selected from hydrogen, C$_{1-4}$alkyl or heterocyclyl;
or a pharmaceutically acceptable salt thereof.

Within the present invention, it is to be understood that, insofar as certain compounds of formula (I) herein defined may exist in optically active or racemic forms by virtue of one or more asymmetric carbon or sulphur atoms, the invention includes in its definition any such optically active or racemic form which possesses Aurora kinase inhibitory activity and in particular Aurora-A and/or Aurora-B kinase inhibitory activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to herein.

Within the present invention it is to be understood that a compound of formula (I) or a salt thereof may exhibit the phenomenon of tautomerism and that the formulae drawings within this specification can represent only one of the possible tautomeric forms. It is to be understood that the invention encompasses any tautomeric form which has Aurora kinase inhibitory activity and in particular Aurora-A and/or Aurora-B kinase inhibitory activity and is not to be limited merely to any one tautomeric form utilised within the formulae drawings.

It is also to be understood that certain compounds of formula (I) and salts thereof can exist in solvated as well as unsolvated forms such as, for example, hydrated forms. It is to be understood that the invention encompasses all such solvated forms which have Aurora kinase inhibitory activity and in particular Aurora-A and/or Aurora-B kinase inhibitory activity.

The present invention relates to the compounds of formula (I) as herein defined as well as to the salts thereof. Salts for use in pharmaceutical compositions will be pharmaceutically acceptable salts, but other salts may be useful in the production of the compounds of formula (I) and their pharmaceutically acceptable salts. Pharmaceutically acceptable salts of the invention may, for example, include acid addition salts of compounds of formula (I) as herein defined which are sufficiently basic to form such salts. Such acid addition salts include but are not limited to furmarate, methanesulphonate, hydrochloride, hydrobromide, citrate and maleate salts and salts formed with phosphoric and sulphuric acid. In addition where compounds of formula (I) are sufficiently acidic, salts are base salts and examples include but are not limited to, an alkali metal salt for example sodium or potassium, an alkaline earth metal salt for example calcium or magnesium, or organic amine salt for example triethylamine, ethanolamine, diethanolamine, triethanolamine, morpholine, N-methylpiperidine, N-ethylpiperidine, dibenzylamine or amino acids such as lysine.

The compounds of formula (I) may also be provided as in vivo hydrolysable esters. An in vivo hydrolysable ester of a compound of formula (I) containing carboxy or hydroxy group is, for example a pharmaceutically acceptable ester which is cleaved in the human or animal body to produce the parent acid or alcohol. Such esters can be identified by administering, for example, intravenously to a test animal, the compound under test and subsequently examining the test animal's body fluid.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable pharmaceutically acceptable esters for hydroxy include inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethylpropionyloxymethoxy. A selection of in vivo hydrolysable ester forming groups for hydroxy include $C_{1-10}$alkanoyl, for example formyl, acetyl, benzoyl, phenylacetyl, substituted benzoyl and phenylacetyl; $C_{1-10}$alkoxycarbonyl (to give alkyl carbonate esters), for example ethoxycarbonyl; di-$C_{1-4}$alkylcarbamoyl and N-(di-$C_{1-4}$alkylaminoethyl)-N—$C_{1-4}$alkylcarbamoyl (to give carbamates); di-$C_{1-4}$alkylaminoacetyl and carboxyacetyl. Examples of ring substituents on phenylacetyl and benzoyl include aminomethyl, $C_{1-4}$alkylaminomethyl and di-($C_{1-4}$alkyl)aminomethyl, and morpholino or piperazino linked from a ring nitrogen atom via a methylene linking group to the 3- or 4-position of the benzoyl ring. Other interesting in vivo hydrolysable esters include, for example, $R^AC(O)OC_{1-6}$alkyl-CO—, wherein $R^A$ is for example, benzyloxy-$C_{1-4}$alkyl, or phenyl. Suitable substituents on a phenyl group in such esters include, for example, 4-$C_{1-4}$piperazino-$C_{1-4}$alkyl, piperazino-$C_{1-4}$alkyl and morpholino-$C_{1-4}$alkyl.

In this specification the generic term "alkyl" includes both straight-chain and branched-chain alkyl groups. However references to individual alkyl groups such as "propyl" are specific for the straight chain version only and references to individual branched-chain alkyl groups such as "tert-butyl" are specific for the branched chain version only. An analogous convention applies to other generic terms, for example "alkenyl" and "alkynyl".

"Cycloalkyl" is a monocyclic, saturated alkyl ring and "aryl" is a monocyclic or bicyclic aromatic ring.

Unless otherwise specified "heteroaryl" is a monocyclic or bicyclic aromatic ring containing 5 to 10 ring atoms of which 1, 2, 3 or 4 ring atoms are chosen from nitrogen, sulphur or oxygen where a ring nitrogen or sulphur may be oxidised.

"Heterocyclyl" is a saturated, unsaturated or partially saturated, monocyclic or bicyclic ring containing 4 to 12 atoms of which 1, 2, 3 or 4 ring atoms are chosen from nitrogen, sulphur or oxygen, which ring may be carbon or nitrogen linked, wherein a —$CH_2$— group can optionally be replaced by a —C(O)—; wherein a ring nitrogen or sulphur atom is optionally oxidised to form the N-oxide or S-oxide(s); wherein a ring —NH is optionally substituted by acetyl, formyl, methyl or mesyl; and wherein a ring is optionally substituted by one or more halo.

"Phosphonooxy" is in one aspect a group of formula —OP(O)(OH)$_2$. However the term "phosphonooxy" also includes salts of this group such as those formed with alkali metal ions such as sodium or potassium ions or alkaline earth metal ions, for example calcium or magnesium ions.

Where optional substituents are chosen from "1 or 2", from "1, 2, or 3" or from "1, 2, 3 or 4" groups or substituents it is to be understood that this definition includes all substituents being chosen from one of the specified groups i.e. all substitutents being the same or the substituents being chosen from two or more of the specified groups i.e. the substitutents not being the same.

Compounds of the present invention have been named with the aid of computer software (ACD/Name version 6.6 or ACD Name Batch version 6.0).

Suitable values for any R group ($R^1$ to $R^{14}$) or any part or substitutent for such groups include:

for $C_{1-4}$alkyl: methyl, ethyl, propyl, isopropyl, butyl, 2-methylpropyl and tert-butyl;

for $C_{1-6}$alkyl: $C_{1-4}$alkyl, pentyl, 2,2-dimethylpropyl, 3-methylbutyl and hexyl;

for $C_{2-4}$alkenyl: vinyl, allyl and 1-propenyl;

for $C_{2-6}$alkenyl: $C_{2-4}$alkenyl, 1-butenyl, 2-butenyl, 3-butenyl, 2-methylbut-2-enyl, 3-methylbut-1-enyl, 1-pentenyl, 3-pentenyl and 4-hexenyl;

for $C_{2-4}$alkynyl: ethynyl, 1-propynyl, 2-propynyl and 3-butynyl;

for $C_{2-6}$alkynyl: $C_{2-4}$alkynyl, 2-pentynyl, hexynyl and 1-methylpent-2-ynyl;

for $C_{3-6}$cycloalkyl: cyclopropyl, cyclobutyl, cyclopentyl and cyclohexyl;

for $C_{3-6}$cycloalkyl$C_{1-4}$alkyl: cyclopropylmethyl, cyclopropylethyl, cyclobutylmethyl, cyclopentylmethyl and cyclohexylmethyl;

for aryl: phenyl and naphthyl;

for aryl$C_{1-4}$alkyl: benzyl, phenethyl, naphthylmethyl and naphthylethyl;

for halo: fluoro, chloro, bromo and iodo;

for $C_{1-4}$alkoxy: methoxy, ethoxy, propoxy and isopropoxy;

for $C_{1-6}$alkoxy: $C_{1-4}$alkoxy, pentyloxy, 1-ethylpropoxy and hexyloxy;

for heteroaryl: pyridyl, imidazolyl, quinolinyl, cinnolyl, pyrimidinyl, thiophenyl, pyrrolyl, pyrazolyl, thiazolyl, triazolyl, oxazolyl, isoxazolyl and pyrazinyl and preferably thiazolyl, pyridyl, imidazolyl and pyrimidinyl;

for heteroaryl$C_{1-4}$alkyl: pyridylmethyl, pyridylethyl, pyrimidinylethyl, pyrimidinylpropyl, pyrimidinylbutyl, imidazolylpropyl, imidazolylbutyl, quinolinylpropyl, 1,3,4-triazolylpropyl and oxazolylmethyl;

for heterocyclyl: furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl, benzofuryl, piperidinyl, N-acetylpiperidinyl, N-methylpiperidinyl, N-formylpiperazinyl, N-mesylpiperazinyl, homopiperazinyl, piperazinyl, azetidinyl, oxetanyl, morpholinyl, tetrahydroisoquinolinyl, tetrahydroquinolinyl, indolinyl, pyranyl, dihydro-2H-pyranyl, tetrahydrofuranyl, 2,5-dioxoimidazolidinyl, 2,2-dimethyl-1,3-dioxolanyl and 3,4-dimethylenedioxybenzyl.

It should be noted that examples given for terms used in the description are not limiting.

Preferred values of A, X, m, Z, $R^3$, $R^4$, $R^5$, $R^6$ and $R^7$ are as follows. Such values may be used where appropriate with any of the definitions, claims or embodiments defined herein.

In one aspect of the invention A is a thiazolyl, thiophenyl or thiadiazolyl. In a further aspect A is a group of formula (a), (b), (c), (d), (e) or (f):

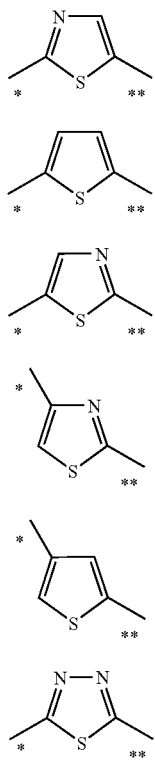

where * is the point of attachment to the X group of formula (I) and ** is the point of attachment to the (CR⁶R⁷) group of formula (I). In another aspect A is a group of formula (a) as defined above.

In one aspect of the invention X is $NR^{14}$, O or S. In another aspect X is $NR^{14}$. In yet another aspect X is NH.

In one aspect of the invention m is 1, 2 or 3. In another aspect m is 0, 1 or 2. In another aspect m is 1. In a further aspect m is 2.

In one aspect of the invention Z is —$NR^1R^2$ or a 4- to 7-membered saturated ring linked via a carbon atom, containing a nitrogen atom, which ring is substituted on carbon or nitrogen by phosphonooxy or $C_{1-4}$alkyl substituted by phosponooxy. In another aspect Z is —$NR^1R^2$.

In one aspect of the invention $R^1$ is $C_{1-5}$alkyl substituted by phosphonooxy. In another aspect $R^1$ is $C_{1-5}$alkyl substituted by phosphonooxy and further substituted by 1 or 2 halo. In a further aspect $R^1$ is 2-phosphonooxyethyl, 2-phosphonooxy-1,1-dimethylethyl, 2-phosphonooxypropyl, 3-phosphonooxy-1,1-dimethylpropyl, 3-phosphonooxypropyl and 4-phosphonooxybutyl. In yet another aspect $R^1$ is 2-phosphonooxyethyl In one aspect of the invention $R^2$ is a group selected from hydrogen and $C_{1-4}$alkyl which $C_{1-4}$alkyl is optionally substituted by halo or $C_{1-4}$alkoxy, or $R^2$ is a group selected from $C_{3-6}$cycloalkyl or $C_{3-6}$cycloalkyl$C_{1-4}$alkyl. In another aspect $R^2$ is hydrogen, 2-propynyl, methyl, ethyl, butyl, cyclopropyl, where the latter four groups are optionally substituted by fluoro, chloro, methoxy and ethoxy. In another aspect of the invention $R^2$ is hydrogen, 2-propynyl, methyl, ethyl, isobutyl, cyclopropyl, 2-fluoroethyl or 2-methoxyethyl. In another aspect of the invention $R^2$ is hydrogen, methyl, ethyl, cyclopropyl, 2-fluoroethyl or 2-methoxyethyl. In a further aspect $R^2$ is hydrogen, methyl or ethyl. In a further aspect $R^2$ is hydrogen.

In one aspect of the invention $R^1$ and $R^2$ together with the nitrogen to which they are attached form a saturated 5- to 6-membered ring optionally containing a further nitrogen atom wherein the ring is substituted on carbon on nitrogen by a group selected from phosphonooxy, and $C_{1-4}$alkyl which $C_{1-4}$alkyl is substituted by phosphonooxy or —$NR^8R^9$ and where the ring is optionally further substituted on carbon or nitrogen, by 1 or 2 $C_{1-4}$alkyl groups. In another aspect of the invention $R^1$ and $R^2$ together with the nitrogen to which they are attached form a piperidine, pyrrolidine or piperazine ring which is substituted by a group selected from phosphonooxy, phosphonooxymethyl, 2-phosphonooxyethyl and N-ethyl-N-(2-phosphonooxyethyl)aminomethyl and N-(2-phosphonooxyethyl)aminomethyl and where the ring is optionally further substituted by 1 or 2 methyl. In a further aspect of the invention $R^1$ and $R^2$ together with the nitrogen to which they are attached form 4-(phosphonooxymethyl)piperidinyl, 2-(phosphonooxymethyl)pyrrolidinyl, 4-(2-phosphonooxyethyl)piperazinyl, 3-(phosphonooxy)pyrrolidinyl, 3-(phosphonooxy)piperidinyl, 2-[N-ethyl-N-(2-phosphonooxyethyl)aminomethyl]pyrrolidinyl, 4-(phosphonooxy)piperidinyl, 2-[N-(2-phosphonooxyethyl)aminomethyl]pyrrolidinyl, 4-(2-phosphonooxyethyl)piperidinyl, 2-(2-phosphonooxyethyl)pyrrolidinyl and 2-(2-phosphonooxyethyl)piperidinyl.

In one aspect of the invention $R^3$ is $C_{1-4}$alkoxy or hydrogen. In another aspect $R^3$ is methoxy. In another aspect $R^3$ is hydrogen.

In one aspect $R^4$ is phenyl optionally substituted by 1 or 2 of fluoro or chloro. In another aspect $R^4$ is 3-fluorophenyl, 3-chlorophenyl, 3,5-difluorophenyl, 3,4-difluorophenyl, 2-fluorophenyl, 2,3-difluorophenyl, 2,4-difluorophenyl and 2,5-difluorophenyl. In another aspect $R^4$ is 3-fluorophenyl. In another aspect $R^4$ is 3-chlorophenyl. In another aspect $R^4$ is 3,5-difluorophenyl. In another aspect $R^4$ is 3,4-difluorophenyl. In another aspect $R^4$ is 2-fluorophenyl. In another aspect $R^4$ is 2,3-difluorophenyl. In another aspect $R^4$ is 2,4-difluorophenyl. In another aspect $R^4$ is 2,5-difluorophenyl.

In one aspect $R^5$ is hydrogen or methyl.

In one aspect of the invention $R^6$ is hydrogen, fluoro, chloro or methyl. In another aspect $R^6$ is hydrogen.

In one aspect of the invention $R^7$ is hydrogen, fluoro, chloro or methyl. In another aspect $R^7$ is hydrogen.

In one aspect $R^8$ is 2-phosphonooxyethyl.

In one aspect of the invention $R^9$ is hydrogen, methyl or ethyl.

In one aspect of the invention $R^{10}$ is hydrogen, methyl or ethyl.

In one aspect of the invention $R^{11}$ is hydrogen, methyl or ethyl.

In one aspect of the invention $R^{12}$ is hydrogen or methyl.
In one aspect of the invention $R^{13}$ is hydrogen or methyl.
In one aspect of the invention $R^{14}$ is hydrogen or methyl.
A preferred class of compounds is of formula (I) wherein:
A is a group of formula (a), (b), (c), (d), (e) or (f) as defined above;
X is NH;
m is 1, 2 or 3;
Z is —$NR^1R^2$;
$R^1$ is $C_{1-5}$alkyl substituted by phosphonooxy;
$R^2$ is hydrogen, 2-propynyl, methyl, ethyl, butyl, cyclopropyl, where the latter four groups are optionally substituted by fluoro, chloro, methoxy and ethoxy;
$R^3$ is $C_{1-4}$alkoxy or hydrogen;

R$^4$ is phenyl optionally substituted by 1 or 2 of fluoro or chloro;
R$^5$ is hydrogen or methyl; and
R$^6$ and R$^7$ are independently hydrogen, fluoro, chloro or methyl;
or a pharmaceutically acceptable salt thereof.

Another preferred class of compounds is of formula (I) wherein:
A is a group of formula (a) as defined above;
X is NH;
m is 0, 1 or 2;
Z is —NR$^1$R$^2$ or a 4- to 7-membered saturated ring linked via a carbon atom, containing a nitrogen atom, which ring is substituted on carbon or nitrogen by phosphonooxy or C$_{1-4}$alkyl substituted by phosponooxy;
R$^1$ is C$_{1-5}$alkyl substituted by phosphonooxy;
R$^2$ is a group selected from hydrogen and C$_{1-4}$alkyl which C$_{1-4}$alkyl is optionally substituted by halo or C$_{1-4}$alkoxy, or R$^2$ is a group selected from C$_{3-6}$cycloalkyl or C$_{3-6}$cycloalkylC$_{1-4}$alkyl;
R$^3$ is C$_{1-4}$alkoxy or hydrogen;
R$^4$ is phenyl optionally substituted by 1 or 2 of fluoro or chloro;
R$^5$ is hydrogen or methyl; and
R$^6$ and R$^7$ are independently hydrogen, fluoro, chloro or methyl;
or a pharmaceutically acceptable salt thereof.

Another preferred class of compounds is of formula (I) wherein:
A is a group of formula (a) as defined above;
X is NH;
m is 0, 1 or 2;
Z is —NR$^1$R$^2$;
R$^1$ is C$_{1-5}$alkyl substituted by phosphonooxy;
R$^2$ is hydrogen, 2-propynyl, methyl, ethyl, butyl, cyclopropyl, where the latter four groups are optionally substituted by fluoro, chloro, methoxy and ethoxy;
R$^3$ is methoxy;
R$^4$ is phenyl optionally substituted by 1 or 2 of fluoro or chloro;
R$^5$ is hydrogen or methyl; and
R$^6$ and R$^7$ are independently hydrogen, fluoro, chloro or methyl;
or a pharmaceutically acceptable salt thereof.

Another preferred class of compounds is of formula (I) wherein:
A is a group of formula (a) as defined above;
X is NH;
m is 0, 1 or 2;
Z is —NR$^1$R$^2$ or a 4- to 7-membered saturated ring linked via a carbon atom, containing a nitrogen atom, which ring is substituted on carbon or nitrogen by phosphonooxy or C$_{1-4}$alkyl substituted by phosponooxy;
R$^1$ is C$_{1-5}$alkyl substituted by phosphonooxy;
R$^2$ is hydrogen, 2-propynyl, methyl, ethyl, butyl, cyclopropyl, where the latter four groups are optionally substituted by fluoro, chloro, methoxy and ethoxy;
R$^3$ is hydrogen;
R$^4$ is phenyl optionally substituted by 1 or 2 of fluoro or chloro;
R$^5$ is hydrogen or methyl; and
R$^6$ and R$^7$ are independently hydrogen, fluoro, chloro or methyl;
or a pharmaceutically acceptable salt thereof.

Another preferred class of compounds is of formula (I) wherein:
A is a group of formula (a), (b), (c), (d), (e) or (f) as defined above;
X is NH;
m is 1, 2 or 3;
Z is —NR$^1$R$^2$;
R$^1$ and R$^2$ together with the nitrogen to which they are attached form a saturated 5- to 6-membered ring optionally containing a further nitrogen atom wherein the ring is substituted on carbon or nitrogen, by a group selected from phosphonooxy, and C$_{1-4}$alkyl which C$_{1-4}$alkyl is substituted by phosphonooxy or —NR$^8$R$^9$ and where the ring is optionally further substituted on carbon on nitrogen, by 1 or 2 C$_{1-4}$alkyl groups;
R$^4$ is phenyl optionally substituted by 1 or 2 of fluoro or chloro;
R$^5$ is hydrogen or methyl; and
R$^6$ and R$^7$ are independently hydrogen, fluoro, chloro or methyl;
R$^8$ is 2-phosphonooxyethyl; and
R$^9$ is hydrogen, methyl or ethyl;
or a pharmaceutically acceptable salt thereof.

A further preferred class of compounds is of formula (I) wherein:
A is a group of formula (a) as defined above;
X is NH;
m is 1, 2 or 3;
Z is —NR$^1$R$^2$ or a 4- to 7-membered saturated ring linked via a carbon atom, containing a nitrogen atom, which ring is substituted on carbon or nitrogen by phosphonooxy or C$_{1-4}$alkyl substituted by phosponooxy;
R$^1$ and R$^2$ together with the nitrogen to which they are attached form a saturated 5- to 6-membered ring optionally containing a further nitrogen atom wherein the ring is substituted on carbon or nitrogen, by a group selected from phosphonooxy, and C$_{1-4}$alkyl which C$_{1-4}$alkyl is substituted by phosphonooxy or —NR$^8$R$^9$ and where the ring is optionally further substituted on carbon or nitrogen, by 1 or 2 C$_{1-4}$alkyl groups;
R$^3$ is C$_{1-4}$alkoxy or hydrogen;
R$^4$ is phenyl optionally substituted by 1 or 2 of fluoro or chloro;
R$^5$ is hydrogen or methyl; and
R$^6$ and R$^7$ are independently hydrogen, fluoro, chloro or methyl;
R$^8$ is 2-phosphonooxyethyl; and
R$^9$ is hydrogen, methyl or ethyl;
or a pharmaceutically acceptable salt thereof.

A further preferred class of compounds is of formula (I) wherein:
A is a group of formula (a) as defined above;
X is NH;
m is 1, 2 or 3;
Z is —NR$^1$R$^2$ or a 4- to 7-membered saturated ring linked via a carbon atom, containing a nitrogen atom, which ring is substituted on carbon or nitrogen by phosphonooxy or C$_{1-4}$alkyl substituted by phosponooxy;
R$^1$ and R$^2$ together with the nitrogen to which they are attached form a piperidine, pyrrolidine or piperazine ring which is substituted by a group selected from phosphonooxy, phosphonooxymethyl, 2-phosphonooxyethyl and N-ethyl-N-(2-phosphonooxyethyl)aminomethyl and N-(2-phosphonooxyethyl)aminomethyl and where the ring is optionally further substituted by 1 or 2 methyl;
R$^3$ is methoxy;

R⁴ is phenyl optionally substituted by 1 or 2 of fluoro or chloro;
R⁵ is hydrogen or methyl; and
R⁶ and R⁷ are independently hydrogen, fluoro, chloro or methyl;
R⁸ is 2-phosphonooxyethyl; and
R⁹ is hydrogen, methyl or ethyl;
or a pharmaceutically acceptable salt thereof.

A further preferred class of compounds is of formula (I) wherein:
A is a group of formula (a) as defined above;
X is NH;
m is 1, 2 or 3;
Z is —NR¹R² or a 4- to 7-membered saturated ring linked via a carbon atom, containing a nitrogen atom, which ring is substituted on carbon or nitrogen by phosphonooxy or C₁₋₄alkyl substituted by phosponooxy;
R¹ and R² together with the nitrogen to which they are attached form a piperidine, pyrrolidine or piperazine ring which is substituted by a group selected from phosphonooxy, phosphonooxymethyl, 2-phosphonooxyethyl and N-ethyl-N-(2-phosphonooxyethyl)aminomethyl and N-(2-phosphonooxyethyl)aminomethyl and where the ring is optionally further substituted by 1 or 2 methyl;
R³ is hydrogen;
R⁴ is phenyl optionally substituted by 1 or 2 of fluoro or chloro;
R⁵ is hydrogen or methyl; and
R⁶ and R⁷ are independently hydrogen, fluoro, chloro or methyl;
R⁸ is 2-phosphonooxyethyl; and
R⁹ is hydrogen, methyl or ethyl;
or a pharmaceutically acceptable salt thereof.

In another aspect of the invention, a preferred compound of the invention is any one selected from:

(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)methyl dihydrogen phosphate;
((2R)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;
2-(4-(3-((4-((5-(2-((3-fluorophenyl)amino)-2-oxoethyl)-1,3-thiazol-2-yl)amino)-6-methoxy-quinazolin-7-yl)oxy)propyl)piperazin-1-yl)ethyl dihydrogen phosphate;
1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-3-yl dihydrogen phosphate;
1-(3-((4-((5-(2-((3-fluorophenyl)amino)-2-oxoethyl)-1,3-thiazol-2-yl)amino)-6-methoxyquinazolin-7-yl)oxy)propyl)piperidin-3-yl dihydrogen phosphate;
2-(ethyl(3-((4-((5-(2-((3-fluorophenyl)amino)-2-oxoethyl)-1,3-thiazol-2-yl)amino)-6-methoxyquinazolin-7-yl)oxy)propyl)amino)ethyl dihydrogen phosphate;
((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;
2-(ethyl(((2S)-1-(3-((4-((5-(2-((3-fluorophenyl)amino)-2-oxoethyl)-1,3-thiazol-2-yl)amino-6-methoxyquinazolin-7-yl)oxy)propyl)pyrrolidin-2-yl)methyl)amino)ethyl dihydrogen phosphate;
1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl dihydrogen phosphate;
2-((((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)amino)ethyl dihydrogen phosphate;
2-((3-((4-((5-(2-((3-fluorophenyl)amino)-2-oxoethyl)-1,3-thiazol-2-yl)amino)-6-methoxyquinazolin-7-yl)oxy)propyl)amino)ethyl dihydrogen phosphate;
3-(ethyl(3-((4-((5-(2-((3-fluorophenyl)amino)-2-oxoethyl)-1,3-thiazol-2-yl)amino)-6-methoxyquinazolin-7-yl)oxy)propyl)amino)propyl dihydrogen phosphate;
2-((2-fluoroethyl)(3-((4-((5-(2-((3-fluorophenyl)amino)-2-oxoethyl)-1,3-thiazol-2-yl)amino-6-methoxyquinazolin-7-yl)oxy)propyl)amino)ethyl dihydrogen phosphate;
2-(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)ethyl dihydrogen phosphate;
2-((3-((4-((5-(2-((3-fluorophenyl)amino)-2-oxoethyl)-1,3-thiazol-2-yl)amino)-6-methoxyquinazolin-7-yl)oxy)propyl)(2-methoxyethyl)amino)ethyl dihydrogen phosphate;
2-((2S)-1-(3-((4-((5-(2-((3-fluorophenyl)amino)-2-oxoethyl)-1,3-thiazol-2-yl)amino-6-methoxyquinazolin-7-yl)oxy)propyl)pyrrolidin-2-yl)ethyl dihydrogen phosphate;
2-((3-((4-((5-(2-((3-fluorophenyl)amino)-2-oxoethyl)-1,3-thiazol-2-yl)amino)-6-methoxyquinazolin-7-yl)oxy)propyl)amino)-2-methylpropyl dihydrogen phosphate;
((2R)-1-(3-((4-((5-(2-((3-chlorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;
2-(1-(3-((4-((5-(2-((3-chlorophenyl)amino)-2-oxoethyl)-1,3-thiazol-2-yl)amino)-6-methoxyquinazolin-7-yl)oxy)propyl)piperidin-4-yl)ethyl dihydrogen phosphate;
2-(4-(3-((4-((5-(2-(3,5-difluorophenyl)amino)-2-oxoethyl)-1,3-thiazol-2-yl)amino)-6-methoxyquinazolin-7-yl)oxy)propyl)piperazin-1-yl)ethyl dihydrogen phosphate;
2-((3-((4-((5-(2-((3,5-difluorophenyl)amino)-2-oxoethyl)-1,3-thiazol-2-yl)amino)-6-methoxyquinazolin-7-yl)oxy)propyl)(methyl)amino)ethyl dihydrogen phosphate;
((2S)-1-(3-((4-((5-(2-((3,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;
(1R)-2-((3-((4-((5-(2-((3,5-difluorophenyl)amino)-2-oxoethyl)-1,3-thiazol-2-yl)amino)-6-methoxyquinazolin-7-yl)oxy)propyl)amino)-1-methylethyl dihydrogen phosphate;
((2R)-1-(3-((4-((5-(2-((3,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;
((2S)-1-(3-((4-((5-(2-((3,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;
1-(3-((4-((5-(2-((3,4-difluorophenyl)amino)-2-oxoethyl)-1,3-thiazol-2-yl)amino)-6-methoxyquinazolin-7-yl)oxy)propyl)piperidin-4-ylmethyl dihydrogen phosphate;
(1-(3-((4-((5-(2-((2-fluorophenyl)amino)-2-oxoethyl)-1,3-thiazol-2yl)amino)-6-methoxyquinazolin-7-yl)oxy)propyl)piperidin-4-yl)methyl dihydrogen phosphate;
((2R)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;
((2S)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;
2-(ethyl(3-((4-((5-(2-((2-fluorophenyl)amino)-2-oxoethyl)-1,3-thiazol-2-yl)amino)-6-methoxyquinazolin-7-yl)oxy)propyl)amino)ethyl dihydrogen phosphate;
2-(1-(3-((4-((5-(2-((2-fluorophenyl)amino)-2-oxoethyl)-1,3-thiazol-2-yl)amino)-6-methoxyquinazolin-7-yl)oxy)propyl)piperidin-2-yl)ethyl dihydrogen phosphate;
((2R)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2S)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)(methyl)amino)ethyl dihydrogen phosphate;

2-(1-(3-((4-((5-(2-((2,3-difluorophenyl)amino)-2-oxoethyl)-1,3-thiazol-2-yl)amino)-6-methoxyquinazolin-7-yl)oxy)propyl)piperidin-2-yl)ethyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)(ethyl)amino)ethyl dihydrogen phosphate;

1-(3-((4-((5-(2-((2,3-difluorophenyl)amino)-2-oxoethyl)-1,3-thiazol-2-yl)amino)-6-methoxyquinazolin-7-yl)oxy)propyl)piperidin-4-ylmethyl dihydrogen phosphate;

2-(4-(3-((4-((5-(2-(2,3-difluorophenyl)amino)-2-oxoethyl)-1,3-thiazol-2-yl)amino)-6-methoxy-quinazolin-7-yl)oxy)propyl)piperazin-1-yl)ethyl dihydrogen phosphate;

3-((3-((4-((5-(2-((2,3-difluorophenyl)amino)-2-oxoethyl)-1,3-thiazol-2-yl)amino)-6-methoxyquinazolin-7-yl)oxy)propyl)amino)-3-methylbutyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)amino)-2-methylpropyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)amino)ethyl dihydrogen phosphate;

((2R)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2S)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-((3-((4-((5-(2-((2,5-difluorophenyl)amino)-2-oxoethyl)-1,3-thiazol-2-yl)amino)-6-methoxyquinazolin-7-yl)oxy)propyl)(ethyl)amino)ethyl dihydrogen phosphate;

((2S)-1-(3-((4-((5-(2-((2,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-(1-(3-((4-((5-(2-((2,4-difluorophenyl)amino)-2-oxoethyl)-1,3-thiazol-2-yl)amino)-6-methoxyquinazolin-7-yl)oxy)propyl)piperidin-2-yl)ethyl dihydrogen phosphate;

2-{cyclopropyl[3-({4-[(5-{2-[(3-fluorophenyl)amino]-2-oxoethyl}-1,3-thiazol-2-yl)amino]-6-methoxyquinazolin-7-yl}oxy)propyl]amino}ethyl dihydrogen phosphate;

2-{cyclopropyl[3-({4-[(5-{2-[(2,3-difluorophenyl)amino]-2-oxoethyl}-1,3-thiazol-2-yl)amino]-6-methoxyquinazolin-7-yl}oxy)propyl]amino}ethyl dihydrogen phosphate;

(1-(2-((4-((5-(2-((2,3-difluorophenyl)amino)-2-oxoethyl)-1,3-thiazol-2-yl)amino)-6-methoxyquinazolin-7-yl)oxy)ethyl)piperidin-4-yl)methyl dihydrogen phosphate;

((2R)-1-(2-((4-((5-(2-((2,3-difluorophenyl)amino)-2-oxoethyl)-1,3-thiazol-2-yl)amino)-6-methoxyquinazolin-7-yl)oxy)ethyl)pyrrolidin-2-yl)methyl dihydrogen phosphate;

2-(4-(2-((4-((5-(2-(2,3-difluorophenyl)amino)-2-oxoethyl)-1,3-thiazol-2-yl)amino)-6-methoxyquinazolin-7-yl)oxy)ethyl)piperazin-1-yl)ethyl dihydrogen phosphate; 2-(1-(2-((4-((5-(2-((3-fluorophenyl)amino)-2-oxoethyl)-1,3-thiazol-2-yl)amino)-6-methoxyquinazolin-7-yl)oxy)ethyl)piperidin-2-yl)ethyl dihydrogen phosphate;

2-(1-(2-((4-((5-(2-((3-fluorophenyl)amino)-2-oxoethyl)-1,3-thiazol-2-yl)amino)-6-methoxyquinazolin-7-yl)oxy)ethyl)piperidin-4-yl)ethyl dihydrogen phosphate;

4-(ethyl(2-((4-((5-(2-((3-fluorophenyl)amino)-2-oxoethyl)-1,3-thiazol-2-yl)amino)-6-methoxyquinazolin-7-yl)oxy)ethyl)amino)butyl dihydrogen phosphate;

2-(ethyl(2-((4-((5-(2-((3-fluorophenyl)amino)-2-oxoethyl)-1,3-thiazol-2-yl)amino)-6-methoxyquinazolin-7-yl)oxy)ethyl)amino)ethyl dihydrogen phosphate;

(1-(3-((4-((5-(2-((3-fluorophenyl)amino)-2-oxoethyl)-1,3-thiazol-2-yl)amino)quinazolin-7-yl)oxy)propyl)piperidin-4-yl)methyl dihydrogen phosphate; and 2-{4-[({4-[({5-{2-[(3-fluorophenyl)amino]-2-oxoethyl}-1,3-thiazol-2-yl)amino]-6-methoxyquinazolin-7-yl}oxy)methyl]piperidin-1-yl}ethyl dihydrogen phosphate;

or a pharmaceutically acceptable salt thereof.

A more preferred compound of the invention is any one selected from:

(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)methyl dihydrogen phosphate;

((2R)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-(4-(3-((4-((5-(2-((3-fluorophenyl)amino)-2-oxoethyl)-1,3-thiazol-2-yl)amino)-6-methoxy-quinazolin-7-yl)oxy)propyl)piperazin-1-yl)ethyl dihydrogen phosphate;

1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-3-yl dihydrogen phosphate;

1-(3-((4-((5-(2-((3-fluorophenyl)amino)-2-oxoethyl)-1,3-thiazol-2-yl)amino)-6-methoxyquinazolin-7-yl)oxy)propyl)piperidin-3-yl dihydrogen phosphate;

((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-(ethyl(((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)amino)ethyl dihydrogen phosphate;

1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl dihydrogen phosphate;

2-(((((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)amino)ethyl dihydrogen phosphate;

2-(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)ethyl dihydrogen phosphate;

2-((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)ethyl dihydrogen phosphate;

((2R)-1-(3-((4-((5-(2-((3-chlorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-(1-(3-((4-((5-(2-((3-chlorophenyl)amino)-2-oxoethyl)-1,3-thiazol-2-yl)amino)-6-methoxyquinazolin-7-yl)oxy)propyl)piperidin-4-yl)ethyl dihydrogen phosphate;

2-(4-(3-((4-((5-(2-(3,5-difluorophenyl)amino)-2-oxoethyl)-1,3-thiazol-2-yl)amino)-6-methoxyquinazolin-7-yl)oxy)propyl)piperazin-1-yl)ethyl dihydrogen phosphate;

((2S)-1-(3-((4-((5-(2-((3,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2R)-1-(3-((4-((5-(2-((3,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2S)-1-(3-((4-((5-(2-((3,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

1-(3-((4-((5-(2-((3,4-difluorophenyl)amino)-2-oxoethyl)-1,
3-thiazol-2-yl)amino)-6-methoxyquinazolin-7-yl)oxy)
propyl)piperidin-4-ylmethyl dihydrogen phosphate;

(1-(3-((4-((5-(2-((2-fluorophenyl)amino)-2-oxoethyl)-1,3-
thiazol-2yl)amino)-6-methoxyquinazolin-7-yl)oxy)pro-
pyl)piperidin-4-yl)methyl dihydrogen phosphate;

((2R)-1-(3-((4-((5-(2-((2-fluorophenyl)amino)-2-oxoethyl)-
1,3-thiazol-2-yl)amino)-6-methoxyquinazolin-7-yl)oxy)
propyl)pyrrolidin-2-yl)methyl dihydrogen phosphate;

((2S)-1-(3-((4-((5-(2-((2-fluorophenyl)amino)-2-oxoethyl)-
1,3-thiazol-2-yl)amino)-6-methoxyquinazolin-7-yl)oxy)
propyl)pyrrolidin-2-yl)methyl dihydrogen phosphate;

2-(1-(3-((4-((5-(2-((2-fluorophenyl)amino)-2-oxoethyl)-1,
3-thiazol-2-yl)amino)-6-methoxyquinazolin-7-yl)oxy)
propyl)piperidin-2-yl)ethyl dihydrogen phosphate;

((2R)-1-(3-((4-((5-(2-((2,3-difluorophenyl)amino)-2-oxoet-
hyl)-1,3-thiazol-2-yl)amino)-6-methoxyquinazolin-7-yl)
oxy)propyl)pyrrolidin-2-yl)methyl dihydrogen phosphate;

((2S)-1-(3-((4-((5-(2-((2,3-difluorophenyl)amino)-2-oxoet-
hyl)-1,3-thiazol-2-yl)amino)-6-methoxyquinazolin-7-yl)
oxy)propyl)pyrrolidin-2-yl)methyl dihydrogen phosphate;

2-(1-(3-((4-((5-(2-((2,3-difluorophenyl)amino)-2-oxoethyl)-
1,3-thiazol-2-yl)amino)-6-methoxyquinazolin-7-yl)oxy)
propyl)piperidin-2-yl)ethyl dihydrogen phosphate;

1-(3-((4-((5-(2-((2,3-difluorophenyl)amino)-2-oxoethyl)-1,
3-thiazol-2-yl)amino)-6-methoxyquinazolin-7-yl)oxy)
propyl)piperidin-4-ylmethyl dihydrogen phosphate;

2-(4-(3-((4-((5-(2-(2,3-difluorophenyl)amino)-2-oxoethyl)-
1,3-thiazol-2-yl)amino)-6-methoxy-quinazolin-7-yl)oxy)
propyl)piperazin-1-yl)ethyl dihydrogen phosphate;

((2R)-1-(3-((4-((5-(2-((2,5-difluorophenyl)amino)-2-oxoet-
hyl)-1,3-thiazol-2-yl)amino)-6-methoxyquinazolin-7-yl)
oxy)propyl)pyrrolidin-2-yl)methyl dihydrogen phosphate;

((2S)-1-(3-((4-((5-(2-((2,5-difluorophenyl)amino)-2-oxoet-
hyl)-1,3-thiazol-2-yl)amino)-6-methoxyquinazolin-7-yl)
oxy)propyl)pyrrolidin-2-yl)methyl dihydrogen phosphate;

((2S)-1-(3-((4-((5-(2-((2,4-difluorophenyl)amino)-2-oxoet-
hyl)-1,3-thiazol-2-yl)amino)-6-methoxyquinazolin-7-yl)
oxy)propyl)pyrrolidin-2-yl)methyl dihydrogen phosphate;

2-(1-(3-((4-((5-(2-((2,4-difluorophenyl)amino)-2-oxoethyl)-
1,3-thiazol-2-yl)amino)-6-methoxyquinazolin-7-yl)oxy)
propyl)piperidin-2-yl)ethyl dihydrogen phosphate;

(1-(2-((4-((5-(2-((2,3-difluorophenyl)amino)-2-oxoethyl)-1,
3-thiazol-2-yl)amino)-6-methoxyquinazolin-7-yl)oxy)
ethyl)piperidin-4-yl)methyl dihydrogen phosphate;

((2R)-1-(2-((4-((5-(2-((2,3-difluorophenyl)amino)-2-oxoet-
hyl)-1,3-thiazol-2-yl)amino)-6-methoxyquinazolin-7-yl)
oxy)ethyl)pyrrolidin-2-yl)methyl dihydrogen phosphate;

2-(4-(2-((4-((5-(2-(2,3-difluorophenyl)amino)-2-oxoethyl)-
1,3-thiazol-2-yl)amino)-6-methoxyquinazolin-7-yl)oxy)
ethyl)piperazin-1-yl)ethyl dihydrogen phosphate;

2-(1-(2-((4-((5-(2-((3-fluorophenyl)amino)-2-oxoethyl)-1,
3-thiazol-2-yl)amino)-6-methoxyquinazolin-7-yl)oxy)
ethyl)piperidin-2-yl)ethyl dihydrogen phosphate;

2-(1-(2-((4-((5-(2-((3-fluorophenyl)amino)-2-oxoethyl)-1,
3-thiazol-2-yl)amino)-6-methoxyquinazolin-7-yl)oxy)
ethyl)piperidin-4-yl)ethyl dihydrogen phosphate;

(1-(3-((4-((5-(2-((3-fluorophenyl)amino)-2-oxoethyl)-1,3-
thiazol-2-yl)amino)quinazolin-7-yl)oxy)propyl)piperi-
din-4-yl)methyl dihydrogen phosphate; and 2-{4-[({4-[({5-{2-[(3-fluorophenyl)amino]-2-oxoethyl}-1,3-
thiazol-2-yl)amino)-6-methoxyquinazolin-7-yl}oxy)me-
thyl]piperidin-1-yl}ethyl dihydrogen phosphate;

or a pharmaceutically acceptable salt thereof.

Another more preferred compound of the invention is any one selected from:

2-(ethyl(3-((4-((5-(2-((3-fluorophenyl)amino)-2-oxoethyl)-
1,3-thiazol-2-yl)amino)-6-methoxyquinazolin-7-yl)oxy)
propyl)amino)ethyl dihydrogen phosphate;

2-((3-((4-((5-(2-((3-fluorophenyl)amino)-2-oxoethyl)-1,3-
thiazol-2-yl)amino)-6-methoxyquinazolin-7-yl)oxy)pro-
pyl)amino)ethyl dihydrogen phosphate;

3-(ethyl(3-((4-((5-(2-((3-fluorophenyl)amino)-2-oxoethyl)-
1,3-thiazol-2-yl)amino)-6-methoxyquinazolin-7-yl)oxy)
propyl)amino)propyl dihydrogen phosphate;

2-((2-fluoroethyl)(3-((4-((5-(2-((3-fluorophenyl)amino)-2-
oxoethyl)-1,3-thiazol-2yl)amino)-6-methoxyquinazolin-
7-yl)oxy)propyl)amino)ethyl dihydrogen phosphate;

2-((3-((4-((5-(2-((3-fluorophenyl)amino)-2-oxoethyl)-1,3-
thiazol-2-yl)amino)-6-methoxyquinazolin-7-yl)oxy)pro-
pyl)(2-methoxyethyl)amino)ethyl dihydrogen phosphate;

2-((3-((4-((5-(2-((3-fluorophenyl)amino)-2-oxoethyl)-1,3-
thiazol-2-yl)amino)-6-methoxyquinazolin-7-yl)oxy)pro-
pyl)amino)-2-methylpropyl dihydrogen phosphate;

2-((3-((4-((5-(2-((3,5-difluorophenyl)amino)-2-oxoethyl)-1,
3-thiazol-2-yl)amino)-6-methoxyquinazolin-7-yl)oxy)
propyl)(methyl)amino)ethyl dihydrogen phosphate;

(1R)-2-((3-((4-((5-(2-((3,5-difluorophenyl)amino)-2-oxoet-
hyl)-1,3-thiazol-2-yl)amino)-6-methoxyquinazolin-7-yl)
oxy)propyl)amino)-1-methylethyl dihydrogen phosphate;

2-(ethyl(3-((4-((5-(2-((2-fluorophenyl)amino)-2-oxoethyl)-
1,3-thiazol-2-yl)amino)-6-methoxyquinazolin-7-yl)oxy)
propyl)amino)ethyl dihydrogen phosphate;

2-((3-((4-((5-(2-((2,3-difluorophenyl)amino)-2-oxoethyl)-1,
3-thiazol-2-yl)amino)-6-methoxyquinazolin-7-yl)oxy)
propyl)(methyl)amino)ethyl dihydrogen phosphate;

2-((3-((4-((5-(2-((2,3-difluorophenyl)amino)-2-oxoethyl)-1,
3-thiazol-2-yl)amino)-6-methoxyquinazolin-7-yl)oxy)
propyl)(ethyl)amino)ethyl dihydrogen phosphate;

3-((3-((4-((5-(2-((2,3-difluorophenyl)amino)-2-oxoethyl)-1,
3-thiazol-2-yl)amino)-6-methoxyquinazolin-7-yl)oxy)
propyl)amino)-3-methylbutyl dihydrogen phosphate;

2-((3-((4-((5-(2-((2,3-difluorophenyl)amino)-2-oxoethyl)-1,
3-thiazol-2-yl)amino)-6-methoxyquinazolin-7-yl)oxy)
propyl)amino)-2-methylpropyl dihydrogen phosphate;

2-((3-((4-((5-(2-((2,3-difluorophenyl)amino)-2-oxoethyl)-1,
3-thiazol-2-yl)amino)-6-methoxyquinazolin-7-yl)oxy)
propyl)amino)ethyl dihydrogen phosphate;

2-((3-((4-((5-(2-((2,5-difluorophenyl)amino)-2-oxoethyl)-1,
3-thiazol-2-yl)amino)-6-methoxyquinazolin-7-yl)oxy)
propyl)(ethyl)amino)ethyl dihydrogen phosphate;

2-{cyclopropyl[3-({4-[(5-{2-[(3-fluorophenyl)amino]-2-
oxoethyl}-1,3-thiazol-2-yl)amino]-6-methoxyquinazolin-
7-yl}oxy)propyl]amino}ethyl dihydrogen phosphate;

2-{cyclopropyl[3-({4-[(5-{2-[(2,3-difluorophenyl)amino]-
2-oxoethyl}-1,3-thiazol-2-yl)amino]-6-methoxyquinazo-
lin-7-yl}oxy)propyl]amino}ethyl dihydrogen phosphate;

4-(ethyl(2-((4-((5-(2-((3-fluorophenyl)amino)-2-oxoethyl)-
1,3-thiazol-2-yl)amino)-6-methoxyquinazolin-7-yl)oxy)
ethyl)amino)butyl dihydrogen phosphate; and 2-(ethyl(2-((4-((5-(2-((3-fluorophenyl)amino)-2-oxoethyl)-
1,3-thiazol-2-yl)amino)-6-methoxyquinazolin-7-yl)oxy)
ethyl)amino)ethyl dihydrogen phosphate;

or a pharmaceutically acceptable salt thereof.

A further more preferred compound of the invention is any one selected from:

(1-(3-((4-((5-(2-((2-fluorophenyl)amino)-2-oxoethyl)-1,3-
thiazol-2yl)amino)-6-methoxyquinazolin-7-yl)oxy)pro-
pyl)piperidin-4-yl)methyl dihydrogen phosphate;

((2R)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2S)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-(ethyl(3-((4-((5-(2-((2-fluorophenyl)amino)-2-oxoethyl)-1,3-thiazol-2-yl)amino)-6-methoxyquinazolin-7-yl)oxy)propyl)amino)ethyl dihydrogen phosphate; and 2-(1-(3-((4-((5-(2-((2-fluorophenyl)amino)-2-oxoethyl)-1,3-thiazol-2-yl)amino)-6-methoxyquinazolin-7-yl)oxy)propyl)piperidin-2-yl)ethyl dihydrogen phosphate;

or a pharmaceutically acceptable salt thereof.

Yet another more preferred compound of the invention is any one selected from:

(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)methyl dihydrogen phosphate;

((2R)-1-(3-((4-((5-(2-((3-fluorophenyl)amino)-2-oxoethyl)-1,3-thiazol-2yl)amino)-6-methoxyquinazolin-7-yl)oxy)propyl)pyrrolidin-2-yl)methyl dihydrogen phosphate;

2-(4-(3-((4-((5-(2-((3-fluorophenyl)amino)-2-oxoethyl)-1,3-thiazol-2-yl)amino)-6-methoxy-quinazolin-7-yl)oxy)propyl)piperazin-1-yl)ethyl dihydrogen phosphate;

1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-3-yl dihydrogen phosphate;

1-(3-((4-((5-(2-((3-fluorophenyl)amino)-2-oxoethyl)-1,3-thiazol-2-yl)amino)-6-methoxyquinazolin-7-yl)oxy)propyl)piperidin-3-yl dihydrogen phosphate;

2-(ethyl(3-((4-((5-(2-((3-fluorophenyl)amino)-2-oxoethyl)-1,3-thiazol-2-yl)amino)-6-methoxyquinazolin-7-yl)oxy)propyl)amino)ethyl dihydrogen phosphate;

((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-(ethyl(((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)amino)ethyl dihydrogen phosphate;

1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl dihydrogen phosphate;

2-((((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)amino)ethyl dihydrogen phosphate;

2-((3-((4-((5-(2-((3-fluorophenyl)amino)-2-oxoethyl)-1,3-thiazol-2-yl)amino)-6-methoxyquinazolin-7-yl)oxy)propyl)amino)ethyl dihydrogen phosphate;

3-(ethyl(3-((4-((5-(2-((3-fluorophenyl)amino)-2-oxoethyl)-1,3-thiazol-2-yl)amino)-6-methoxyquinazolin-7-yl)oxy)propyl)amino)propyl dihydrogen phosphate;

2-((2-fluoroethyl)(3-((4-((5-(2-((3-fluorophenyl)amino)-2-oxoethyl)-1,3-thiazol-2-yl)amino)-6-methoxyquinazolin-7-yl)oxy)propyl)amino)ethyl dihydrogen phosphate;

2-(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)ethyl dihydrogen phosphate;

2-((3-((4-((5-(2-((3-fluorophenyl)amino)-2-oxoethyl)-1,3-thiazol-2-yl)amino)-6-methoxyquinazolin-7-yl)oxy)propyl)(2-methoxyethyl)amino)ethyl dihydrogen phosphate;

2-((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)ethyl dihydrogen phosphate;

2-((3-((4-((5-(2-((3-fluorophenyl)amino)-2-oxoethyl)-1,3-thiazol-2-yl)amino)-6-methoxyquinazolin-7-yl)oxy)propyl)amino)-2-methylpropyl dihydrogen phosphate;

2-{cyclopropyl[3-({4-[(5-{2-[(3-fluorophenyl)amino]-2-oxoethyl}-1,3-thiazol-2-yl)amino]-6-methoxyquinazolin-7-yl}oxy)propyl]amino}ethyl dihydrogen phosphate;

2-(1-(2-((4-((5-(2-((3-fluorophenyl)amino)-2-oxoethyl)-1,3-thiazol-2-yl)amino)-6-methoxyquinazolin-7-yl)oxy)ethyl)piperidin-2-yl)ethyl dihydrogen phosphate;

2-(1-(2-((4-((5-(2-((3-fluorophenyl)amino)-2-oxoethyl)-1,3-thiazol-2-yl)amino)-6-methoxyquinazolin-7-yl)oxy)ethyl)piperidin-4-yl)ethyl dihydrogen phosphate;

4-(ethyl(2-((4-((5-(2-((3-fluorophenyl)amino)-2-oxoethyl)-1,3-thiazol-2-yl)amino)-6-methoxyquinazolin-7-yl)oxy)ethyl)amino)butyl dihydrogen phosphate;

2-(ethyl(2-((4-((5-(2-((3-fluorophenyl)amino)-2-oxoethyl)-1,3-thiazol-2-yl)amino)-6-methoxyquinazolin-7-yl)oxy)ethyl)amino)ethyl dihydrogen phosphate;

(1-(3-((4-((5-(2-((3-fluorophenyl)amino)-2-oxoethyl)-1,3-thiazol-2-yl)amino)quinazolin-7-yl)oxy)propyl)piperidin-4-yl)methyl dihydrogen phosphate; and 2-{4-[({4-[(5-{2-[(3-fluorophenyl)amino]-2-oxoethyl}-1,3-thiazol-2-yl)amino]-6-methoxyquinazolin-7-yl}oxy)methyl]piperidin-1-yl}ethyl dihydrogen phosphate;

or a pharmaceutically acceptable salt thereof.

Yet a further more preferred compound of the invention is any one selected from:

((2R)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2S)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)(methyl)amino)ethyl dihydrogen phosphate;

2-(1-(3-((4-((5-(2-((2,3-difluorophenyl)amino)-2-oxoethyl)-1,3-thiazol-2-yl)amino)-6-methoxyquinazolin-7-yl)oxy)propyl)piperidin-2-yl)ethyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)(ethyl)amino)ethyl dihydrogen phosphate;

1-(3-((4-((5-(2-((2,3-difluorophenyl)amino)-2-oxoethyl)-1,3-thiazol-2-yl)amino)-6-methoxyquinazolin-7-yl)oxy)propyl)piperidin-4-ylmethyl dihydrogen phosphate;

2-(4-(3-((4-((5-(2-(2,3-difluorophenyl)amino)-2-oxoethyl)-1,3-thiazol-2-yl)amino)-6-methoxy-quinazolin-7-yl)oxy)propyl)piperazin-1-yl)ethyl dihydrogen phosphate;

3-((3-((4-((5-(2-((2,3-difluorophenyl)amino)-2-oxoethyl)-1,3-thiazol-2-yl)amino)-6-methoxyquinazolin-7-yl)oxy)propyl)amino)-3-methylbutyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)amino)-2-methylpropyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)amino)ethyl dihydrogen phosphate;

2-{cyclopropyl[3-({4-[(5-{2-[(2,3-difluorophenyl)amino]-2-oxoethyl}-1,3-thiazol-2-yl)amino]-6-methoxyquinazolin-7-yl}oxy)propyl]amino}ethyl dihydrogen phosphate;

(1-(2-((4-((5-(2-((2,3-difluorophenyl)amino)-2-oxoethyl)-1,3-thiazol-2-yl)amino)-6-methoxyquinazolin-7-yl)oxy)ethyl)piperidin-4-yl)methyl dihydrogen phosphate;

((2R)-1-2-((4-((5-(2-((2,3-difluorophenyl)amino)-2-oxoethyl)-1,3-thiazol-2-yl)amino)-6-methoxyquinazolin-7-yl)oxy)ethyl)pyrrolidin-2-yl)methyl dihydrogen phosphate; and 2-(4-(2-((4-((5-(2-(2,3-difluorophenyl)amino)-2-oxoethyl)-1,3-thiazol-2-yl)amino)-6-methoxyquinazolin-7-yl)oxy)ethyl)piperazin-1-yl)ethyl dihydrogen phosphate;

or a pharmaceutically acceptable salt thereof.

Another more preferred compound of the invention is:

((2S)-1-(3-((4-((5-(2-((2,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate; or 2-(1-(3-((4-((5-(2-((2,4-difluorophenyl)amino)-2-oxoethyl)-1,3-thiazol-2-yl)amino)-6-methoxyquinazolin-7-yl)oxy)propyl)piperidin-2-yl)ethyl dihydrogen phosphate;

or a pharmaceutically acceptable salt thereof.

A further more preferred compound is any one selected from:

((2R)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2S)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate; and 2-((3-((4-((5-(2-((2,5-difluorophenyl)amino)-2-oxoethyl)-1,3-thiazol-2-yl)amino)-6-methoxyquinazolin-7-yl)oxy)propyl)(ethyl)amino)ethyl dihydrogen phosphate;

or a pharmaceutically acceptable salt thereof.

Another more preferred compound is any one selected from:

((2R)-1-(3-((4-((5-(2-((3,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2S)-1-(3-((4-((5-(2-((3,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate; and 1-(3-((4-((5-(2-((3,4-difluorophenyl)amino)-2-oxoethyl)-1,3-thiazol-2-yl)amino)-6-methoxyquinazolin-7-yl)oxy)propyl)piperidin-4-ylmethyl dihydrogen phosphate;

or a pharmaceutically acceptable salt thereof.

Yet a further more preferred compound of the invention is any one selected from:

2-(4-(3-((4-((5-(2-(3,5-difluorophenyl)amino)-2-oxoethyl)-1,3-thiazol-2-yl)amino)-6-methoxyquinazolin-7-yl)oxy)propyl)piperazin-1-yl)ethyl dihydrogen phosphate;

2-((3-((4-((5-(2-((3,5-difluorophenyl)amino)-2-oxoethyl)-1,3-thiazol-2-yl)amino)-6-methoxyquinazolin-7-yl)oxy)propyl)(methyl)amino)ethyl dihydrogen phosphate;

((2S)-1-(3-((4-((5-(2-((3,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate; and (1R)-2-((3-((4-((5-(2-((3,5-difluorophenyl)amino)-2-oxoethyl)-1,3-thiazol-2-yl)amino)-6-methoxyquinazolin-7-yl)oxy)propyl)amino)-1-methylethyl dihydrogen phosphate;

or a pharmaceutically acceptable salt thereof.

Another preferred compound is:

((2R)-1-(3-((4-((5-(2-((3-chlorophenyl)amino)-2-oxoethyl)-1,3-thiazol-2-yl)amino)-6-methoxyquinazolin-7-yl)oxy)propyl)pyrrolidin-2-yl)methyl dihydrogen phosphate; or 2-(1-(3-((4-((5-(2-((3-chlorophenyl)amino)-2-oxoethyl)-1,3-thiazol-2-yl)amino)-6-methoxyquinazolin-7-yl)oxy)propyl)piperidin-4-yl)ethyl dihydrogen phosphate;

An especially preferred compound is any one selected from:

((2R)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-(4-(3-((4-((5-(2-((3-fluorophenyl)amino)-2-oxoethyl)-1,3-thiazol-2-yl)amino)-6-quinazolin-7-yl)oxy)propyl)piperazin-1-yl)ethyl dihydrogen phosphate;

2-(ethyl(3-((4-((5-(2-((3-fluorophenyl)amino)-2-oxoethyl)-1,3-thiazol-2-yl)amino)-6-methoxyquinazolin-7-yl)oxy)propyl)amino)ethyl dihydrogen phosphate;

((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-(ethyl(((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)amino)ethyl dihydrogen phosphate;

1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl dihydrogen phosphate;

2-(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)ethyl dihydrogen phosphate;

2-((3-((4-((5-(2-((3-fluorophenyl)amino)-2-oxoethyl)-1,3-thiazol-2-yl)amino)-6-methoxyquinazolin-7-yl)oxy)propyl)(2-methoxyethyl)amino)ethyl dihydrogen phosphate;

2-((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)ethyl dihydrogen phosphate;

2-(4-(3-((4-((5-(2-(3,5-difluorophenyl)amino)-2-oxoethyl)1,3-thiazol-2-yl)amino)-6-methoxyquinazolin-7-yl)oxy)propyl)piperazin-1-yl)ethyl dihydrogen phosphate;

2-((3-((4-((5-(2-((3,5-difluorophenyl)amino)-2-oxoethyl)-1,3-thiazol-2-yl)amino)-6-methoxyquinazolin-7-yl)oxy)propyl)(methyl)amino)ethyl dihydrogen phosphate;

((2S)-1-(3-((4-((5-(2-((3,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2R)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2S)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)(methyl)amino)ethyl dihydrogen phosphate;

2-(1-(3-((4-((5-(2-((2,3-difluorophenyl)amino)-2-oxoethyl)-1,3-thiazol-2-yl)amino)-6-methoxyquinazolin-7-yl)oxy)propyl)piperidin-2-yl)ethyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)(ethyl)amino)ethyl dihydrogen phosphate;

1-(3-((4-((5-(2-((2,3-difluorophenyl)amino)-2-oxoethyl)-1,3-thiazol-2-yl)amino)-6-methoxyquinazolin-7-yl)oxy)propyl)piperidin-4-ylmethyl dihydrogen phosphate;

2-(4-(3-((4-((5-(2-(2,3-difluorophenyl)amino)-2-oxoethyl)-1,3-thiazol-2-yl)amino)-6-methoxy-quinazolin-7-yl)oxy)propyl)piperazin-1-yl)ethyl dihydrogen phosphate;

3-((3-((4-((5-(2-((2,3-difluorophenyl)amino)-2-oxoethyl)-1,3-thiazol-2-yl)amino)-6-methoxyquinazolin-7-yl)oxy)propyl)amino)-3-methylbutyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)amino)-2-methylpropyl dihydrogen phosphate;

(1-(3-((4-((5-(2-((3-fluorophenyl)amino)-2-oxoethyl)-1,3-thiazol-2-yl)amino)quinazolin-7-yl)oxy)propyl)piperidin-4-yl)methyl dihydrogen phosphate; and 2-{4-[({4-[(5-{2-[(3-fluorophenyl)amino]-2-oxoethyl}-1,3-thiazol-2-yl)amino]-6-methoxyquinazolin-7-yl}oxy)methyl]piperidin-1-yl}ethyl dihydrogen phosphate;

or a pharmaceutically acceptable salt thereof.

In another aspect the present invention provides a process for the preparation of a compound of formula (I) or a pharmaceutically acceptable salt thereof, which process comprises converting a compound of formula (II) into a compound of formula (I) by phosphorylation of an appropriate hydroxy group:

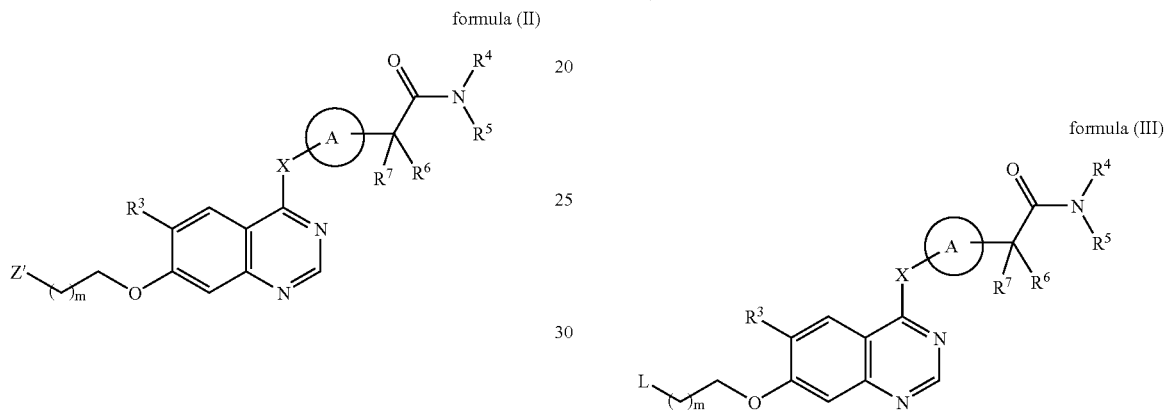

formula (II)

where A, X, m, $R^3$, $R^4$, $R^5$, $R^6$, $R^7$ and $R^9$ are as defined for formula (I); Z' is a group selected from —$NR^{1'}R^{2'}$, hydroxy, $C_{3-6}$cycloalkyl which $C_{3-6}$cycloalkyl is substituted by hydroxy or $C_{1-4}$alkyl substituted by hydroxy, and a 4- to 7-membered ring linked via a carbon atom, containing a nitrogen atom and optionally containing a further nitrogen atom which ring may be saturated, unsaturated or partially saturated, wherein the ring is substituted on carbon or nitrogen by hydroxy or $C_{1-4}$alkyl substituted by hydroxy, and wherein the ring is optionally further substituted by 1, 2 or 3 halo or $C_{1-4}$alkyl groups; and $R^{1'}$ is —$COR^{8'}$, —$CONR^{8'}R^9$ or $C_{1-6}$alkyl which $C_{1-6}$alkyl is substituted by hydroxy and optionally further substituted on carbon or nitrogen by 1 or 2 halo or methoxy groups; $R^{2'}$ is a group selected from hydrogen, —$COR^{10}$, —$CONR^{10}R^{11}$ and $C_{1-6}$alkyl which $C_{1-6}$alkyl is optionally substituted by 1, 2, or 3 halo or $C_{1-4}$alkoxy groups or —$S(O)_pR^{11}$ (where p is 0, 1 or 2) or hydroxy, or $R^{2'}$ is a group selected from $C_{2-6}$alkenyl, $C_{2-6}$alkynyl, $C_{3-6}$cycloalkyl and $C_{3-6}$cycloalkyl$C_{1-4}$alkyl; or $R^{1'}$ and $R^{2'}$ together with the nitrogen to which they are attached form a 4- to 7-membered ring optionally containing a further nitrogen atom which may be saturated, unsaturated or partially saturated, wherein the ring is substituted on carbon or nitrogen by a group selected from hydroxy and $C_{1-4}$alkyl substituted by hydroxy or —$NR^{8'}R^9$ and where the ring is optionally further substituted on carbon or nitrogen by 1, 2 or 3 halo or $C_{1-4}$alkyl groups; and where $R^{8'}$ is $C_{1-4}$alkyl substituted by hydroxy and optionally further substituted by 1 or 2 halo or methoxy groups:

and thereafter if necessary:
i) converting a compound of the formula (I) into another compound of the formula (I); and/or
ii) removing any protecting groups; and/or
iii) forming a pharmaceutically acceptable salt thereof.

Phosphorylation may be suitably performed by treatment with 1-H tetrazole (or a suitable replacement such as S-ethyl tetrazole or pyridinium hydrochloride) and di-tert-butyldiethylphosphoramidite or dibenzyldiethylphosphoramidite at 5 to 35° C. under an inert atmosphere for 30 minutes to 4 hours followed by treatment with an oxidizing agent such as meta-chloroperbenzoic acid (mCPBA) or 30% aqueous hydrogen peroxide at −10 to 25° C. for 2 to 18 hour. Deprotection of the tert-butyl groups to yield the phosphate group is required as a final step with these reagents and may be readily achieved by treatment with 4.0 N hydrochloric acid in 1,4-dioxane at 10 to 35° C. for 12 to 18 hours.

This process may further comprise a method for the preparation of a compound of formula (II) where Z is —$NR^1R^{2'}$ which method comprises the reaction of a compound of formula (III) where L is a leaving group such as halo (e.g. chloro):

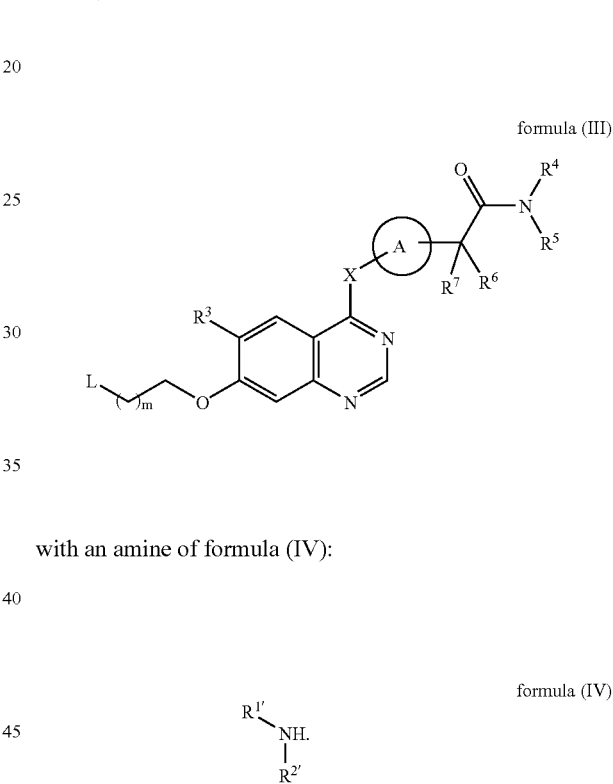

formula (III)

with an amine of formula (IV):

$$\begin{array}{c} R^{1'} \\ | \\ NH. \\ | \\ R^{2'} \end{array}$$

formula (IV)

Suitable reaction conditions for this method include heating a compound of formula (III) with an excess of amine of formula (IV) in an inert solvent such as dimethylacetamide, with or without the addition of a suitable catalyst (such as tetra-n-butylammoniuim iodide or potassium iodide) at a temperature of 50 to 100° C. for 12 to 72 hours. In an alternative procedure, the leaving group L in formula (III) may be a carboxaldehyde and the reaction with amine (IV) may be carried out under reductive conditions using a reducing agent such as sodium cyanoborohydride.

The amines of formula (IV) are known in the art or may be prepared by the skilled person using methods known in the art.

The process may further comprise a method for the preparation of a compound of formula (III) where X is $NR^{14}$, O or S, which method comprises the reaction of a compound of formula (V) where R' and R" are alkyl groups such as methyl and ethyl and L is as defined in relation to formula (III):

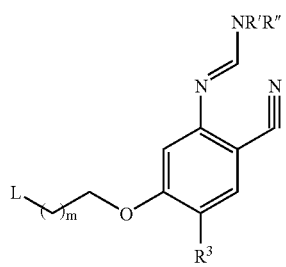

formula (V)

with a compound of formula (VI) where R may be either hydrogen or a group such as tert-butoxycarbonyl (Boc) or trityl:

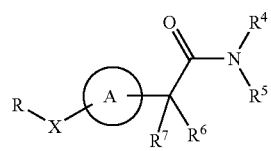

formula (VI)

Such a reaction can be achieved under a range of conditions described in the literature, such as heating a compound of formula (V) with a compound of formula (VI) in a solvent such as acetic acid at a temperature of 100 to 130° C. for 2 to 18 hours.

Alternatively, the process may further comprise a method for the preparation of a compound of formula (III) where X is $NR^{14}$, O or S, which method comprises the reaction of a compound of formula (VII) where R* is a leaving group such as halo (e.g. chloro):

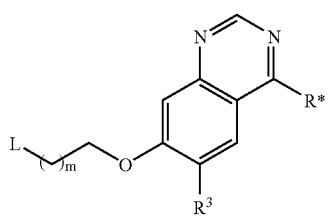

formula (VII)

with a compound of formula (VI) where R is either hydrogen or tert-butoxycarbonyl (Boc) or trityl. Such a reaction can be achieved under a range of conditions described in the literature, such as heating a compound of formula (VII) with a compound of formula (VI) in a solvent such as isopropanol or dimethylacetamide, in the presence of an acid catalyst such as hydrochloric acid, at a temperature of 80 to 100° C. for 2 to 6 hours. Alternatively the reaction may be effected using a base such as sodium hydride; carrying out the reaction in an inert solvent such as dimethylformamide at a temperature of 50 to 80° C. for 2 to 6 hours.

Compounds of formula (V) can be prepared from a compound of formula (VIII) where P is a hydroxy protecting group such as benzyl:

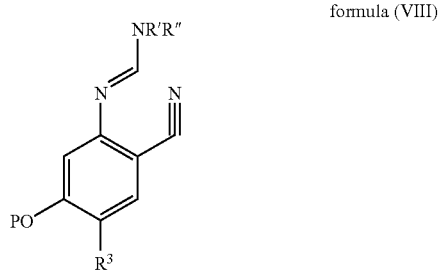

formula (VIII)

by reaction with a compound of formula (IX) where L' is a leaving group such as halo (e.g. bromo) and L is as defined in relation to formula (III):

formula (IX)

Such a reaction can be achieved (after removal of the protecting group using a method selected from those already described in the literature) under a range of conditions described in the literature such as heating a compound of formula (VIII) with a compound of formula (IX) in the presence of a catalyst such as caesium carbonate in a solvent such as acetonitrile at a temperature of 80 to 100° C. for 1 to 4 hours.

A method for the preparation of a compound of formula (VIII) comprises the reaction of a compound of formula (X) where P is as defined in relation for formula (VIII):

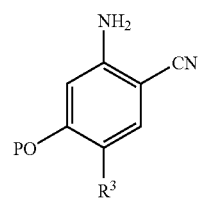

formula (X)

with an appropriate acetal such as N,N-dimethylformamide dimethyl acetal. The reaction is suitably effected in an organic solvent such as toluene or benzene, at elevated temperature, conveniently at the reflux temperature of the solvent.

Compounds of formula (X) are either known compounds or they can be prepared by the skilled person using conventional methods. In particular, compounds of formula (X) may be prepared reduction of the corresponding nitro compound of formula (XI) where P is as described in relation to formula (VIII):

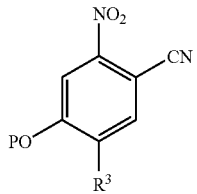

formula (XI)

Suitable reaction conditions are illustrated herein.

Compounds of formula (XI) may be obtained by nitration of a compound of formula (XII) where P is as defined in relation to formula (VIII)

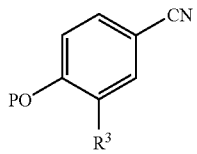

formula (XII)

for example, using nitric acid as the nitrating agent. Again, suitable reaction conditions are illustrated herein.

The nitrile of formula (XII) may be derived by reaction of the corresponding aldehyde of formula (XIII) with hydroxylamine as illustrated herein.

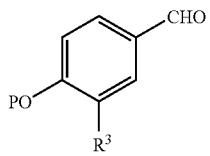

formula (XIII)

The process may further comprise a method for the preparation of a compound according to formula (VII) which method comprises the reaction of a compound of formula (XIV)

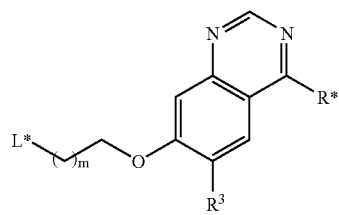

formula (XIV)

where L* is a hydroxy group, with a suitable chlorinating agent such as thionyl chloride, phoshoryl chloride or phoshorus pentachloride. Again, suitable reaction conditions are illustrated herein.

Compounds of formula (XI) are either known compounds or they can be prepared by the skilled person using conventional methods. In particular, compounds of formula (XIV) may be prepared by reaction of a compound of formula (XV) where L" is a leaving group such as halo (fluoro)

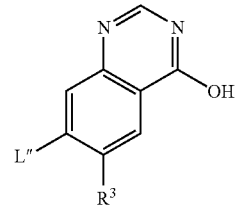

formula (XV)

with a compound of formula (XVI) where L* is a hydroxy group:

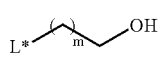

formula (XVI)

Suitable reaction conditions are illustrated herein.

Compounds of formula (XV) are either known compounds or they can be prepared by the skilled person using conventional methods. In particular, compounds of formula (XV) may be prepared by reaction of a compound of formula (XVII) (where L" is a leaving group such as halo (fluoro) and L''' is an alkoxy or hydroxy group) by reaction with neat formamide at a temperature of 140 to 200° C. for 3 to 6 hours.

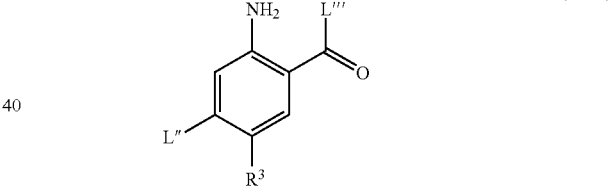

formula (XVII)

Suitable reaction conditions are illustrated herein.

Compounds of formula (XVII) are either known compounds or they can be prepared by the skilled person using conventional methods. In particular, compounds of formula (XVII) may be prepared by reduction of a compound of formula (XVIII) (where L" is a leaving group such as halo (fluoro) and L''' is an alkoxy or hydroxy group) using a reducing agent such as sodium dithionite in a water:dichloromethane solvent system at ambient temperature for 1 to 3 hours.

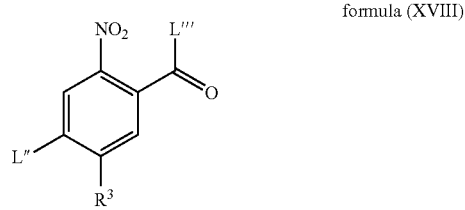

formula (XVIII)

Compounds of formula (XVIII) may be obtained by nitration of a compound of formula (XIX) where L" and L'" are as defined in relation to formula (XVIII)

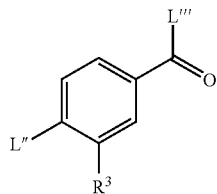

formula (XIX)

for example, using nitric acid as the nitrating agent. Again, suitable reaction conditions are illustrated herein.

The process may further comprise a method for the preparation of a compound according to formula (VI) where X is $NR^{14}$, O or S, which method comprises the reaction of a compound of formula (XX), where P is a suitable protecting group:

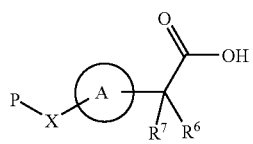

formula (XX)

with an amine of formula $HNR^4R^5$ in the presence of a coupling reagent (such as O-(7-azabenzotriazol-1-yl)-N,N,N',N'-tetramethyluronium hexafluorophosphate) and diisopropylethylamine in a solvent (such as dimethylacetamide) under inert and anhydrous conditions.

A compound of formula (XX) where X is NH may be prepared from a compound of formula (XXI):

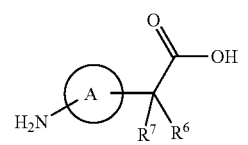

formula (XXI)

with a compound of formula (XXII) where L is an appropriate leaving group:

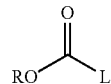

formula (XXII)

Suitable reagent and reaction conditions for this reaction include the use of di(tert-butyldicarbonate and triethylamine in tetrahydrofuran at 0° C. under a nitrogen atmosphere.

A compound of formula (III) may also be prepared (following deprotection) from a compound of formula (XX) by reacting it with a compound of formula (V) under a range of conditions described in the literature, such as heating the reaction mixture in a solvent such as acetic acid at a temperature of 100 to 130° C. for 2 to 18 hours. The product, a compound of formula (XXIII):

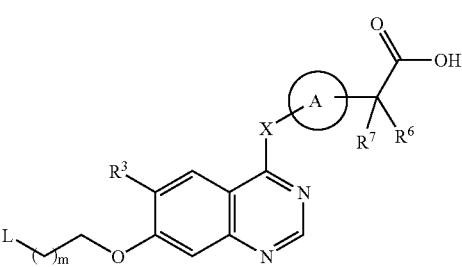

formula (XXIII)

may then be reacted with an amine of formula $HNR^4R^5$ in the presence of a coupling agent (such as O-(7-azabenzotriazol-1-yl)-N,N,N',N'-tetramethyluronium hexafluorophosphate) and diisopropylethylamine in a solvent (such as dimethylacetamide) under inert and anhydrous conditions.

Further a compound of formula (XXII) may also be prepared by reacting a deprotected compound of formula (XX) with a compound of formula (VII) under a range of conditions described in the literature, such as heating the reaction mixture in a solvent such as isopropanol or dimethylacetamide, in the presence of an acid catalyst such as hydrochloric acid, at a temperature of 80 to 100° C. for 2 to 6 hours. Alternatively the reaction may be effected using a base such as sodium hydride; carrying out the reaction in an inert solvent such as dimethylformamide at a temperature of 50 to 80° C. for 2 to 6 hours.

Compounds of formula (XXI) which comprise a heteroaromatic ring are made according to the literature. However for illustrative purpose, when A is a thiazole ring, a compound of formula (XXI) may be prepared according to the following scheme:

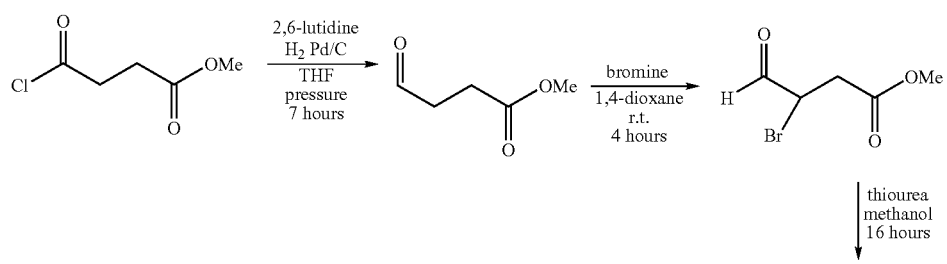

-continued

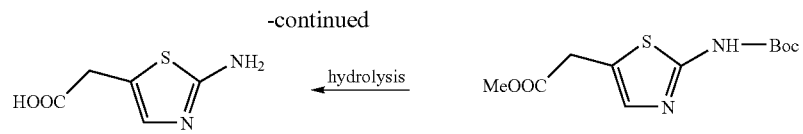

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

According to a further aspect of the invention there is provided a pharmaceutical composition which comprises a compound of formula (I), or a pharmaceutically acceptable salt thereof, as defined herein in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, soya bean oil, coconut oil, or preferably olive oil, or any other acceptable vehicle Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible or lyophilised powders and granules suitable for preparation of an aqueous suspension or solution by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, solutions, emulsions or particular systems, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in polyethylene glycol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30 µm or much less preferably 5 µm or less and more preferably between 5 µm and 1 µm, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

Therefore in a further aspect of the invention there is provided a compound of formula (I), or a pharmaceutically acceptable salt thereof, for use in therapy. Further provided is a compound of formula (I), or a pharmaceutically acceptable salt thereof, for use as a medicament. A compound of formula (I), or a pharmaceutically acceptable salt thereof, is also provided for use in the treatment of a disease where the inhibition of one or more Aurora kinase is beneficial. In particular it is envisaged that inhibition of Aurora-A kinase and/or Aurora-B kinase may be beneficial. Preferably inhibition of Aurora-B kinase is beneficial. A compound of formula (I), or a pharmaceutically acceptable salt thereof, has further use in the treatment of hyperproliferative diseases such as cancer and in particular colorectal, breast, lung, prostate, pancreatic or bladder and renal cancer or leukemias or lymphomas.

Additionally a compound of formula (I), or a pharmaceutically acceptable salt thereof is provided for use in a method of treatment of a warm-blooded animal such as man by therapy. According to this aspect, there is provided a compound of formula (I) or a pharmaceutically acceptable salt thereof for use in the method of treating a human suffering from a disease in which the inhibition of one or more Aurora kinases is beneficial, comprising the steps of administering to a person in need thereof a therapeutically effective amount of a compound of formula (I) or a pharmaceutically acceptable salt thereof. In particular it is envisaged that inhibition of Aurora-A kinase and/or Aurora-B kinase may be beneficial. Preferably inhibition of Aurora-B kinase is beneficial. Further provided is a compound of formula (I) or a pharmaceutically acceptable salt thereof for use in the method of treating a human suffering from a hyperproliferative disease such as cancer and in particular particular colorectal, breast, lung, prostate, pancreatic or bladder and renal cancer or leukemias or lymphomas, comprising the steps of administering to a person in need thereof a therapeutically effective amount of a compound of formula (I) or a pharmaceutically acceptable salt thereof.

In another aspect of the invention, there is provided the use of a compound of formula (I) or a pharmaceutically acceptable salt thereof, in the preparation of a medicament for the treatment of a disease where the inhibition of one or more Aurora kinase is beneficial. In particular it is envisaged that inhibition of Aurora-A kinase and/or Aurora-B kinase may be beneficial. Preferably inhibition of Aurora-B kinase is beneficial. In another aspect of the invention, there is provided the use of a compound of formula (I) or a pharmaceutically acceptable salt thereof, in the preparation of a medicament for the treatment of hyperproliferative diseases such as cancer and in particular colorectal, breast, lung, prostate, pancreatic or bladder and renal cancer or leukemias or lymphomas.

For the above mentioned therapeutic uses the dose administered will vary with the compound employed, the mode of administration, the treatment desired, the disorder indicated and the age and sex of the animal or patient. The size of the dose would thus be calculated according to well known principles of medicine.

In using a compound of formula (I) for therapeutic or prophylactic purposes it will generally be administered so that a daily dose in the range, for example, 0.05 mg/kg to 50 mg/kg body weight is received, given if required in divided doses. In general lower doses will be administered when a parenteral route is employed. Thus, for example, for intravenous administration, a dose in the range, for example, 0.05 mg/kg to 25 mg/kg body weight will generally be used. Similarly, for administration by inhalation, a dose in the range, for example, 0.05 mg/kg to 25 mg/kg body weight will be used.

The treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine-threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multidrug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In addition a compound of the invention may be used in combination with one or more cell cycle inhibitors. In particular with cell cycle inhibitors which inhibit bub1, bubR1 or CDK. Such conjoint treatment may be achieved by way of the simultaneous, sequential or separate dosing of the individual components of the treatment. Such combination products employ the compounds of this invention within the dosage range described herein and the other pharmaceutically active agent within its approved dosage range.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

The compounds of the invention inhibit the serine-threonine kinase activity of the Aurora kinases, in particular Aurora-A and/or Aurora-B and thus inhibit the cell cycle and cell proliferation. These properties may be assessed for example, using one or more of the procedures set out below. Whilst not wishing to be bound by theoretical constraints, it is believed that the compounds of formula (I) described herein may act as prodrugs. In procedures (c) and (d) set out below it is believed that a phosphonooxy group present in the compound of formula (I) is cleaved in situ to yield a hydroxy group and that such cleavage is necessary for activity is these assays.

(a) In Vitro Aurora-A Kinase Inhibition Test

This assay determines the ability of a test compound to inhibit serine-threonine kinase activity. DNA encoding Aurora-A may be obtained by total gene synthesis or by cloning. This DNA may then be expressed in a suitable expression system to obtain polypeptide with serine-threonine kinase activity. In the case of Aurora-A, the coding sequence was isolated from cDNA by polymerase chain reaction (PCR) and cloned into the BamH1 and Not1 restriction endonuclease sites of the baculovirus expression vector pFastBac HTc (GibcoBRL/Life technologies). The 5' PCR primer contained a recognition sequence for the restriction endonuclease BamH1 5' to the Aurora-A coding sequence. This allowed the insertion of the Aurora-A gene in frame with the 6 histidine residues, spacer region and rTEV protease cleavage site encoded by the pFastBac HTc vector. The 3' PCR primer replaced the Aurora-A stop codon with additional coding sequence followed by a stop codon and a recognition sequence for the restriction endonuclease Not1. This additional coding sequence (5' TAC CCA TAC GAT GTT CCA GAT TAC GCT TCT TAA 3') encoded for the polypeptide sequence YPYDVPDYAS. This sequence, derived from the influenza hemagglutin protein, is frequently used as a tag epitope sequence that can be identified using specific monoclonal antibodies. The recombinant pFastBac vector therefore encoded for an N-terminally 6 his tagged, C terminally influenza hemagglutin epitope tagged Aurora-A protein. Details of the methods for the assembly of recombinant DNA molecules can be found in standard texts, for example Sambrook et al. 1989, Molecular Cloning—A Laboratory Manual, 2$^{nd}$ Edition, Cold Spring Harbor Laboratory press and Ausubel et al. 1999, Current Protocols in Molecular Biology, John Wiley and Sons Inc.

Production of recombinant virus can be performed following manufacturer's protocol from GibcoBRL. Briefly, the pFastBac-1 vector carrying the Aurora-A gene was transformed into E. coli DH10Bac cells containing the baculovirus genome (bacmid DNA) and via a transposition event in the cells, a region of the pFastBac vector containing gentamycin resistance gene and the Aurora-A gene including the baculovirus polyhedrin promoter was transposed directly into the bacmid DNA. By selection on gentamycin, kanamycin, tetracycline and X-gal, resultant white colonies should contain recombinant bacmid DNA encoding Aurora-A. Bacmid DNA was extracted from a small scale culture of several BH10Bac white colonies and transfected into Spodoptera frugiperda Sf21 cells grown in TC100 medium (GibcoBRL) containing 10% serum using CellFECTIN reagent (GibcoBRL) following manufacturer's instructions. Virus particles were harvested by collecting cell culture medium 72 hrs post transfection. 0.5 mls of medium was used to infect 100 ml suspension culture of Sf21s containing $1 \times 10^7$ cells/ml. Cell culture medium was harvested 48 hrs post infection and virus titre determined using a standard plaque assay procedure. Virus stocks were used to infect Sf9 and "High 5" cells at a multiplicity of infection (MOI) of 3 to ascertain expression of recombinant Aurora-A protein.

For the large scale expression of Aurora-A kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached $1.2 \times 10^6$ cells ml$^{-1}$ they were infected with plaque-pure Aurora-A recombinant virus at a multiplicity of infection of 1 and harvested 48 hours later. All subsequent purification steps were performed at 4° C. Frozen insect cell pellets containing a total of $2.0 \times 10^8$ cells were thawed and diluted with lysis buffer (25 mM HEPES (N-[2-hydroxyethyl]piperazine-N'-[2-ethanesulphonic acid]) pH 7.4 at 4° C., 100 mM KCl, 25 mM NaF, 1 mM Na$_3$VO$_4$, 1 mM PMSF (phenylmethylsulphonyl fluoride), 2 mM 2-mercaptoethanol, 2 mM imidazole, 1 µg/ml aprotinin, 1 µg/ml pepstatin, 1 µg/ml leupeptin), using 1.0 ml per $3 \times 10^7$ cells. Lysis was achieved using a dounce homogeniser, following which the lysate was centrifuged at 41,000 g for 35 minutes. Aspirated supernatant was pumped onto a 5 mm diameter chromatography column containing 500 µl Ni NTA (nitrilo-tri-acetic acid) agarose (Qiagen, product no. 30250) which had been equilibrated in lysis buffer. A baseline level of UV absorbance for the eluent was reached after washing the column with 12 ml of lysis buffer followed by 7 ml of wash buffer (25 mM HEPES pH 7.4 at 4° C., 100 mM KCl, 20 mM imidazole, 2 mM 2-mercaptoethanol). Bound Aurora-A protein was eluted from the column using elution buffer (25 mM HEPES pH 7.4 at 4° C., 100 mM KCl, 400 mM imidazole, 2 mM 2-mercaptoethanol). An elution fraction (2.5 ml) corresponding to the peak in UV absorbance was collected. The elution fraction, containing active Aurora-A kinase, was dialysed exhaustively against dialysis buffer (25 mM HEPES pH 7.4 at 4° C., 45% glycerol (v/v), 100 mM KCl, 0.25% Nonidet P40 (v/v), 1 mM dithiothreitol).

Each new batch of Aurora-A enzyme was titrated in the assay by dilution with enzyme diluent (25 mM Tris-HCl pH 7.5, 12.5 mM KCl, 0.6 mM DTT). For a typical batch, stock enzyme is diluted 1 in 666 with enzyme diluent and 20 µl of dilute enzyme is used for each assay well. Test compounds (at 10 mM in dimethylsulphoxide (DMSO) were diluted with water and 10 µl of diluted compound was transferred to wells in the assay plates. "Total" and "blank" control wells contained 2.5% DMSO instead of compound. Twenty microlitres of freshly diluted enzyme was added to all wells, apart from "blank" wells. Twenty microlitres of enzyme diluent was added to "blank" wells. Twenty microlitres of reaction mix (25 mM Tris-HCl, 78.4 mM KCl, 2.5 mM NaF, 0.6 mM dithiothreitol, 6.25 mM MnCl$_2$, 6.25 mM ATP, 7.5 µM peptide substrate [biotin-LRRWSLGLRRWSLGLRRWSLGL-RRWSLG]) containing 0.2 µCi [γ$^{33}$P]ATP (Amersham Pharmacia, specific activity ≧2500 Ci/mmol) was then added to all test wells to start the reaction. The plates were incubated at room temperature for 60 minutes. To stop the reaction 100 μl 20% v/v orthophosphoric acid was added to all wells. The peptide substrate was captured on positively-charged nitrocellulose P30 filtermat (Whatman) using a 96-well plate harvester (TomTek) and then assayed for incorporation of $^{33}$P with a Beta plate counter. "Blank" (no enzyme) and "total" (no compound) control values were used to determine the dilution range of test compound which gave 50% inhibition of enzyme activity.

In this test, the compounds of the invention give 50% inhibition of enzyme activity at concentrations of 0.3 nM to 1000 nM and in particular compound 2 in Table 1 gave 50% inhibition of enzyme activity at a concentration of 10.2 nM.

(b) In Vitro Aurora-B Kinase Inhibition Test

This assay determines the ability of a test compound to inhibit serine-threonine kinase activity. DNA encoding Aurora-B may be obtained by total gene synthesis or by cloning. This DNA may then be expressed in a suitable expression system to obtain polypeptide with serine-threonine kinase activity. In the case of Aurora-B, the coding sequence was isolated from cDNA by polymerase chain reaction (PCR) and cloned into the pFastBac system in a manner similar to that described above for Aurora-A (i.e. to direct expression of a 6-histidine tagged Aurora-B protein).

For the large scale expression of Aurora-B kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached $1.2 \times 10^6$ cells ml$^{-1}$ they were infected with plaque-pure Aurora-B recombinant virus at a multiplicity of infection of 1 and harvested 48 hours later. All subsequent purification steps were performed at 4° C. Frozen insect cell pellets containing a total of $2.0 \times 10^8$ cells were thawed and diluted with lysis buffer (50 mM HEPES (N-[2-hydroxyethyl]piperazine-N'-[2-ethanesulphonic acid]) pH 7.5 at 4° C., 1 mM Na$_3$VO$_4$, 1 mM PMSF (phenylmethylsulphonyl fluoride), 1 mM dithiothreitol, 1 μg/ml aprotinin, 1 μg/ml pepstatin, 1 μg/ml leupeptin), using 1.0 ml per $2 \times 10^7$ cells. Lysis was achieved using a sonication homogeniser, following which the lysate was centrifuged at 41,000 g for 35 minutes. Aspirated supernatant was pumped onto a 5 mm diameter chromatography column containing 1.0 ml CM sepharose Fast Flow (Amersham Pharmacia Biotech) which had been equilibrated in lysis buffer. A baseline level of UV absorbance for the eluent was reached after washing the column with 12 ml of lysis buffer followed by 7 ml of wash buffer (50 mM HEPES pH 7.4 at 4° C., 1 mM dithiothreitol). Bound Aurora-B B protein was eluted from the column using a gradient of elution buffer (50 mM HEPES pH 7.4 at 4° C., 0.6 M NaCl, 1 mM dithiothreitol, running from 0% elution buffer to 100% elution buffer over 15 minutes at a flowrate of 0.5 ml/min). Elution fractions (1.0 ml) corresponding to the peak in UV absorbance was collected. Elution fractions were dialysed exhaustively against dialysis buffer (25 mM HEPES pH 7.4 at 4° C., 45% glycerol (v/v), 100 mM KCl, 0.05% (v/v) IGEPAL CA630 (Sigma Aldrich), 1 mM dithiothreitol). Dialysed fractions were assayed for Aurora-B kinase activity.

Each new batch of Aurora-B enzyme was titrated in the assay by dilution with enzyme diluent (25 mM Tris-HCl pH 7.5, 12.5 mM KCl, 0.6 mM DTT). For a typical batch, stock enzyme is diluted 1 in 40 with enzyme diluent and 20 μl of dilute enzyme is used for each assay well. Test compounds (at 10 mM in dimethylsulphoxide (DMSO) were diluted with water and 10 μl of diluted compound was transferred to wells in the assay plates. "Total" and "blank" control wells contained 2.5% DMSO instead of compound. Twenty microlitres of freshly diluted enzyme was added to all wells, apart from "blank" wells. Twenty microlitres of enzyme diluent was added to "blank" wells. Twenty microlitres of reaction mix (25 mM Tris-HCl, 78.4 mM KCl, 2.5 mM NaF, 0.6 mM dithiothreitol, 6.25 mM MnCl$_2$, 37.5 mM ATP, 25 μM peptide substrate [biotin-LRRWSLGLRRWSLGLRRWSLGLRRWSLG]) containing 0.2 μCi [γ$^{33}$P]ATP (Amersham Pharmacia, specific activity ≧2500 Ci/mmol) was then added to all test wells to start the reaction. The plates were incubated at room temperature for 60 minutes. To stop the reaction 100 μl 20% v/v orthophosphoric acid was added to all wells. The peptide substrate was captured on positively-charged nitrocellulose P30 filtermat (Whatman) using a 96-well plate harvester (TomTek) and then assayed for incorporation of $^{33}$P with a Beta plate counter. "Blank" (no enzyme) and "total" (no compound) control values were used to determine the dilution range of test compound which gave 50% inhibition of enzyme activity.

In this test, the compounds of the invention give 50% inhibition of enzyme activity at concentrations of 0.3 nM to 1000 nM and in particular compound 2 in Table 1 gave 50% inhibition of enzyme activity at a concentration of 9 nM.

(c) In Vitro Cell Proliferation Assay

This and other assays can be used to determine the ability of a test compound to inhibit the growth of adherent mammalian cell lines, for example the human tumour cell line SW620 (ATCC CCL-227). This assay determines the ability of at test compound to inhibit the incorporation of the thymidine analogue, 5'-bromo-2'-deoxy-uridine (BrdU) into cellular DNA. SW620 or other adherent cells were typically seeded at $1 \times 10^5$ cells per well in L-15 media (GIBCO) plus 5% foetal calf serum, 1% L-glutamine (100 μl/well) in 96 well tissue culture treated 96 well plates (Costar) and allowed to adhere overnight. The following day the cells were dosed with compound (diluted from 10 mM stock in DMSO using L-15 (with 5% FCS, 1% L-glutamine). Untreated control wells and wells containing a compound known to give 100% inhibition of BrdU incorporation were included on each plate. After 48 hours in the presence/absence of test compound the ability of the cells to incorporate BrdU over a 2 hour labelling period was determined using a Boehringer (Roche) Cell Proliferation BrdU ELISA kit (cat. No. 1 647 229) according to manufacturers directions. Briefly, 15 μl of BrdU labelling reagent (diluted 1:100 in media—L-15, 5% FCS, 1% L-glutamine) was added to each well and the plate returned to a humidified (+5% CO$_2$) 37° C. incubator for 2 hours. After 2 hours the labelling reagent was removed by decanting and tapping the plate on a paper towel. FixDenat solution (50 μl per well) was added and the plates incubated at room temperature for 45 minutes with shaking. The FixDenat solution was removed by decanting and tapping the inverted plate on a paper towel. The plate was then washed once with phosphate buffered saline (PBS) and 100 μl/well of Anti-BrdU-POD antibody solution (diluted 1:100 in antibody dilution buffer) added. The plate was then incubated at room temperature with shaking for 90 minutes. Unbound Anti-BrdU-POD antibody was removed by decanting and washing the plate 4 times with PBS before being blotted dry. TMB substrate solution was added (100 μl/well) and incubated for approximately 10 minutes at room temperature with shaking until a colour change was apparent. The optical density of the wells was then determined at 690 nm wavelength using a Titertek Multiscan plate reader. The values from compound treated, untreated and 100% inhibition controls were used to determine the dilution range of a test compound that gave 50% inhibition of BrdU incorporation. The compounds of the invention are active at 0.3 nM to 10000 nM in this test and in particular compound 2 in table 1 was active at 6 nM.

(d) In Vitro Cell Cycle Analysis Assay

This assay determines the ability of a test compound to arrest cells in specific phases of the cell cycle. Many different mammalian cell lines could be used in this assay and SW620 cells are included here as an example. SW620 cells were seeded at $7 \times 10^5$ cells per T25 flask (Costar) in 5 ml L-15 (5% FCS, 1% L-glutamine). Flasks were then incubated overnight in a humidified 37° C. incubator with 5% $CO_2$. The following day, 5 µl of L-15 (5% FCS, 1% L-glutamine) carrying the appropriate concentration of test compound solubilised in DMSO was added to the flask. A no compound control treatments was also included (0.5% DMSO). The cells were then incubated for a defined time (24 hours) with compound. After this time the media was aspirated from the cells and they were washed with 5 ml of prewarmed (37° C.) sterile PBSA, then detached from the flask by brief incubation with trypsin and followed by resuspension in 5 ml of 1% Bovine Serum Albumin (BSA, Sigma-Aldrich Co.) in sterile PBSA. The samples were then centrifuged at 2200 rpm for 10 minutes. The supernatant was aspirated to leave 200 µl of the PBS/BSA solution. The pellet was resuspended in this 200 µl of solution by pipetting 10 times to create a single cell suspension. One ml of ice-cold 80% ethanol was slowly added to each cell suspension and the samples stored at −20° C. overnight or until required for staining. Cells were pelleted by centrifugation, ethanol aspirated off and pellets resuspended in 200 µl PBS containing 100 µg/ml RNAse (Sigma Aldrich) and 10 µg/ml Propidium Iodide (Sigma Aldrich). Cell suspensions were incubated at 37° C. for 30 min, a further 200 µl PBS added and samples stored in the dark at 4° C. overnight.

Each sample was then syringed 10 times using 21-guage needle. The samples were then transferred to LPS tubes and DNA content per cell analysed by Fluorescence activated cell sorting (FACS) using a FACScan flow cytometer (Becton Dickinson). Typically 30,000 events were counted and recorded using CellQuest v1.1 software (Verity Software). Cell cycle distribution of the population was calculated using Modfit software (Verity Software) and expressed as percentage of cells with 2N (G0/G1), 2N-4N (S phase) and with 4N (G2/M) DNA content.

The compounds of the invention are active at 0.3 nM to 10000 nM in this test and in particular compound 2 in table 1 was active at 20 nM.

The invention will now be illustrated in the following non limiting examples, in which standard techniques known to the skilled chemist and techniques analogous to those described in these examples may be used where appropriate, and in which, unless otherwise stated:

(i) evaporations were carried out by rotary evaporation in vacuo and work up procedures were carried out after removal of residual solids such as drying agents by filtration;

(ii) operations were carried out at ambient temperature, typically in the range 18-25° C. and in air unless stated, or unless the skilled person would otherwise operate under an atmosphere of an inert gas such as argon;

(iii) column chromatography (by the flash procedure) and medium pressure liquid chromatography (MPLC) were performed on Merck Kieselgel silica (Art. 9385) or on Merck Lichroprep RP-18 (Art. 9303) reversed-phase silica, obtained from E. Merck, Darmstadt, Germany; bond elute chromatography was performed using Varian Mega Bond Elut cartridges (10 g, order code 1225-6034), obtained from Varian Sample Preparation Products, California, USA;

(iv) yields are given for illustration only and are not necessarily the maximum attainable;

(v) the structures of the end products of the formula (I) were generally confirmed by nuclear (generally proton) magnetic resonance (NMR) and mass spectral techniques; proton magnetic resonance chemical shift values were measured in deuterated DMSO $d_6$ (unless otherwise stated) on the delta scale (ppm downfield from tetramethylsilane) using a Varian Gemini 2000 spectrometer operating at a field strength of 300 MHz, or a Bruker DPX300 spectrometer operating at a field strength of 300 MHz; and peak multiplicities are shown as follows: s, singlet; d, doublet; dd, double doublet; t, triplet; q, quartet; qu, quintet; m, multiplet; bs, broad singlet; mass spectrometry (MS) was performed by electrospray on a VG platform;

(vi) robotic synthesis was carried out using a Zymate XP robot, with solution additions via a Zymate Master Laboratory Station and stirred via a Stem RS5000 Reacto-Station at 25° C.;

(vii) work up and purification of reaction mixtures from robotic synthesis was carried out as follows: evaporations were carried out in vacuo using a Savant AES 2000; column chromatography was performed using either an Anachem Sympur MPLC-or Jones Flashmaster MPLC systems on silica using Varian Mega Bond Elut cartridges; the structures of the final products were confirmed by LCMS on a Micromass OpenLynx system using the following and are quoted as retention time (RT) in minutes:

Column: 4.6 mm×3 cm Hichrom RPB

Solvent A: 5% Methanol in Water+0.1% formic acid

Solvent B: 5% Methanol in Acetonitrile+0.1% formic acid

Flow rate: 1.4 ml/min

Run time: 5 minutes with a 4.5 minute gradient from 0-100% B

Wavelength: 254 nm, bandwidth 10 nm

Mass detector: Micromass Platform LC

Injection volume 0.002 ml (vii) Analytical LCMS for compounds which had not been prepared by robotic synthesis was performed on a a Waters Alliance HT system using the following and are quoted as retention time (RT) in minutes:

Column: 2.0 mm×5 cm Phenomenex Max-RP 80A

Solvent A: Water

Solvent B: Acetonitrile

Solvent C: Methanol+1% formic acid

Flow rate: 1.1 ml/min

Run time: 5 minutes with a 4.5 minute gradient from 0-95% B+constant 5% solvent C Wavelength: 254 nm, bandwidth 10 nm Injection volume 0.005 ml Mass detector: Micromass ZMD (viii) Preparative high performance liquid chromatography (HPLC) was performed on a Gilson instrument using the following and are quoted as retention time (RT) in minutes:

Column: 21 mm×10 cm Hichrom RPB

Solvent A: Water+0.1% trifluoracetic acid,

Solvent B: Acetonitrile+0.1% trifluoracetic acid
Flow rate: 18 ml/min
Run time: 15 minutes with a 10 minute gradient from 5-100% B
Wavelength: 254 nm, bandwidth 10 nm
Injection volume 2.0-4.0 ml (ix) intermediates were not generally fully characterised and purity was assessed by thin layer chromatography (TLC), HPLC, infra-red (IR), MS or NMR analysis.

Particular examples of compounds of formula (I) are set out in the following tables, in which

TABLE 1

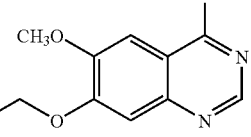

| N°. | Rˣ | Rʸ | Rᶻ |
|---|---|---|---|
| 1 | 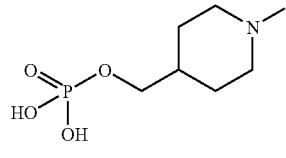 | H | 3-fluorophenyl |
| 2 | 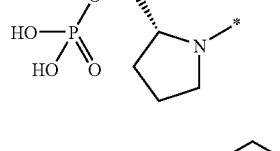 | H | 3-fluorophenyl |
| 3 | 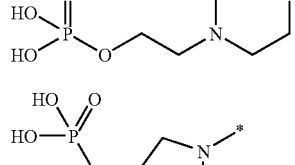 | H | 3-fluorophenyl |
| 4 | 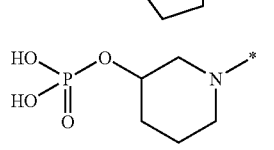 | H | 3-fluorophenyl |
| 5 | 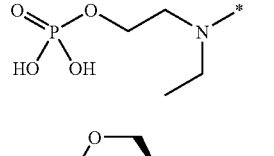 | H | 3-fluorophenyl |
| 6 | 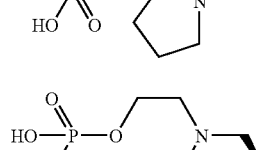 | H | 3-fluorophenyl |
| 7 |  | H | 3-fluorophenyl |
| 8 |  | H | 3-fluorophenyl |

TABLE 1-continued
| N°. | Rx | Ry | Rz |
|---|---|---|---|
| 9 | 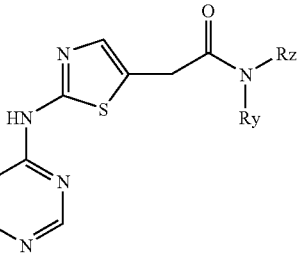 | H | 3-fluorophenyl |
| 10 | 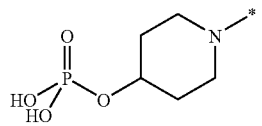 | H | 3-fluorophenyl |
| 11 | 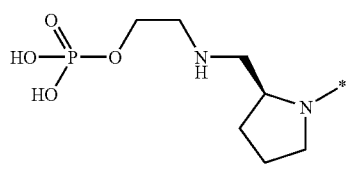 | H | 3-fluorophenyl |
| 12 | 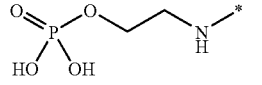 | H | 3-fluorophenyl |
| 13 | 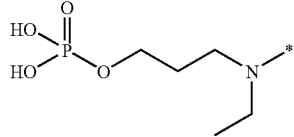 | H | 3-fluorophenyl |
| 14 | 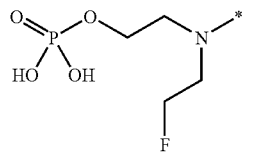 | H | 3-fluorophenyl |
| 15 | 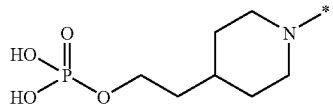 | H | 3-fluorophenyl |
| 16 | 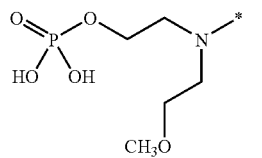 | H | 3-fluorophenyl |
| 17 | 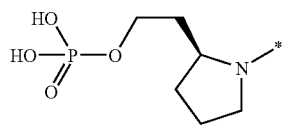 | H | 3-fluorophenyl |

TABLE 1-continued
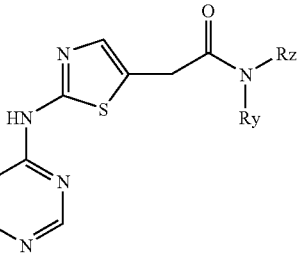
| N°. | R$^x$ | R$^y$ | R$^z$ |
|---|---|---|---|
| 18 | 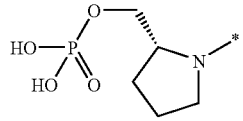 | H | 3-chlorophenyl |
| 19 | 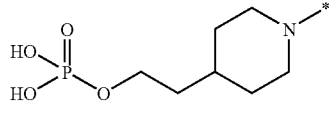 | H | 3-chlorophenyl |
| 20 | 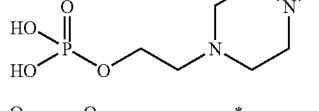 | H | 3,5-difluorophenyl |
| 21 | 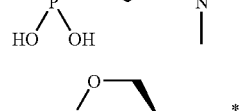 | H | 3,5-difluorophenyl |
| 22 | 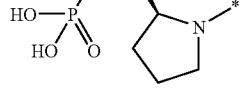 | H | 3,5-difluorophenyl |
| 23 | 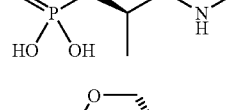 | H | 3,5-difluorophenyl |
| 24 | 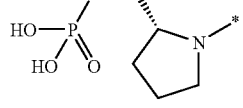 | H | 3,4-difluorophenyl |
| 25 | 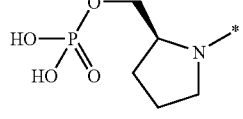 | H | 3,4-difluorophenyl |
| 26 | 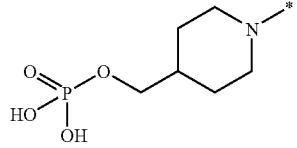 | H | 3,4-difluorophenyl |
| 27 | 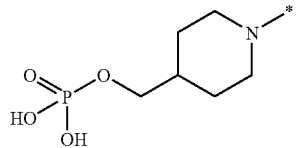 | H | 2-fluorophenyl |

TABLE 1-continued
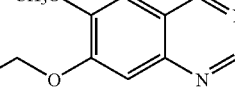
| Nº. | Rx | Ry | Rz |
|---|---|---|---|
| 28 | 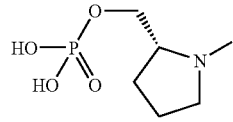 | H | 2-fluorophenyl |
| 29 | 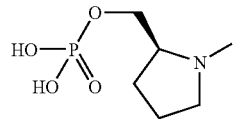 | H | 2-fluorophenyl |
| 30 | 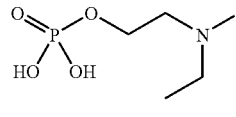 | H | 2-fluorophenyl |
| 31 | 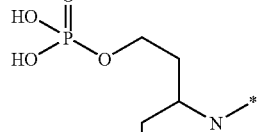 | H | 2-fluorophenyl |
| 32 | 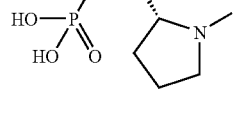 | H | 2,3-difluorophenyl |
| 33 | 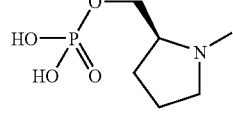 | H | 2,3-difluorophenyl |
| 34 | 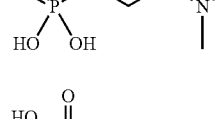 | H | 2,3-difluorophenyl |
| 35 | 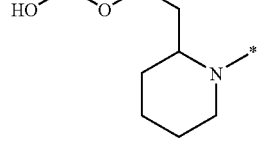 | H | 2,3-difluorophenyl |

TABLE 1-continued
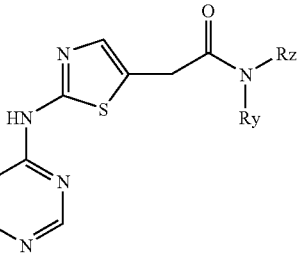
| N°. | R<sup>x</sup> | R<sup>y</sup> | R<sup>z</sup> |
|---|---|---|---|
| 36 | 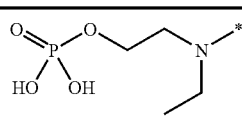 | H | 2,3-difluorophenyl |
| 37 | 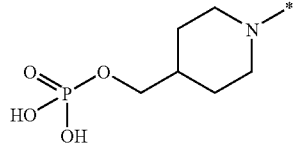 | H | 2,3-difluorophenyl |
| 38 | 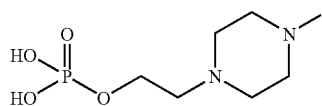 | H | 2,3-difluorophenyl |
| 39 | 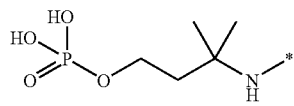 | H | 2,3-difluorophenyl |
| 40 | 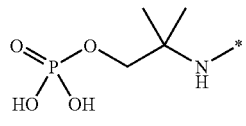 | H | 2,3-difluorophenyl |
| 41 | 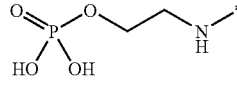 | H | 2,3-difluorophenyl |
| 42 | 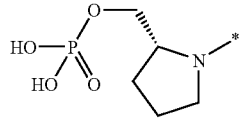 | H | 2,5-difluorophenyl |
| 43 | 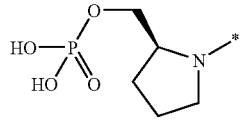 | H | 2,5-difluorophenyl |
| 44 | 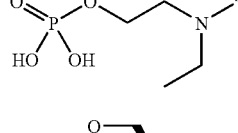 | H | 2,5-difluorophenyl |
| 45 | 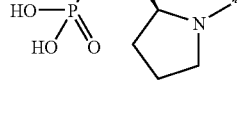 | H | 2,4-difluorophenyl |

TABLE 1-continued

[Structure: quinazoline core with CH3O- and Rx-O-CH2CH2CH2- substituents, linked via HN to thiazole-CH2-C(=O)-N(Ry)(Rz)]

| N°. | Rx | Ry | Rz |
|-----|----|----|----|
| 46 | (HO)2P(=O)-O-CH2CH2-[2-piperidinyl, N-*] | H | 2,4-difluorophenyl |
| 47 | (HO)2P(=O)-O-CH2CH2-N(cyclopropyl)-* | H | 3-fluorophenyl |
| 48 | (HO)2P(=O)-O-CH2CH2-N(cyclopropyl)-* | H | 2,3-difluorophenyl |

TABLE 2

[Structure: quinazoline core with CH3O- and Rx-CH2CH2-O- substituents, linked via HN to thiazole-CH2-C(=O)-N(Ry)(Rz)]

| N°. | Rx | Ry | Rz |
|-----|----|----|----|
| 49 | 4-[(HO)2P(=O)-O-CH2]-piperidin-1-yl-* | H | 2,3-difluorophenyl |
| 50 | (2S)-2-[(HO)2P(=O)-O-CH2]-pyrrolidin-1-yl-* | H | 2,3-difluorophenyl |
| 51 | 4-[2-((HO)2P(=O)-O)-ethyl]-piperazin-1-yl-* | H | 2,3-difluorophenyl |

TABLE 2-continued
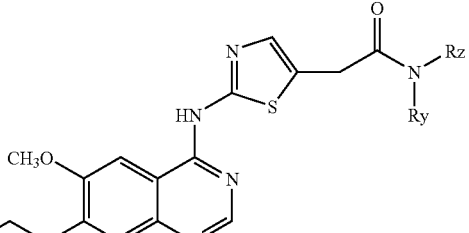
| Nº. | Rx | Ry | Rz |
|---|---|---|---|
| 52 | 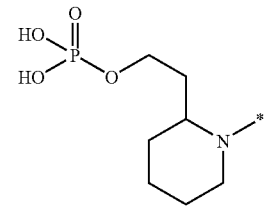 | H | 3-fluorophenyl |
| 53 | 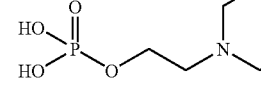 | H | 3-fluorophenyl |
| 54 | 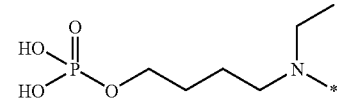 | H | 3-fluorophenyl |
| 55 | 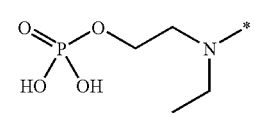 | H | 3-fluorophenyl |
TABLE 3
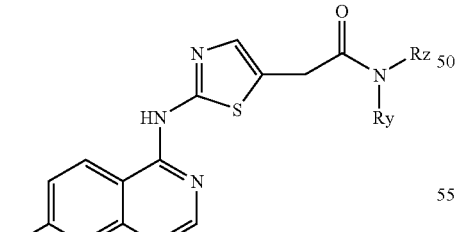
| Nº. | Rx | Ry | Rz |
|---|---|---|---|
| 56 | 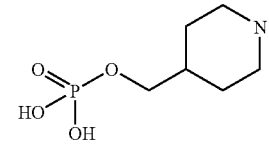 | H | 3-fluorophenyl |
TABLE 4
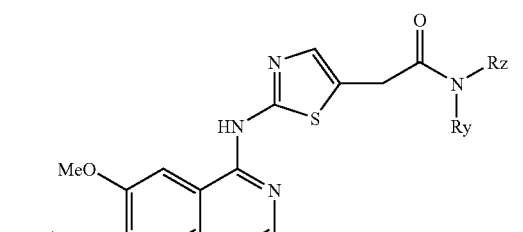
| Nº. | Rx | Ry | Rz |
|---|---|---|---|
| 57 | 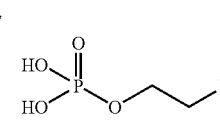 | H | 3-fluorophenyl |

EXAMPLE 1

Preparation of Compound 1 in Table 1—(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)methyl dihydrogen phosphate Di(tert-butyl) (1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)methyl phosphate (6.64 g, 8.6 mmol), in 1,4-dioxane (250 ml) was treated with 4.0 N hydrochloric acid in 1,4-dioxane (15 ml, 60 mmol) at 20° C. for 18 hours. The solid product was collected by suction filtration and washed with i) 1,4-dioxane (100 ml), ii) acetonitrile (100 ml) and iii) diethyl ether (100 ml), Prolonged drying in vacuo yielded the title compound (6.73 g, 98% yield) as a yellow dihydrochloride salt:

$^1$H-NMR (DMSO d$_6$): 10.95 (s, 1H), 10.60 (br s, 1H), 9.00 (s, 1H), 7.85 (s, 1H), 7.65 (m, 1H), 7.60 (s, 1H), 7.45 (s, 1H), 7.38 (m, 2H), 6.90 (m, 1H), 4.30 (m, 2H), 4.03 (s, 2H), 3.95 (s, 3H), 3.70 (m, 2H), 3.55 (m, 2H), 3.20 (m, 2H), 2.97 (m, 2H), 2.35 (m, 2H), 1.90 (m, 3H), 1.60 (m, 2H):

MS (+ve ESI): 661 (M+H)$^+$

MS (−ve ESI): 659 (M−H)$^−$.

Di(tert-butyl) (1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)methyl phosphate used as the starting material was obtained as follows:

a) A mixture of 4-benzyloxy-3-methoxybenzaldehyde (157 g, 649 mmol), sodium acetate (106 g, 1.29 mol), hydroxylamine hydrochloride (90 g, 1.29 mol) and acetic acid (500 ml) was heated at reflux for 21 hours. The solvent was evaporated in vacuo and ice/water (1000 ml) was added to the residue, forming a sticky solid. The mixture was neutralised by addition of aqueous sodium hydroxide solution then extracted with dichloromethane (2×500 ml). The organic solution was washed with 1.0 N sodium hydroxide (100 ml) and brine (100 ml) and then dried over magnesium sulphate. Solvent evaporation in vacuo, followed by trituration of the residue with hexane:ethyl acetate (3:1) and collection of the solid by suction filtration yielded 4-benzyloxy-3-methoxybenzonitrile (123 g, 80% yield) as a brown solid:

$^1$H-NMR (DMSO d$_6$): 7.38 (m, 7H), 7.19 (m, 1H), 5.18 (s, 2H), 3.80 (s, 3H):

MS (−ve ESI): 238 (M−H)$^−$.

b) Acetic acid (17 ml) was added slowly to nitric acid (40 ml, 440 mmol) at 5° C. Powdered 4-benzyloxy-3-methoxybenzonitrile (10 g, 42 mmol) was added and the mixture warmed to 23° C. over 10 minutes. An exotherm occurred and the temperature was controlled at <30° C. using an ice bath. The reaction was stirred at 23° C. for 20 hours then poured into ice/water (1000 ml). After stirring for two hours the yellow solid was collected by suction filtration, washed with water and dried to yield 4-benzyloxy-3-methoxy-6-nitrobenzonitrile (10.1 g, 85% yield) as a yellow solid:

$^1$H-NMR (DMSO d$_6$): 7.95 (s, 1H), 7.70 (s, 1H), 7.40 (m, 5H), 5.30 (s, 2H), 3.95 (s, 3H):

MS (−ve ESI): 283 (M−H)$^−$.

c) A mixture of 4-benzyloxy-3-methoxy-6-nitrobenzonitrile (46.0 g, 162 mmol), sodium bicarbonate (95.0 g, 1.13 mol), water (750 ml), dichloromethane (550 ml) and tetrabutylammonium chloride (30.0 g, 108 mmol) was rapidly stirred at 20° C. and treated with sodium dithionite (66.0 g, 379 mmol) portionwise over 2 hours. The mixture was stirred for a further 1 hour then the phases separated. The aqueous phase was extracted with dichloromethane (2×200 ml) and then the combined organic solution was washed with water (300 ml) and dried over magnesium sulphate. The solution was concentrated to 250 ml and 4.0N hydrochloric acid in 1,4-dioxane (150 ml, 0.6 mol) was added. Diethyl ether (1000 ml) was added and the reaction cooled with ice. The resulting solid was collected by suction filtration and washed with diethyl ether. The resultant solid was stirred in methanol (1000 ml), sodium bicarbonate solution (800 ml) was added (until pH >8) and the reaction was stirred for 1 hour. The solid was collected by suction filtration, washed with water and methanol and dried in vacuo to yield 2-cyano-5-benzyloxy-4-methoxyaniline (34 g, 82% yield) as light brown solid:

$^1$H-NMR (DMSO d$_6$): 7.40 (m, 5H), 6.90 (s, 1H), 6.50 (s, 1H), 5.60 (br s, 2H), 5.02 (s, 2H), 3.65 (s, 3H):

MS (+ve ESI): 254 (M+H)$^+$.

d) 2-cyano-5-benzyloxy-4-methoxyaniline (100 g, 394 mmol) in toluene (1400 ml) was heated with dimethylformamide dimethylacetal (100 ml, 940 mmol) at reflux with slow distillation of solvent to maintain the internal temperature at 105° C. After 3 hours the solution was cooled and filtered to remove a small amount of solid. The filtrate was evaporated in vacuo, the residue was triturated with diethyl ether and the solid collected by suction filtration. Prolonged drying in vacuo yielded N'-(5-(benzyloxy)-2-cyano-4-methoxyphenyl)-N,N-dimethylimidoformamide (110 g, 90% yield) as a brown solid:

$^1$H-NMR (DMSO d$_6$): 7.90 (s, 1H), 7.40 (m, 5H), 7.10 (s, 1H), 6.88 (s, 1H), 5.15 (s, 2H), 3.70 (s, 3H), 3.02 (s, 3H), 2.95 (s, 3H):

MS (+ve ESI): 310 (M+H)$^+$

MS (−ve ESI): 308 (M−H)$^−$.

e) N'-(5-(benzyloxy)-2-cyano-4-methoxyphenyl)-N,N-dimethylimidoformamide (110 g, 356 mmol) and trifluoroacetic acid (600 ml) were heated at reflux for 15 minutes. Evaporation and co-evaporation with toluene, trituration with diethyl ether and collection of the solid by suction filtration, followed by prolonged drying in vacuo, yielded N'-(2-cyano-5-hydroxy-4-methoxyphenyl)-N,N-dimethylimidoformamide (112 g, 95% yield) as a light brown trifluoroacetate salt:

$^1$H-NMR (DMSO d$_6$): 8.39 (s, 1H), 7.38 (s, 1H), 6.90 (s, 1H), 3.80 (s, 3H), 3.25 (s, 3H), 3.17 (s, 3H):

MS (+ve ESI): 220 (M+H)$^+$

MS (−ve ESI): 218 (M−H)$^−$.

f) A mixture of N'-(2-cyano-5-hydroxy-4-methoxyphenyl)-N,N-dimethylimidoformamide (21.9 g, 66 mmol), caesium carbonate (998 g, 300 mmol) and 1-bromo-3-chloropropane (11 ml, 110 mmol) in acetonitrile (300 ml) was heated at reflux for 1 hour. The reaction mixture was cooled and the solvent evaporated in vacuo. The residue was dissolved in water (200 ml) and extracted with dichloromethane (2×150 ml). The organic solution was washed with brine (50 ml) and dried over magnesium sulphate. The solvent was evaporated in vacuo and the resultant solid was triturated (with diethyl ether) and collected by suction filtration. Drying in vacuo yielded N'-(5-(3-chloropropoxy)-2-cyano-4-methoxyphenyl)-N,N-dimethylimidoformamide (17.7 g, 91% yield) as a white solid:

$^1$H-NMR (DMSO d$_6$): 8.89 (s, 1H), 7.07 (s, 1H), 6.75 (s, 1H), 4.15 (t, 2H), 3.77 (t, 2H), 3.70 (s, 3H), 3.05 (s, 3H), 2.95 (s, 3H), 2.18 (m, 2H):

MS (+ve ESI): 296.4 (M+H)$^+$.

g) A mixture of tert-butyl 5-(2-((3-fluorophenyl)amino)-2-oxoethyl)-1,3-thiazol-2-ylcarbamate (3.82 g, 10 mmol)

and N'-(5-(3-chloropropoxy)-2-cyano-4-methoxyphenyl)-N,N-dimethylimidoformamide (2.95 g, 10 mmol) in acetic acid (10 ml) was heated at reflux for 2 hours. The mixture was cooled and the solid product collected by suction filtration, washed with acetic acid then diethyl ether. The solid was dissolved in dimethyl acetamide (20 ml) and filtered. Aqueous sodium bicarbonate solution (50 ml) was added slowly to the filtrate and the solid product was collected by suction filtration, washed with water and dried to yield N-(3-fluorophenyl)-2-(2-(7-(3-chloropropoxy)-6-methoxyquinazolin-4-yl-amino-1,3-thiazol-5-yl)acetamide (3.63 g, 73% yield) as a pale yellow solid:
$^1$H-NMR (DMSO $d_6$): 12.00 (br s, 1H), 10.42 (br s, 1H), 8.63 (s, 1H), 8.10 (s, 1H), 7.60 (m, 1H), 7.30 (m, 4H), 6.85 (m, 1H), 4.25 (t, 2H), 3.95 (s, 3H), 3.85 (s, 2H), 3.80 (t, 2H), 2.25 (m, 2H):
MS (+ve ESI): 502 (M+H)$^+$
MS (−ve ESI): 500 (M−H)$^-$.

h) N-(3-fluorophenyl)-2-(2-(7-(3-chloropropoxy)-6-methoxyquinazolin-4-yl-amino-1,3-thiazol-5-yl)acetamide (13.1 g, 26.1 mmol) in dimethyl acetamide (180 ml) was reacted with piperidin-4-ylmethanol (6.01 g, 52.3 mmol) in the presence of tetrabutylammonium iodide (1.3 g, 10 mol %) at 60° C., under an inert atmosphere, for 20 hours. The cooled reaction solution was diluted with aqueous sodium bicarbonate solution and the resulting solid was collected by suction filtration. Purification by chromatography on silica gel, eluting with methanol:ammonia:dichloromethane (7:1:92), evaporation of solvents and drying in vacuo yielded N-(3-fluorophenyl)-2-(2-((7-(3-(4-(hydroxymethyl)piperidin-1-yl)propoxy)-6-methoxyquinazolin-4-yl)amino)-1,3-thiazol-5-yl)acetamide (6.01 g, 40% yield) as an orange solid:
$^1$H-NMR (DMSO $d_6$): 10.42 (br s, 1H), 8.65 (s, 1H), 8.10 (s, 1H), 7.60 (m, 1H), 7.35 (m, 3H), 7.20 (s, 1H), 6.85 (m, 1H), 4.35 (t, 1H), 4.17 (t, 2H), 3.95 (s, 3H), 3.85 (s, 2H), 3.20 (t, 2H), 2.85 (m, 2H), 2.43 (m, 2H), 1.90 (m, 4H), 1.60 (m, 2H), 1.30 (m, 1H), 1.10 (m, 2H):
MS (+ve ESI): 581 (M+H)$^+$
MS (−ve ESI): 579 (M−H)$^-$.

i) N-(3-fluorophenyl)-2-(2-((7-(3-(4-(hydroxymethyl)piperidin-1-yl)propoxy)-6-methoxyquinazolin-4-yl)amino)-1,3-thiazol-5-yl)acetamide (5.41 g, 9.33 mmol) in dimethyl acetamide (50 ml) was treated with tetrazole (1.33 g, 19.0 mmol) and di-tert-butyldiethylphosphoramidite (5.8 g, 22 mmol) at 20° C., under an inert atmosphere, for 2 hours. The reaction solution was cooled to −10° C. and 30% hydrogen peroxide solution (2.3 ml, 20 mmol) was added dropwise over 5 minutes. After stirring for 2 hours at 20° C. the reaction was quenched at −10° C. with 0.5N aqueous sodium thiosulphate solution. The mixture was extracted twice with ethyl acetate (300 ml) and the organic solution dried over magnesium sulphate, evaporated and the resulting oil purified by chromatography on silica gel, eluting with methanol:ammonia:dichloromethane (4:1:97). Evaporation of solvent and drying in vacuo yielded di(tert-butyl) (1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)methyl phosphate (6.66 g, 84% yield) as an orange foam:
$^1$H-NMR (DMSO $d_6$): 12.00 (br s, 1H), 10.45 (s, 1H), 8.65 (s, 1H), 8.20 (s, 1H), 7.60 (m, 1H), 7.38 (s, 1H), 7.35 (m, 2H), 7.25 (s, 1H), 6.88 (m, 1H), 4.18 (m, 2H), 3.95 (s, 3H), 3.89 (s, 2H), 3.70 (m, 2H), 2.90 (m, 2H), 2.45 (m, 2H), 1.95 (m, 4H), 1.60 (m, 3H), 1.40 (m, 18H), 1.22 (m, 2H):
MS (+ve ESI): 773 (M+H)$^+$.
MS (−ve ESI): 771 (M−H)$^-$.

tert-butyl 5-(2-((3-fluorophenyl)amino)-2-oxoethyl)-1,3-thiazol-2-ylcarbamate, used as the starting material (in example 1g) was obtained as follows:
j) 2,6-Lutidine (158 g, 1.48 mol) and 10% palladium on carbon (15 g) were added to a solution of methyl 4-chloro-4-oxobutanoate (220 g, 1.46 mol) in tetrahydrofuran (3600 ml). The mixture was stirred under a hydrogen atmosphere at 1.6 bar for 7 hours at ambient temperature. The reaction mixture was filtered through glass fibre paper washing with diethyl ether. The filtrate was concentrated under reduced pressure and the residue purified by vacuum distillation (72° C., 13 mmHg) to yield methyl 4-oxobutanoate (130.8 g, 76% yield) as an oil:
$^1$H-NMR (DMSO $d_6$): 9.60 (s, 1H), 3.60 (s, 3H), 2.70 (t, 2H), 2.50 (t, 2H).

k) Bromine (180 g, 1.12 mol) was added, over 3 hours, to a solution of methyl 4-oxobutanoate (123.6 g, 1.07 mol) in diethyl ether (1000 ml) and 1,4-dioxane (9.10 ml) and the reaction mixture stirred for one hour at ambient temperature. The reaction mixture was poured into dichloromethane (1000 ml) and calcium carbonate (250 g, 2.50 mol) and sodium hydrogen carbonate (80 g, 0.95 mol) were added before the mixture was stirred for 21 hours at ambient temperature. The inorganic solids were removed by suction filtration and the filtrate was concentrated under reduced pressure to yield methyl 3-bromo-4-oxobutanoate (208 g, quantitative yield) as a brown oil:
$^1$H-NMR (DMSO $d_6$): 9.55 (s, 1H), 4.45 (t, 1H), 3.70 (s, 3H), 3.22 (m, 1H), 2.95 (m, 1H).

l) Methyl 3-bromo-4-oxobutanoate (1.07 mol assumed) was added to a suspension of thiourea (73 g, 0.96 mol) in methanol, giving an exotherm. The reaction was heated at 80° C. for 6 hours, cooled and then allowed to stand at ambient temperature for 4 days. The product was collected by suction filtration and washed with methanol to give methyl (2-amino-1,3-thiazol-5-yl)acetate hydrobromide (173 g, 69% yield) as a yellow crystalline solid:
$^1$H-NMR (DMSO $d_6$): 9.25 (bs, 2H), 7.20 (s, 1H), 3.80 (s, 2H), 3.60 (s, 3H).

m) A solution of di(tert-butyl)dicarbonate (43.9 g, 0.201 mol) in tetrahydrofuran (200 ml) was added, at 0° C. under a nitrogen atmosphere, to a solution of methyl (2-amino-1,3-thiazol-5-yl)acetate hydrobromide (30 g, 0.12 mol) in tetrahydrofuran (600 ml), water (150 ml) and triethylamine (54 ml, 0.39 mol). Di(tert-butyl)dicarbonate (4.4 g, 20 mmol) and triethylamine (5.4 ml, 0.039 mol) were added and the reaction stirred for 20 hours at ambient temperature before the reaction was concentrated under reduced pressure. The residue was dissolved in ethyl acetate. The organic phase was washed with brine, dried over magnesium sulphate, concentrated under reduced pressure and triturated with diethyl ether and hexane to yield methyl (2-((tert-butoxycarbonyl)amino)-1,3-thiazol-5-yl)acetate (31.8 g, 98% yield) as a pale orange solid:
$^1$H-NMR (DMSO $d_6$): 11.30 (s, 1H), 7.15 (s, 1H), 3.80 (s, 2H), 3.60 (s, 3H), 1.40 (s, 9H):
MS (−ve ESI): 271 (M−H)$^-$.

n) Sodium hydroxide (234 ml of a 1.0 N solution in water) was added to a solution of methyl (2-((tert-butoxycarbonyl)amino)-1,3-thiazol-5-yl)acetate (31.8 g, 117 mmol) in tetrahydrofuran (240 ml) and methanol (240 ml). The solution was stirred overnight at ambient temperature. The organic solvents were removed under reduced pressure. The residue was acidified with aqueous citric acid to pH 3.5. The product was extracted into ethyl acetate, dried over magnesium sulphate, filtered, concentrated under reduced pressure and triturated with diethyl ether to give (2-((tert-butoxycarbonyl)amino)-1,3-thiazol-5-yl)acetic acid (23.1 g, 76% yield) as a pale orange solid:

$^1$H-NMR (DMSO d$_6$): 7.10 (s, 1H), 3.70 (s, 2H), 1.40 (s, 9H):

MS (−ve ESI): 257 (M−H)$^−$.

p) A solution of (2-((tert-butoxycarbonyl)amino)-1,3-thiazol-5-yl)acetic acid (100 g, 0.388 mol), 3-fluoroaniline (60 g, 0.504 mol) and diisopropylethylamine (88 ml, 0.504 mol) in dimethylacetamide (360 ml) under inert and anhydrous conditions, was treated portionwise with O-(7-azabenzotriazol-1-yl)-N,N,N',N'-tetramethyluronium hexafluoro-phosphate (191.6 g, 0.504 mol) at 30° C. for 19 hours. The solvent was removed in vacuo and the residue taken up in ethyl acetate (1500 ml) and washed with aqueous sodium bicarbonate solution (500 ml) then water (2×250 ml). The organic solution was dried over magnesium sulphate, the solvent was removed in vacuo and the residue was triturated with diethyl ether and dried. The solid was triturated with dimethyl formamide (500 ml) and a white solid was collected by filtration, washed with water and dried in vacuo to yield tert-butyl 5-(2-((3-fluorophenyl)amino)-2-oxoethyl)-1,3-thiazol-2-ylcarbamate (78.9 g, 53% yield). The filtrate was diluted with water (1500 ml) and a light brown solid collected by suction filtration, washed with water and dried in vacuo to yield a second crop of tert-butyl 5-(2-((3-fluorophenyl)amino)-2-oxoethyl)-1,3-thiazol-2-ylcarbamate (51 g, 33% yield):

$^1$H-NMR (DMSO d$_6$): 7.58 (m, 1H), 7.30 (m, 2H), 7.15 (s, 1H), 6.85 (m, 1H), 3.79 (s, 2H), 1.45 (s, 9H):

MS (+ve ESI): 352 (M+H)$^+$

MS (−ve ESI): 350 (M−H)$^−$.

EXAMPLE 2

Preparation of Compound 2 in Table 1—((2R)-1-(3-((4-((5-(2-((3-fluorophenyl)amino)-2-oxoethyl)-1,3-thiazol-2-yl)amino)-6-methoxyquinazolin-7-yl)oxy) propyl)pyrrolidin-2-yl)methyl dihydrogen phosphate An analogous reaction to that described in example 1, but starting with di(tert-butyl) ((2R)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl phosphate (400 mg, 0.528 mmol) yielded the title compound (313 mg, 81% yield):

$^1$H-NMR (DMSO d$_6$): 9.03 (s, 1H), 7.89 (s, 1H), 7.65 (d, 1H), 7.62 (s, 1H), 7.44 (s, 1H), 7.44 (s, 1H), 7.36 (m, 2H), 6.90 (m, 1H), 4.32 (m, 2H), 4.25 (m, 2H), 4.02 (s, 2H), 3.99 (s, 3H), 3.80 (m, 1H), 3.70 (m, 1H), 3.60 (m, 1H), 3.30 (m, 1H), 3.23 (q, 1H), 2.35 (m, 2H), 2.20 (m, 1H), 2.04 (m, 1H), 1.96 (m, 1H), 1.83 (m, 1H):

MS (+ve ESI): 647 (M+H)$^+$.

di(tert-butyl) ((2R)-1-(3-((4-((5-(2-((3-fluorophenyl) amino)-2-oxoethyl)-1,3-thiazol-2-yl)amino)-6-methoxyquinazolin-7-yl)oxy)propyl)pyrrolidin-2-yl)methyl phosphate used as the starting material was obtained as follows:

a) An analogous reaction to that described in example 1h, but starting with (R)-(−)-2-pyrrolidinylmethanol (334 mg, 3.3 mmol) yielded N-(3-fluorophenyl)-2-(2-((7-(3-((2R)-2-(hydroxymethyl)pyrrolidin-1-yl)propoxy)-6-methoxyquinazolin-4-yl)amino)-1,3-thiazol-5-yl)acetamide (66 mg, 53% yield):

$^1$H-NMR (DMSO d$_6$): 12.01 (br s, 1H), 10.48 (s, 1H), 8.68 (s, 1H), 8.13 (s, 1H), 7.64 (d, 1H), 7.39 (s, 1H), 7.31-7.42 (m, 2H), 7.26 (s, 1H), 6.91 (t, 1H), 4.35 (br s, 1H), 4.22 (t, 2H), 3.98 (s, 3H), 3.91 (s, 2H), 3.41 (m, 1H), 3.20 (m, 1H), 3.10 (m, 1H), 2.98 (m, 1H), 2.45 (m, 2H), 2.18 (m, 1H), 2.82 (m, 1H), 1.96 (m, 2H), 1.67 (m, 2H), 1.57 (m, 1H):

MS (+ve ESI): 567 (M+H)$^+$.

b) An analogous reaction to that described in example 1i, but starting with N-(3-fluorophenyl)-2-(2-((7-(3-((2R)-2-(hydroxymethyl)pyrrolidin-1-yl)propoxy)-6-methoxyquinazolin-4-yl)amino)-1,3-thiazol-5-yl)acetamide (600 mg, 1.06 mmol) yielded di(tert-butyl) ((2R)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl phosphate (400 mg, 50% yield):

$^1$H-NMR (DMSO d$_6$): 8.67 (s, 1H), 8.11 (s, 1H), 7.63 (d, 1H), 7.38 (s, 1H), 7.35 (m, 2H), 7.25 (s, 1H), 6.90 (m, 1H), 4.21 (m, 2H), 3.97 (s, 3H), 3.90 (s, 2H), 3.79 (m, 1H), 3.67 (m, 1H), 3.10 (m, 1H), 2.97 (m, 1H), 2.70 (m, 1H), 2.50 (m, 1H), 2.23 (q, 1H), 1.97 (m, 2H), 1.88 (m, 1H), 1.70 (m, 2H), 1.63 (m, 1H), 1.38 (s, 18H):

MS (+ve ESI): 759 (M+H)$^+$.

EXAMPLE 3

Preparation of Compound 3 in Table 1—2-(4-(3-((4-((5-(2-((3-fluorophenyl)amino)-2-oxoethyl)-1,3-thiazol-2-yl)amino)-6-methoxy-quinazolin-7-yl)oxy) propyl)piperazin-1-yl)ethyl dihydrogen phosphate An analogous reaction to that described in example 1, but starting with di(tert-butyl) 2-(4-(3-((4-((5-(2-((3-fluorophenyl)amino)-2-oxoethyl)-1,3-thiazol-2-yl)amino)-6-methoxyquinazolin-7-yl)oxy)propyl)piperazin-1-yl)ethyl phosphate (450 mg, 0.57 mmol) yielded the title compound (430 mg, 96% yield):

$^1$H-NMR (DMSO d$_6$, CD$_3$COOD): 8.89 (s, 1H), 7.81 (s, 1H), 7.56 (d, 1H), 7.48 (s, 1H), 7.27 (m, 3H), 6.80 (m, 1H), 4.27 (m, 4H), 3.95 (s, 5H), 3.67 (m, 8H), 3.47 (m, 2H), 3.39 (t, 2H), 2.34 (m, 2H):

MS (+ve ESI): 676.5 (M+H)$^+$.

Di(tert-butyl) 2-(4-(3-((4-((5-(2-((3-fluorophenyl)amino)-2-oxoethyl)-1,3-thiazol-2-yl)amino)-6-methoxyquinazolin-7-yl)oxy)propyl)piperazin-1-yl)ethyl phosphate used as the starting material was obtained as follows:

a) An analogous reaction to that described in example 1h, but starting with 1-(2-hydroxyethyl)piperazine (430 mg, 3.3 mmol) yielded N-(3-fluorophenyl)-2-(2-((7-3(4-(2-hydroxyethyl)piperazin-1-yl)propoxy)-6-methoxyquinazolin-4-yl)amino)-1,3-thiazol-5-yl)acetamide (91 mg, 69% yield):

$^1$H-NMR (DMSO d$_6$): 12.04 (br s, 1H), 10.48 (s, 1H), 8.68 (s, 1H), 8.12 (s, 1H), 7.65 (d, 1H), 7.39 (s, 1H), 7.32-7.42 (m, 2H), 7.25 (s, 1H), 6.91 (t, 1H), 4.37 (t, 1H), 4.20 (t, 2H), 3.97 (s, 3H), 3.91 (s, 2H), 3.50 (q, 2H), 2.41 (m, 12H), 1.96 (m, 2H):

MS (+ve ESI): 596 (M+H)$^+$.

b) N-(3-fluorophenyl)-2-(2-((7-3-(4-(2-hydroxyethyl)piperazin-1-yl)propoxy)-6-methoxyquinazolin-4-yl)amino)-1,3-thiazol-5-yl)acetamide (595 mg, 1 mmol) was dissolved in dimethylformamide (3 ml). Tetrazole (280 mg, 4 mmol) and di-tert-butyl-diethylphosphoramidite (598 µl, 2 mmol) were added to the mixture at ambient temperature, and stirring was continued for 2 hours under argon. The mixture was cooled to −60° C. and a solution of monoperoxyphtalic acid magnesium salt (371 mg, 0.6 mmol) in dimethylformamide (2 ml) was slowly added. This mixture was stirred for 1.5 hours at −60° C., sodium metabisulfite (1.9 g, 10 mmol) in water (2 ml) was added, and the mixture was slowly allowed to warm to ambient temperature, evaporated, and purified by chromatography on silica gel, eluting with dichloromethane: 3.0 N methanolic ammonia (0-10%), to give di(tert-butyl) 2-(4-(3-((4-((5-(2-((3-fluorophenyl)amino)-2-oxoethyl)-1,3-thiazol-2-yl)amino)-6-methoxyquinazolin-7-yl)oxy)propyl)piperazin-1-yl)ethyl phosphate (600 mg, 76% yield):

$^1$H-NMR (DMSO d$_6$): 8.68 (s, 1H), 8.11 (s, 1H), 7.63 (d, 1H), 7.39 (s, 1H), 7.34 (t, 2H), 7.25 (s, 1H), 6.91 (t, 1H), 4.19 (t, 2H), 3.97 (s, 3H), 3.92 (m, 2H), 3.90 (s, 2H), 2.52 (m, 4H), 2.42

8H), 1.95 (m, 2H), 1.42 (s, 18H):

MS (+ve ESI): 788.6 (M+H)$^+$.

EXAMPLE 4

Preparation of Compound 4 in Table 1—1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-3-yl dihydrogen phosphate An analogous reaction to that described in example 1, but starting with di(tert-butyl) 1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-3-yl phosphate (435 mg, 0.58 mmol) yielded the title compound (325 mg, 78% yield):

$^1$H-NMR (DMSO d$_6$, CD$_3$COOD): 9.02 (s, 1H), 7.87 (s, 1H), 7.66 (m, 1H), 7.61 (s, 1H), 7.36 (m, 3H), 6.90 (m, 1H), 4.97 (m, 1H), 4.30 (m, 2H), 3.97 (s, 2H), 3.90 (s, 3H), 3.75 (m, 1H), 3.40 (m, 3H), 3.26 (m, 2H), 2.45 (m, 1H), 2.31 (m, 3H), 2.18 (m, 1H):

MS(+ve ESI): 633.5 (M+H)$^+$.

Di(tert-butyl) 1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-3-yl phosphate used as the starting material was obtained as follows:

a) An analogous reaction to that described in example 1h, but starting with 3-pyrrolidinol (288 mg, 3.3 mmol) yielded N-(3-fluorophenyl)-2-(2-((7-(3-(3-hydroxypyrrolidin-1-yl)propoxy)-6-methoxyquinazolin-4-yl)amino)-1,3-thiazol-5-yl)acetamide (18 mg, 15% yield):

$^1$H-NMR (DMSO d$_6$, TFA): 9.09 (s, 1H), 7.91 (s, 1H), 7.64 (s, 1H), 7.63 (d, 1H), 7.31-7.41 (m, 2H), 7.28 (d, 1H), 6.91 (m, 1H), 4.41-4.51 (m, 1H), 4.29 (m, 2H), 4.00 (s, 2H), 3.99 (s, 3H), 3.02-3.79 (m, 6H), 2.27 (m, 2H), 1.84-2.03 (m, 2H):

MS (+ve ESI): 553 (M+H)$^+$.

b) An analogous reaction to that described in example 1i, but starting with N-(3-fluorophenyl)-2-(2-((7-(3-(3-hydroxypyrrolidin-1-yl)propoxy)-6-methoxyquinazolin-4-yl)amino)-1,3-thiazol-5-yl)acetamide (552 mg, 1 mmol) yielded di(tert-butyl) 1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-3-yl phosphate (440 mg, 59% yield).

$^1$H-NMR (DMSO d$_6$): 8.68 (s, 1H), 8.13 (s, 1H), 7.63 (d, 1H), 7.39 (s, 1H), 7.35 (m, 2H), 7.25 (s, 1H), 6.91 (m, 1H), 4.76 (m, 1H), 4.22 (t, 2H), 3.98 (s, 3H), 3.90 (s, 2H), 2.75 (m, 3H), 2.63 (m, 2H), 2.45 (m, 1H), 2.16 (m, 1H), 1.98 (m, 2H), 1.85 (m, 1H), 1.40 (s, 18H):

MS (+ve ESI): 745.6 (M+H)$^+$.

EXAMPLE 5

Preparation of Compound 5 in Table 1—1-(3-((4-((5-(2-((3-fluorophenyl)amino)-2-oxoethyl)-1,3-thiazol-2-yl)amino)-6-methoxyquinazolin-7-yl)oxy)propyl)piperidin-3-yl dihydrogen phosphate An analogous reaction to that described in example 1, but starting with di(tert-butyl) 1-(3-((4-((5-(2-((3-fluorophenyl)amino)-2-oxoethyl)-1,3-thiazol-2-yl)amino)-6-methoxyquinazolin-7-yl)oxy)propyl)piperidin-3-yl phosphate (470 mg, 0.62 mmol) yielded the title compound (340 mg, 75% yield):

$^1$H-NMR (DMSO d$_6$, CD$_3$COOD): 9.05 (s, 1H), 7.86 (s, 1H), 7.64 (m, 1H), 7.63 (s, 1H), 7.37 (m, 3H), 6.90 (m, 1H), 4.55-4.67 (m, 1H), 4.30 (m, 2H), 4.02 (s, 2H), 3.90 (s, 3H), 3.60 (m, 1H), 3.47 (m, 1H), 3.30 (m, 2H), 3.00 (m, 2H), 1.50-2.40 (m, 6H):

MS (+ve ESI): 647.6 (M+H)$^+$.

Di(tert-butyl) 1-(3-((4-((5-(2-((3-fluorophenyl)amino)-2-oxoethyl)-1,3-thiazol-2-yl)amino)-6-methoxyquinazolin-7-yl)oxy)propyl)piperidin-3-yl phosphate used as the starting material was obtained as follows:

a) An analogous reaction to that described in example 1h, but starting with 3-hydroxypiperidine (334 mg, 3.3 mmol) yielded N-(3-fluorophenyl)-2-(2-((7-(3-(3-hydroxypiperidin-1-yl)propoxy)-6-methoxyquinazolin-4-yl)amino)-1,3-thiazol-5-yl)acetamide (72 mg, 58% yield):

$^1$H-NMR (DMSO d$_6$): 12.02 (br s, 1H), 10.48 (s, 1H), 8.68 (s, 1H), 8.13 (br s, 1H), 7.64 (s, 1H), 7.40 (s, 1H), 7.31-7.42 (m, 2H), 7.26 (s, 1H), 6.91 (t, 1H), 4.60 (d, 1H), 4.20 (t, 2H), 3.98 (s, 3H), 3.91 (s, 2H), 3.49 (m, 1H), 2.85 (m, 1H), 2.69 (m, 1H), 2.47 (m, 2H), 1.96 (t, 2H), 1.87 (m, 1H), 1.78 (m, 2H), 1.63 (m, 1H), 1.43 (m, 1H), 1.09 (m, 1H):

MS (+ve ESI): 567 (M+H)$^+$.

b) An analogous reaction to that described in example 1i, but starting with N-(3-fluorophenyl)-2-(2-((7-(3-(3-hydroxypiperidin-1-yl)propoxy)-6-methoxyquinazolin-4-yl)amino)-1,3-thiazol-5-yl)acetamide (680 mg, 1.2 mmol) yielded di(tert-butyl) 1-(3-((4-((5-(2-((3-fluorophenyl)amino)-2-oxoethyl)-1,3-thiazol-2-yl)amino)-6-methoxyquinazolin-7-yl)oxy)propyl)piperidin-3-yl phosphate (500 mg, 55% yield):

$^1$H-NMR (DMSO d$_6$): 8.68 (s, 1H), 8.12 (s, 1H), 7.63 (d, 1H), 7.35 (m, 3H), 7.25 (s, 1H), 6.90 (m, 1H), 3.97 (s, 3H), 3.90 (s, 2H), 3.40 (m, 1H), 2.90 (m, 1H), 2.60 (m, 1H), 2.50 (m, 1H), 2.20 (m, 2H), 1.95 (m, 3H), 1.70 (m, 1H), 1.45 (m, 2H), 1.39 (s, 18H):

MS (+ve ESI): 759.6 (M+H)$^+$.

EXAMPLE 6

Preparation of Compound 6 in Table 1—2-(ethyl(3-((4-((5-(2-((3-fluorophenyl)amino)-2-oxoethyl)-1,3-thiazol-2-yl)amino)-6-methoxyquinazolin-7-yl)oxy)propyl)amino)ethyl dihydrogen phosphate An analogous reaction to that described in example 1, but starting with di(tert-butyl) 2-(ethyl(3-((4-((5-(2-((3-fluorophenyl)amino)-2-oxoethyl)-1,3-thiazol-2-yl)amino)-6-methoxyquinazolin-7-yl)oxy)propyl)amino)ethyl phosphate (284 mg, 0.38 mmol) yielded the title compound (270 mg, 38% yield):

$^1$H-NMR (DMSO d$_6$, TFA): 9.08 (s, 1H), 7.90 (s, 1H), 7.64 (s, 1H), 7.62 (m, 1H), 7.36 (m, 3H), 6.90 (m, 1H), 4.30 (m,

2H), 4.22 (m, 2H), 3.99 (s, 2H), 3.98 (s, 3H), 3.48 (m, 2H), 3.35 (m, 4H), 2.28 (m, 2H), 1.27 (t, 3H):

MS (+ve ESI): 635 (M+H)+.

Di(tert-butyl) 2-(ethyl(3-((4-((5-(2-((3-fluorophenyl) amino)-2-oxoethyl)-1,3-thiazol-2-yl)amino)-6-methoxyquinazolin-7-yl)oxy)propyl)amino)ethyl phosphate used as the starting material was obtained as follows:

a) An analogous reaction to that described in example 1h, but starting with 2-(2-((7-(3-chloropropoxy)-6-methoxyquinazolin-4-yl)amino)-1,3-thiazol-5-yl)-N-(3-fluorophenyl)acetamide (2 g, 4 mmol) and 2-(ethylamino) ethanol (2 ml, 20 mmol) yielded N-(3-fluorophenyl)-2-(2-((7-(3-((2-hydroxyethyl)(ethyl)amino)propoxy)-6-methoxyquinazolin-4-yl)amino)-1,3-thiazol-5-yl) acetamide (1.49 g, 67% yield):

$^1$H-NMR (DMSO d$_6$, TFA): 9.09 (s, 1H), 7.90 (s, 1H), 7.65 (s, 1H), 7.61 (d, 1H), 7.35 (m, 2H), 7.3 (s, 1H), 6.91 (m, 1H), 4.3 (t, 2H), 4.00 (s, 2H), 3.99 (s, 3H), 3.77 (m, 2H), 3.3 (m, 6H), 2.28 (m, 2H), 1.26 (t, 3H):

MS (+ve ESI): 555.6 (M+H)+.

b) An analogous reaction to that described in example 1i, but starting with N-(3-fluorophenyl)-2-(2-((7-(3-((2-hydroxyethyl)(ethyl)amino)propoxy)-6-methoxyquinazolin-4-yl) amino)-1,3-thiazol-5-yl)acetamide (560 mg, 1 mmol) yielded di(tert-butyl) 2-(ethyl(3-((4-((5-(2-((3-fluorophenyl)amino)-2-oxoethyl)-1,3-thiazol-2-yl)amino)-6-methoxyquinazolin-7-yl)oxy)propyl)amino)ethyl phosphate (255 mg, 34% yield):

$^1$H-NMR (DMSO d$_6$): 8.68 (s, 1H), 8.12 (s, 1H), 7.63 (m, 1H), 7.37 (m, 3H), 7.24 (s, 1H), 6.90 (m, 1H), 4.21 (t, 2H), 3.97 (s, 3H), 3.90 (s, 2H), 3.87 (m, 2H), 2.64 (m, 6H), 1.92 (m, 2H), 1.39 (s, 18H), 0.98 (t, 3H):

MS (+ve ESI): 747.6 (M+H)+.

EXAMPLE 7

Preparation of Compound 7 in Table 1—((2S)-1-(3-((4-((5-(2-((3-fluorophenyl)amino)-2-oxoethyl)-1,3-thiazol-2-yl)amino)-6-methoxyquinazolin-7-yl)oxy) propyl)pyrrolidin-2-yl)methyl dihydrogen phosphate Hydrochloric acid (10.4 ml of a 4.0 N solution in 1,4-dioxane, 41.5 mmol) was added, dropwise to a solution of di(tert-butyl) ((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl phosphate (4.49 g, 5.92 mmol) in 1,4-dioxane (180 ml) upon which a light yellow solid precipitated from the reaction mixture. The resulting heterogeneous reaction mixture was stirred for a further 20 hours before the precipitate was collected, washed with 1,4-dioxane (80 ml) and acetonitrile (2×100 ml) and dried in vacuo to yield ((2S)-1-(3-((4-((5-(2-((3-fluorophenyl) amino)-2-oxoethyl)-1,3-thiazol-2-yl)amino)-6-methoxyquinazolin-7-yl)oxy)propyl)pyrrolidin-2-yl)methyl dihydrogen phosphate bis-hydrochloride as a light yellow solid (4.40 g, 97% yield):

$^1$H-NMR (DMSO d$_6$): 10.96 (s, 1H), 9.05 (s, 1H), 7.82 (s, 1H), 7.62 (m, 2H), 7.38 (m, 3H), 6.90 (t, 1H), 4.25 (m, 4H), 4.05 (s, 2H), 3.96 (s, 3H), 3.80 (m, 1H), 3.69 (m, 1H), 3.60 (m, 1H), 3.28 (m, 1H), 3.19 (q, 1H), 2.35 (m, 2H), 2.20 (m, 1H), 2.04 (m, 1H), 1.95 (m, 1H), 1.81 (m, 1H):

$^{31}$P-NMR (DMSO d$_6$): –0.04 (s, 1P):

MS (+ve ESI): 647 (M+H)+.

Di(tert-butyl) ((2S)-1-(3-((4-((5-(2-((3-fluorophenyl) amino)-2-oxoethyl)-1,3-thiazol-2-yl)amino)-6-methoxyquinazolin-7-yl)oxy)propyl)pyrrolidin-2-yl)methyl phosphate used as the starting material was obtained as follows:

a) An analogous reaction to that described in example 1h, but starting with (S)-(+)-2-pyrrolidinylmethanol (334 mg, 3.3 mmol) yielded N-(3-fluorophenyl)-2-(2-((7-(3-((2S)-2-(hydroxymethyl)pyrrolidin-1-yl)propoxy-6-methoxyquinazolin-4-yl)amino)-1,3-thiazol-5-yl)acetamide (59 mg, 48% yield):

$^1$H-NMR (DMSO d$_6$, TFA): 9.08 (s, 1H), 7.91 (s, 1H), 7.64 (s, 1H), 7.63 (d, 1H), 7.30-7.40 (m, 2H), 7.29 (s, 1H), 6.89 (t, 1H), 4.29 (t, 2H), 3.99 (s, 2H), 3.98 (s, 3H), 3.77 (q, 1H), 3.61 (m, 4H), 3.23 (m, 2H), 2.31 (m, 2H), 2.13 (m, 1H), 2.03 (m, 1H), 1.90 (m, 1H), 1.78 (m, 1H):

MS (+ve ESI): 567 (M+H)+.

b) 1H-tetrazole (897 mg, 12.8 mmol) and di-tert-butyl diethylphosphoramidite (4.37 ml, 15.7 mmol) were added, directly to a stirred mixture of N-(3-fluorophenyl)-2-(2-((7-(3-((2S)-2-(hydroxymethyl)pyrrolidin-1-yl)propoxy-6-methoxyquinazolin-4-yl)amino)-1,3-thiazol-5-yl)acetamide (3.63 g, 6.41 mmol) in dry dimethylacetamide (35 ml) maintained under a nitrogen atmosphere. After stirring for 2 hours, further equivalents of 1H-tetrazole (897 mg, 12.8 mmol) and di-tert-butyl diethylphosphoramidite (4.37 ml, 15.7 mmol) were added. Stirring was continued for a further 2 hours upon which time the reaction mixture was cooled (–10° C.) and hydrogen peroxide (4.16 ml of a 30% w/w aqueous solution, 36.6 mmol) was introduced dropwise then the reaction mixture warmed to ambient temperature over 10 minutes and stirred for a further 18 hours. The reaction was then cooled (0° C.) and quenched with sodium thiosulphite (0.53 N aqueous solution) until the reaction mixture tested negative for peroxide. The reaction mixture was then diluted with ethyl acetate (200 ml) and sodium hydrogen carbonate (100 ml of a saturated aqueous solution) was added, the phases separated and the aqueous layer further extracted with ethyl acetate (3×100 ml). The combined organic layers were dried over sodium sulphate, filtered and concentrated under reduced pressure to afford a yellow oil. This material was subjected to chromatography on silica gel, eluting with methanol:dichloromethane (0-10%) and concentration of the appropriate fractions yielded di(tert-butyl) ((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl phosphate (as a yellow foam) which was used in the next step of the reaction sequence:

MS (+ve ESI): 759 (M+H)+.

EXAMPLE 8

Preparation of Compound 8 in Table 1—2-(ethyl (((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl) amino)ethyl dihydrogen phosphate An analogous reaction to that described in example 1, but starting with di(tert-butyl) 2-(ethyl(((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)amino)ethyl phosphate (230 mg, 0.277 mmol) yielded the title compound (199 mg, 100% yield):

$^1$H-NMR (DMSO d$_6$, TFA): 9.08 (s, 1H), 7.91 (s, 1H), 7.65 (s, 1H), 7.63 (m, 1H), 7.41 (s, 1H), 7.35 (m, 2H), 6.90 (m, 1H), 4.32 (m, 2H), 4.28 (m, 2H), 3.88 (d, 1H), 3.72 (m, 2H), 3.6 (m, 2H), 3.52 (m, 2H), 3.37 (q, 2H), 3.27 (m, 2H), 2.38 (m, 3H), 2.07 (m, 2H), 1.98 (m, 1H), 1.29 (t, 3H):

MS (+ve ESI): 718.4 (M+H)+.

Di(tert-butyl) 2-(ethyl(((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)amino) ethyl phosphate used as the starting material was obtained as follows:

a) tert-butyl (2S)-2-(((methylsulfonyl)oxy)methyl)pyrrolidin-1-ylcarboxylate (4.75 g, 17 mmol) was condensed with 2-(ethylamino)ethanol (8.3 ml, 85.1 mmol) at 65° C. for 4 hours and over night at ambient temperature. The crude reaction mixture was purified by chromatography on silica gel, eluting with dichloromethane:7.0N methanolic ammonia (0-7%), to give tert-butyl (2S)-2-((ethyl(2-hydroxyethyl)amino)methyl)pyrrolidin-1-ylcarboxylate (1.54 g, 33% yield):

$^1$H-NMR (DMSO $d_6$): 4.30 (t, 1H), 3.68 (m, 1H), 3.42 (m, 2H), 3.20 (m, 2H), 2.51 (m, 4H), 2.21 (t, 1H), 1.80 (m, 4H), 1.42 (s, 9H), 0.96 (t, 3H).

b) tert-butyl (2S)-2-((ethyl(2-hydroxyethyl)amino)methyl)pyrrolidin-1-ylcarboxylate (1.52 g, 5.58 mmol) in solution in dioxane (20 ml) was treated with a solution of hydrochloric acid (4.0 N) in dioxane (6 ml, 24 mmol) at ambient temperature for 18 hours. The solvent was evaporated, and the residue was taken up in a mixture of dichloromethane:methanol (9:1) and was treated with 7.0N methanolic ammonia (10 ml, 70 mmol). The solid was removed by filtration, and the residue was purified by chromatography on silica gel, eluting with dichloromethane:7.0N methanolic ammonia (0-12%), to give 2-(ethyl((2S)-pyrrolidin-2-ylmethyl)amino)ethanol (950 mg, 99% yield):

$^1$H-NMR (DMSO $d_6$, TFA): 3.97 (m, 1H), 3.78 (m, 2H), 3.55 (m, 2H), 3.27 (m, 6H), 2.22 (m, 1H), 1.98 (m, 1H), 1.90 (m, 1H), 1.70 (m, 1H), 1.26 (t, 3H):

MS (+ve ESI): 173.4 (M+H)$^+$.

c) 2-(2-((7-(3-chloropropoxy)-6-methoxyquinazolin-4-yl)amino)-1,3-thiazol-5-yl)-N-(3-fluorophenyl)acetamide (1.4 g, 2.79 mmol) in N-methyl pyrrolidine (2 ml) was condensed with 2-(ethyl((2S)-pyrrolidin-2-ylmethyl)amino)ethanol (1.45 g, 8.42 mmol) at 85° C. for 10 hours. The solvent was evaporated, and the crude was purified by chromatography on silica gel, eluting with dichloromethane:7.0N methanolic ammonia (0-8%), to give 2-(2-((7-(3-((2S)-2-((ethyl(2-hydroxyethyl)amino)methyl)pyrrolidin-1-yl)propoxy)-6-methoxyquinazolin-4-yl)amino)-1,3-thiazol-5-yl)-N-(3-fluorophenyl)acetamide (670 mg, 37% yield):

$^1$H-NMR (DMSO $d_6$): 4.21 (m, 2H), 3.97 (s, 3H), 3.90 (s, 2H), 3.41 (m, 2H), 3.10 (m, 2H), 2.46 (m, 6H), 2.32 (m, 1H), 2.20 (m, 1H), 2.12 (q, 1H), 1.95 (m, 2H), 1.83 (m, 1H), 1.67 (m, 2H), 1.50 (m, 1H), 0.90 (t, 3H):

MS (+ve ESI): 638.6 (M+H)$^+$.

d) An analogous reaction to that described in example 1i, but starting with 2-(2-((7-(3-((2S)-2-((ethyl(2-hydroxyethyl)amino)methyl)pyrrolidin-1-yl)propoxy)-6-methoxyquinazolin-4-yl)amino)-1,3-thiazol-5-yl)-N-(3-fluorophenyl)acetamide (650 mg, 1.02 mmol) yielded di(tert-butyl) 2-(ethyl(((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)amino)ethyl phosphate (235 mg, 28% yield):

$^1$H-NMR (DMSO $d_6$): 8.67 (s, 1H), 8.11 (s, 1H), 7.63 (m, 1H), 7.38 (m, 3H), 7.24 (s, 1H), 6.90 (m, 1H), 4.20 (m, 2H), 3.97 (s, 3H), 3.90 (s, 2H), 3.82 (q, 1H), 3.10 (m, 2H), 2.55 (m, 7H), 2.32 (m, 1H), 2.22 (m, 1H), 2.10 (q, 1H), 1.95 (m, 2H), 1.83 (m, 1H), 1.65 (m, 2H), 1.52 (m, 1H), 1.40 (s, 18H), 0.91 (t, 3H):

MS (+ve ESI): 830 (M+H)$^+$.

EXAMPLE 9

Preparation of Compound 9 in Table 1—1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl dihydrogen phosphate An analogous reaction to that described in example 1, but starting with di(tert-butyl) 1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl phosphate (650 mg, 0.85 mmol) yielded the title compound (553 mg, 100% yield):

$^1$H-NMR (DMSO $d_6$): 9.06 (s, 1H), 7.90 (s, 1H), 7.65 (m, 1H), 7.64 (s, 1H), 7.40 (s, 1H), 7.32 (m, 2H), 6.91 (m, 1H), 4.55 (m, 1H), 4.32 (m, 2H), 3.99 (s, 3H), 3.58 (s, 3H), 3.48 (m, 2H), 3.28 (m, 2H), 3.10 (m, 2H), 2.35 (m, 2H), 2.15 (m, 2H), 2.05 (m, 2H):

MS (+ve ESI): 647.5 (M+H)$^+$.

di(tert-butyl) 1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl phosphate used as the starting material was obtained as follows:

a) An analogous reaction to that described in example 1h, but starting with 4-hydroxypiperidine (334 mg, 3.3 mmol) yielded N-(3-fluorophenyl)-2-(2-((7-(3-(4-hydroxypiperidin-1-yl)propoxy)-6-methoxyquinazolin-4-yl)amino)-1,3-thiazol-5-yl)acetamide (21 mg, 17% yield):

$^1$H-NMR (DMSO $d_6$, TFA): 9.09 (s, 1H), 7.91 (s, 1H), 7.64 (s,1H), 7.63 (d, 1H), 7.30-7.40 (m, 2H), 7.29 (s, 1H), 6.90 (t, 1H), 4.28 (t, 2H), 3.99 (s, 2H), 3.98 (s, 3H), 3.68 (m, 1H), 3.57 (d, 1H), 3.40 (m, 1H), 3.28 (m, 2H), 3.21 (m, 1H), 3.03 (t, 1H), 2.28 (m, 2H), 2.01 (d, 1H), 1.85 (m, 2H), 1.59 (m, 1H):

MS (+ve ESI): 567 (M+H)$^+$.

b) An analogous reaction to that described in example 1i, but starting with N-(3-fluorophenyl)-2-(2-((7-(3-(4-hydroxypiperidin-1-yl)propoxy)-6-methoxyquinazolin-4-yl)amino)-1,3-thiazol-5-yl)acetamide (900 mg, 1.59 mmol) yielded di(tert-butyl) 1-(3-((4-((5-(2-((3-fluorophenyl)amino)-2-oxoethyl)-1,3-thiazol-2-yl)amino)-6-methoxyquinazolin-7-yl)oxy)propyl)piperidin-4yl phosphate (700 mg, 58% yield):

$^1$H-NMR (DMSO $d_6$): 8.68 (s, 1H), 8.12 (s, 1H), 7.62 (m, 1H), 7.39 (s, 1H), 7.35 (m, 2H), 7.26 (s, 1H), 6.92 (m, 1H), 4.21 (m, 2H), 3.97 (s, 3H), 3.90 (s, 2H), 3.38 (m, 1H), 2.56 (m, 2H), 2.46 (t, 2H), 2.25 (m, 2H), 1.96 (m, 2H), 1.87 (m, 2H), 1.67 (m, 2H), 1.42 (s, 18 H):

MS (+ve ESI): 759.7 (M+H)$^+$.

EXAMPLE 10

Preparation of Compound 10 in Table 1—2-((((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)amino)ethyl dihydrogen phosphate An analogous reaction to that described in example 1, but starting with tert-butyl 2-((di(tert-butoxy)phosphoryl)oxy)ethyl(((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)carbamate (535 mg, 0.67 mmol) yielded the title compound (416 mg, 68% yield):

$^1$H-NMR (DMSO $d_6$, TFA): 9.07 (s, 1H), 7.90 (s, 1H), 7.64 (s, 1H), 7.62 (m, 1H), 7.40 (s, 1H), 7.38 (m, 2H), 6.90 (m, 1H), 4.32 (m, 2H), 4.16 (m, 2H), 4.00 (s, 2H), 3.99 (s, 3H), 3.82 (m, 1H), 3.68 (m, 3H), 3.43 (m, 1H), 3.32 (m, 4H), 2.35 (m, 3H), 2.20 (m, 3H):

MS (+ve ESI): 690.5 (M+H)$^+$.

tert-butyl 2-((di(tert-butoxy)phosphoryl)oxy)ethyl(((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)carbamate used as the starting material was obtained as follows:

a) tert-butyl (2S)-2-(((methylsulfonyl)oxy)methyl)pyrrolidin-1-ylcarboxylate (7 g, 25 mmol) was reacted with ethanolamine (7.5 ml, 124 mmol) at 85° C. for 2 hours. The crude reaction mixture was purified by chromatography on silica gel, eluting with dichloromethane:7.0N methanolic ammonia (0-6%), to give tert-butyl (2S)-2-(((2-hydroxyethyl)amino)methyl)pyrrolidin-1-ylcarboxylate (3.56 g, 58% yield):

$^1$H-NMR (DMSO d$_6$, TFA): 4.03 (m, 1H), 3.66 (m, 2H), 3.28 (m, 2H), 3.03 (m, 4H), 1.82 (m, 4H), 1.44 (s, 9H):

MS (+ve ESI): 245.6 (M+H)$^+$.

b) tert-butyl (2S)-2-(((2-hydroxyethyl)amino)methyl)pyrrolidin-1-ylcarboxylate (3.55 g, 14.5 mmol) in dioxane (10 ml) was treated with a solution of hydrochloric acid (4.0 N) in dioxane (20 ml, 5.5 eq) for 20 hours at ambient temperature. The dioxane was evaporated, the residue was dissolved in methanol and treated with 7.0 N methanolic ammonia (10 ml, 70 mmol). The solid was collected by suction filtration and, after evaporation of the solvent, the residual oil was purified by chromatography on HP20SS support, eluting with water:aqueous potassium carbonate solution (6.0 N). The fractions containing compound were collected, evaporated and the residue extracted with dichloromethane:methanol before the organic phase was dried and concentrated in vacuo to yield 2-(((2S)-pyrrolidin-2-ylmethyl)amino)ethanol (1.99 g, 95% yield):

$^1$H-NMR (DMSO d$_6$, TFA): 3.84 (m, 1H), 3.69 (t, 2H), 3.30 (m, 4H), 3.10 (m, 2H), 2.15 (m, 1H), 1.92 (m, 2H), 1.72 (m, 1H):

MS (+ve ESI): 145.3 (M+H)$^+$.

c) 2-(2-((7-(3-chloropropoxy)-6-methoxyquinazolin-4-yl)amino)-1,3-thiazol-5-yl)-N-(3-fluorophenyl)acetamide (1 g, 2 mmol) in solution in N-methyl pyrrolidine (4 ml) was reacted with 2-(((2S)-pyrrolidin-2-ylmethyl)amino)ethanol (1.15 g, 8 mmol) at 85° C. for 2.5 hours. The crude mixture was purified by chromatography on silica gel, eluting with dichloromethane:7.0N methanolic ammonia (0-10%), to yield N-(3-fluorophenyl)-2-(2-((7-(3-((2S)-2-(((2-hydroxyethyl)amino)methyl)pyrrolidin-1-yl)propoxy)-6-methoxyquinazolin-4-yl)amino)-1,3-thiazol-5-yl)acetamide (0.77 g, 64% yield):

$^1$H-NMR (DMSO d$_6$, TFA): 9.09 (s, 1H), 7.91 (s, 1H), 7.65 (s, 1H), 7.62 (m, 1H), 7.36 (m, 3H), 6.90 (m, 1H), 4.31 (m, 2H), 4.00 (s, 2H), 3.99 (s, 3H), 3.77 (m, 3H), 3.70 (t, 2H), 3.60 (m, 2H), 3.30 (m, 3H), 3.13 (m, 2H), 2.33 (m, 2H), 2.00 (m, 3H):

MS (+ve ESI): 610.6 (M+H)$^+$.

d) N-(3-fluorophenyl)-2-(2-((7-(3-((2S)-2-(((2-hydroxyethyl)amino)methyl)pyrrolidin-1-yl)propoxy)-6-methoxyquinazolin-4-yl)amino)-1,3-thiazol-5-yl)acetamide (760 mg, 1.25 mmol) in dimethylformamide (5 ml) and dichloromethane (10 ml) was reacted with di-tert-butyl dicarbonate (300 mg, 1.37 mmol). The mixture was stirred at ambient temperature for 18 hours, the solvent was evaporated and the residue purified by chromatography on silica gel, eluting with dichloromethane:7.0N methanolic ammonia (0-6%), to give tert-butyl ((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl(2-hydroxyethyl)carbamate (517 mg, 58% yield):

$^1$H-NMR (DMSO d$_6$): 8.65 (s, 1H), 8.10 (s, 1H), 7.61 (d, 1H), 7.37 (s, 1H), 7.32 (m, 2H), 7.23 (s, 1H), 6.90 (m, 1H), 4.19 (m, 2H), 3.95 (s, 3H), 3.89 (s, 2H), 3.42 (m, 4H), 3.25 (m, 1H), 3.17 (m, 1H), 3.09 (m, 1H), 2.95 (m, 1H), 2.60 (m, 1H), 2.37 (m, 1H), 2.18 (q, 1H), 1.97 (m, 2H), 1.80 (m, 1H), 1.68 (m, 2H), 1.50 (m, 1H):

MS (+ve ESI): 710.5 (M+H)$^+$.

e) An analogous reaction to that described in example 1i, but starting with tert-butyl ((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl(2-hydroxyethyl)carbamate (510 mg, 0.72 mmol) yielded tert-butyl 2-((di(tert-butoxy)phosphoryl)oxy)ethyl (((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)carbamate (535 mg, 93% yield):

$^1$H-NMR (DMSO d$_6$): 8.66 (s, 1H), 8.10 (s, 1H), 7.61 (d, 1H), 7.37 (s, 1H), 7.33 (m, 2H), 7.20 (s, 1H), 6.90 (m, 1H), 4.18 (m, 2H), 3.95 (s, 3H), 3.88 (m, 4H), 3.40 (m, 2H), 3.09 (m, 2H), 2.95 (m, 2H), 2.60 (m, 1H), 2.37 (m, 1H), 2.18 (m, 1H), 1.98 (m, 2H), 1.78 (m, 1H), 1.70 (m, 2H), 1.52 (m, 1H), 1.38 (s, 18H), 1.34 (s, 9H).

EXAMPLE 11

Preparation of Compound 11 in Table 1—2-((3-((4-((5-(2-((3-fluorophenyl)amino)-2-oxoethyl)-1,3-thiazol-2-yl)amino)-6-methoxyquinazolin-7-yl)oxy)propyl)amino)ethyl dihydrogen phosphate An analogous reaction to that described in example 1 but starting with tert-butyl 2-((di(tert-butoxy)phosphoryl)oxy)ethyl(3-((4-((5-(2-((3-fluorophenyl)amino)-2-oxoethyl)-1,3-thiazol-2-yl)amino)-6-methoxyquinazolin-7-yl)oxy)propyl)carbamate (350 mg, 0.428 mmol) yielded the title compound (290 mg, 72% yield):

$^1$H-NMR (DMSO d$_6$, CD$_3$COOD): 8.99 (s, 1H), 7.89 (s, 1H), 7.64 (d, 1H), 7.60 (s, 1H), 7.37 (m, 3H), 6.89 (m, 1H), 4.31 (m, 2H), 4.16 (m, 2H), 4.01 (s, 2H), 3.99 (s, 3H), 3.26 (m, 2H), 3.20 (m, 2H), 2.27 (m, 2H):

MS (+ve ESI): 607.4 (M+H)$^+$.

tert-butyl 2-((di(tert-butoxy)phosphoryl)oxy)ethyl(3-((4-((5-(2-((3-fluorophenyl)amino)-2-oxoethyl)-1,3-thiazol-2-yl)amino)-6-methoxyquinazolin-7-yl)oxy)propyl)carbamate used as the starting material was obtained as follows:

a) An analogous reaction to that described in example 1h, but starting with 2-(2-((7-(3-chloropropoxy)-6-methoxyquinazolin-4-yl)amino)-1,3-thiazol-5-yl)-N-(3-fluorophenyl)acetamide (249 mg, 0.4 mmol) and ethanolamine (122 mg, 2 mmol) yielded N-((3-fluorophenyl)-2-(2-((7-(3-((2-hydroxyethyl)amino)propoxy)-6-methoxyquinazolin-4-yl)amino)-1,3-thiazol-5-yl)acetamide, (90 mg, 43% yield):

$^1$H-NMR (DMSO d$_6$): 8.67 (s, 1H), 8.11 (s, 1H), 7.63 (d, 1H), 7.38 (s,1H), 7.35 (m, 2H), 7.26 (s, 1H), 6.91 (t,1H), 4.23 (t, 2H), 3.97 (s, 3H), 3.90 (s, 2H), 3.47 (t, 2H), 2.72 (t, 2H), 2.62 (t, 2H), 1.95 (m, 2H):

MS (+ve ESI): 527.59 (M+H)$^+$.

b) A solution of N-((3-fluorophenyl)-2-(2-((7-(3-((2-hydroxyethyl)amino)propoxy)-6-methoxyquinazolin-4-yl)amino)-1,3-thiazol-5-yl)acetamide (650 mg, 1.23 mmol) in dimethylformamide (5 ml) was reacted with di-tertbutyl dicarbonate (590 mg, 2.7 mmol) at 50° C. for 48 hours. The solvent was evaporated and the residue purified by chromatography on silica gel, eluting with dichloromethane:3.0 N methanolic ammonia (0-5%), to yield tert-butyl 3-((4-((5-(2-((3-fluorophenyl)amino)-2-oxoethyl)-1,3-thiazol-2-yl)amino)-6-methoxyquinazolin-7-yl)oxy)propyl(2-hydroxyethyl)carbamate (330 mg, 43% yield):

$^1$H-NMR (DMSO d$_6$, TFA): 8.68 (s, 1H), 8.12 (s, 1H), 7.62 (d, 1H), 7.36 (m, 3H), 7.24 (s, 1H), 6.90 (m, 1H), 4.68 (m, 2H), 4.14 (m, 2H), 3.96 (s, 3H), 3.89 (s, 2H), 3.47 (m, 2H), 3.24 (m, 2H), 2.02 (m, 2H), 1.35 (m, 9H):

MS (+ve ESI): 627.5 (M+H)$^+$.

c) An analogous reaction to that described in example 1i, but starting with tert-butyl 3-((4-((5-(2-((3-fluorophenyl)amino)-2-oxoethyl)-1,3-thiazol-2-yl)amino)-6-methoxyquinazolin-7-yl)oxy)propyl(2-hydroxyethyl)carbamate (330 mg, 0.53 mmol) yielded tert-butyl 2-((di(tert-butoxy)phosphoryl)oxy)ethyl(3-((4-((5-(2-((3-fluorophenyl)amino)-2-oxoethyl)-1,3-thiazol-2-yl)amino)-6-methoxyquinazolin-7-yl)oxy)propyl)carbamate (350 mg, 81% yield):

$^1$H-NMR (DMSO d$_6$, TFA): 9.40 (s, 1H), 9.07 (s, 1H), 7.61 (m, 2H), 7.35 (m, 2H), 7.24 (s, 1H), 6.89 (t, 1H), 4.19 (t, 2H), 3.96 (m, 7H), 3.41 (m, 4H), 2.05 (m, 2H), 1.40 (m, 27H).

EXAMPLE 12

Preparation of Compound 12 in Table 1—3-(ethyl(3-((4-((5-(2-((3-fluorophenyl)amino)-2-oxoethyl)-1,3-thiazol-2-yl)amino)-6-methoxyquinazolin-7-yl)oxy)propyl)amino)propyl dihydrogen phosphate An analogous reaction to that described in example 1 but starting with di(tert-butyl) 3-(ethyl(3-((4-((5-(2-((3-fluorophenyl)amino)-2-oxoethyl)-1,3-thiazol-2-yl)amino)-6-methoxyquinazolin-7-yl)oxy)propyl)amino)propyl phosphate (430 mg, 0.56 mmol) yielded the title compound (415 mg, 99% yield):

$^1$H-NMR (DMSO d$_6$, CD$_3$COOD): 9.04 (s, 1H), 7.88 (s, 1H), 7.63 (m, 2H), 7.36 (m, 3H), 6.90 (m, 1H), 4.31 (m, 2H), 4.00 (m, 7H), 3.25 (m, 6H), 2.32 (m, 2H), 2.07 (m, 2H), 1.30 (t, 3H).

di(tert-butyl) 3-(ethyl(3-((4((5-(2-((3-fluorophenyl)amino)-2-oxoethyl)-1,3-thiazol-2-yl)amino)-6-methoxyquinazolin-7-yl)oxy)propyl)amino)propyl phosphate used as the starting material was obtained as follows:

a) An analogous reaction to that described in example 1h, but starting with 2-(2-((7-(3-chloropropoxy)-6-methoxyquinazolin-4-yl)amino)-1,3-thiazol-5-yl)-N-(3-fluorophenyl)acetamide (1 g, 2 mmol) and 3-(ethylamino)propan-1-ol (687 mg, 3 mmol) yielded 2-(2-((7-(3-(ethyl(3-hydroxypropyl)amino)propoxy)-6-methoxyquinazolin-4-yl)amino)-1,3-thiazol-5-yl)-N-(3-fluorophenyl)acetamide, (520 mg, 46% yield):

$^1$H-NMR (DMSO d$_6$): 8.68 (s, 1H), 8.12 (s, 1H), 7.63 (d, 1H), 7.39 (s, 1H), 7.36 (m, 2H), 7.24 (s, 1H), 6.91 (m, 1H), 4.20 (t, 2H), 3.97 (s, 3H), 3.90 (s, 2H), 3.42 (t, 2H), 2.56 (m, 2H), 2.47 (m, 4H), 1.92 (m, 2H), 1.53 (m, 2H), 0.96 (t, 3H):

MS (+ve ESI): 569.5 (M+H)$^+$.

b) An analogous reaction to that described in example 1i, but starting with 2-(2-((7-(3-(ethyl(3-hydroxypropyl)amino)propoxy)-6-methoxyquinazolin-4-yl)amino)-1,3-thiazol-5-yl)-N-(3-fluorophenyl)acetamide (470 mg, 0.827 mmol) yielded di(tert-butyl) 3-(ethyl(3-((4-((5-(2-((3-fluorophenyl)amino)-2-oxoethyl)-1,3-thiazol-2-yl)amino)-6-methoxyquinazolin-7-yl)oxy)propyl)amino)propyl phosphate (430 mg, 68% yield):

$^1$H-NMR (DMSO d$_6$): 8.68 (s, 1H), 8.12 (s, 1H), 7.63 (m, 1H), 7.37 (m, 3H), 7.24 (s, 1H), 6.91 (m, 1H), 4.20 (t, 2H), 3.97 (s, 3H), 3.90 (s, 2H), 3.85 (q, 2H), 2.50 (m, 6H), 1.91 (m, 2H), 1.70 (m, 2H), 1.37 (s, 18H), 0.97 (t, 3H):

EXAMPLE 13

Preparation of Compound 13 in Table 1—2-((2-fluoroethyl)(3-((4-((5-(2-((3-fluorophenyl)amino)-2-oxoethyl)-1,3-thiazol-2-yl)amino)-6-methoxyquinazolin-7-yl)oxy)propyl)amino)ethyl dihydrogen phosphate An analogous reaction to that described in example 1, but starting with di(tert-butyl) 2-((2-fluoroethyl)(3-((4-((5-(2-((3-fluorophenyl)amino)-2-oxoethyl)-1,3-thiazol-2yl)amino)-6-methoxyquinazolin-7-yl)oxy)propyl)amino)ethyl phosphate (635 mg, 0.83 mmol) yielded the title compound (550 mg, 80% yield):

$^1$H-NMR (DMSO d$_6$, TFA): 9.07 (s, 1H), 7.89 (s, 1H), 7.63 (s, 1H), 7.62 (m, 1H), 7.34 (m, 3H), 6.90 (m, 1H), 4.98 (m, 1H), 4.87 (m, 1H), 4.30 (m, 4H), 3.99 (s, 2H), 3.98 (s, 3H), 3.73 (m, 1H), 3.66 (m, 1H), 3.58 (m, 2H), 3.48 (m, 2H), 2.33 (m, 2H):

MS (+ve ESI): 653.5 (M+H)$^+$.

Di(tert-butyl) 2-((2-fluoroethyl)(3-((4-((5-(2-((3-fluorophenyl)amino)-2-oxoethyl)-1,3-thiazol-2-yl)amino)-6-methoxyquinazolin-7-yl)oxy)propyl)amino)ethyl phosphate used as the starting material was obtained as follows:

a) 2-(2-((7-(3-chloropropoxy)-6-methoxyquinazolin-4-yl)amino)-1,3-thiazol-5-yl)-N-(3-fluorophenyl)acetamide (1.26 g, 2.5 mmol) in N-methyl pyrrolidine (5 ml) was reacted with 2-((2-fluoroethyl)amino)ethanol (1.07 g, 10 mmol) at 90° C. for 16 hours. The reaction was purified by chromatography on silica gel, eluting with dichloromethane:7.0 N methanolic ammonia (3-4%), to yield 2-(2-((7-(3-((2-fluoroethyl)(2-hydroxyethyl)amino)propoxy)-6-methoxyquinazolin-4-yl)amino)-1,3-thiazol-5-yl)-N-(3-fluorophenyl)acetamide (0.506 g, 35% yield):

$^1$H-NMR (DMSO d$_6$): 8.57 (s, 1H), 8.01 (s, 1H), 7.53 (d, 1H), 7.28 (m, 3H), 7.14 (s, 1H), 6.81 (M, 1H), 4.45 (t, 1H), 4.33 (t, 1H), 4.28 (m, 1H), 4.11 (t, 2H), 3.87 (s, 3H), 3.80 (s, 2H), 3.36 (m, 2H), 2.74 (t, 1H), 2.68 (t, 1H), 2.61 (t, 1H), 2.50 (t, 2H):

MS (+ve ESI): 573.5 (M+H)$^+$.

b) An analogous reaction to that described in example 1i, but starting with 2-(2-((7-(3-((2-fluoroethyl)(2-hydroxyethyl)amino)propoxy)-6-methoxyquinazolin-4-yl)amino)-1,3-thiazol-5-yl)-N-(3-fluorophenyl)acetamide (493 mg, 0.86 mmol) yielded di(tert-butyl) 2-((2-fluoroethyl)(3-((4-((5-(2-((3-fluorophenyl)amino)-2-oxoethyl)-1,3-thiazol-2-yl)amino)-6-methoxyquinazolin-7-yl)oxy)propyl)amino)ethyl phosphate (635 mg, 97% yield):

$^1$H-NMR (DMSO d$_6$): 8.67 (s, 1H), 8.11 (s, 1H), 7.63 (d, 1H), 7.39 (s, 1H), 7.34 (m, 2H), 6.90 (m, 1H), 4.55 (t, 1H), 4.44 (t, 1H), 4.21 (t, 2H), 3.97 (2, 3H), 2.87 (t, 1H), 2.78 (m, 3), 2.74 (t, 2H), 1.94 (m, 2H), 1.39 (s, 18H):

MS (+ve ESI): 765.5 (M+H)$^+$.

EXAMPLE 14

Preparation of Compound 14 in Table 1—2-(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)ethyl dihydrogen phosphate An analogous reaction to that described in example 1 but starting with di(tert-butyl)-2-(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)ethyl phosphate (300 mg, 0.42 mmol) yielded the title compound (300 mg, 95% yield):
$^1$H-NMR (DMSO d$_6$, CD$_3$COOD): 9.00 (s, 1H), 7.86 (s, 1H), 7.62 (m, 1H), 7.58 (s, 1H), 7.34 (m, 3H), 6.87 (m, 1H), 4.28 (m, 2H), 4.01 (s, 2H), 3.96 (s, 3H), 3.92 (m, 2H), 3.55 (d, 2H), 3.23 (t, 2H), 2.93 (t, 2H), 2.33 (m, 2H), 1.90 (d, 2H), 1.70 (m, 2H):
MS (+ve ESI): 675.3 (M+H)$^+$.

di(tert-butyl)-2-(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)ethyl phosphate used as the starting material was obtained as follows:
a) An analogous reaction to that described in example 1h but starting with 4-(2-hydroxyethyl)piperidine (426 mg, 3.3 mmol) yielded N-(3-fluorophenyl)-2-(2-((7-(3-(4-(2-hydroxyethyl)piperidin-1-yl)propoxy)-6-methoxyquinazolin-4-yl)amino)-1,3-thiazol-5-yl)acetamide (65 mg, 50% yield):
$^1$H-NMR (DMSO d$_6$): 12.03 (s, 1H), 10.48 (s, 1H), 8.68 (s, 1H), 8.12 (br s, 1H), 7.63 (d, 1H), 7.40 (s, 1H), 7.32-7.42 (m, 2H), 7.25 (s, 1H), 6.91 (t, 1H), 4.33 (t, 1H), 4.20 (t, 2H), 3.97 (s, 3H), 3.91 (s, 2H), 3.44 (m, 2H), 2.87 (d, 2H), 1.96 (m, 2H), 1.88 (m, 2H), 1.63 (d, 2H), 1.36 (m, 3H), 1.15 (m, 2H):
MS (+ve ESI): 595 (M+H)$^+$.
b) An analogous reaction to that described in example 1i, but starting with N-(3-fluorophenyl)-2-(2-((7-(3-(4-(2-hydroxyethyl)piperidin-1-yl)propoxy)-6-methoxyquinazolin-4-yl)amino)-1,3-thiazol-5-yl)acetamide (500 mg, 0.84 mmol) yielded di(tert-butyl)-2-(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)ethyl phosphate (330 mg, 50% yield):
$^1$H-NMR (DMSO d$_6$): 8.66 (s, 1H), 8.10 (s, 1H), 7.61 (d, 1H), 7.39 (s, 1H), 7.33 (m, 2H), 7.23 (s, 1H), 6.89 (t, 2H), 4.18 (t, 2H), 3.88 (s, 3H), 3.86 (m, 4H), 2.86 (d, 2H), 2.42 (t, 2H), 1.88 (m, 2H), 1.85 (t, 2H), 1.63 (d, 2H), 1.52 (m, 2H), 1.39 (s, 18H), 1.14 (m, 3H):
MS (+ve ESI): 787.5 (M+H)$^+$.

EXAMPLE 15

Preparation of Compound 15 in Table 1—2-((3-((4-((5-(2-((3-fluorophenyl)amino)-2-oxoethyl)-1,3-thiazol-2-yl)amino)-6-methoxyquinazolin-7-yl)oxy)propyl)(2-methoxyethyl)amino)ethyl dihydrogen phosphate An analogous reaction to that described in example 1, but starting with di(tert-butyl) 2-((3-((4-((5-(2-((3-fluorophenyl)amino)-2-oxoethyl)-1,3-thiazol-2-yl)amino)-6-methoxyquinazolin-7-yl)oxy)propyl)(2-methoxyethyl)amino)ethyl phosphate (360 mg, 0.463 mmol) yielded the title compound (341 mg, 100% yield):
$^1$H-NMR (DMSO d$_6$, TFA): 9.06 (s, 1H), 7.92 (s, 1H), 7.62 (d, 1H), 7.60 (s, 1H), 6.83 (m, 1H), 6.32 (m, 2H), 6.28 (s, 1H), 4.30 (m, 4H), 3.98 (s, 5H), 3.72 (m, 2H), 3.56 (m, 2H), 3.50 (m, 2H), 3.42 (m, 2H), 2.30 (m, 2H):
MS (+ve ESI): 665.2 (M+H)$^+$.

di(tert-butyl) 2-((3-((4-((5-(2-((3-fluorophenyl)amino)-2-oxoethyl)-1,3-thiazol-2-yl)amino)-6-methoxyquinazolin-7-yl)oxy)propyl)(2-methoxyethyl)amino)ethyl phosphate used as the starting material was obtained as follows:
a) 2-(2-((7-(3-chloropropoxy)-6-methoxyquinazolin-4-yl)amino)-1,3-thiazol-5-yl)-N-(3-fluorophenyl)acetamide (2 g, 4 mmol) in dimethylacetamide (15 ml) was reacted with 2-((2-methoxyethyl)amino)ethanol (1.9 g, 16 mmol) and potassium iodide (1.32 g, 8 mmol) under argon at 70° C. for 4 hours. The solvent was evaporated, and the residue was purified by chromatography on silica gel, eluting with dichloromethane:7.0N methanolic ammonia (2-5%), to yield N-(3-fluorophenyl)-2-(2-((7-(3-((2-hydroxyethyl)(2-methoxyethyl)amino)propoxy)-6-methoxyquinazolin-4-yl)amino)-1,3-thiazol-5-yl)acetamide (1.0 g, 43% yield):
$^1$H-NMR (DMSO d$_6$): 8.68 (s, 1H) 8.12 (s, 1H), 7.63 (d, 1H), 4.21 (t, 2H), 3.98 (s, 3H), 3.91 (s, 2H), 3.43 (m, 2H), 3.38 (m, 2H), 2.68 (m, 4H), 2.54 (t, 2H), 1.90 (m, 2H):
MS (+ve ESI): 585.2 (M+H)$^+$.
b) An analogous reaction to that described in example 1i, but starting with N-(3-fluorophenyl)-2-(2-((7-(3-((2-hydroxyethyl)(2-methoxyethyl)amino)propoxy)-6-methoxyquinazolin-4-yl)amino)-1,3-thiazol-5-yl)acetamide (900 mg, 1.54 mmol) yielded di(tert-butyl) 2-((3-((4-((5-(2-((3-fluorophenyl)amino)-2-oxoethyl)-1,3-thiazol-2-yl)amino)-6-methoxyquinazolin-7-yl)oxy)propyl)(2-methoxyethyl)amino)ethyl phosphate (360 mg, 30% yield):
$^1$H-NMR (DMSO d$_6$): 8.68 (s, 1H), 8.14 (s, 1H), 7.63 (d, 1H), 7.37 (m, 3H), 7.25 (s, 1H), 6.90 (m, 1H), 4.21 (m, 2H), 3.97 (s, 3H), 3.91 (s, 2H), 3.88 (m, 2H), 3.40 (m, 2H), 3.32 (m, 2H), 3.22 (s, 3H), 2.70 (m, 4H), 1.92 (m, 2H), 1.40 (s, 18H):
MS (+ve ESI): 777.4 (M+H)$^+$.

EXAMPLE 16

Preparation of Compound 16 in Table 1—2-((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)ethyl dihydrogen phosphate An analogous reaction to that described in example 1, but starting with di(tert-butyl) 2-((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)ethyl phosphate (110 mg, 0.14 mmol) yielded the title compound (85 mg, 82% yield):
$^1$H-NMR (DMSO-d$_6$): 10.70 (s, 1H), 9.0 (s, 1H), 7.90 (s, 1H), 7.50-7.60 (m, 2H), 7.30-7.40 (m, 3H), 6.90 (m, 1H), 4.40 (t, 2H), 4.00 (s, 3H), 3.99 (s, 2H), 3.95 (m, 1H), 3.60-3.70 (m, 1H), 3.40-3.50 (m, 3H), 3.10-3.20 (m, 2H), 2.30-2.40 (m, 4H), 1.90-2.10 (m, 3H), 1.70-1.80 (m, 1H):
MS (+ve ESI): 661 (M+H)$^+$.

di(tert-butyl) 2-((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)ethyl phosphate used as the starting material was obtained as follows:
a) An analogous reaction to that described in example 1h, but starting with (S)-2-(2-hydroxyethyl)pyrrolidine (689 mg, 5.99 mmol) yielded N-(3-fluorophenyl)-2-(2-((7-(3-((2S)-2-(2-hydroxyethyl)pyrrolidin-1-yl)propoxy-6-methoxyquinazolin-4-yl)amino)-1,3-thiazol-5-yl)acetamide (377 mg, 43% yield): ¹H-NMR (DMSO-d₆): 10.40 (s, 1H), 8.60 (s, 1H), 8.05 (s, 1H), 7.55-7.65 (m, 1H), 7.30-7.40 (m, 3H), 7.20 (s, 1H), 6.80-6.90 (m, 1H), 4.20 (t, 2H) 3.95 (s, 3H), 3.80 (s, 2H), 3.30-3.50 (m, 2H), 3.00-3.10 (m, 1H), 2.90-3.00 (m, 1H), 2.30-2.40 (m, 1H), 2.10-2.20 (m, 1H), 2.05 (m, 1H), 1.80-1.90 (m, 2H), 1.67 (m, 1H), 1.63 (m, 2H), 1.20-1.40 (m, 2H):
MS (+ve ESI): 581 (M+H)⁺
MS (−ve ESI): 579 (M+H)⁻ b) An analogous reaction to that described in example 1i, but starting with N-(3-fluorophenyl)-2-(2-((7-(3-((2S)-2-(2-hydroxyethyl)pyrrolidin-1-yl)propoxy-6-methoxyquinazolin-4-yl)amino)-1,3-thiazol-5-yl)acetamide (142 mg, 0.245 mmol) yielded di(tert-butyl) 2-((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)ethyl phosphate (110 mg, 58% yield):
¹H-NMR (DMSO-d₆): 12.00 (s, 1H), 10.40 (s, 1H), 8.70 (s, 1H), 8.10 (s, 1H), 7.72 (m, 1H), 7.40 (s, 1H), 7.33 (m, 2H), 7.20 (s, 1H), 6.92 (m, 1H), 4.20 (t, 2H), 3.90 (s, 3H), 3.90 (s, 2H), 3.82 (m, 1H), 3.10-3.20 (m, 1H), 2.90-3.00 (m, 1H), 2.44 (m, 1H), 2.20-2.30 (m, 1H), 2.00-2.15 (m, 1H), 1.80-2.00 (m, 4H), 1.60-1.70 (m, 2H), 1.40-1.50 (m, 1H), 1.35 (s, 18H), 0.80-0.90 (m, 2H):
MS (+ve ESI): 331 (N+H-ᵗButyl)⁺/2

EXAMPLE 17

Preparation of Compound 17 in Table 1—2-((3-((4-((5-(2-((3-fluorophenyl)amino)-2-oxoethyl)-1,3-thiazol-2-yl)amino)-6-methoxyquinazolin-7-yl)oxy)propyl)amino)-2-methylpropyl dihydrogen phosphate An analogous reaction to that described in example 1, but starting with di(tert-butyl) 2-((3-((4-((5-(2-((3-fluorophenyl)amino)-2-oxoethyl)-1,3-thiazol-2-yl)amino)-6-methoxyquinazolin-7-yl)oxy)propyl)amino)-2-methylpropyl phosphate (185 mg, 0.248 mmol) yielded the title compound (145 mg, 83% yield):
¹H-NMR (DMSO-d₆): 10.80 (s, 1H), 9.20 (br s, 1H), 9.00 (s, 1H), 7.80 (s, 1H), 7.60-7.70 (m, 2H), 7.45 (s, 1H), 7.30-7.40 (m, 2H), 6.80-6.90 (m, 1H), 4.30 (t, 2H), 4.01 (s, 2H), 3.95 (s, 3H), 3.88 (m, 2H), 3.00-3.20 (m, 2H), 2.30-2.40 (m, 2H), 1.40 (s, 6H):
MS (+ve ESI): 635 (M+H)⁺ di(tert-butyl) 2-((3-((4-((5-(2-((3-fluorophenyl)amino)-2-oxoethyl)-1,3-thiazol-2-yl)amino)-6-methoxyquinazolin-7-yl)oxy)propyl)amino)-2-methylpropyl phosphate used as the starting material was obtained as follows:

a) An analogous reaction to that described in example 1h, but starting with 2-amino-2-methylpropanol (888 mg, 10 mmol) yielded N-(3-fluorophenyl)-2-(2-((7-(3-((1-hydroxy-2-methylprop-2-yl)amino)propoxy)-6-methoxyquinazolin-4-yl)amino)-1,3-thiazol-5-yl)acetamide (306 mg, 28% yield):
¹H-NMR (DMSO-d₆): 10.45 (s, 1H), 8.60 (s, 1H), 8.05 (s, 1H), 7.62 (m, 1H), 7.40 (s, 1H), 7.25-7.35 (m, 2H), 7.20 (s, 1H), 6.80-6.90 (m, 1H), 4.20 (t, 2H), 3.95 (s, 3H), 3.90 (s, 2H), 3.20 (s, 2H), 2.70 (t, 2H), 1.80-1.95 (m, 2H), 1.00 (s, 6H):
MS (+ve ESI): 555 (M+H)⁺
MS (−ve ESI): 553 (M+H)⁻ b) An analogous reaction to that described in example 1i, but starting with N-(3-fluorophenyl)-2-(2-((7-(3-((1-hydroxy-2-methylprop-2-yl)amino)propoxy)-6-methoxyquinazolin-4-yl)amino)-1,3-thiazol-5-yl)acetamide (306 mg, 0.55 mmol) yielded di(tert-butyl) 2-((3-((4-((5-(2-((3-fluorophenyl)amino)-2-oxoethyl)-1,3-thiazol-2-yl)amino)-6-methoxyquinazolin-7-yl)oxy)propyl)amino)-2-methylpropyl phosphate (185 mg, 45% yield):
¹H-NMR (DMSO-d₆): 10.50 (s, 1H), 8.70 (s, 1H), 8.20 (s, 1H), 7.80-7.90 (m, 1H), 7.30-7.40 (m, 3H), 7.20 (s, 1H), 6.93 (m, 1H), 4.20 (t, 2H), 3.90 (s, 3H), 3.70 (d, 2H), 2.70-2.75 (m, 2H), 1.92 (m, 2H), 1.40 (s, 18H), 1.05 (t, 6H):
MS (+ve ESI): 747 (M+H)⁺

EXAMPLE 18

Preparation of Compound 18 in Table 1—((2R)-1-(3-((4-((5-(2-((3-chlorophenyl)amino)-2-oxoethyl)-1,3-thiazol-2-yl)amino)-6-methoxyquinazolin-7-yl)oxy)propyl)pyrrolidin-2-yl)methyl dihydrogen phosphate An analogous reaction to that described in example 1, but starting with di(tert-butyl) ((2R)-1-(3-((4-((5-(2-((3-chlorophenyl)amino)-2-oxoethyl)-1,3-thiazol-2-yl)amino)-6-methoxyquinazolin-7-yl)oxy)propyl)pyrrolidin-2-yl)methyl phosphate (228 mg, 0.294 mmol) yielded the title compound (185 mg, 85% yield):
¹H-NMR (DMSO d₆): 9.05 (s, 1H), 7.90 (s, 1H), 7.87 (s, 1H), 7.64 (s, 1H), 7.52 (t, 1H), 7.41 (s, 1H), 7.37 (t, 1H), 7.15 (d, 1H), 4.32 (m, 2H), 4.21 (m, 2H), 3.79 (m, 1H), 3.70 (m, 1H), 3.31 (m, 1H), 3.23 (m, 1H), 2.34 (m, 2H), 2.20 (m, 1H), 2.06 (m, 1H), 1.96 (m, 1H), 1.82 (m, 1H):
MS (+ve ESI): 663.5 (M+H)⁺.

di(tert-butyl) ((2R)-1-(3-((4-((5-(2-((3-chlorophenyl)amino)-2-oxoethyl)-1,3-thiazol-2-yl)amino)-6-methoxyquinazolin-7-yl)oxy)propyl)pyrrolidin-2-yl)methyl phosphate used as the starting material was obtained as follows:

a) Triethylamine (26.7 ml, 0.192 mol) and triphenylmethyl chloride (52.0 g, 0.187 mol) were added to a suspension of methyl (2-amino-1,3-thiazol-5-yl)acetate (30.0 g, 0.174 mol—for method see example 1l) in dichloromethane (450 ml) at 0° C. The reaction mixture was stirred for 15 minutes and then allowed to warm to ambient temperature over 3 hours before solvent evaporation in vacuo. Water (300 ml) was added and the aqueous phase was extracted with ethyl acetate. The organic phase was washed with brine, dried over magnesium sulphate, and concentrated under reduced pressure to yield methyl (2-((N-triphenylmethyl)amino)-1,3-thiazol-5-yl)acetate (64.1 g, 89% yield) as a white solid:
¹H-NMR (DMSO d₆): 8.41 (s, 1H), 7.18-7.37 (m, 15H), 6.60 (s, 1H), 3.61 (m, 5H):
MS (−ve ESI): 413 (M−H)⁻.

b) Sodium hydroxide (300 ml of a 1.0 N solution in water) was added to a solution of methyl (2-((N-triphenylmethyl)amino)-1,3-thiazol-5-yl)acetate (80.9 g, 0.195 mol) in ethanol (600 ml) at 0° C. Tetrahydrofuran (200 ml) was added and the reaction was allowed to warm to ambient temperature over 3 hours before solvent evaporation in vacuo. The residue was acidified with aqueous hydrochloric acid (6.0 N) to pH 2 and the product collected by suction filtration to yield (2-((N-triphenylmethyl)amino)-1,3-thiazol-5-yl)acetic acid (70.0 g, 88% yield) as a white solid:
¹H-NMR (DMSO d₆): 8.41 (s, 1H), 7.18-7.37 (m, 15H), 6.58 (s, 1H), 3.60 (s, 2H):
MS (−ve ESI): 399 (M−H)⁻.

c) A solution of (2-((N-triphenylmethyl)amino)-1,3-thiazol-5-yl)acetic acid (8.0 g, 20 mmol), 3-chloroaniline (3.30 g, 26 mmol) and diisopropylethylamine (4.5 ml, 26 mmol) in dimethylformamide (50 ml) under inert and anhydrous conditions, was treated portionwise with O-(7-azabenzotriazol-1-yl)-N,N,N',N'-tetramethyluronium hexafluorophosphate (9.88 g, 26 mmol) at 50° C. for 19 hours. The reaction was cooled to ambient temperature and poured into aqueous sodium bicarbonate solution. A small amount of methanol was added to resolubilise the brown solid and then iced water was added to precipitate the product. Drying in vacuo yielded N-(3-chlorophenyl)-2-(2-((N-triphenylmethyl)amino)-1,3-thiazol-5-yl)acetamide as a beige solid (8.63 g, 65% yield):

$^1$H-NMR (DMSO d$_6$): 10.24 (br s, 1H), 8.49 (br s, 1H), 7.74 (s, 1H), 7.08-7.39 (m, 18H), 6.61 (s, 1H), 3.56 (s, 2H):

MS (+ve ESI): 510 (M+H)$^+$.

d) A mixture of N-(3-chlorophenyl)-2-(2-((N-triphenylmethyl)amino)-1,3-thiazol-5-yl)acetamide (8.50 g, 16.7 mmol) and N'-(5-(3-chloropropoxy)-2-cyano-4-methoxyphenyl)-N,N-dimethylimidoformamide (4.46 g, 16.7 mmol) were heated in acetic acid (75 ml) at 140° C. for 7 hours. The reaction mixture was evaporated to dryness, the residue was triturated with diethyl ether and the yellow solid collected by suction filtration and washed with diethyl ether. Extended drying in vacuo yielded N-(3-chlorophenyl)-2-(2-(7-(3-chloropropoxy)-6-methoxyquinazolin-4-yl-amino-1,3-thiazol-5-yl)acetamide (6.63 g, 77% yield) as a pale yellow solid:

$^1$H-NMR (DMSO d$_6$): 12.01 (br s, 1H), 10.42 (br s, 1H), 8.65 (s, 1H), 8.05 (s, 1H), 7.80 (s, 1H), 7.45 (d, 1H), 7.35 (m, 2H), 7.25 (s, 1H), 7.05 (d, 1H), 4.25 (t, 2H), 3.98 (s, 3H), 3.85 (s, 2H), 3.80 (t, 2H), 2.25 (m, 2H):

MS (+ve ESI): 518, 520 (M+H)$^+$

MS (-ve ESI): 516, 518 (M-H)$^-$.

e) An analogous reaction to that described in example 1h, but starting with (R)-(-)-2-pyrrolidinylmethanol (334 mg, 3.3 mmol) yielded N-(3-chlorophenyl)-2-(2-((7-(3-((2R)-2-hydroxymethyl)pyrrolidin-1-yl)propoxy)-6-methoxyquinazolin-4-yl)amino)-1,3-thiazol-5-yl)acetamide (76 mg, 59% yield):

$^1$H-NMR (DMSO d$_6$, TFA): 9.08 (s, 1H), 7.90 (s, 1H), 7.85 (t, 1H), 7.63 (s, 1H), 7.46 (dd, 1H), 7.35 (t, 1H), 7.29 (s, 1H), 7.13 (dd, 1H), 4.29 (t, 2H), 3.99 (s, 2H), 3.98 (s, 3H), 3.76 (m, 1H), 3.62 (m, 4H), 3.21 (m, 2H), 2.29 (m, 2H), 2.40 (m, 1H), 2.02 (m, 1H), 1.89 (m, 1H), 1.77 (m, 1H):

MS (+ve ESI): 583 (M+H)$^+$.

f) An analogous reaction to that described in example 1i but starting with N-(3-chlorophenyl)-2-(2-((7-(3-((2R)-2-hydroxymethyl)pyrrolidin-1-yl)propoxy)-6-methoxyquinazolin)amino)-1,3-thiazol-5-yl)acetamide (600 mg, 1.01 mmol) yielded di(tert-butyl) ((2R)-1-(3-((4-((5-2-((3-chlorophenyl)amino)-2-oxoethyl)-1,3-thiazol-2-yl)amino)-6-methoxyquinazolin-7-yl)oxy)propyl)pyrrolidin-2-yl)methyl phosphate (228 mg, 29% yield):

$^1$H-NMR (DMSO d$_6$): 8.67 (s, 1H), 8.11 (s, 1H), 7.86 (m, 1H), 7.48 (d, 1H), 7.37 (m, 2H), 7.25 (s, 1H), 7.14 (d, 1H), 4.21 (m, 2H), 3.97 (s, 3H), 3.89 (s, 2H), 3.78 (m, 1H), 3.57 (m, 1H), 3.09 (m, 1H), 2.98 (m, 1H), 2.68 (m, 1H), 2.46 (m, 1H), 2.22 (q, 1H), 1.98 (m, 2H), 1.88 (m, 1H), 1.70 (m, 2H), 1.62 (m, 1H), 1.37 (s, 18H):

MS (+ve ESI): 775.6 (M+H)$^+$.

EXAMPLE 19

Preparation of Compound 19 in Table 1—2-(1-(3-((4-((5-(2-((3-chlorophenyl)amino)-2-oxoethyl)-1,3-thiazol-2-yl)amino)-6-methoxyquinazolin-7-yl)oxy)propyl)piperidin-4-yl)ethyl dihydrogen phosphate An analogous reaction to that described in example 1 but starting with di(tert-butyl)-2-(1-(3-((4-((5-(2-((3-chlorophenyl)amino)-2-oxoethyl)-1,3-thiazol-2-yl)amino)-6-methoxyquinazolin-7-yl)oxy)propyl)piperidin-4-yl)ethyl phosphate (153 mg, 0.19 mmol) yielded the title compound (136 mg, 94% yield):

$^1$H-NMR (DMSO d$_6$): 10.92 (br s, 1H), 9.00 (s, 1H), 7.90 (s, 1H), 7.80 (s, 1H), 7.65 (d, 2H), 7.60 (s, 1H), 7.40 (s, 1H), 7.33 (m, 1H), 7.10 (d, 1H), 4.20-4.40 (m, 2H), 4.00 (s, 2H), 3.95 (s, 3H), 3.85 (m, 2H), 3.32 (m, 1H), 3.17 (m, 1H), 2.95 (m, 2H), 2.30 (m, 2H), 1.85 (m, 2H), 1.65 (m, 2H), 1.52 (m, 2H):

MS (+ve ESI): 691, 693 (M+H)$^+$.

di(tert-butyl)-2-(1-(3-((4-((5-(2-((3-chlorophenyl)amino)-2-oxoethyl)-1,3-thiazol-2-yl)amino)-6-methoxyquinazolin-7-yl)oxy)propyl)piperidin-4-yl)ethyl phosphate used as the starting material was obtained as follows:

a) An analogous reaction to that described in example 18e, but starting with 4-(2-hydroxyethyl)piperidine (426 mg, 3.3 mmol) yielded N-(3-chlorophenyl)-2-(2-((7-(3-(4-(2-hydroxyethyl)piperidin-1-yl)propoxy)-6-methoxyquinazolin-4-yl)amino)-1,3-thiazol-5-yl)acetamide (78 mg, 58% yield):

$^1$H-NMR (DMSO d$_6$): 10.42 (br s, 1H), 8.65 (s, 1H), 7.80 (s, 1H), 7.47 (m, 1H), 7.33 (m, 2H), 7.22 (s, 1H), 7.11 (m, 1H), 4.28 (m, 1H), 4.17 (m, 2H), 3.94 (s, 3H), 3.85 (s, 2H), 3.41 (m, 2H), 2.82 (m, 2H), 2.40 (m, 2H), 1.92 (m, 4H), 1.60 (m, 2H), 1.36 (m, 3H), 1.16 (m, 2H):

MS (+ve ESI): 611 (M+H)$^+$.

b) An analogous reaction to that described in example 1i, but starting with N-(3-chlorophenyl)-2-(2-((7-(3-(4-(2-hydroxyethyl)piperidin-1-yl)propoxy)-6-methoxyquinazolin-4-yl)amino)-1,3-thiazol-5-yl)acetamide (170 mg, 0.28 mmol) yielded di(tert-butyl)-2-(1-(3-((4-((5-(2-((3-chlorophenyl)amino)-2-oxoethyl)-1,3-thiazol-2-yl)amino)-6-methoxyquinazolin-7-yl)oxy)propyl)piperidin-4-yl)ethyl phosphate (153 mg, 69% yield):

$^1$H-NMR (DMSO d$_6$): 10.92 (br s, 1H), 8.60 (s, 1H), 8.10 (s, 1H), 7.80 (s, 1H), 7.45 (d, 1H), 7.35 (m, 2H), 7.20 (s, 1H), 7.10 (d, 1H), 4.20 (t, 2H), 3.95 (s, 3H), 3.85 (m, 4H), 2.90 (m, 2H), 1.90 (m, 4H), 2.30 (m, 2H), 1.65 (m, 2H), 1.48 (m, 2H), 1.40 (s, 18H), 1.17 (m, 2H);

MS (+ve ESI): 801, 803 (M+H)$^+$.

EXAMPLE 20

Preparation of Compound 20 in Table 1—2-(4-(3-((4-((5-(2-(3,5-difluorophenyl)amino)-2-oxoethyl)-1,3-thiazol-2-yl)amino)-6-methoxyquinazolin-7-yl)oxy)propyl)piperazin-1-yl)ethyl dihydrogen phosphate An analogous reaction to that described in example 1, but starting with di(tert-butyl) 2-(4-(3-((4-((5-(2-(3,5-difluorophenyl)amino)-2-oxoethyl)-1,3-thiazol-2-yl)amino)-6-methoxyquinazolin-7-yl)oxy)propyl)piperazin-1-yl)ethyl phosphate (340 mg, 0.42 mmol) yielded the title compound (320 mg, 94% yield):

¹H-NMR (DMSO d$_6$, CD$_3$COOD): 9.03 (s, 1H), 7.88 (s, 1H), 7.61 (s, 1H), 7.37 (m, 3H), 6.87 (m, 1H), 4.33 (m, 2H), 4.29 (m, 2H), 4.03 (s, 2H), 3.99 (s, 3H), 3.67 (m, 8H), 3.50 (m, 2H), 3.41 (m, 2H), 2.37 (m, 2H):

MS (+ve ESI): 694.6 (M+H)$^+$.

di(tert-butyl) 2-(4-(3-((4-((5-(2-(3,5-difluorophenyl)amino)-2-oxoethyl)-1,3-thiazol-2-yl)amino)-6-methoxyquinazolin-7-yl)oxy)propyl)piperazin-1-yl)ethyl phosphate used as the starting material was obtained as follows:

a) An analogous reaction to that described in example 18c, but starting with 3,5-difluoroaniline (2.09 g, 16.3 mmol) and (2-((N-triphenylmethyl)amino)-1,3-thiazol-5-yl)acetic acid (5.00 g, 12.5 mmol) yielded N-(3,5-difluorophenyl)-2-(2-((N-triphenylmethyl)amino)-1,3-thiazol-5-yl)acetamide (4.75 g, 74% yield):

¹H-NMR (DMSO d$_6$): 7.30 (m, 2H), 6.92 (m, 1H), 7.10 (m, 2H), 6.75 (br s, 2H), 6.72 (s, 1H), 3.65 (s, 2H):

MS (+ve ESI): 511.9 (M+H)$^+$.

b) A mixture of N-(3,5-difluorophenyl)-2-(2-((N-triphenylmethyl)amino)-1,3-thiazol-5-yl)acetamide (5.38 g, 20.0 mmol) and N'-(5-(3-chloropropoxy)-2-cyano-4-methoxyphenyl)-N,N-dimethylimidoformamide (5.91 g, 20.0 mmol) were heated in acetic acid (50 ml) at 140° C. for 4.5 hours. The reaction mixture was evaporated to dryness, the residue was triturated with acetonitrile and the yellow solid collected by suction filtration and washed with diethyl ether. Extended drying in vacuo yielded N-(3,5-difluorophenyl)-2-(2-(7-(3-chloropropoxy)-6-methoxyquinazolin-4-yl-amino-1,3-thiazol-5-yl)acetamide (5.88 g, 57% yield) as a pale yellow solid:

¹H-NMR (DMSO d$_6$): 12.00 (br s, 1H), 10.59 (br s, 1H), 8.64 (s, 1H), 8.11 (s, 1H), 7.38 (s, 1H), 7.34 (m, 2H), 7.26 (s, 1H), 6.89 (m, 1H), 4.25 (t, 2H), 3.98 (s, 3H), 3.85 (s, 2H), 3.80 (t, 2H), 2.25 (m, 2H):

MS (+ve ESI): 520 (M+H)$^+$

MS (−ve ESI): 518 (M−H)$^−$.

c) An analogous reaction to that described in example 1h, but starting with 1-(2-hydroxyethyl)piperazine (430 mg, 3.3 mmol) and N-(3,5-difluorophenyl)-2-(2-(7-(3-chloropropoxy)-6-methoxyquinazolin-4-yl-amino-1,3-thiazol-5-yl)acetamide (114 mg, 0.22 mmol) yielded N-(3,5-difluorophenyl)-2-(2-((7-(3-(4-(2-hydroxyethyl)piperazin-1-yl)propoxy)-6-methoxyquinazolin-4-yl)amino)-1,3-thiazol-5-yl)acetamide (124 mg, 92% yield):

¹H-NMR (DMSO d$_6$, TFA): 10.63 (s, 1H), 8.66 (s, 1H), 8.10 (s, 1H), 7.38 (s, 1H), 7.34 (dd, 2H), 7.23 (s, 1H), 6.43 (m, 1H), 4.35 (m, 1H), 4.18 (t, 2H), 3.95 (s, 3H), 3.90 (s, 2H), 3.48 (m, 2H), 2.70 (m, 1H), 2.40 (m, 12H), 1.96 (m, 2H):

MS (+ve ESI): 614 (M+H)$^+$ d) An analogous reaction to that described in example 1i, but starting with N-(3,5-difluorophenyl)-2-(2-((7-(3-(4-(2-hydroxyethyl)piperazin-1-yl)propoxy)-6-methoxyquinazolin-4-yl)amino)-1,3-thiazol-5-yl)acetamide (460 mg; 0.75 mmol) yielded di(tert-butyl) 2-(4-(3-((4-((5-(2-(3,5-difluorophenyl)amino)-2-oxoethyl)-1,3-thiazol-2-yl)amino)-6-methoxyquinazolin-7-yl)oxy)propyl)piperazin-1-yl)ethyl phosphate (340 mg, 56% yield):

¹H-NMR: 8.67 (s, 1H), 8.11 (s, 1H), 7.39 (s, 1H), 7.35 (m, 2H), 7.24 (s, 1H), 6.94 (m, 1H), 4.20 (t, 2H), 3.97 (s, 3H), 3.94 (m, 2H), 3.91 (s, 2H), 2.55 (m, 4H), 2.45 (m, 8H), 1.97 (m, 2H), 1.42 (s, 18H):

EXAMPLE 21

Preparation of Compound 21 in Table 1—2-((3-((4-((5-(2-((3,5-difluorophenyl)amino)-2-oxoethyl)-1,3-thiazol-2-yl)amino)-6-methoxyquinazolin-7-yl)oxy)propyl)(methyl)amino)ethyl dihydrogen phosphate An analogous reaction to that described in example 1, but starting with di(tert-butyl) 2-((3-((4-((5-(2-((3,5-difluorophenyl)amino)-2-oxoethyl)-1,3-thiazol-2-yl)amino)-6-methoxyquinazolin-7-yl)oxy)propyl)(methyl)amino)ethyl phosphate (470 mg, 0.62 mmol) yielded the title compound (378 mg, 94% yield):

¹H-NMR (DMSO d$_6$): 9.06 (s, 1H), 7.88 (s, 1H), 7.64 (s, 1H), 7.43 (m, 3H), 6.95 (m, 1H), 4.31 (m, 4H), 4.05 (s, 2H), 3.99 (s, 3H), 3.46 (m, 2H), 3.34 (m, 2H), 2.88 (s, 3H), 2.33 (m, 2H):

MS (+ve ESI): 639.5 (M+H)$^+$.

di(tert-butyl) 2-((3-((4-((5-(2-((3,5-difluorophenyl)amino)-2-oxoethyl)-1,3-thiazol-2-yl)amino)-6-methoxyquinazolin-7-yl)oxy)propyl)(methyl)amino)ethyl phosphate used as the starting material was obtained as follows:

a) An analogous reaction to that described in example 20c but starting with 2-methylaminoethanol (248 mg, 3.3 mmol) yielded N-(3,5-difluorophenyl)-2-(2-((7-(3-((2-hydroxyethyl)(methyl)amino)propoxy)-6-methoxyquinazolin-4-yl)amino)-1,3-thiazol-5-yl)acetamide (33 mg, 27% yield):

¹H-NMR (DMSO d$_6$): 12.04 (br s, 1H), 10.65 (s, 1H), 8.69 (s, 1H), 8.13 (br s, 1H), 7.40 (s, 1H), 7.36 (dd, 2H), 7.27 (s, 1H), 6.95 (m, 1H), 4.38 (m, 1H), 4.21 (t, 2H), 3.98 (s, 3H), 3.93 (s, 2H), 3.49 (m, 2H), 2.48 (m, 2H), 2.45 (m, 2H), 2.24 (s, 3H), 1.95 (m, 2H):

MS (+ve ESI): 559 (M+H)$^+$.

b) An analogous reaction to that described in example 1i, but starting with N-(3,5-difluorophenyl)-2-(2-((7-(3-((2-hydroxyethyl)(methyl)amino)propoxy)-6-methoxyquinazolin-4-yl)amino)-1,3-thiazol-5-yl)acetamide (500 mg, 0.896 mmol) yielded di(tert-butyl) 2-((3-((4-((5-(2-((3,5-difluorophenyl)amino)-2-oxoethyl)-1,3-thiazol-2-yl)amino)-6-methoxyquinazolin-7-yl)oxy)propyl)(methyl)amino)ethyl phosphate (375 mg, 56% yield):

¹H-NMR (DMSO d$_6$): 8.68 (s, 1H), 8.12 (s, 1H), 7.40 (s, 1H), 7.36 (m, 2H), 7.24 (s, 1H), 6.94 (m, 1H), 4.21 (t, 2H), 3.97 (s, 3H), 3.92 (m, 4H), 2.62 (t, 2H), 2.57 (t, 2H), 2.25 (s, 3H), 1.95 (m, 2H), 1.39 (s, 18H):

MS (+ve ESI): 751.6 (M+H)$^+$.

EXAMPLE 22

Preparation of Compound 22 in Table 1—((2S)-1-(3-((4-((5-(2-((3,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate An analogous reaction to that described in example 1, but starting with di(tert-butyl) ((2S)-1-(3-((4-((5-(2-((3,5-difluorophenyl)amino)-2-oxoethyl)-1,3-thiazol-2-yl)amino)-6-methoxyquinazolin-7-yl)oxy)propyl)pyrrolidin-2-yl)methyl phosphate (500 mg, 0.644 mmol) yielded the title compound (402 mg, 82% yield):

¹H-NMR (DMSO d$_6$): 9.05 (s, 1H), 7.89 (s, 1H), 7.64 (s, 1H), 7.40, (m, 3H), 6.95 (m, 1H), 4.31 (m, 2H), 4.23 (m, 2H), 4.05 (s, 2H), 3.99 (s, 3H), 3.80 (m, 1H), 3.70 (m, 1H), 3.60 (m, 1H), 3.30 (m, 1H), 3.23 (q, 1H), 2.35 (m, 2H), 2.20 (m, 1H), 2.04 (m, 1H), 1.97 (m, 1H), 1.83 (m, 1H):

MS (+ve ESI): 665.5 (M+H)$^+$.

di(tert-butyl) ((2S)-1-(3-((4-((5-(2-((3,5-difluorophenyl) amino)-2-oxoethyl)-1,3-thiazol-2-yl)amino)-6-methoxyquinazolin-7-yl)oxy)propyl)pyrrolidin-2-yl)methyl phosphate used as the starting material was obtained as follows:

a) An analogous reaction to that described in example 20c but starting with (S)-(+)-2-pyrrolidinylmethanol (334 mg, 3.3 mmol) yielded N-(3,5-difluorophenyl)-2-(2-((7-(3-((2S)-2-(hydroxymethyl)pyrrolidin-1-yl)propoxy)-6-methoxyquinazolin-4-yl)amino)-1,3-thiazol-5-yl)acetamide (58 mg, 45% yield):
 ¹H-NMR (DMSO d₆, TFA): 9.09 (s, 1H), 7.91 (s, 1H), 7.64 (s, 1H), 7.35 (dd, 2H), 7.30 (s, 1H), 6.91 (t, 1H), 4.30 (m, 2H), 4.01 (s, 2H), 3.99 (s, 3H), 3.77 (dd, 1H), 3.62 (m, 4H), 3.33 (m, 2H), 2.30 (m, 2H), 2.13 (m, 1H), 2.02 (m, 1H), 1.90 (m, 1H), 1.79 (m, 1H);
 MS (+ve ESI): 585 (M+H)⁺.

b) An analogous reaction to that described in example 1i, but starting with N-(3,5-difluorophenyl)-2-(2-((7-(3-((2S)-2-(hydroxymethyl)pyrrolidin-1-yl)propoxy)-6-methoxyquinazolin-4-yl)amino)-1,3-thiazol-5-yl)acetamide (759 mg, 1.3 mmol) yielded di(tert-butyl) ((2S)-1-(3-((4-((5-(2-((3,5-difluorophenyl)amino)-2-oxoethyl)-1,3-thiazol-2-yl)amino)-6-methoxyquinazolin-7-yl)oxy)propyl)pyrrolidin-2-yl)methyl phosphate (500 mg, 50% yield):
 ¹H-NMR (DMSO d₆): 8.68 (s, 1H), 8.12 (s, 1H), 7.39 (s, 1H), 7.35 (m, 2H), 7.24 (s, 1H), 6.95 (m, 1H), 4.22 (m, 2H), 3.97 (s, 3H), 3.92 (s, 2H), 3.80 (m, 1H), 3.61 (m, 1H), 3.12 (m, 1H), 3.00 (m, 1H), 2.72 (m, 1H), 2.50 (m, 1H), 2.25 (q, 1H), 1.98 (m, 2H), 1.90 (m, 1H), 1.70 (m, 2H), 1.63 (m, 1H), 1.37 (s, 18H):
 MS (+ve ESI): 777.5 (M+H)⁺.

EXAMPLE 23

Preparation of Compound 23 in Table 1—(1R)-2-((3-((4-((5-(2-((3,5-difluorophenyl)amino)-2-oxoethyl)-1,3-thiazol-2-yl)amino)-6-methoxyquinazolin-7-yl)oxy)propyl)amino)-1-methylethyl dihydrogen phosphate An analogous reaction to that described in example 1, but starting with di(tert-butyl) (1R)-2-((3-((4-((5-(2-((3,5-difluorophenyl)amino)-2-oxoethyl)-1,3-thiazol-2-yl)amino)-6-methoxyquinazolin-7-yl)oxy)propyl)amino)-1-methylethyl phosphate (470 mg, 0.553 mmol) yielded the title compound (350 mg, 89% yield):
 ¹H-NMR (DMSO d₆, CD₃COOD): 9.00 (s, 1H), 7.86 (s, 1H), 7.59 (s, 1H), 7.37 (m, 3H), 6.85 (m, 1H), 4.61 (m, 1H), 4.29 (m, 2H), 4.01 (s, 2H), 3.96 (s, 3H), 3.20 (m, 4H), 2.28 (m, 2H), 1.32 (d, 3H):
 MS (+ve ESI): 639.6 (M+H)⁺.

di(tert-butyl) (1R)-2-((3-((4-((5-(2-((3,5-difluorophenyl) amino)-2-oxoethyl)-1,3-thiazol-2-yl)amino)-6-methoxyquinazolin-7-yl)oxy)propyl)amino)-1-methylethyl phosphate used as the starting material was obtained as follows:

a) An analogous reaction to that described in example 20c, but starting with (R)-(−)-1-amino-2-propanol (248 mg, 3.3 mmol) yielded N-(3,5-difluorophenyl)-2-(2-((7-(3-(((2R)-2-hydroxypropyl)amino)propoxy)-6-methoxyquinazolin-4-yl)amino)-1,3-thiazol-5-yl)acetamide (40 mg, 32% yield):
 ¹H-NMR (DMSO d₆, TFA): 9.09 (s, 1H), 7.91 (s, 1H), 7.64 (s, 1H), 7.34 (dd, 2H), 7.28 (s, 1H), 6.90 (m, 1H), 4.29 (t, 1H), 4.01 (s, 3H), 3.99 (s, 3H), 3.95 (m, 1H), 3.15 (t, 2H), 3.06 (dd, 1H), 2.83 (dd, 1H), 2.24 (m, 2H), 1.15 (d, 3H):
 MS (+ve ESI): 559 (M+H)⁺.

b) An analogous reaction to that described in example 1i, but starting with N-(3,5-difluorophenyl)-2-(2-((7-(3-(((2R)-2-hydroxypropyl)amino)propoxy)-6-methoxyquinazolin-4-yl)amino)-1,3-thiazol-5-yl)acetamide (470 mg, 0.714 mmol) yielded di(tert-butyl) (1R)-2-((3-((4-((5-(2-((3,5-difluorophenyl)amino)-2-oxoethyl)-1,3-thiazol-2-yl) amino)-6-methoxyquinazolin-7-yl)oxy)propyl)amino)-1-methylethyl phosphate (470 mg, 77% yield):
 ¹H-NMR (DMSO d₆): 8.68 (s, 1H), 8.12 (s, 1H), 7.40 (s, 1H), 7.35 (m, 2H) 7.25 (s, 1H); 6.95 (m, 1H), 4.50 (m, 1H), 4.17 (m, 2H), 3.96 (s, 3H), 3.91 (s, 2H), 2.32 (m, 2H), 2.05 (m, 2H), 1.42 (s, 18H), 1.22 (d, 3H).

EXAMPLE 24

Preparation of Compound 24 in Table 1—((2R)-1-(3-((4-((5-(2-((3,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate Di(tert-butyl) ((2R)-1-(3-((4-((5-(2-((3,4-difluorophenyl) amino)-2-oxoethyl)-1,3-thiazol-2-yl)amino)-6-methoxyquinazolin-7-yl)oxy)propyl)pyrrolidin-2-yl)methyl phosphate (450 mg, 0.58 mmol) in dioxane (20 ml) was treated with a solution of HCl (4N) in dioxane (940 μl) at ambient temperature for 15 hours. The solid was recovered by filtration, washed with dioxane, dried in vacuo at 50° C. to yield the title compound (270 mg, 63% yield):
 ¹H-NMR (DMSO d₆, CD₃COOD): 9.07 (s, 1H), 7.90 (s, 1H), 7.80 (m, 1H), 7.62 (s, 1H), 7.35 (m, 3H), 7.30 (s, 1H), 4.29 (t, 2H), 4.21 (m, 1H), 4.14 (m, 1H), 3.97 (s, 5H), 3.82 (m, 1H), 3.70 (m, 1H), 3.58 (m, 1H), 3.27 (m, 2H), 2.30 (m, 3H), 2.20 (m, 1H), 1.89 (m, 2H):
 MS (+ve ESI): 665 (M+H)⁺.

Di(tert-butyl) ((2R)-1-(3-((4-((5-(2-((3,4-difluorophenyl) amino)-2-oxoethyl)-1,3-thiazol-2-yl)amino)-6-methoxyquinazolin-7-yl)oxy)propyl)pyrrolidin-2-yl)methyl phosphate used as the starting material was obtained as follows:

a) An analogous reaction to that described in example 18c, but starting with (2-((N-triphenylmethyl)amino)-1,3-thiazol-5-yl)acetic acid (10.0 g, 25.0 mmol) and 3,4-difluoroaniline (3.0 ml, 30 mol) yielded N-(3,4-difluorophenyl)-2-(2-((N-triphenylmethyl)amino)-1,3-thiazol-5-yl) acetamide (9.61 g, 75% yield):
 ¹H-NMR (DMSO d₆): 8.36 (s, 1H), 7.70 (m, 1H), 7.13-7.37 (m, 17H), 6.58 (s, 1H), 3.53 (s, 2H):
 MS (−ve ESI): 510 (M−H)⁻.

b) A mixture of N-(3,4-difluorophenyl)-2-(2-((N-triphenylmethyl)amino)-1,3-thiazol-5-yl)acetamide (9.51 g, 18.6 mmol) and N'-(5-(3-chloropropoxy)-2-cyano-4-methoxyphenyl)-N,N-dimethylimidoformamide (5.50 g, 18.6 mmol) were heated in acetic acid (50 ml) at 140° C. for 5.5 hours. The reaction was allowed to stir at ambient temperature for 16 hours, the yellow solid was collected by suction filtration and was then washed with i) acetic acid, ii) acetonitrile and iii) diethyl ether. Extended drying in vacuo yielded N-(3,4-difluorophenyl)-2-(2-(7-(3-chloropropoxy)-6-methoxyquinazolin-4-yl-amino-1,3-thiazol-5-yl) acetamide (5.81 g, 60% yield) as a pale yellow solid:
 ¹H-NMR (DMSO d₆): 10.42 (br s, 1H), 8.63 (s, 1H), 8.11 (s, 1H), 7.79 (m, 1H), 7.32-7.41 (m, 4H), 4.25 (t, 2H), 3.98 (s, 3H), 3.85 (s, 2H), 3.79 (t, 2H), 2.25 (m, 2H):
 MS (+ve ESI): 520 (M+H)⁺
 MS (−ve ESI): 518 (M−H)⁻.

c) An analogous reaction to that described in example 1h, but starting with N-(3,4-difluorophenyl)-2-(2-(7-(3-chloropropoxy)-6-methoxyquinazolin-4-yl-amino-1,3-thiazol-5-yl)acetamide and (R)-(−)-2-pyrrolidinylmethanol (334 mg, 3.3 mmol) yielded N-(3,4-difluorophenyl)-2-(2-((7-(3-((2R)-2-(hydroxymethyl)pyrrolidin-1-yl)propoxy)-6-methoxyquinazolin-4-yl)amino)-1,3-thiazol-5-yl)acetamide (90 mg, 70% yield):

$^1$H-NMR (DMSO d$_6$, TFA): 9.08 (s, 1H), 7.90 (s, 1H), 7.80 (m, 1H), 7.64 (s, 1H), 7.39 (dd, 1H), 7.32 (m, 1H), 7.30 (s, 1H), 4.29 (t, 2H), 3.98 (s, 5H), 3.77 (m, 1H), 3.62 (m, 4H), 3.21 (m, 2H), 2.29 (m, 2H), 2.11 (m, 1H), 2.03 (m, 1H), 1.91 (m, 1H), 1.79 (m, 1H):

MS (+ve ESI): 585 (M+H)$^+$.

d) N-(3,4-difluorophenyl)-2-(2-((7-(3-((2R)-2-(hydroxymethyl)pyrrolidin-1-yl)propoxy)-6-methoxyquinazolin-4-yl)amino)-1,3-thiazol-5-yl)acetamide (600 mg, 1.02 mmol) was dissolved in dimethylacetamide (3 ml). Tetrazole (144 mg, 2.05 mmol) and di-tert-butyl-diethylphosphoramidite (571 µl, 2.05 mmol) were added to the mixture, which was stirred at ambient temperature under argon for 20 hours. The mixture was then diluted with dichloromethane (60 ml) and washed with a saturated solution of sodium bicarbonate (25 ml). The organic phase was recovered, dried over magnesium sulphate, filtered and concentrated in vacuo. The crude product was dissolved in tetrahydrofuran (15 ml) at 0° C., hydrogen peroxide (30%, 210 µl) was added to the solution which was stirred for two hours, warming from 0° C. to ambient temperature. The mixture was then cooled to 0° C., sodium metabisulfite (390 mg, 2.05 mmol) was added, the mixture was stirred at 0° C. for 15 minutes, diluted with ethyl acetate, washed with a saturated solution of sodium bicarbonate, the organic phase was recovered, dried over magnesium sulphate, filtered, concentrated. The crude product was purified by chromatography on silica gel, eluting with dichloromethane:7.0N methanolic ammonia (2-5%), to yield di(tert-butyl) ((2R)-1-3-((4-((5-(2-((3,4-difluorophenyl)amino)-2-oxoethyl-1,3-thiazol-2-yl)amino)-6-methoxyquinazolin-7-yl)oxy)propyl)pyrrolidin-2-yl)methyl phosphate (490 mg, 61% yield):

$^1$H-NMR (DMSO d$_6$): 8.67 (s, 1H), 8.11 (s, 1H), 7.82 (m, 1H), 7.42 (m, 1H), 7.40 (s, 1H), 7.33 (m, 1H), 7.25 (s, 1H), 4.22 (m, 2H), 3.97 (s, 3H), 3.89 (s, 2H), 3.78 (m, 1H), 3.57 (m, 1H), 3.10 (m, 1H), 2.96 (m, 1H), 2.68 (m, 1H), 2.46 (m, 1H), 2.22 (q, 1H), 1.97 (m, 2H), 1.88 (m, 1H), 1.70 (m, 2H), 1.62 (m, 1H), 1.37 (s, 18H):

MS (+ve ESI): 777.7 (M+H)$^+$.

EXAMPLE 25

Preparation of Compound 25 in Table 1—((2S)-1-(3-((4-((5-(2-((3,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate Di(tert-butyl) ((2S)-1-3-((4-((5-(2-((3,4-difluorophenyl)amino)-2-oxoethyl)-1,3-thiazol-2-yl)amino)-6-methoxyquinazolin-7-yl)oxy)propyl)pyrrolidin-2-yl)methyl phosphate (537 mg, 0.69 mmol) in dioxane (10 ml) was treated with a solution of HCl (4N) in dioxane (1.2 ml) at ambient temperature for 15 hours. The solid was recovered by filtration, washed with dioxane, dried under vacuum at 50° C. to give the title compound (413 mg, 81% yield):

$^1$H-NMR (DMSO d$_6$, CD$_3$COOD): 9.07 (s, 1H), 7.90 (s, 1H), 7.80 (m, 1H), 7.62 (s, 1H), 7.35 (m, 3H), 7.30 (s, 1H), 4.29 (t, 2H), 4.21 (m, 1H), 4.14 (m, 1H), 3.97 (s, 5H), 3.82 (m, 1H), 3.70 (m, 1H), 3.58 (m, 1H), 3.27 (m, 2H), 2.30 (m, 3H), 2.20 (m, 1H), 1.89 (m, 2H);

MS (+ve ESI): 665 (M+H)$^+$.

Di(tert-butyl) ((2S)-1-3-((4-((5-(2-((3,4-difluorophenyl)amino)-2-oxoethyl)-1,3-thiazol-2-yl)amino)-6-methoxyquinazolin-7-yl)oxy)propyl)pyrrolidin-2-yl)methyl phosphate used as the starting material was obtained as follows:

a) An analogous reaction to that described in example 24c, but starting with (S)-(+)-2-pyrrolidinylmethanol (1.42 ml, 14.5 mmol) yielded N-(3,4-difluorophenyl)-2-(2-((7-(3-((2S)-2-(hydroxymethyl)pyrrolidin-1-yl)propoxy)-6-methoxyquinazolin-4-yl)amino)-1,3-thiazol-5-yl)acetamide (825 mg, 49% yield):

$^1$H-NMR (DMSO d$_6$, TFA): 9.08 (s, 1H), 7.90 (s, 1H), 7.80 (m, 1H), 7.64 (s, 1H), 7.39 (dd, 1H), 7.32 (m, 1H), 7.30 (s, 1H), 4.29 (t, 2H), 3.98 (s, 5H), 3.77 (m, 1H), 3.62 (m, 4H), 3.21 (m, 2H), 2.29 (m, 2H), 2.11 (m, 1H), 2.03 (m, 1H), 1.91 (m, 1H), 1.79 (m, 1H):

MS (+ve ESI): 585 (M+H)$^+$.

b) An analogous reaction to that described in example 1i, but starting with N-(3,4-difluorophenyl)-2-(2-((7-(3-((2S)-2-(hydroxymethyl)pyrrolidin-1-yl)propoxy)-6-methoxyquinazolin-4-yl)amino)-1,3-thiazol-5-yl)acetamide (794 mg, 1.36 mmol) yielded di(tert-butyl) ((2R)-1-3-((4-((5-(2-((3,4-difluorophenyl)amino)-2-oxoethyl-1,3-thiazol-2-yl)amino)-6-methoxyquinazolin-7-yl)oxy)propyl)pyrrolidin-2-yl)methyl phosphate (537 mg, 51% yield):

$^1$H-NMR (DMSO d$_6$): 8.67 (s, 1H), 8.11 (s, 1H), 7.82 (m, 1H), 7.42 (m, 1H), 7.40 (s, 1H), 7.33 (m, 1H), 7.25 (s, 1H), 4.22 (m, 2H), 3.97 (s, 3H), 3.89 (s, 2H), 3.78 (m, 1H), 3.57 (m, 1H), 3.10 (m, 1H), 2.96 (m, 1H), 2.68 (m, 1H), 2.46 (m, 1H), 2.22 (q, 1H), 1.97 (m, 2H), 1.88 (m, 1H), 1.70 (m, 2H), 1.62 (m, 1H), 1.37 (s, 18H):

MS (+ve ESI): 777 (M+H)$^+$.

EXAMPLE 26

Preparation of Compound 26 in Table 1—1-(3-((4-((5-(2-((3,4-difluorophenyl)amino)-2-oxoethyl)-1,3-thiazol-2-yl)amino)-6-methoxyquinazolin-7-yl)oxy)propyl)piperidin-4-ylmethyl dihydrogen phosphate An analogous reaction to that described in example 1, but starting with di(tert-butyl) (1-(3-((4-((5-(2-((3,4-difluorophenyl)amino)-2-oxoethyl)-1,3-thiazol-2-yl)amino)-6-methoxyquinazolin-7-yl)oxy)propyl)piperidin-4-yl)methyl phosphate (321 mg, 0.41 mmol) yielded the title compound (258 mg, 85% yield):

$^1$H-NMR (DMSO d$_6$): 11.20 (s, 1H), 10.70 (s, 1H), 8.97 (s, 1H), 7.84 (m, 1H), 7.76 (s, 1H), 7.59 (s, 1H), 7.43 (m, 3H), 4.30 (m, 2H), 4.04 (s, 2H), 3.95 (s, 3H), 3.70 (t, 2H), 3.56 (m, 2H), 3.50-3.40 (m, 2H), 3.23 (m, 2H), 2.98 (m, 2H), 2.37 (m, 2H), 1.90 (m, 3H), 1.65 (m, 2H):

MS (+ve ESI): 679 (M+H)$^+$.

di(tert-butyl) (1-(3-((4-((5-(2-((3,4-difluorophenyl)amino)-2-oxoethyl)-1,3-thiazol-2-yl)amino)-6-methoxyquinazolin-7-yl)oxy)propyl)piperidin-4-yl)methyl phosphate used as the starting material was obtained as follows:

a) An analogous reaction to that described in example 1h, but starting with N-(3,4-difluorophenyl)-2-(2-(7-(3-chloropropoxy)-6-methoxyquinazolin-4-yl-amino-1,3-thiazol-5-yl)acetamide (1.50 g, 2.89 mmol) and piperidin-4-ylmethanol (1.66 g, 14.4 mmol) yielded N-(3,4-difluorophenyl)-2-(2-((7-(3-(4-(hydroxymethyl)piperidin-1-yl)propoxy)-6-methoxyquinazolin-4-yl)

amino)-1,3-thiazol-5-yl)acetamide (989 mg, 57% yield) as a pale yellow solid after drying in vacuo:

$^1$H-NMR (DMSO-d$_6$): 12.00 (s, 1H), 10.45 (s, 1H), 8.70 (s, 1H), 8.15 (s, 1H), 7.65-7.75 (m, 1H), 7.40-7.50 (m, 3H), 7.25 (s, 1H), 4.40 (br s, 1H), 4.20 (t, 2H), 3.98 (s, 3H), 3.90 (s, 2H), 3.22 (m, 2H), 2.80-2.90 (m, 2H), 2.50 (t, 2H), 1.80-2.00 (m, 4H), 1.50-1.60 (m, 2H), 1.32 (m, 1H), 1.12 (m, 2H):

MS (+ve ESI): 599 (M+H)$^+$

MS (−ve ESI): 597(M−H)$^-$.

b) An analogous reaction to that described in example 1i, but starting with N-(3,4-difluorophenyl)-2-(2-((7-(3-(4-(hydroxymethyl)piperidin-1-yl)propoxy)-6-methoxyquinazolin-4-yl)amino)-1,3-thiazol-5-yl)acetamide (963 mg, 1.61 mmol) yielded di(tert-butyl) (1-(3-((4-((5-(2-((3,4-difluorophenyl)amino)-2-oxoethyl)-1,3-thiazol-2-yl)amino)-6-methoxyquinazolin-7-yl)oxy)propyl)piperidin-4-yl)methyl phosphate (343 mg, 34% yield):

$^1$H-NMR (DMSO d$_6$): 12.00 (s, 1H), 10.45 (s, 1H), 8.65 (s, 1H), 8.20 (s, 1H), 7.67 (m, 1H), 7.25-7.45 (m, 3H), 7.25 (s, 1H), 4.20 (t, 2H), 3.95 (s, 3H), 3.90 (s, 2H), 3.74 (m, 1H), 2.80-2.90 (m, 1H), 2.40-2.50 (m, 2H), 1.80-2.00 (m, 4H), 1.60-1.70 (m, 3H), 1.40 (s, 18H), 1.18 (m, 2H):

MS (+ve ESI): 791 (M+H)$^+$.

EXAMPLE 27

Preparation of Compound 27 in Table 1—(1-(3-((4-((5-(2-((2-fluorophenyl)amino)-2-oxoethyl)-1,3-thiazol-2yl)amino)-6-methoxyquinazolin-7-yl)oxy)propyl)piperidin-4-yl)methyl dihydrogen phosphate Hydrochloric acid (1 ml of a 4.0 N solution in 1,4-dioxane, 4 mmol) was added, dropwise to a solution of di(tert-butyl) (1-(3-((4-((5-(2-((2-fluorophenyl)amino)-2-oxoethyl)-1,3-thiazol-2-yl)amino)-6-methoxyquinazolin-7-yl)oxy)propyl) piperidin-4-yl)methyl phosphate (assumed 379 mg, 0.49 mmol) in 1,4-dioxane (15 ml) upon which a light yellow solid precipitated from the reaction mixture. The resulting heterogeneous reaction mixture was stirred for a further 20 hours and the precipitate was filtered and washed with 1,4-dioxane (2×5 ml) then dried under high vacuum for 48 hours to furnish (1-(3-((4-((5-(2-((2-fluorophenyl)amino)-2-oxoethyl)-1,3-thiazol-2yl)amino)-6-methoxyquinazolin-7-yl)oxy)propyl) piperidin-4-yl)methyl dihydrogen phosphate bis-hydrochloride as a light yellow solid (302 mg, 84% yield):

$^1$H-NMR (DMSO d$_6$): 10.52 (m, 1H), 10.19 (s, 1H), 9.02 (s, 1H), 7.83 (m, 2H), 7.58 (s, 1H), 7.42 (s, 1H), 7.24 (m, 1H), 7.17 (m, 2H), 4.27 (t, 2H), 4.05 (s, 2H), 3.95 (s, 3H), 3.70 (t, 2H), 3.53 (m, 2H), 3.20 (m, 2H), 2.93 (q, 2H), 2.34 (m, 2H), 2.86 (br d, 3H), 1.60 (m, 1H):

MS (+ve ESI): 661 (M+H)$^+$.

di(tert-butyl) (1-(3-((4-((5-(2-((2-fluorophenyl)amino)-2-oxoethyl)-1,3-thiazol-2-yl)amino)-6-methoxyquinazolin-7-yl)oxy)propyl)piperidin-4-yl)methyl phosphate used as the starting material was obtained as follows:

a) An analogous reaction to that described in example 1p, but starting with 2-((tert-butoxycarbonyl)amino)-1,3-thiazol-5-yl)acetic acid (1.50 g, 5.81 mmol) and 2-fluoroaniline (0.73 ml, 7.56 mol) yielded tert-butyl 5-(2-((2-fluorophenyl)amino)-2-oxoethyl)-1,3-thiazol-2-ylcarbamate (1.25 g, 61% yield):

MS (+ve ESI): 352 (M+H)$^+$.

b) A mixture of tert-butyl 5-(2-((2-fluorophenyl)amino)-2-oxoethyl)-1,3-thiazol-2-ylcarbamate (9.88 g, 20.0 mmol) and N'-(5-(3-chloropropoxy)-2-cyano-4-methoxyphenyl)-N,N-dimethylimidoformamide (5.91 g, 20.0 mmol) were heated in acetic acid (75 ml) at 140° C. for 4 hours. The reaction mixture was cooled to ambient temperature, the yellow solid was collected by suction filtration and washed with i) acetic acid, ii) acetontrile and iii) diethyl ether. Extended drying in vacuo yielded N-(2-fluorophenyl)-2-(2-(7-(3-chloropropoxy)-6-methoxyquinazolin-4-yl-amino-1,3-thiazol-5-yl)acetamide (7.57 g, 76% yield) as a pale yellow solid:

$^1$H-NMR (DMSO d$_6$): 10.00 (br s, 1H), 8.63 (s, 1H), 8.11 (s, 1H), 7.88 (m, 1H), 7.38 (s, 1H), 7.25 (m, 2H), 7.16 (m, 2H), 4.25 (t, 2H), 3.95 (m, 5H), 3.80 (t, 2H), 2.25 (m, 2H):

MS (+ve ESI): 502 (M+H)$^+$

MS (−ve ESI): 500 (M−H)$^-$.

c) An analogous reaction to that described in example 1h, but starting with N-(2-fluorophenyl)-2-(2-(7-(3-chloropropoxy)-6-methoxyquinazolin-4-yl-amino-1,3-thiazol-5-yl) acetamide (0.50 g, 1.0 mmol) and piperidin-4-ylmethanol (0.60 ml, 5.0 mmol) yielded N-(2-fluorophenyl)-2-(2-((7-(3-(4-(hydroxymethyl)piperidin-1-yl)propoxy)-6-methoxyquinazolin-4-yl)amino)-1,3-thiazol-5-yl)acetamide (325 mg, 55% yield) as a pale yellow solid after drying in vacuo:

$^1$H-NMR (DMSO d$_6$): 9.98 (br s, 1H), 8.63 (s, 1H), 8.06 (s, 1H), 7.88 (m, 1H), 7.37 (s, 1H), 7.25 (m, 1H), 7.21 (s, 1H), 7.15 (m, 2H), 4.32 (m, 1H), 4.17 (t, 2H), 3.93 (s, 3H), 3.12 (m, 2H), 2.89 (m, 2H), 2.40 (m, 2H), 1.81-1.96 (m, 4H), 1.60 (m, 2H), 1.30 (m, 1H), 1.10 (m, 2H):

MS (+ve ESI): 581 (M+H)$^+$.

d) N-(2-fluorophenyl)-2-(2-((7-(3-(4-(hydroxymethyl)piperidin-1-yl)propoxy)-6-methoxyquinazolin-4-yl)amino)-1,3-thiazol-5-yl)acetamide (285 mg, 0.49 mmol) and dry 1H-tetrazole (104 mg, 1.47 mmol) were dissolved in dry dimethylacetamide (10 ml) under a nitrogen atmosphere. Di-tert-butyl diethylphosphoramidite (210 µl, 0.74 mmol) was added, in one portion, to the stirred homogeneous reaction mixture and left to stir at ambient temperature for 2 hours upon which time the reaction mixture was diluted with dichloromethane (20 ml) and washed with sodium hydrogen carbonate (20 ml of a saturated aqueous solution). The aqueous layer was further extracted with dichloromethane (3×20 ml) and the combined organic layers were dried over sodium sulphate, filtered and concentrated under reduced pressure to yield a viscous, yellow oil which was used promptly in the next step of the reaction sequence without further purification:

MS (+ve ESI): 701 (M+H-tBu)$^+$.

Hydrogen peroxide (120 µl of a 30% w/w aqueous solution, 0.98 mmol) was added dropwise to a stirred and cooled (0° C.) solution of the crude phosphite in tetrahydrofuran (5 ml) and warmed to ambient temperature over 10 minutes. The resulting homogeneous solution was stirred for 2 hours upon which time the reaction was then cooled (0° C.) and a solution of sodium thiosulphite (3 ml of a 0.53 N aqueous solution) was introduced, dropwise. The reaction was warmed to ambient temperature over 10 minutes then diluted with ethyl acetate (20 ml) and sodium hydrogen carbonate (20 ml of a saturated aqueous solution), the phases separated and the aqueous layer further extracted with ethyl acetate (2×20 ml). The combined organic layers were dried over sodium sulphate, filtered and concentrated under reduced pressure to furnish di(tert-butyl) (1-(3-((4-((5-(2-((2-fluorophenyl) amino)-2-oxoethyl)-1,3-thiazol-2-yl)amino)-6-methoxyquinazolin-7-yl)oxy)propyl)piperidin-4-yl)methyl phosphate as a viscous, yellow oil which was used in the next step of the reaction sequence without further, purification (assumed 379 mg, quantitative yield):

MS (+ve ESI): 773 (M+H)$^+$.

EXAMPLE 28

Preparation of Compound 28 in Table 1—((2R)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate Di(tert-butyl) ((2R)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl phosphate (310 mg, 0.41 mmol) in 1,4-dioxane (25 ml) was treated with 4.0 N hydrochloric acid in 1,4-dioxane (0.7 ml, 2.86 mmol) at 20° C. for 18 hours. The solid product was collected by suction filtration and washed successively with 1,4-dioxane (50 ml), acetonitrile (50 ml) then diethyl ether (50 ml), dried in vacuo to give the title compound (287 mg, 97% yield) as a yellow dihydrochloride salt:

$^1$H-NMR (DMSO d$_6$): 10.08 (s, 1H), 8.90 (s, 1H), 7.80 (m, 2H), 7.50 (s, 1H), 7.35 (s, 1H), 7.18 (m, 1H), 7.07 (m, 2H), 4.22 (m, 2H), 4.12 (m, 2H), 3.95 (s, 2H), 3.90 (s, 3H), 3.70 (m, 1H), 3.59 (m, 1H), 3.48 (m, 1H), 3.20 (m, 1H), 3.10 (m, 1H), 2.21 (m, 2H), 2.10 (m, 1H), 1.95 (m, 1H), 1.85 (m, 1H), 1.72 (m, 1H):

MS (+ve ESI): 647 (M+H)$^+$.
MS (−ve ESI): 645 (M−H)$^−$.

di(tert-butyl) ((2R)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl phosphate, used as the starting material was obtained as follows:

a) N-(2-fluorophenyl)-2-(2-(7-(3-chloropropoxy)-6-methoxyquinazolin-4-yl-amino-1,3-thiazol-5-yl)acetamide (884 mg, 1.5 mmol) in dimethylacetamide (5 ml) was reacted with 2(R)-pyrrolidinylmethanol (D-prolinol) (307 mg, 3.0 mmol) in the presence of tetrabutylammonium iodide (100 mg) at 60° C., under an inert atmosphere, for 6 hours. The cooled reaction solution was purified by chromatography on silica gel, eluting with dichloromethane: 7.0N methanolic ammonia (2-8%); evaporation of solvent and drying in vacuo yielded N-(2-fluorophenyl)-2-(2-((7-(3-((2R)-2-(hydroxymethyl)pyrrolidin-1-yl)propoxy)-6-methoxyquinazolin-4-yl)amino)-1,3-thiazol-5-yl)acetamide (583 mg, 69% yield) as an orange solid:

$^1$H-NMR (DMSO d$_6$): 10.01 (s, 1H), 8.66 (s, 1H), 8.10 (s, 1H), 7.90 (m, 1H), 7.37 (s, 1H), 7.25 (m, 1H), 7.23 (s, 1H), 7.15 (m, 2H), 4.29 (br s, 1H), 4.20 (t, 2H), 3.95 (s, 2H), 3.95 (s, 3H), 3.39 (m, 1H), 3.20 (m, 1H), 3.05 (m, 1H), 2.95 (m, 1H), 2.42 (m, 2H), 2.15 (m, 1H), 1.49-1.98 (m, 6H):

MS (+ve ESI): 567 (M+H)$^+$.
MS (−ve ESI): 565 (M−H)$^−$.

b) N-(2-fluorophenyl)-2-(2-((7-(3-((2R)-2-(hydroxymethyl)pyrrolidin-1-yl)propoxy)-6-methoxyquinazolin-4-yl)amino)-1,3-thiazol-5-yl)acetamide (427 mg, 0.75 mmol) in dimethyl acetamide (4 ml) was treated with tetrazole (105 mg, 1.5 mmol) and di-tert-butyl-diethylphosphoramidite (493 mg, 1.84 mmol) at 20° C., under an inert atmosphere, for 3 hours. The reaction solution was cooled to −10° C. and 30% hydrogen peroxide solution (0.22 ml, 1.84 mmol) was added dropwise over 5 minutes. After stirring for 2 hours at 20° C. the reaction was quenched at −10° C. with 0.5N sodium thiosulphate solution. The mixture was extracted twice with ethyl acetate (20 ml) and the organic solution dried over magnesium sulphate, evaporated and the resulting oil purified by chromatography on silica gel, eluting with dichloromethane:7.0 N methanolic ammonia (0-4%). Evaporation of solvent and drying in vacuo yielded di(tert-butyl) ((2R)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl phosphate (310 mg, 55% yield) as a yellow gum:

MS (+ve ESI): 759 (M+H)$^+$.
MS (−ve ESI): 757 (M−H)$^−$.

EXAMPLE 29

Preparation of Compound 29 in Table 1—((2S)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate An analogous reaction to that described in example 28 but starting with di(tert-butyl) ((2S)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl phosphate (612 mg, 0.81 mmol) yielded the title compound (527 mg, 86% yield) as a yellow dihydrochloride salt:

$^1$H-NMR (DMSO d$_6$): 10.29 (s, 1H), 9.00 (s, 1H), 7.85 (m, 1H), 7.80 (s, 1H), 7.60 (s, 1H), 7.45 (s, 1H), 7.28 (m, 1H), 7.18 (m, 2H), 4.30 (m, 3H), 4.20 (m, 1H), 4.05 (s, 2H), 3.95 (s, 3H), 3.80 (m, 1H), 3.65 (m, 1H), 3.60 (m, 1H), 3.28 (m, 1H), 3.20 (m, 1H), 2.25 (m, 2H), 2.20 (m, 1H), 2.05 (m, 1H), 1.95 (m, 1H), 1.80 (m, 1H):

MS (+ve ESI): 647 (M+H)$^+$.
MS (−ve ESI): 645 (M−H)$^−$.

di(tert-butyl) ((2S)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl phosphate, used as the starting material was obtained as follows:

a) An analogous reaction to that described in example 28a, but starting with 2-(S)-pyrrolidinylmethanol (L-prolinol) (615 mg, 6.0 mmol) and N-(2-fluorophenyl)-2-(2-(7-(3-chloropropoxy)-6-methoxyquinazolin-4-yl-amino-1,3-thiazol-5-yl)acetamide (1.12 g, 2.0 mmol). Purification by reverse phase HPLC eluting with 40% acetonitrile in water containing 0.1% TFA and basification of the product fractions with ammonia. After concentration to low volume the solid product was collected by suction filtration, washed with water and dried in vacuo to yield N-(2-fluorophenyl)-2-(2-((7-(3-((2S)-2-(hydroxymethyl)pyrrolidin-1-yl)propoxy)-6-methoxyquinazolin-4-yl)amino)-1,3-thiazol-5-yl)acetamide (697 mg, 62% yield):

$^1$H-NMR (DMSO d$_6$): 11.95 (br s, 1H), 9.95 (s, 1H), 8.57 (s, 1H), 8.00 (s, 1H), 7.85 (m, 1H), 7.29 (s, 1H), 7.20 (m, 1H), 7.15 (s, 1H), 7.08 (m, 2H), 4.25 (br s, 1H), 4.10 (t, 2H), 3.85 (s, 2H), 3.85 (s, 3H), 3.30 (m, 1H), 3.10 (m, 1H), 3.00 (m, 1H), 2.85 (m, 1H), 2.30 (m, 2H), 2.08 (m, 1H), 1.40-1.90 (m, 6H):

MS (+ve ESI): 567 (M+H)$^+$.
MS (−ve ESI): 565 (M−H)$^−$.

b) An analogous reaction to that described in example 28b, but starting with N-(2-fluorophenyl)-2-(2-((7-(3-((2S)-2-(hydroxymethyl)pyrrolidin-1-yl)propoxy)-6-methoxyquinazolin-4-yl)amino)-1,3-thiazol-5-yl)acetamide (600 mg, 1.06 mmol) yielded di(tert-butyl) ((2S)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl phosphate (625 mg, 78% yield) as a yellow gum:

$^1$H-NMR (DMSO d$_6$): 10.08 (s, 1H), 8.65 (s, 1H), 8.10 (s, 1H), 7.92 (m, 1H), 7.37 (s, 1H), 7.25 (m, 1H), 7.22 (s, 1H), 7.18 (m, 2H), 4.20 (m, 2H), 3.95 (s, 2H), 3.95 (s, 3H), 3.78 (m,

1H), 3.55 (m, 1H), 3.10 (m, 1H), 2.95 (m, 1H), 2.68 (m, 1H), 2.47 (m, 1H), 2.20 (m, 1H), 1.80-2.00 (m, 3H), 1.50-1.70 (m, 3H), 1.35 (s, 18H):
MS (+ve ESI): 759 (M+H)$^+$.
MS (−ve ESI): 757 (M−H)$^-$.

EXAMPLE 30

Preparation of Compound 30 in Table 1—2-(ethyl(3-((4-((5-(2-((2-fluorophenyl)amino)-2-oxoethyl)-1,3-thiazol-2-yl)amino)-6-methoxyquinazolin-7-yl)oxy)propyl)amino)ethyl dihydrogen phosphate An analogous reaction to that described in example 28 but starting with di(tert-butyl) 2-(ethyl(3-((4-((5-(2-((2-fluorophenyl)amino)-2-oxoethyl)-1,3-thiazol-2-yl)amino)-6-methoxyquinazolin-7-yl)oxy)propyl)amino)ethyl phosphate (888 mg, 1.19 mmol) yielded the title compound (544 mg, 61% yield) as a yellow dihydrochloride salt:
$^1$H-NMR (DMSO d$_6$): 10.80 (br s, 1H), 10.17 (s, 1H), 8.95 (s, 1H), 7.78 (m, 2H), 7.50 (s, 1H), 7.38 (s, 1H), 7.20 (m, 1H), 7.09 (m, 2H), 4.20 (m, 4H), 4.00 (s, 2H), 3.90 (s, 3H), 3.35 (m, 2H), 3.22 (m, 4H), 2.24 (m, 2H), 1.20 (t, 3H):
MS (+ve ESI): 635 (M+H)$^+$
MS (−ve ESI): 633 (M−H)$^-$.

di(tert-butyl) 2-(ethyl(3-((4-((5-(2-((2-fluorophenyl)amino)-2-oxoethyl)-1,3-thiazol-2-yl)amino)-6-methoxyquinazolin-7-yl)oxy)propyl)amino)ethyl phosphate, used as the starting material was obtained as follows:
a) An analogous reaction to that described in example 28a, but starting with 2-ethylaminoethanol (802 mg, 9.0 mmol) and N-(2-fluorophenyl)-2-(2-(7-(3-chloropropoxy)-6-methoxyquinazolin-4-yl-amino-1,3-thiazol-5-yl)acetamide (1.68 g, 3.0 mmol), and purifying the product by reverse phase HPLC eluting with 40% acetonitrile in water containing 0.1% TFA, yielded 2-(2-((7-(3-(ethyl(2-hydroxyethyl)amino)propoxy)-6-methoxyquinazolin-4-yl)amino)-1,3-thiazol-5-yl)-N-(2-fluorophenyl)acetamide (972 mg, 58% yield):
$^1$H-NMR (DMSO d$_6$): 9.89 (s, 1H), 8.37 (s, 1H), 7.92 (m, 1H), 7.85 (s, 1H), 7.25 (m, 1H), 7.15 (m, 3H), 7.00 (s, 1H), 4.35 (br s, 1H), 4.10 (t, 2H), 3.90 (s, 3H), 3.82 (s, 2H), 3.40 (t, 2H), 2.60 (m, 2H), 2.47 (m, 2H), 1.88 (m, 2H), 0.95 (t, 3H):
MS (+ve ESI): 555 (M+H)$^+$
MS (−ve ESI): 553 (M−H)$^-$.
b) An analogous reaction to that described in example 28b, but starting with 2-(2-((7-(3-(ethyl(2-hydroxyethyl)amino)propoxy)-6-methoxyquinazolin-4-yl)amino)-1,3-thiazol-5-yl)-N-(2-fluorophenyl)acetamide (1.15 g, 1.7 mmol) yielded di(tert-butyl) 2-(ethyl(3-((4-((5-(2-((2-fluorophenyl)amino)-2-oxoethyl)-1,3-thiazol-2-yl)amino)-6-methoxyquinazolin-7-yl)oxy)propyl)amino)ethyl phosphate (888 mg, 70% yield) as a yellow oil:
MS (+ve ESI): 747 (M+H)$^+$
MS (−ve ESI): 745 (M−H)$^-$.

EXAMPLE 31

Preparation of Compound 31 in Table 1—2-(1-(3-((4-((5-(2-((2-fluorophenyl)amino)-2-oxoethyl)-1,3-thiazol-2-yl)amino)-6-methoxyquinazolin-7-yl)oxy)propyl)piperidin-2-yl)ethyl dihydrogen phosphate An analogous reaction to that described in example 28, but starting with di(tert-butyl) 2-(1-(3-((4-((5-(2-((2-fluorophenyl)amino)-2-oxoethyl)-1,3-thiazol-2-yl)amino)-6-methoxyquinazolin-7-yl)oxy)propyl)piperidin-2-yl)ethyl phosphate (484 mg, 0.615 mmol) and the resulting yellow solid was purified by silica chromatography, eluting with 100:40:8:8 dichloromethane:methanol:water:formic acid, evaporation of solvent and drying in vacuo yielded the title compound (300 mg, 62% yield) as a yellow dihydrochloride salt:
$^1$H-NMR (DMSO d$_6$): 10.10 (s, 1H), 8.65 (s, 1H), 8.10 (s, 1H), 7.90 (m, 1H), 7.38 (s, 1H), 7.25 (m, 2H), 7.17 (m, 2H), 4.20 (m, 2H), 4.00 (s, 3H), 3.99 (s, 2H), 3.76 (m, 1H), 3.10 (m, 4H), 2.75 (m,1H), 2.15 (m, 2H), 1.95 (m, 1H), 1.85 (m, 1H), 1.65 (m, 5H), 1.40 (m, 1H):
MS (+ve ESI): 675 (M+H)$^+$
MS (−ve ESI): 673 (M−H)$^-$.

di(tert-butyl) 2-(1-(3-((4-((5-(2-((2-fluorophenyl)amino)-2-oxoethyl)-1,3-thiazol-2-yl)amino)-6-methoxyquinazolin-7-yl)oxy)propyl)piperidin-2-yl)ethyl phosphate, used as the starting material was obtained as follows:
a) An analogous reaction to that described in example 28a, but starting with 2-piperidinylethanol (1.61 g, 9.0 mmol) and N-(2-fluorophenyl)-2-(2-(7-(3-chloropropoxy)-6-methoxyquinazolin-4-yl-amino-1,3-thiazol-5-yl)acetamide (1.68 g, 3.0 mmol), and purifying the product by reverse phase HPLC eluting with 40% acetonitrile in water containing 0.1% TFA, yielded N-(2-fluorophenyl)-2-(2-((7-(3-(2-(2-hydroxyethyl)piperidin-1-yl)propoxy)-6-methoxyquinazolin-4-yl)amino)-1,3-thiazol-5-yl)acetamide (565 mg, 32% yield):
$^1$H-NMR (DMSO d$_6$): 9.95 (s, 1H), 8.48 (s, 1H), 7.90 (m, 2H), 7.25 (m, 2H), 7.13 (m, 2H), 7.08 (s, 1H), 4.40 (br s, 1H), 4.10 (t, 2H), 3.90 (s, 3H), 3.88 (s, 2H), 3.40 (m, 2H), 2.77 (m, 2H), 2.45 (m, 2H), 2.20 (m, 1H), 1.90 (m, 2H), 1.75 (m, 1H), 1.57 (m, 2H), 1.47 (m, 3H),
1.27 (m, 2H):
MS (+ve ESI): 595 (M+H)$^+$
MS (−ve ESI): 593 (M−H)$^-$.
b) An analogous reaction to that described in example 28b, but starting with N-(2-fluorophenyl)-2-(2-((7-(3-(2-(2-hydroxyethyl)piperidin-1-yl)propoxy)-6-methoxyquinazolin-4-yl)amino)-1,3-thiazol-5-yl)acetamide (517 mg, 0.87 mmol) yielded di(tert-butyl) 2-(1-(3-((4-((5-(2-((2-fluorophenyl)amino)-2-oxoethyl)-1,3-thiazol-2-yl)amino)-6-methoxyquinazolin-7-yl)oxy)propyl)piperidin-2-yl)ethyl phosphate (484 mg, 71% yield) as a yellow gum:
MS (+ve ESI): 787 (M+H)$^+$
MS (−ve ESI): 785 (M−H)$^-$.

EXAMPLE 32

Preparation of Compound 32 in Table 1—((2R)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate Di(tert-butyl) ((2R)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl phosphate (230 mg, 0.296 mmol) in 1,4-dioxane (15 ml) was treated with 4.0 N hydrochloric acid in 1,4-dioxane (0.9 ml, 3.43 mmol) at 20° C. for 18 hours. The solid product was collected by suction filtration, washed with i) 1,4-dioxane (50 ml), ii) acetonitrile (50 ml) and iii) diethyl ether (50 ml) and then dried in vacuo to yield the title compound (166 mg, 72% yield) as a yellow dihydrochloride salt:
$^1$H-NMR (DMSO d$_6$): 10.45 (s, 1H), 9.00 (s, 1H), 7.85 (s, 1H), 7.67 (m, 1H), 7.60 (s, 1H), 7.43 (s, 1H), 7.20 (m, 2H), 4.28 (m, 2H), 4.20 (m, 2H), 4.09 (s, 2H), 3.95 (s, 3H), 3.80 (m, 1H), 3.68 (m, 1H), 3.58 (m, 1H), 3.25 (m, 2H), 2.30 (m, 2H), 2.20 (m, 1H), 2.00 (m, 2H), 1.85 (m, 1H):
MS (+ve ESI): 665 (M+H)⁺
MS (–ve ESI): 663 (M–H)⁻.

di(tert-butyl) ((2R)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl phosphate, used as the starting material was obtained as follows:

a) An analogous reaction to that described in example 1p, but starting with (2-((N-triphenylmethyl)amino)-1,3-thiazol-5-yl)acetic acid (26.7 g, 67 mmol) and 2,3-difluoroaniline (8.80 ml, 87 mmol) yielded N-(2,3-difluorophenyl)-2-(2-((N-triphenylmethyl)amino)-1,3-thiazol-5-yl)acetamide (15.4 g, 95% yield):

¹H-NMR (DMSO d₆): 10.02 (s, 1H), 8.33 (s, 1H), 7.60 (m, 1H), 7.11-7.31 (m, 16H), 6.58 (s, 1H), 3.63 (s, 2H):
MS (+ve ESI): 512 (M+H)⁺ b) An analogous reaction to that described in example 1g, but starting with N-(2,3-difluorophenyl)-2-(2-((N-triphenylmethyl)amino)-1,3-thiazol-5-yl)acetamide (4.70 g, 9.2 mmol) yielded N-(2,3-difluorophenyl)-2-(2-(7-(3-chloropropoxy)-6-methoxyquinazolin-4-yl-amino-1,3-thiazol-5-yl)acetamide (2.20 g, 46% yield):

¹H-NMR (DMSO d₆): 11.96 (br s, 1H), 10.20 (br s, 1H), 8.66 (s, 1H), 8.10 (s, 1H), 7.70 (m, 1H), 7.36 (s, 1H), 7.28 (s, 1H), 7.18 (m, 2H), 4.26 (t, 2H), 3.95 (s, 2H), 3.93 (s, 3H), 3.81 (t, 2H), 2.25 (m, 2H):
MS (+ve ESI): 520 (M+H)⁺
MS (–ve ESI): 518 (M–H)⁻.

c) N-(2,3-difluorophenyl)-2-(2-(7-(3-chloropropoxy)-6-methoxyquinazolin-4-yl-amino-1,3-thiazol-5-yl)acetamide (1.04 g, 2.0 mmol) in dimethylacetamide (5 ml) was reacted with D-prolinol (615 mg, 6.0 mmol) in the presence of tetrabutylammonium iodide (100 mg, 0.27 mmol) at 60° C., under an inert atmosphere, for 17 hours. The cooled reaction solution was purified by reverse phase HPLC eluting with 40% acetonitrile in water containing 0.1% TFA. After basification of the product fractions with sodium carbonate and concentration to low volume, the solid product was collected by suction filtration, washed with water and dried in vacuo, to yield N-(2,3-difluorophenyl)-2-(2-((7-(3-((2R)-2-(hydroxymethyl)pyrrolidin-1-yl)propoxy)-6-methoxyquinazolin-4-yl)amino)-1,3-thiazol-5-yl)acetamide (687 mg, 59% yield):

¹H-NMR (DMSO d₆): 10.20 (s, 1H), 8.55 (s, 1H), 8.00 (s, 1H), 7.70 (m, 1H), 7.30 (s, 1H), 7.20 (m, 3H), 4.35 (br s, 1H), 4.20 (m, 2H), 3.90 (s, 2H), 3.90 (s, 3H), 3.40 (m, 1H), 3.18 (m, 1H), 3.07 (m, 1H), 2.95 (m, 1H), 2.40 (m, 2H), 2.15 (m, 1H), 1.93 (m, 2H), 1.80 (m, 1H), 1.67 (m, 2H), 1.55 (m, 1H):
MS (+ve ESI): 585 (M+H)⁺.

d) N-(2,3-difluorophenyl)-2-(2-((7-(3-((2R)-2-(hydroxymethyl)pyrrolidin-1-yl)propoxy)-6-methoxyquinazolin-4-yl)amino)-1,3-thiazol-5-yl)acetamide (620 mg, 1.06 mmol) in dimethylacetamide (6 ml) was treated with tetrazole (148 mg, 2.12 mmol) and di-tert-butyl-diethylphosphoramidite (800 mg, 2.6 mmol) at 20° C., under an inert atmosphere, for 6 hours. The reaction solution was cooled to –10° C. and 30% hydrogen peroxide solution (0.3 ml, 2.6 mmol) was added dropwise over 5 minutes. After stirring for 2 hours at 20° C. the reaction was quenched at –10° C. with 0.5 N sodium thiosulphate solution (3 ml). The mixture was extracted twice with ethyl acetate (25 ml) and the organic solution dried over magnesium sulphate, evaporated and the resulting oil purified by chromatography on silica gel, eluting with dichloromethane:7.0 N methanolic ammonia (0-5%); evaporation of solvent and drying in vacuo yielded di(tert-butyl) ((2R)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl phosphate (393 mg, 48% yield) as a yellow gum:

¹H-NMR (DMSO d₆): 12.00 (br s, 1H), 10.27 (s, 1H), 8.66 (s, 1H), 8.10 (s, 1H), 7.72 (m, 1H), 7.39 (s, 1H), 7.25 (s, 1H), 7.19 (m, 1H), 4.18 (m, 2H), 3.99 (s, 2H), 3.95 (s, 3H), 3.79 (m, 1H), 3.55 (m, 1H), 3.10 (m, 1H), 2.95 (m, 1H), 2.68 (m, 1H), 2.47 (m, 1H), 2.20 (m, 1H), 1.80-2.00 (m, 3H), 1.50-1.75 (m, 3H), 1.35 (s, 18H):
MS (+ve ESI): 777 (M+H)⁺
MS (–ve ESI): 775 (M–H)⁻.

EXAMPLE 33

Preparation of Compound 33 in Table 1—((2S)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate An analogous reaction to that described in example 32, but starting with di(tert-butyl) ((2S)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl phosphate (202 mg, 0.26 mmol) yielded the title compound (177 mg, 88% yield) as a yellow dihydrochloride salt:

¹H-NMR (DMSO d₆): 10.45 (s, 1H), 9.00 (s, 1H), 7.85 (s, 1H), 7.65 (m, 1H), 7.60 (s, 1H), 7.49 (s, 1H), 7.20 (m, 2H), 4.30 (m, 2H), 4.20 (m, 2H), 4.08 (s, 2H), 3.98 (s, 3H), 3.55-3.80 (m, 3H), 3.15-3.35 (m, 2H), 2.15-2.45 (m, 3H), 1.78-2.08 (m, 3H):
MS (+ve ESI): 665 (M+H)⁺
MS (–ve ESI): 663 (M–H)⁻.

di(tert-butyl) ((2S)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl phosphate, used as the starting material was obtained as follows:

a) An analogous reaction to that described in example 32c, but starting with L-prolinol (583 mg, 5.7 mmol) and N-(2,3-difluorophenyl)-2-(2-(7-(3-chloropropoxy)-6-methoxyquinazolin-4-yl-amino-1,3-thiazol-5-yl)acetamide (982 mg, 1.89 mmol). Purification was by reverse phase HPLC, eluting with 40% acetonitrile in water containing 0.1% TFA. After basification of the product fractions with sodium carbonate and concentration to low volume, the solid product was collected by suction filtration, washed with water and dried in vacuo, to yield N-(2,3-difluorophenyl)-2-(2-((7-(3-((2S)-2-(hydroxymethyl)pyrrolidin-1-yl)propoxy)-6-methoxyquinazolin-4-yl)amino)-1,3-thiazol-5-yl)acetamide (562 mg, 51% yield):

¹H-NMR (DMSO d₆): 10.25 (s, 1H), 8.60 (s, 1H), 8.05 (s, 1H), 7.70 (m, 1H), 7.35 (s, 1H), 7.17 (m, 3H), 4.32 (br s, 1H), 4.15 (m, 2H), 3.95 (s, 2H), 3.90 (s, 3H), 3.38 (m, 1H), 3.15 (m, 1H), 3.05 (m, 1H), 2.95 (m, 1H), 2.40 (m, 2H), 2.12 (m, 1H), 1.95 (m, 2H), 1.78 (m, 1H), 1.60 (m, 2H), 1.55 (m, 1H):
MS (+ve ESI): 585 (M+–H)⁺
MS (–ve ESI): 583 (M–H)⁻.

b) An analogous reaction to that described in example 32d, but starting with N-(2,3-difluorophenyl)-2-(2-((7-(3-((2S)-2-(hydroxymethyl)pyrrolidin-1-yl)propoxy)-6-methoxyquinazolin-4-yl)amino)-1,3-thiazol-5-yl)acetamide (501 mg, 0.858 mmol) yielded di(tert-butyl) ((2S)-1-(3-((4-((5-(2-((2,3-difluorophenyl)amino)-2-oxoethyl)-1, 3-thiazol-2-yl)amino)-6-methoxyquinazolin-7-yl)oxy) propyl)pyrrolidin-2-yl)methyl phosphate (205 mg, 31% yield) as a yellow gum:
MS (+ve ESI): 777 (M+H)⁺
MS (−ve ESI): 775 (M−H)⁻.

EXAMPLE 34

Preparation of Compound 34 in Table 1—2-((3-((4-((5-(2-((2,3-difluorophenyl)amino)-2-oxoethyl)-1,3-thiazol-2-yl)amino)-6-methoxyquinazolin-7-yl)oxy) propyl)(methyl)amino)ethyl dihydrogen phosphate An analogous reaction to that described in example 32, but starting with di(tert-butyl) 2-((3-((4-((5-(2-((2,3-difluorophenyl)amino)-2-oxoethyl)-1,3-thiazol-2-yl)amino)-6-methoxyquinazolin-7-yl)oxy)propyl)(methyl)amino)ethyl phosphate (503 mg, 0.67 mmol) yielded the title compound (478 mg, 96% yield) as a yellow dihydrochloride salt:
¹H-NMR (DMSO d₆): 10.45 (s, 1H), 9.00 (s, 1H), 7.85 (s, 1H), 7.65 (m, 1H), 7.60 (s, 1H), 7.45 (s, 1H), 7.18 (m, 2H), 4.25 (m, 4H), 4.05 (s, 2H), 3.95 (s, 3H), 3.42 (m, 2H), 3.30 (m, 2H), 2.85 (s, 3H), 2.30 (m, 2H):
MS (+ve ESI): 639 (M+H)⁺
MS (−ve ESI): 637 (M−H)⁻.

di(tert-butyl) 2-((3-((4-((5-(2-((2,3-difluorophenyl)amino)-2-oxoethyl)-1,3-thiazol-2-yl)amino)-6-methoxyquinazolin-7-yl)oxy)propyl)(methyl)amino)ethyl phosphate, used as the starting material was obtained as follows:
a) An analogous reaction to that described in example 32c, but starting with 2-(methylamino)ethanol (496 mg, 6.6 mmol) and N-(2,3-difluorophenyl)-2-(2-(7-(3-chloropropoxy)-6-methoxyquinazolin-4-yl-amino-1,3-thiazol-5-yl)acetamide (1.14 g, 2.2 mmol) yielded N-(2,3-difluorophenyl)-2-(2-((7-(3-((2-hydroxyethyl)(methyl)amino)propoxy)-6-methoxyquinazolin-4yl)amino)-1,3-thiazol-5-yl) acetamide (681 mg, 55% yield):
¹H-NMR (DMSO d₆): 10.15 (s, 1H), 8.53 (s, 1H), 7.98 (s, 1H), 7.70 (m, 1H), 7.28 (s, 1H), 7.15 (m, 2H), 4.15 (m, 2H), 3.92 (s, 2H), 3.90 (s, 3H), 3.48 (m, 2H), 2.50 (m, 2H), 7.42 (m, 2H), 2.20 (s, 3H), 1.90 (m, 2H):
MS (+ve ESI): 559 (M+H)⁺
MS (−ve ESI): 557 (M−H)⁻.
b) An analogous reaction to that described in example 32d, but starting with N-(2,3-difluorophenyl)-2-(2-((7-(3-((2-hydroxyethyl)(methyl)amino)propoxy)-6-methoxyquinazolin-4-yl)amino)-1,3-thiazol-5-yl)acetamide (617 mg, 1.106 mmol) yielded di(tert-butyl) 2-((3-((4-((5-(2-((2,3-difluorophenyl)amino)-2-oxoethyl)-1,3-thiazol-2-yl)amino)-6-methoxyquinazolin-7-yl)oxy)propyl)(methyl)amino)ethyl phosphate (503 mg, 61% yield) as a yellow gum:
MS (+ve ESI): 751 (M+H)⁺
MS (−ve ESI): 749 (M−H)⁻.

EXAMPLE 35

Preparation of Compound 35 in Table 1—2-(1-(3-((4-((5-(2-((2,3-difluorophenyl)amino)-2-oxoethyl)-1,3-thiazol-2-yl)amino)-6-methoxyquinazolin-7-yl) oxy)propyl)piperidin-2-yl)ethyl dihydrogen phosphate An analogous reaction to that described in example 32 but starting with di(tert-butyl) 2-(1-(3-((4-((5-(2-((2,3-difluorophenyl)amino)-2-oxoethyl)-1,3-thiazol-2-yl)amino)-6-methoxyquinazolin-7-yl)oxy)propyl)piperidin-2-yl)ethyl phosphate (133 mg, 0.166 mmol) yielded the title compound (136 mg, 98% yield) as a yellow dihydrochloride salt:
¹H-NMR (DMSO d₆): 10.75 (s, 1H), 10.40 (s, 1H), 9.00 (s, 1H), 7.87 (s, 1H), 7.65 (m, 1H), 7.60 (s, 1H), 7.42 (s, 1H), 7.19 (m, 2H), 4.28 (m, 2H), 4.05 (s, 2H), 3.95 (s, 3H), 3.95 (m, 2H), 3.02-3.50 (m, 5H), 2.30 (m, 2H), 1.40-2.10 (m, 6H):
MS (+ve ESI): 693 (M+H)⁺
MS (−ve ESI): 691 (M−H)⁻.

di(tert-butyl) 2-(1-(3-((4-((5-(2-((2,3-difluorophenyl) amino)-2-oxoethyl)-1,3-thiazol-2-yl)amino)-6-methoxyquinazolin-7-yl)oxy)propyl)piperidin-2-yl)ethyl phosphate, used as the starting material was obtained as follows:
a) An analogous reaction to that described in example 32c, but starting with 2-(2-hydroxyethyl)piperidine (588 mg, 6.6 mmol) and N-(2,3-difluorophenyl)-2-(2-(7-(3-chloropropoxy)-6-methoxyquinazolin-4-yl-amino-1,3-thiazol-5-yl) acetamide (1.14 g, 2.2 mmol), yielded N-(2,3-difluorophenyl)-2-(2-((7-(3-(2-(2-hydroxyethyl)piperidin-1-yl) propoxy)-6-methoxyquinazolin-4-yl)amino)-1,3-thiazol-5-yl)acetamide (260 mg, 19% yield):
¹H-NMR (DMSO d₆): 10.10 (s, 1H), 8.50 (s, 1H), 7.95 (s, 1H), 7.70 (m, 1H), 7.25 (s, 1H), 7.18 (m, 2H), 7.09 (s, 1H), 4.35 (br s, 1H), 4.10 (m, 2H), 3.90 (s, 3H), 3.89 (s, 2H), 3.45 (m, 1H), 2.75 (m, 2H), 2.45 (m, 2H), 2.25 (m, 1H), 1.90 (m, 2H), 1.75 (m, 1H), 1.57 (m, 2H), 1.45 (m, 3H), 1.28 (m, 2H):
MS (+ve ESI): 613 (M+H)⁺
MS (−ve ESI): 611 (M−H)⁻.
b) An analogous reaction to that described in example 32d, but starting with N-(2,3-difluorophenyl)-2-(2-((7-(3-(2-(2-hydroxyethyl)piperidin-1-yl)propoxy)-6-methoxyquinazolin-4-yl)amino)-1,3-thiazol-5-yl)acetamide (219 mg, 0.358 mmol) yielded di(tert-butyl) 2-(1-(3-((4-((5-(2-((2,3-difluorophenyl)amino)-2-oxoethyl)-1,3-thiazol-2-yl)amino)-6-methoxyquinazolin-7-yl)oxy)propyl)piperidin-2-yl)ethyl phosphate (133 mg, 46% yield) as a yellow gum:
MS (+ve ESI): 805 (M+H)⁺
MS (−ve ESI): 803 (M−H)⁻.

EXAMPLE 36

Preparation of Compound 36 in Table 1—2-((3-((4-((5-(2-((2,3-difluorophenyl)amino)-2-oxoethyl)-1,3-thiazol-2-yl)amino)-6-methoxyquinazolin-7-yl)oxy) propyl)(ethyl)amino)ethyl dihydrogen phosphate An analogous reaction to that described in example 32 but starting with di(tert-butyl) 2-((3-((4-((5-(2-((2,3-difluorophenyl)amino)-2-oxoethyl)-1,3-thiazol-2-yl)amino)-6-methoxyquinazolin-7-yl)oxy)propyl)(ethyl)amino)ethyl phosphate (354 mg, 0.46 mmol) and the resulting yellow solid was purified by chromatography on silica gel, eluting with dichloromethane:methanol:water:formic acid (100:40:8:8); evaporation of solvent and drying in vacuo yielded the title compound (194 mg, 55% yield) as a yellow dihydrochloride salt:
¹H-NMR (DMSO d₆): 10.30 (s, 1H), 8.65 (s, 1H), 8.10 (s, 1H), 7.70 (m, 1H), 7.35 (s, 1H), 7.25 (s, 1H), 7.18 (m, 2H), 4.20 (m, 2H), 3.95 (s, 2H), 3.93 (s, 3H), 3.90 (m, 2H), 2.95 (m, 4H), 2.87 (m, 2H), 2.10 (m, 2H), 1.10 (t, 3H):
MS (+ve ESI): 653 (M+H)⁺
MS (−ve ESI): 651 (M−H)⁻.

di(tert-butyl) 2-((3-((4-((5-(2-((2,3-difluorophenyl)amino)-2-oxoethyl)-1,3-thiazol-2-yl)amino)-6-methoxyquinazolin- 7-yl)oxy)propyl)(ethyl)amino)ethyl phosphate, used as the starting material was obtained as follows:

a) An analogous reaction to that described in example 32c, but starting with 2-(ethylamino)ethanol (588 mg, 6.6 mmol) and N-(2,3-difluorophenyl)-2-(2-(7-(3-chloropropoxy)-6-methoxyquinazolin-4-yl-amino-1,3-thiazol-5-yl)acetamide (1.14 g, 2.2 mmol), yielded N-(2,3-difluorophenyl)-2-(2-((7-(3-(ethyl(2-hydroxyethyl)amino)propoxy)-6-methoxyquinazolin-4-yl)amino)-1,3-thiazol-5-yl) acetamide (345 mg, 28% yield):

$^1$H-NMR (DMSO d$_6$): 10.20 (s, 1H), 8.60 (s, 1H), 8.05 (s, 1H), 7.70 (m, 1H), 7.35 (m, 1H), 7.15 (m, 3H), 4.28 (br s, 1H), 4.16 (m, 2H), 3.94 (s, 2H), 3.93 (s, 3H), 3.42 (m, 2H), 2.60 (m, 2H), 2.50 (m, 6H), 1.90 (m, 2H), 0.95 (t, 3H):

MS (+ve ESI): 572 (M+H)$^+$
MS (−ve ESI): 571 (M−H)$^−$.

b) An analogous reaction to that described in example 32d, but starting with N-(2,3-difluorophenyl)-2-(2-((7-(3-(ethyl(2-hydroxyethyl)amino)propoxy)-6-methoxyquinazolin-4-yl)amino)-1,3-thiazol-5-yl)acetamide (293 mg, 0.512 mmol) yielded di(tert-butyl) 2-((3-((4-((5-(2-((2,3-difluorophenyl)amino)-2-oxoethyl)-1,3-thiazol-2-yl)amino)-6-methoxyquinazolin-7-yl)oxy)propyl)(ethyl) amino)ethyl phosphate (354 mg, 91% yield) as a yellow gum:

MS (+ve ESI): 765(M+H)$^+$
MS (−ve ESI): 763 (M−H)$^−$.

EXAMPLE 37

Preparation of Compound 37 in Table 1—1-(3-((4-((5-(2-((2,3-difluorophenyl)amino)-2-oxoethyl)-1,3-thiazol-2-yl)amino)-6-methoxyquinazolin-7-yl)oxy) propyl)piperidin-4-ylmethyl dihydrogen phosphate An analogous reaction to that described in example 32, but starting with di(tert-butyl) 1-(3-((4-((5-(2-((2,3-difluorophenyl)amino)-2-oxoethyl)-1,3-thiazol-2-yl)amino)-6-methoxyquinazolin-7-yl)oxy)propyl)piperidin-4-ylmethyl phosphate (983 mg, 1.24 mmol) yielded the title compound (993 mg, 100% yield):

$^1$H-NMR (DMSO d$_6$): 10.45 (br s, 2H), 9.00 (s, 1H), 7.90 (s, 1H), 7.60-7.70 (m, 1H), 7.55 (s, 1H), 7.40 (s, 1H), 7.10-7.25 (m, 1H), 4.30-4.40 (m, 2H), 4.10 (s, 2H), 3.98 (m, 3H), 3.68 (m, 2H), 3.50-3.60 (m, 2H), 3.22 (m, 2H), 2.90-3.00 (m, 2H), 2.30-2.45 (m, 2H), 1.80-1.90 (m, 2H), 1.55-1.65 (m, 2H):

MS (+ve ESI): 679.4 (M+H)$^+$.

di(tert-butyl) 1-(3-((4-((5-(2-((2,3-difluorophenyl)amino)-2-oxoethyl)-1,3-thiazol-2-yl)amino)-6-methoxyquinazolin-7-yl)oxy)propyl)piperidin-4-ylmethyl phosphate used as the starting material was obtained as follows:

a) An analogous reaction to that described in example 32c, but starting with N-(2,3-difluorophenyl)-2-(2-(7-(3-chloropropoxy)-6-methoxyquinazolin-4-yl-amino-1,3-thiazol-5-yl)acetamide (2.00 g, 3.85 mmol) and 4-(hydroxymethyl)piperidine (2.22 g, 19.3 mmol) yielded N-(2,3-difluorophenyl)-2-(2-((7-(3-(4-(hydroxymethyl)piperidin-1-yl)propoxy)-6-methoxyquinazolin-4-yl) amino)-1,3-thiazol-5-yl)acetamide (1.30 g, 56% yield):

$^1$H-NMR (DMSO d$_6$): 12.00 (s, 1H), 10.25 (s, 1H), 8.70 (s, 1H), 8.15 (s, 1H), 7.65-7.75 (m, 1H), 7.35 (s, 1H), 7.25 (s, 1H), 7.00-7.10 (m, 2H), 4.40 (br s, 1H), 4.10-4.20 (m, 2H), 3.98 (s, 3H), 3.96 (s, 2H), 3.33 (m, 6H), 1.80-2.00 (m, 2H), 1.60-1.70 (m, 2H), 1.40-1.50 (m, 1H), 1.10-1.20 (m, 2H):

MS (+ve ESI): 599.6 (M+H)$^+$
MS (−ve ESI): 597.6 (M−H)$^−$.

b) An analogous reaction to that described in example 32d, but starting with N-(2,3-difluorophenyl)-2-(2-((7-(3-(4-(hydroxymethyl)piperidin-1-yl)propoxy)-6-methoxyquinazolin-4-yl)amino)-1,3-thiazol-5-yl)acetamide (1.34 g, 2.25 mmol) yielded di(tert-butyl) 1-(3-((4-((5-(2-((2,3-difluorophenyl)amino)-2-oxoethyl)-1,3-thiazol-2-yl)amino)-6-methoxyquinazolin-7-yl)oxy)propyl)piperidin-4-ylmethyl phosphate (983 mg, 55% yield):

$^1$H-NMR (DMSO d$_6$): 11.80 (s, 1H), 10.20 (s, 1H), 8.65 (s, 1H), 8.10 (s, 1H), 7.67 (m, 1H), 7.45 (s, 1H), 7.25 (s, 1H), 7.18 (m, 2H), 4.20 (t, 2H), 3.98 (s, 3H), 3.96 (s, 2H), 3.75 (m, 1H), 2.80-2.90 (m, 1H), 2.40-2.50 (m, 4H), 1.90-2.00 (m, 4H), 1.60-1.70 (m, 2H), 1.56 (m, 1H), 1.40 (s, 18H), 1.10-1.20 (m, 2H):

MS (+ve ESI): 791 (M+H)$^+$.

EXAMPLE 38

Preparation of Compound 38 in Table 1—2-(4-(3-((4-((5-(2-((2,3-difluorophenyl)amino)-2-oxoethyl)-1,3-thiazol-2-yl)amino)-6-methoxyquinazolin-7-yl) oxy)propyl)piperazin-1-yl)ethyl dihydrogen phosphate An analogous reaction to that described in example 32, but starting with di(tert-butyl) 2-(4-(3-((4-((5-(2-((2,3-difluorophenyl)amino)-2-oxoethyl)-1,3-thiazol-2-yl)amino)-6-methoxy-quinazolin-7-yl)oxy)propyl)piperazin-1-yl)ethyl phosphate (866 mg, 1.08 mmol) yielded the title compound (898 mg, quantitative yield):

$^1$H-NMR (DMSO d$_6$): 10.50 (s, 1H), 9.00 (s, 1H), 7.90 (s, 1H), 7.78 (m, 1H), 7.60 (s, 1H), 7.45 (s, 1H), 7.10-7.25 (m, 2H), 4.30-4.40 (m, 4H), 4.10 (s, 2H), 4.00 (s, 3H), 3.50-3.90 (m, 8H), 3.42 (m, 2H), 3.30 (m, 2H), 2.30-2.40 (m, 2H):

$^{31}$P-NMR ($^1$H) (DMSO d$_6$): 0.46 (s, 1P):
MS (+ve ESI): 694 (M+H)$^+$.

di(tert-butyl) 2-(4-(3-((4-((5-(2-((2,3-difluorophenyl) amino)-2-oxoethyl)-1,3-thiazol-2-yl)amino)-6-methoxyquinazolin-7-yl)oxy)propyl)piperazin-1-yl)ethyl phosphate used as the starting material was obtained as follows:

a) An analogous reaction to that described in example 32c, but starting with N-(2-hydroxyethyl)piperazine (2.50 g, 19.2 mmol) yielded N-(2,3-difluorophenyl)-2-(2-((7-(3-(1-(4-(2-hydroxyethyl))piperazin-1-yl)propoxy)-6-methoxyquinazolin-4-yl)amino)-1,3-thiazol-5-yl)acetamide (1.08 g, 46% yield):

$^1$H-NMR (DMSO d$_6$): 12.02 (s, 1H), 10.30 (s, 1H), 8.70 (s, 1H), 8.01 (s, 1H), 7.60-7.70 (m, 1H), 7.40 (s, 1H), 7.20 (s, 1H), 7.13 (m, 2H), 4.40 (br s, 1H), 4.20 (t, 2H), 3.98 (s, 2H), 3.95 (s, 3H), 3.57 (m, 2H), 2.40-2.50 (m, 10H), 1.90-2.00 (m, 2H):

MS (+ve ESI): 614 (M+H)$^+$
MS (−ve ESI): 612 (M−H)$^−$.

b) An analogous reaction to that described in example 32d, but starting with N-(2,3-difluorophenyl)-2-(2-((7-(3-(1-(4-(2-hydroxyethyl))piperazin-1-yl)propoxy)-6-methoxyquinazolin-4-yl)amino)-1,3-thiazol-5-yl)acetamide (1.08 g, 1.76 mmol) yielded di(tert-butyl) 2-(4-3-((4-((5-(2-((2,3-difluorophenyl)amino)-2-oxoethyl)-1,3-thiazol-2-yl)amino)-6-methoxy-quinazolin-7-yl)oxy)propyl)piperazin-1-yl)ethyl phosphate (866 mg, 61% yield):

$^1$H-NMR (DMSO d$_6$): 12.01 (s, 1H), 10.30 (s, 1H), 8.70 (s, 1H), 8.20 (s, 1H), 7.60-7.70 (m, 1H), 7.40 (s, 1H), 7.20 (s, 1H), 7.14 (m, 2H), 4.20 (t, 2H), 3.98 (s, 2H), 3.90 (s, 3H), 3.82 (m, 2H), 2.66 (m, 2H), 2.30-2.40 (m, 8H), 1.90-2.00 (m, 2H), 1.40 (s, 18H):

MS (+ve ESI): 806 (M+H)$^+$.

EXAMPLE 39

Preparation of Compound 39 in Table 1—3-((3-((4-((5-(2-((2,3-difluorophenyl)amino)-2-oxoethyl)-1,3-thiazol-2-yl)amino)-6-methoxyquinazolin-7-yl)oxy)propyl)amino)-3-methylbutyl dihydrogen phosphate An analogous reaction to that described in example 32, but starting with di(tert-butyl) 3-((3-((4-((5-(2-((2,3-difluorophenyl)amino)-2-oxoethyl)-1,3-thiazol-2-yl)amino)-6-methoxyquinazolin-7-yl)oxy)propyl)amino)-3-methylbutyl phosphate (168 mg, 0.22 mmol) yielded the title compound (160 mg, quantitative yield):

$^1$H-NMR (DMSO d$_6$): 10.50 (s, 1H), 9.15 (br s, 2H), 9.02 (s, 1H), 7.90 (s, 1H), 7.60-7.70 (m, 1H), 7.60 (s, 1H), 7.40 (s, 1H), 7.10-7.20 (m, 2H), 4.40 (t, 2H), 4.10 (s, 2H), 4.01 (s, 3H), 3.92 (m, 2H), 3.00-3.10 (m, 2H), 2.30-2.50 (m, 2H), 2.00-2.10 (m, 2H), 1.45 (s, 6H):

MS (+ve ESI): 667 (M+H)$^+$.

di(tert-butyl) 3-((3-((4-((5-(2-((2,3-difluorophenyl)amino)-2-oxoethyl)-1,3-thiazol-2-yl)amino)-6-methoxyquinazolin-7-yl)oxy)propyl)amino)-3-methylbutyl phosphate used as the starting material was obtained as follows:

a) An analogous reaction to that described in example 32c but starting with 3-amino-3-methyl-1-butanol (1.98 g, 19.3 mmol) yielded N-(2,3-difluorophenyl)-2-(2-((7-(3-((1-hydroxy-3-methylbut-3-yl)amino)propoxy)-6-methoxyquinazolin-4-yl)amino)-1,3-thiazol-5-yl)acetamide (168 mg, 7% yield):

$^1$H-NMR (DMSO d$_6$): 10.40 (s, 1H), 8.70 (s, 1H), 8.10 (s, 1H), 7.60-7.70 (m, 1H), 7.35 (s, 1H), 7.10-7.20 (m, 2H), 4.20 (t, 2H), 3.98 (s, 3H), 3.95 (s, 2H), 3.50 (t, 2H), 2.60-2.70 (m, 2H), 1.90-2.00 (m, 2H), 1.50 (t, 2H), 1.01 (s, 6H):

MS (+ve ESI): 587(M+H)$^+$

MS (−ve ESI): 585 (M+H)$^-$.

b) An analogous reaction to that described in example 32d, but starting with N-(2,3-difluorophenyl)-2-(2-((7-(3-((1-hydroxy-3-methylbut-3-yl)amino)propoxy)-6-methoxyquinazolin-4-yl)amino)-1,3-thiazol-5-yl)acetamide (168 mg, 0.29 mmol) yielded di(tert-butyl) 3-((3-((4-((5-(2-((2,3-difluorophenyl)amino)-2-oxoethyl)-1,3-thiazol-2-yl)amino)-6-methoxyquinazolin-7-yl)oxy)propyl)amino)-3-methylbut-3-yl phosphate (168 mg, 75% yield):

MS (+ve ESI): 779 (M+H)$^+$.

EXAMPLE 40

Preparation of Compound 40 in Table 1—2-((3-((4-((5-(2-((2,3-difluorophenyl)amino)-2-oxoethyl)-1,3-thiazol-2-yl)amino)-6-methoxyquinazolin-7-yl)oxy)propyl)amino)-2-methylpropyl dihydrogen phosphate An analogous reaction to that described in example 32, but starting with di(tert-butyl) 2-((3-((4-((5-(2-((2,3-difluorophenyl)amino)-2-oxoethyl)-1,3-thiazol-2-yl)amino)-6-methoxyquinazolin-7-yl)oxy)propyl)amino)-2-methylpropyl phosphate (230 mg, 0.30 mmol) yielded the title compound (150 mg, 70% yield):

$^1$H-NMR (DMSO d$_6$): 10.50 (s, 1H), 9.15 (br s, 2H), 9.00 (s, 1H), 7.90 (s, 1H), 7.60-7.70 (m, 1H), 7.55 (s, 1H), 7.40 (s, 1H), 7.10-7.20 (m, 2H), 4.35 (t, 2H), 4.10 (s, 2H), 4.00 (s, 3H), 3.92 (m, 2H), 3.00-3.10 (m, 2H), 2.30-2.40 (m, 2H), 1.45 (s, 6H):

MS (+ve ESI): 653 (M+H)$^+$.

di(tert-butyl) 2-((3-((4-((5-(2-((2,3-difluorophenyl)amino)-2-oxoethyl)-1,3-thiazol-2-yl)amino)-6-methoxyquinazolin-7-yl)oxy)propyl)amino)-2-methylpropyl phosphate used as the starting material was obtained as follows:

a) An analogous reaction to that described in example 32c, but starting with 2-amino-2-methyl-1-propanol (1.71 g, 19.3 mmol) yielded N-(2,3-difluorophenyl)-2-(2-((7-(3-((3-hydroxy-2-methylprop-2-yl)amino)propoxy)-6-methoxyquinazolin-4-yl)amino)-1,3-thiazol-5-yl)acetamide (478 mg, 23% yield):

$^1$H-NMR (DMSO d$_6$): 10.20 (s, 1H), 8.70 (s, 1H), 8.20 (s, 1H), 7.70-7.80 (m, 1H), 7.40 (s, 1H), 7.35 (s, 1H), 7.17 (m, 2H), 4.40 (br s, 1H), 4.20 (t, 2H), 3.98 (s, 2H), 3.95 (s, 3H), 3.20 (s, 2H), 2.70 (t, 2H), 1.90-2.00 (m, 2H), 1.01 (s, 6H):

MS (+ve ESI): 573 (M+H)$^+$

MS (−ve ESI): 571 (M+H)$^-$.

b) An analogous reaction to that described in example 32d, but starting with N-(2,3-difluorophenyl)-2-(2-((7-(3-((3-hydroxy-2-methylprop-2-yl)amino)propoxy)-6-methoxyquinazolin-4-yl)amino)-1,3-thiazol-5-yl)acetamide (430 mg, 0.75 mmol) yielded di(tert-butyl) 2-((3-((4-((5-(2-((2,3-difluorophenyl)amino)-2-oxoethyl)-1,3-thiazol-2-yl)amino)-6-methoxyquinazolin-7-yl)oxy)propyl)amino)-2-methylpropyl phosphate (230 mg, 40% yield):

MS (+ve ESI): 765 (M+H)$^+$.

EXAMPLE 41

Preparation of Compound 41 in Table 1—2-((3-((4-((5-(2-((2,3-difluorophenyl)amino)-2-oxoethyl)-1,3-thiazol-2-yl)amino)-6-methoxyquinazolin-7-yl)oxy)propyl)amino)ethyl dihydrogen phosphate An analogous reaction to that described in example 32, but starting with di(tert-butyl) 2-((3-((4-((5-(2-((2,3-difluorophenyl)amino)-2-oxoethyl)-1,3-thiazol-2-yl)amino)-6-methoxyquinazolin-7-yl)oxy)propyl)amino)ethyl phosphate (716 mg, 0.877 mmol) yielded the title compound (200 mg, 36% yield):

$^1$H-NMR (DMSO d$_6$): 10.00 (br s, 1H), 8.60 (s, 1H), 8.09 (s, 1H), 7.65 (m, 1H), 7.30 (s, 1H), 7.27 (s, 1H), 7.13 (m, 2H), 4.25 (m, 2H), 3.95 (m, 7H), 3.00 (m, 4H), 2.10 (m, 2H):

MS (+ve ESI): 625 (M−H)$^+$

MS (−ve ESI): 623 (M−H)$^-$.

di(tert-butyl) 2-((3-((4-((5-(2-((2,3-difluorophenyl)amino)-2-oxoethyl)-1,3-thiazol-2-yl)amino)-6-methoxyquinazolin-7-yl)oxy)propyl)amino)ethyl phosphate used as the starting material was obtained as follows:

a) An analogous reaction to that described in example 32c, but starting with ethanolamine (403 mg, 6.60 mmol) yielded N-(2,3-difluorophenyl)-2-(2-((7-(3-((2-hydroxyethyl)amino)propoxy)-6-methoxyquinazolin-4-yl)amino)-1,3-thiazol-5-yl)acetamide (503 mg, 81% yield):

$^1$H-NMR (DMSO d$_6$): 10.31 (s, 1H), 8.89 (s, 1H), 8.55 (br s, 2H), 8.01 (br s, 1H), 7.70 (m, 1H), 7.50 (s, 1H), 7.31 (s, 1H), 7.18 (m, 2H), 4.26 (m, 2H), 4.02 (s, 2H), 3.96 (s, 3H), 3.67 (m, 2H), 3.15 (m, 2H), 3.08 (m, 2H), 2.20 (m, 2H):

MS (+ve ESI): 545 (M−H)$^+$

MS (−ve ESI): 543 (M−H)$^-$.

b) An analogous reaction to that described in example 32d, but starting with N-(2,3-difluorophenyl)-2-(2-((7-(3-((2-hydroxyethyl)amino)propoxy)-6-methoxyquinazolin-4-yl)amino)-1,3-thiazol-5-yl)acetamide (450 mg, 0.83 mmol) yielded di(tert-butyl) 2-((3-((4-((5-(2-((2,3-difluorophenyl)amino)-2-oxoethyl)-1,3-thiazol-2-yl)amino)-6- methoxyquinazolin-7-yl)oxy)propyl)amino)ethyl phosphate (716 mg) as an off-white solid which was used without further purification.

EXAMPLE 42

Preparation of Compound 42 in Table 1—((2R)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate An analogous reaction to that described in example 1, but starting with di(tert-butyl) ((2R)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl phosphate (448 mg, 0.577 mmol) yielded the title compound as the dihydrochloride salt (424 mg, 99% yield):

$^1$H-NMR (DMSO d$_6$): 10.45 (s, 1H), 9.10 (s, 1H), 8.00 (m, 2H), 7.70 (s, 1H), 7.35-7.45 (m, 1H), 7.05 (m, 1H), 4.15-4.40 (m, 1H), 4.10 (s, 2H), 4.00 (s, 3H), 3.80 (t, 1H), 3.50-3.70 (m, 2H), 3.20-3.40 (m, 2H), 2.35-2.50 (m, 2H), 2.25 (m, 2H), 1.97 (m, 2H), 1.85 (m, 1H);

MS (+ve ESI): 665(M+H)$^+$.

di(tert-butyl) ((2R)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl phosphate used as the starting material was obtained as follows:

a) An analogous reaction to that described in example 1p, but starting with (2-((N-triphenylmethyl)amino)-1,3-thiazol-5-yl)acetic acid (10.0 g, 25 mmol) and 2,5-difluoroaniline (0.73 ml, 7.56 mol) yielded N-(2,5-difluorophenyl)-2-(2-((N-triphenylmethyl)amino)-1,3-thiazol-5-yl)acetamide (1.25 g, 61% yield):

MS (+ve ESI): 352 (M+H)$^+$.

b) Trifluoroacetic acid (20 ml) was added to a solution of N-(2,5-difluorophenyl)-2-(2-((N-triphenylmethyl)amino)-1,3-thiazol-5-yl)acetamide (12.8 g, 25 mmol) in dichloromethane (200 ml) and the reaction allowed to stir for 16 hours at ambient temperature before solvent evaporation in vacuo. The crude product was washed with saturated aqueous sodium hydrogen carbonate solution and then purified by chromatography on silica gel, eluting with 5-20% methanol in dichloromethane to yield 2-(2-amino-1,3-thiazol-5-yl)-N-(2,5-difluorophenyl)acetamide (2.64 g, 39% yield) as a beige solid:

$^1$H-NMR (DMSO d$_6$): 7.82 (m, 1H), 7.28 (m, 1H), 6.93 (m, 1H), 6.70 (m, 3H), 3.74 (s, 2H), 2.25 (m, 2H):

MS (+ve ESI): 270 (M+H)$^+$
MS (-ve ESI): 268 (M-H)$^-$.

c) A mixture of 2-(2-amino-1,3-thiazol-5-yl)-N-(2,5-difluorophenyl)acetamide (2.64 g, 9.8 mmol) and 1-(5-(3-chloropropoxy)-2-cyano-4-methoxyphenyl)-N,N-dimethylimidoformamide (2.90 g, 9.8 mmol) was heated in acetic acid (15 ml) at 145° C. for 5 hours. The reaction mixture was cooled to ambient temperature, methanol (2 ml) and diethyl ether (30 ml) were added and the yellow solid was collected by suction filtration. The crude product was washed with i) acetic acid, ii) acetonitrile and iii) diethyl ether and then taken up in dimethylacetamide (15 ml). Saturated aqueous sodium hydrogen carbonate solution (200 ml) was added and the reaction stirred for 30 minutes at ambient temperature before a solid was collected by suction filtration. Drying in vacuo yielded N-(2,5-difluorophenyl)-2-(2-(7-(3-chloropropoxy)-6-methoxyquinazolin-4-yl-amino-1,3-thiazol-5-yl)acetamide (3.23 g, 63% yield) as a pale yellow solid:

$^1$H-NMR DMSO d$_6$): 10.15 (br s, 1H), 8.58 (s, 1H), 8.01 (s, 1H), 7.89 (m, 1H), 7.36 (m, 2H), 7.19 (s, 1H), 6.95 (m, 1H), 4.25 (t, 2H), 3.95 (m, 5H), 3.80 (t, 2H), 2.25 (m, 2H);

MS (+ve ESI): 520 (M+H)$^+$
MS (-ve ESI): 518 (M-H)$^-$.

d) An analogous reaction to that described in example 1h, but starting with N-(2,5-difluorophenyl)-2-(2-(7-(3-chloropropoxy)-6-methoxyquinazolin-4-yl-amino-1,3-thiazol-5-yl)acetamide (1.00 g, 1.93 mmol) and D-prolinol (0.95 ml, 9.60 mmol) yielded N-(2,5-difluorophenyl)-2-(2-((7-(3-(((2R)-2-(hydroxymethyl)pyrrolidin-1-yl)propoxy)-6-methoxyquinazolin-4-yl)amino)-1,3-thiazol-5-yl)acetamide (745 mg, 63% yield) as a pale yellow solid after drying in vacuo:

$^1$H-NMR (DMSO d$_6$): 10.32 (s, 1H), 9.23 (br s, 1H), 8.94 (s, 1H), 8.00 (s, 1H), 7.91 (m, 1H), 7.58 (s, 1H), 7.31-7.40 (m, 2H), 7.04 (m, 1H), 4.29 (m, 2H), 4.04 (s, 2H), 3.96 (s, 3H), 3.60 (m, 3H), 3.22 (m, 2H), 2.29 (m, 2H), 2.00-2.18 (m, 2H), 1.92 (m, 1H), 1.79 (m, 1H):

MS (+ve ESI): 585 (M+H)$^+$
MS (-ve ESI): 583 (M-H)$^-$.

e) An analogous reaction to that described in example 1i, but starting with N-(2,5-difluorophenyl)-2-(2-((7-(3-(((2R)-2-(hydroxymethyl)pyrrolidin-1-yl)propoxy)-6-methoxyquinazolin-4-yl)amino)-1,3-thiazol-5-yl)acetamide (704 mg, 1.20 mmol) yielded di(tert-butyl) ((2R)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl phosphate (448 mg, 48% yield):

$^1$H-NMR (DMSO d$_6$): 8.62 (s, 1H), 8.10 (m, 1H), 7.89 (m, 1H), 7.20-7.38 (m, 3H), 6.96 (m, 1H), 4.20 (m, 2H), 4.10 (s, 2H), 3.97 (s, 2H), 3.93 (s, 3H), 3.74 (m, 1H), 3.55 (m, 1H), 3.06 (m, 1H), 2.93 (m, 1H), 2.65 (m, 1H), 2.20 (m, 1H), 1.80-1.96 (m, 3H), 1.52-1.70 (m, 3H), 1.36 (s, 18H):

MS (+ve ESI): 777.5 (M+H)$^+$.

EXAMPLE 43

Preparation of Compound 43 in Table 1—((2S)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate An analogous reaction to that described in example 1, but starting with di(tert-butyl) ((2S)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl phosphate (500 mg, 0.644 mmol) yielded the title compound as the dihydrochloride salt (459 mg, 99% yield):

$^1$H-NMR (DMSO d$_6$): 10.45 (s, 1H), 9.10 (s, 1H), 8.0 (m, 2H), 7.70 (s, 1H), 7.35-7.45 (m, 1H), 7.05 (m, 1H), 4.15-4.40 (m, 1H), 4.10 (s, 2H), 4.00 (s, 3H), 3.80 (t, 1H), 3.50-3.70 (m, 2H), 3.20-3.40 (m, 2H), 2.35-2.50 (m, 2H), 2.25 (m, 2H), 1.97 (m, 2H), 1.85 (m, 1H);

MS (+ve ESI): 665(M+H)$^+$.

di(tert-butyl) ((2S)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl phosphate used as the starting material was obtained as follows:

a) An analogous reaction to that described in example 42d, but starting with L-prolinol (0.95 ml, 9.60 mmol) yielded N-(2,5-difluorophenyl)-2-(2-((7-(3-(((2S)-2-(hydroxymethyl)pyrrolidin-1-yl)propoxy)-6-methoxyquinazolin-4-yl)amino)-1,3-thiazol-5-yl)acetamide (612 mg, 52% yield) as a pale yellow solid after drying in vacuo:

¹H-NMR (DMSO d₆): 10.07 (s, 1H), 8.95 (br s, 1H), 8.70 (s, 1H), 7.81 (s, 1H), 7.70 (m, 1H), 7.34 (s, 1H), 7.05-7.25 (m, 2H), 6.81 (m, 1H), 4.08 (m, 2H), 3.80 (s, 2H), 3.72 (s, 3H), 3.50 (m, 3H), 2.99 (m, 2H), 2.04 (m, 2H), 1.80-1.98 (m, 2H), 1.65 (m, 1H), 1.55 (m, 1H):

MS (+ve ESI): 585 (M+H)⁺

MS (−ve ESI): 583 (M−H)⁻.

b) An analogous reaction to that described in example 42e, but starting with N-(2,5-difluorophenyl)-2-(2-((7-(3-((2S)-2-(hydroxymethyl)pyrrolidin-1-yl)propoxy)-6-methoxyquinazolin-4-yl)amino)-1,3-thiazol-5-yl)acetamide (571 mg, 0.98 mmol) yielded di(tert-butyl) ((2S)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl phosphate (500 mg, 66% yield):

¹H-NMR (DMSO d₆): 8.62 (s, 1H), 8.09 (m, 1H), 7.90 (m, 1H), 7.37 (s, 1H), 7.32 (m, 1H), 7.21 (s, 1H), 6.96 (m, 1H), 4.20 (m, 2H), 4.10 (s, 2H), 3.98 (s, 2H), 3.93 (s, 3H), 3,74 (m, 1H), 3.55 (m, 1H), 3.06 (m, 1H), 2.93 (m, 1H), 2.65 (m, 1H), 2.20 (m, 1H), 1.80-1.96 (m, 3H), 1.52-1.70 (m, 3H), 1.36 (s, 18H):

MS (+ve ESI): 777.5 (M+H)⁺.

EXAMPLE 44

Preparation of Compound 44 in Table 1—2-((3-((4-((5-(2-((2,5-difluorophenyl)amino)-2-oxoethyl)-1,3-thiazol-2-yl)amino)-6-methoxyquinazolin-7-yl)oxy)propyl)(ethyl)amino)ethyl dihydrogen phosphate An analogous reaction to that described in example 1, but starting with di(tert-butyl) 2-((3-((4-((5-(2-((2,5-difluorophenyl)amino)-2-oxoethyl)-1,3-thiazol-2-yl)amino)-6-methoxyquinazolin-7-yl)oxy)propyl)(ethyl)amino)ethyl phosphate (233 mg, 0.305 mmol) yielded the title compound as the dihydrochloride salt (222 mg, 99% yield):

¹H-NMR (DMSO d₆): 10.50 (s, 1H), 9.05 (s, 1H), 7.96 (m, 2H), 7.70 (s, 1H), 7.60 (s, 1H), 7.40-7.50 (m, 1H), 6.90-7.10 (m, 1H), 4.30-4.40 (m, 4H), 4.10 (s, 2H), 4.02 (s, 3H), 3.40-3.50 (m, 2H), 3.20-3.30 (m, 4H), 2.30-2.40 (m, 2H), 1.30 (t, 3H):

MS (+ve ESI): 653 (M+H)⁺.

di(tert-butyl) 2-((3-((4-((5-(2-((2,5-difluorophenyl)amino)-2-oxoethyl)-1,3-thiazol-2-yl)amino)-6-methoxyquinazolin-7-yl)oxy)propyl)(ethyl)amino)ethyl phosphate used as the starting material was obtained as follows:

a) An analogous reaction to that described in example 42d, but starting with N-ethylethanolamine (0.66 ml, 6.75 mmol) yielded N-(2,5-difluorophenyl)-2-(2-((7-(3-(ethyl(2-hydroxyethyl)amino)propoxy)-6-methoxyquinazolin-4-yl)amino)-1,3-thiazol-5-yl)acetamide (312 mg, 40% yield) as a pale yellow solid after drying in vacuo:

¹H-NMR (DMSO d₆): 10.15 (s, 1H), 8.60 (s, 1H), 8.00 (s, 1H), 7.80-7.90 (m, 1H), 7.25-7.40 (m, 1H), 7.20 (s, 1H), 6.90-7.00 (m, 1H), 4.25 (br s, 1H), 4.20 (t, 2H), 3.98 (s, 2H), 3.95 (s, 3H), 3.42 (m, 2H), 2.57 (m, 2H), 2.40-2.50 (m, 4H), 1.80-1.95 (m, 2H), 1.30 (t, 3H):

MS (+ve ESI): 573 (M+H)⁺

MS (−ve ESI): 571 (M−H)⁻.

b) An analogous reaction to that described in example 42e, but starting with N-(2,5-difluorophenyl)-2-(2-((7-(3-(ethyl(2-hydroxyethyl)amino)propoxy)-6-methoxyquinazolin-4-yl)amino)-1,3-thiazol-5-yl)acetamide (294 mg, 0.51 mmol) yielded di(tert-butyl) 2-((3-((4-((5-(2-((2,5-difluorophenyl)amino)-2-oxoethyl)-1,3-thiazol-2-yl)amino)-6-methoxyquinazolin-7-yl)oxy)propyl)(ethyl)amino)ethyl phosphate (233 mg, 60% yield):

¹H-NMR (DMSO d₆): 12.00 (s, 1H), 10.30 (s, 1H), 8.70 (s, 1H), 8.20 (s, 1H), 7.80-7.90 (m, 1H), 7.40 (s, 1H), 7.33 (m, 1H), 7.20 (s, 1H), 6.95 (m, 1H), 4.20 (t, 2H), 3.90 (s, 2H), 3.80 (s, 3H), 3.75 (m, 2H), 2.68 (m, 4H), 2.50-2.60 (m, 2H), 1.88 (m, 2H), 1.40 (s, 18H), 1.30 (t, 3H):

MS (+ve ESI): 765 (M+H)⁺.

EXAMPLE 45

Preparation of Compound 45 in Table 1—((2S)-1-(3-((4-((5-(2-((2,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate An analogous reaction to that described in example 1, but starting with di(tert-butyl) ((2S)-1-(3-((4-((5-(2-((2,4-difluorophenyl)amino)-2-oxoethyl)-1,3-thiazol-2-yl)amino)-6-methoxyquinazolin-7-yl)oxy)propyl)pyrrolidin-2-yl)methyl phosphate (261 mg, 0.336 mmol) yielded the title compound (218 mg, 88% yield):

¹H-NMR (DMSO d₆): 10.15 (br s, 1H), 9.00 (s, 1H), 7.90 (s, 1H), 7.70-7.80 (m, 1H), 7.60 (s, 1H), 7.40 (s, 1H), 7.20-7.30 (m, 1H), 7.12 (m, 1H), 4.30-4.40 (m, 2H), 4.15-4.25 (m, 2H), 4.10 (s, 2H), 3.95 (s, 3H), 3.50-3.90 (m, 3H), 3.10-3.40 (m, 2H), 1.80-2.40 (m, 8H):

MS (+ve ESI): 665 (M+H)⁺.

di(tert-butyl) ((2S)-1-(3-((4-((5-(2-((2,4-difluorophenyl)amino)-2-oxoethyl)-1,3-thiazol-2-yl)amino)-6-methoxyquinazolin-7-yl)oxy)propyl)pyrrolidin-2-yl)methyl phosphate used as the starting material was obtained as follows:

a) A solution of sodium hydroxide (30 g, 760 mmol) in water (60 ml) was added to a solution of methyl (2-amino-1,3-thiazol-5-yl)acetate hydrobromide (see example 11)) (64 g, 250 mmol) in methanol (600 ml) and the reaction was stirred at ambient temperature for 3 hours. The methanol was removed in vacuo and the residue acidified to pH 3.5 by addition of 1.0 N hydrochloric acid. The orange solid was collected by suction filtration, washed with water and dried in vacuo to yield (2-amino-1,3-thiazol-5-yl)acetic acid (48.4 g, quantitative yield) as a pale orange solid:

¹H-NMR (DMSO d₆): 6.72 (br s, 2H), 6.69 (s, 1H), 3.54 (s, 2H):

MS (+ve ESI): 159 (M+H)⁺.

b) A solution of N'-(5-(3-chloropropoxy)-2-cyano-4-methoxyphenyl)-N,N-dimethylimidoformamide (22.6 g, 76.7 mmol) and (2-amino-1,3-thiazol-5-yl)acetic acid (12.1 g, 76.7 mmol) in acetic acid (230 ml) was heated at reflux for 5 hours. The reaction was cooled to ambient temperature, the solid was collected by suction filtration and then taken up in water (250 ml) and heated at 100° C. for 20 minutes. The reaction was cooled, the solid was filtered off and washed with water. Drying in vacuo yielded 2-(2-(7-(3-chloropropoxy)-6-methoxyquinazolin-4-yl-amino-1,3-thiazol-5-yl)acetic acid (24.7 g, 79% yield) as a cream solid:

¹H-NMR (DMSO d₆): 8.65 (s, 1H), 8.08 (s, 1H), 7.33 (s, 1H), 7.27 (s, 1H), 4.37 (t, 2H), 3.95 (s, 3H), 3.80 (m, 4H), 2.25 (m, 2H):

MS (+ve ESI): 409 (M+H)⁺.

c) 2,4-Difluoroaniline (2.99 ml, 29.4 mmol) and 4-(4,6-dimethoxy-1,3,5-triazin-2-yl)-4-methylmorpholinium chloride (7.46 g, 27.0 mmol) were added to a stirred solution of 2-(2-(7-(3-chloropropoxy)-6-methoxyquinazolin- 4-yl-amino-1,3-thiazol-5-yl)acetic acid (10.0 g, 24.5 mmol) in dimethylacetamide (150 ml) and the reaction stirred for 45 hours at ambient temperature under an inert atmosphere. The reaction was filtered and the filtrate diluted with saturated aqueous sodium hydrogen carbonate solution (300 ml). The product was collected by suction filtration and washed with i) water, ii) acetonitrile and iii) ethyl acetate/hexane to give a beige solid. This was stirred in water (500 ml) at 80° C. for 10 minutes, cooled to ambient temperature and the solid filtered off. Drying in vacuo yielded N-(2,4-difluorophenyl)-2-(2-(7-(3-chloropropoxy)-6-methoxyquinazolin-4-yl-amino-1,3-thiazol-5-yl)acetamide (6.34 g, 50% yield) as an off-white solid:
$^1$H-NMR (DMSO d$_6$): 9.80 (s, 1H), 8.20 (s, 1H), 7.70-7.80 (m, 1H), 7.60 (s, 1H), 7.20-7.30 (m, 1H), 7.00-7.10 (m, 2H), 6.90 (s, 1H), 4.00 (t, 2H), 3.80 (s, 3H), 3.70 (t, 2H), 3.60 (s, 2H), 2.10-2.20 (m, 2H):
MS (+ve ESI): 520/522 (M+H)$^+$
MS (−ve ESI): 518/520 (M−H)$^-$.

d) An analogous reaction to that described in example 1h, but starting with (S)-(+)-2-pyrrolidinylmethanol (1.46 g, 14.5 mmol) and N-(2,4-difluorophenyl)-2-(2-(7-(3-chloropropoxy)-6-methoxyquinazolin-4-yl-amino-1,3-thiazol-5-yl)acetamide (1.49 g, 2.87 mmol) yielded N-(2,4-difluorophenyl)-2-(2-((7-(3-((2S)-2-(hydroxymethyl)pyrrolidin-1-yl)propoxy-6-methoxyquinazolin-4-yl)amino)-1,3-thiazol-5-yl)acetamide (670 mg, 40% yield):
$^1$H-NMR (DMSO d$_6$): 12.00 (s, 1H), 10.00 (s, 1H), 8.70 (s, 1H), 8.10 (s, 1H), 7.80-7.90 (m, 1H), 7.40 (s, 1H), 7.32 (m, 1H), 7.25 (s, 1H), 7.00-7.10 (m, 1H), 4.40 (br s, 1H), 4.17 (m, 2H), 4.00 (s, 3H), 3.98 (s, 2H), 3.30-3.40 (m, 1H), 3.18 (m, 1H), 3.06 (m, 1H), 2.90-3.00 (m, 1H), 2.40-2.50 (m, 2H), 2.19 (m, 1H), 1.90-2.00 (m, 2H), 1.70-1.80 (m, 1H), 1.50-1.60 (m, 2H), 1.35-1.45 (m, 1H):
MS (+ve ESI): 585 (M+H)$^+$
MS (−ve ESI): 583 (M−H)$^-$.

e) An analogous reaction to that described in example 1i, but starting with N-(2,4-difluorophenyl)-2-(2-((7-(3-((2S)-2-(hydroxymethyl)pyrrolidin-1-yl)propoxy-6-methoxyquinazolin-4-yl)amino)-1,3-thiazol-5-yl)acetamide (614 mg, 1.05 mmol) yielded di(tert-butyl) ((2S)-1-(3-((4-((5-(2-((2,4-difluorophenyl)amino)-2-oxoethyl)-1,3-thiazol-2-yl)amino)-6-methoxyquinazolin-7-yl)oxy)propyl)pyrrolidin-2-yl)methyl phosphate (280 mg, 34% yield):
$^1$H-NMR (DMSO d$_6$): 12.00 (s, 1H), 10.00 (s, 1H), 8.65 (s, 1H), 8.20 (s, 1H), 7.80-7.90 (m, 1H), 7.40 (s, 1H), 7.35 (m, 1H), 7.25 (s, 1H), 7.00-7.10 (m, 1H), 4.15 (m, 2H), 4.00 (s, 3H), 3.98 (s, 2H), 3.70-3.80 (m, 1H), 3.50-3.60 (m, 2H), 3.17 (m, 1H), 3.08 (m, 1H), 2.90-3.00 (m, 1H), 2.60-2.70 (m, 1H), 2.17 (m, 1H), 1.80-2.00 (m, 2H), 1.50-1.60 (m, 3H), 1.30 (s, 18H):
MS (+ve ESI): 777.7 (M+H)$^+$.

EXAMPLE 46

Preparation of Compound 46 in Table 1—2-(1-(3-((4-((5-(2-((2,4-difluorophenyl)amino)-2-oxoethyl)-1,3-thiazol-2-yl)amino)-6-methoxyquinazolin-7-yl)oxy)propyl)piperidin-2-yl)ethyl dihydrogen phosphate An analogous reaction to that described in example 1, but starting with di(tert-butyl) 2-(1-(3-((4-((5-(2-((2,4-difluorophenyl)amino)-2-oxoethyl)-1,3-thiazol-2-yl)amino)-6-methoxyquinazolin-7-yl)oxy)propyl)piperidin-2-yl)ethyl phosphate (181 mg, 0.225 mmol) yielded the title compound (134 mg, 78% yield):

$^1$H-NMR (DMSO d$_6$): 10.45 (s, 1H), 10.20 (s, 1H), 9.00 (s, 1H), 7.90 (s, 1H), 7.82 (m, 1H), 7.60 (s, 1H), 7.40 (s, 1H), 7.45 (m, 1H), 7.00-7.10 (m, 1H), 4.32 (m, 2H), 4.00 (s, 2H), 3.95 (s, 3H), 3.80-3.90 (m, 2H), 3.55-3.65 (m, 1H), 3.10-3.50 (m, 6H), 2.30-2.40 (m, 2H), 1.50-2.10 (m, 6H):
MS (+ve ESI): 693 (M+H)$^+$.

di(tert-butyl) 2-(1-(3-((4-((5-(2-((2,4-difluorophenyl)amino)-2-oxoethyl)-1,3-thiazol-2-yl)amino)-6-methoxyquinazolin-7-yl)oxy)propyl)piperidin-2-yl)ethyl phosphate used as the starting material was obtained as follows:

a) An analogous reaction to that described in example 45d, but starting with 2-piperidinylethanol (1.86 g, 14.4 mmol) and N-(2,4-difluorophenyl)-2-(2-(7-(3-chloropropoxy)-6-methoxyquinazolin-4-yl-amino-1,3-thiazol-5-yl)acetamide (1.50 g, 2.89 mmol yielded N-(2,4-difluorophenyl)-2-(2-((7-(3-(2-(2-hydroxyethyl)piperidin-1-yl)propoxy)-6-methoxyquinazolin-4-yl)amino)-1,3-thiazol-5-yl) acetamide (314 mg, 18% yield):
$^1$H-NMR (DMSO d$_6$): 12.00 (s, 1H), 10.10 (s, 1H), 8.70 (s, 1H), 8.10 (s, 1H), 7.88 (m, 1H), 7.40 (s,1H), 7.33 (m, 1H), 7.25 (s, 1H), 7.00-7.10 (m, 1H), 4.20 (t, 2H), 3.98 (s, 3H), 3.96 (s, 2H), 3.40-3.50 (m, 2H), 2.70-2.80 (m, 2H), 2.40-2.50 (m, 2H), 2.25 (m, 1H), 1.90-2.00 (m, 2H), 1.70-1.80 (m, 1H), 1.30-1.60 (m, 5H), 1.20-1.30 (m, 2H):
MS (+ve ESI): 613 (M+H)$^+$
MS (−ve ESI): 611 (M−H)$^-$.

b) An analogous reaction to that described in example 1i, but starting with N-(2,4-difluorophenyl)-2-(2-((7-(3-(2-(2-hydroxyethyl)piperidin-1-yl)propoxy)-6-methoxyquinazolin-4-yl)amino)-1,3-thiazol-5-yl)acetamide (279 mg, 0.46 mmol) yielded di(tert-butyl) 2-(1-(3-((4-((5-(2-((2,4-difluorophenyl)amino)-2-oxoethyl)-1,3-thiazol-2-yl)amino)-6-methoxyquinazolin-7-yl)oxy)propyl)piperidin-2-yl)ethyl phosphate (181 mg, 49% yield):
$^1$H-NMR (DMSO d$_6$): 12.00 (s, 1H), 10.00 (s, 1H), 8.65 (s, 1H), 8.20 (s, 1H), 7.80-7.90 (m, 1H), 7.40 (s, 1H), 7.33 (m, 1H), 7.25 (s, 1H), 7.00-7.10 (m, 1H), 4.18 (m, 2H), 4.00 (s, 3H), 3.98 (s, 2H), 3.80-3.90 (m, 2H), 2.80-2.90 (m, 2H), 2.52 (m, 2H), 2.23 (m, 1H), 1.90-2.00 (m, 3H), 1.50-1.70 (m, 5H), 1.40 (s, 18H), 1.32 (m, 2H):
MS (+ve ESI): 805 (M+H)$^+$.

EXAMPLE 47

Preparation of Compound 47 in Table 1—2-{cyclopropyl[3-({4-[(5-{2-[(3-fluorophenyl)amino]-2-oxoethyl}-1,3-thiazol-2-yl)amino]-6-methoxyquinazolin-7-yl}oxy)propyl]amino}ethyl dihydrogen phosphate An analogous reaction to that described in example 1 but starting with di-tert-butyl 2-{cyclopropyl[3-({4-[(5-{2-[(3-fluorophenyl)amino]-2-oxoethyl}-1,3-thiazol-2-yl)amino]-6-methoxyquinazolin-7-yl}oxy)propyl]amino}ethyl phosphate (634 mg, 0.83 mmol) yielded the title compound (595 mg, 97% yield):
$^1$H-NMR (DMSO d$_6$, TFA): 9.08 (s, 1H), 7.90 (s, 1H), 7.64 (s, 1H), 7.63 (m, 1H), 7.36 (m, 2H), 7.35 (s, 1H), 6.91 (m, 1H), 4.31 (m, 4H), 4.01 (s, 2H), 3.99 (s, 3H), 3.61 (m, 2H), 3.49 (m, 2H), 2.99 (m, 1H), 2.38 (m, 2H), 1.10 (m, 2H), 0.94 (m, 2H):
MS (+ve ESI): 647 (M+H)$^+$.

di-tert-butyl 2-{cyclopropyl[3-({4-[(5-{2-[(3-fluorophenyl)amino]-2-oxoethyl}-1,3-thiazol-2-yl)amino]-6-methoxyquinazolin-7-yl}oxy)propyl]amino}ethyl phosphate, used as the starting material was obtained as follows:

a) An analogous reaction to that described in example 1h, but starting with cyclopropylamine (758 mg, 7.50 mmol) yielded 2-{2-[(7-{3-[cyclopropyl(2-hydroxyethyl)amino]propoxy}-6-methoxyquinazolin-4-yl)amino]-1,3-thiazol-5-yl}-N-(3-fluorophenyl)acetamide (1.10 g, 77% yield) as a pale yellow solid after drying in vacuo:
$^1$H-NMR (DMSO d$_6$): 8.67 (s, 1H), 8.12 (s, 1H), 7.61 (d, 1H), 7.35 (m, 3H), 7.24 (s, 1H), 6.90 (m, 1H), 4.30 (t, 1H), 3.16 (t, 2H), 3.96 (s, 3H), 3.89 (s, 2H), 4.50 (m, 2H), 2.76 (t, 2H), 2.65 (t, 2H), 1.95 (m, 2H), 1.82 (m, 1H), 0.42 (m, 2H), 0.30 (m, 2H):
MS (+ve ESI): 567 (M+H)$^+$.

b) An analogous reaction to that described in example 1i, but starting with 2-{2-[(7-{3-[cyclopropyl(2-hydroxyethyl)amino]propoxy}-6-methoxyquinazolin-4-yl)amino]-1,3-thiazol-5-yl}-N-(3-fluorophenyl)acetamide (793 mg, 1.40 mmol) yielded di-tert-butyl 2-{cyclopropyl[3-({4-[(5-{2-[(3-fluorophenyl)amino]-2-oxoethyl}-1,3-thiazol-2yl)amino]-6-methoxyquinazolin-7-yl}oxy)propyl]amino}ethyl phosphate (630 mg, 59% yield):
$^1$H-NMR (DMSO d$_6$, TFA): 9.09 (s, 1H), 7.91 (s, 1H), 7.65 (s, 1H), 7.63 (m, 1H), 7.36 (m, 2H), 7.32 (s, 1H), 6.91 (m, 1H), 4.31 (m, 4H), 4.00 (s, 2H), 3.99 (s, 3H), 3.64 (m, 2H), 3.51 (m, 2H), 2.99 (m, 1H), 2.36 (m, 2H), 1.45 (s, 18H), 1.04 (m, 2H), 0.96 (m, 2H):
MS (+ve ESI): 759.7 (M+H)$^+$.

EXAMPLE 48

Preparation of Compound 48 in Table 1—2-{cyclopropyl[3-({4-[(5-{2-[(2,3-difluorophenyl)amino]-2-oxoethyl}-1,3-thiazol-2-yl)amino]-6-methoxyquinazolin-7-yl}oxy)propyl]amino}ethyl dihydrogen phosphate An analogous reaction to that described in example 1 but starting with di-tert-butyl 2-{cyclopropyl[3-({4-[(5-{2-[(2,3-difluorophenyl)amino]-2-oxoethyl}-1,3-thiazol-2-yl)amino]-6-methoxyquinazolin-7-yl}oxy)propyl]amino}ethyl phosphate (605 mg, 0.78 mmol) yielded the title compound (570 mg, 97% yield):
$^1$H-NMR (DMSO d$_6$, TFA): 9.08 (s, 1H), 7.91 (s, 1H), 7.71 (m, 1H), 7.64 (s, 1H), 7.36 (s, 1H), 7.20 (m, 2H), 4.32 (m, 4H), 4.09 (s, 2H), 4.00 (s, 3H), 3.62 (m, 2H), 3.51 (m, 2H), 3.00 (m, 1H), 2.39 (m, 2H), 1.11 (m, 2H), 0.95 (m, 2H):
MS (+ve ESI): 665 (M+H)$^+$.

di-tert-butyl 2-{cyclopropyl[3-({4-[(5-{2-[(2,3-difluorophenyl)amino]-2-oxoethyl}-1,3-thiazol-2-yl)amino]-6-methoxyquinazolin-7-yl}oxy)propyl]amino}ethyl phosphate, used as the starting material was obtained as follows:

a) An analogous reaction to that described in example 1h, but starting with N-(2,3-difluorophenyl)-2-(2-(7-(3-chloropropoxy)-6-methoxyquinazolin-4-yl-amino-1,3-thiazol-5-yl)acetamide (1.25 g, 2.50 mmol) and cyclopropylamine (758 mg, 7.50 mmol) yielded 2-{2-[(7-{3-[cyclopropyl(2-hydroxyethyl)amino]propoxy}-6-methoxyquinazolin-4-yl)amino]-1,3-thiazol-5-yl}-N-(2,3-difluorophenyl)acetamide (1.10 g, 77% yield) as a pale yellow solid after drying in vacuo:
$^1$H-NMR (DMSO d$_6$, TFA): 9.08 (s, 1H), 7.91 (s, 1H), 7.71 (m, 1H), 7.65 (s, 1H), 7.31 (s, 1H), 7.20 (m, 2H), 4.31 (m, 2H), 4.09 (s, 2H), 3.99 (s, 3H), 3.85 (m, 1H), 3.81 (m, 1H), 3.44 (m, 4H), 2.96 (m, 1H), 2.37 (m, 2H), 1.04 (m, 2H), 0.92 (m, 2H):
MS (+ve ESI): 585 (M+H)$^+$.

b) An analogous reaction to that described in example 1i, but starting with 2-{2-[(7-{3-[cyclopropyl(2-hydroxyethyl)amino]propoxy}-6-methoxyquinazolin-4-yl)amino]-1,3-thiazol-5-yl}-N-(2,3-difluorophenyl)acetamide (670 mg, 1.15 mmol) yielded di-tert-butyl 2-{cyclopropyl[3-({4-[(5-{2-[(2,3-difluorophenyl)amino]-2-oxoethyl}-1,3-thiazol-2-yl)amino]-6-methoxyquinazolin-7-yl}oxy)propyl]amino}ethyl phosphate (605 mg, 66% yield):
$^1$H-NMR (DMSO d$_6$, TFA): 9.08 (s, 1H), 7.91 (s, 1H), 7.71 (m, 1H), 7.65 (s, 1H), 7.32 (s, 1H), 7.21 (m, 2H), 4.31 (m, 4H), 4.08 (s, 2H), 3.99 (s, 3H), 3.63 (m, 2H), 3.50 (m, 2H), 2.99 (m, 1H), 2.38 (m, 2H), 1.03 (m, 2H), 0.96 (m, 2H):
MS (+ve ESI): 777.6 (M+H)$^+$.

EXAMPLE 49

Preparation of Compound 49 in Table 2—(1-(2-((4-((5-(2-((2,3-difluorophenyl)amino)-2-oxoethyl)-1,3-thiazol-2-yl)amino)-6-methoxyquinazolin-7-yl)oxy)ethyl)piperidin-4-yl)methyl dihydrogen phosphate An analogous reaction to that described in example 1 but starting with di(tert-butyl) (1-(2-((4-((5-(2-((2,3-difluorophenyl)amino)-2-oxoethyl)-1,3-thiazol-2-yl)amino)-6-methoxyquinazolin-7-yl)oxy)ethyl)piperidin-4-yl)methyl phosphate (350 mg, 0.45 mmol) yielded the title compound (190 mg, 64% yield):
$^1$H-NMR (DMSO d$_6$, CD$_3$COOD): 8.69 (s, 1H), 8.14 (s, 1H), 7.72 (m, 1H), 7.37 (m, 2H), 7.18 (m, 2H), 4.55 (m, 2H), 3.99 (s, 2H), 3.97 (s, 3H), 3.65 (m, 2H), 3.50 (m, 4H), 2.98 (m, 2H), 1.80 (m, 3H), 1.56 (m, 2H):
MS (+ve ESI): 665 (M+H).$^+$ di(tert-butyl) (1-(2-((4-((5-(2-((2,3-difluorophenyl)amino)-2-oxoethyl)-1,3-thiazol-2-yl)amino)-6-methoxyquinazolin-7-yl)oxy)ethyl)piperidin-4-yl)methyl phosphate used as the starting material was obtained as follows:

a) A mixture of N'-(2-cyano-5-hydroxy-4-methoxyphenyl)-N,N-dimethylimidoformamide (see example 1e) (6.00 g, 18.1 mmol), caesium carbonate (26 g, 82.2 mmol) and 1-bromo-2-chloroethane (2.51 ml, 30.2 mmol) in acetonitrile (80 ml) was heated at reflux for 2 hours. The reaction mixture was cooled, the solvent was evaporated in vacuo and the residue taken up in water (200 ml). The aqueous phase was extracted with dichloromethane (2×150 ml), the organic solution was washed with brine (50 ml) and dried over magnesium sulphate. Solvent evaporated in vacuo, trituration with diethyl ether and drying in vacuo yielded N'-(5-(2-chloroethoxy)-2-cyano-4-methoxyphenyl)-N,N-dimethylimidoformamide (4.12 g, 81% yield) as a white solid:
MS (+ve ESI): 282 (M+H)$^+$
MS (−ve ESI): 280 (M−H)$^-$.

b) An analogous reaction to that described in example 42c, but starting with N-(2,3-difluorophenyl)-2-(2-((N-triphenylmethyl)amino)-1,3-thiazol-5-yl)acetamide (1.65 g, 3.23 mmol) and N'-(5-(2-chloroethoxy)-2-cyano-4-methoxyphenyl)-N,N-dimethylimidoformamide (1.00 g, 3.55 mmol), yielded N-(2,3-difluorophenyl)-2-(2-(7-(2-chloroethoxy)-6-methoxyquinazolin-4-yl-amino-1,3-thiazol-5-yl)acetamide (820 mg, 51% yield) as a pale yellow solid after drying in vacuo:
$^1$H-NMR DMSO d$_6$): 10.21 (s, 1H), 8.65 (s, 1H), 8.13 (s, 1H), 7.69 (m, 1H), 7.37 (s, 1H), 7.29 (s, 1H), 7.17 (m, 2H), 4.43 (t, 2H), 4.03 (t, 2H), 3.97 (s, 3H), 3.94 (s, 2H):
MS (+ve ESI): 505.9 (M+H)$^+$
MS (−ve ESI): 503.9 (M−H)$^-$.

c) An analogous reaction to that described in example 1h, but starting with N-(2,3-difluorophenyl)-2-(2-(7-(2-chloroethoxy)-6-methoxyquinazolin-4-yl-amino-1,3-thiazol-5-yl) acetamide (680 mg, 1.35 mmol) and 4-(hydroxymethyl) piperidine (622 mg, 5.40 mmol) yielded N-(2,3-difluorophenyl)-2-(2-((7-(3-(4-(hydroxymethyl)piperidin-1-yl)ethoxy)-6-methoxyquinazolin-4-yl) amino)-1,3-thiazol-5-yl)acetamide (565 mg, 72% yield) as a pale yellow solid after drying in vacuo:

$^1$H-NMR (DMSO d$_6$): 10.32 (s, 1H), 9.50 (m, 1H), 8.95 (s, 1H), 8.02 (m, 1H), 7.70 (m, 1H), 7.56 (s, 1H), 7.38 (s, 1H), 7.21 (m, 2H), 4.59 (t, 2H), 4.06 (s, 2H), 4.00 (s, 3H), 3.68 (m, 5H), 3.29 (d, 2H), 3.12 (m, 2H), 1.88 (m, 2H), 1.63 (m, 1H), 1.42 (m, 2H):

MS (+ve ESI): 585 (M+H)$^+$

MS (−ve ESI): 583 (M−H)$^−$.

d) An analogous reaction to that described in example 1i, but starting with N-(2,3-difluorophenyl)-2-(2-((7-(2-((2S)-2-(hydroxymethyl)pyrrolidin-1-yl)ethoxy)-6-methoxyquinazolin-4-yl)amino)-1,3-thiazol-5-yl)acetamide (565 mg, 0.97 mmol) yielded di(tert-butyl) (1-(2-((4-((5-(2-((2,3-difluorophenyl)amino)-2-oxoethyl)-1,3-thiazol-2-yl)amino)-6-methoxyquinazolin-7-yl)oxy)ethyl)piperidin-4-yl)methyl phosphate (350 mg, 47% yield):

MS (+ve ESI): 777 (M+H)$^+$.

EXAMPLE 50

Preparation of Compound 50 in Table 2—((2R)-1-(2-((4-((5-(2-((2,3-difluorophenyl)amino)-2-oxoethyl)-1,3-thiazol-2-yl)amino)-6-methoxyquinazolin-7-yl)oxy)ethyl)pyrrolidin-2-yl)methyl dihydrogen phosphate An analogous reaction to that described in example 42e, but starting with N-(2,3-difluorophenyl)-2-(2-((7-(2-((2R)-2-(hydroxymethyl)pyrrolidin-1-yl)ethoxy)-6-methoxyquinazolin-4-yl)amino)-1,3-thiazol-5-yl)acetamide (571 mg, 0.98 mmol) yielded di(tert-butyl) ((2R)-1-(2-((4-((5-(2-((2,3-difluorophenyl)amino)-2-oxoethyl)-1,3-thiazol-2-yl)amino)-6-methoxyquinazolin-7-yl)oxy)ethyl)pyrrolidin-2-yl)methyl phosphate. This material was not isolated but immediately subjected to an analogous reaction to that described in example 1 to yield the title compound as a dihydrochloride salt (110 mg, 64% yield over the two steps):

$^1$H-NMR (DMSO d$_6$, CD$_3$COOD): 8.67 (s, 1H), 8.15 (s, 1H), 7.68 (m, 1H), 7.31 (m, 2H), 7.15 (m, 2H), 4.48 (m, 2H), 4.10 (m, 1H), 3.98 (s, 3H), 3.96 (s, 2H), 3.83 (m, 2H), 3.65 (m, 1H), 3.50 (m, 1H), 3.41 (m, 1H), 3.03 (m, 1H), 2.05 (m, 2H), 1.82 (m, 2H):

MS (+ve ESI): 651 (M+H)$^+$.

N-(2,3-difluorophenyl)-2-(2-((7-(2-((2R)-2-(hydroxymethyl)pyrrolidin-1-yl)ethoxy)-6-methoxyquinazolin-4-yl) amino)-1,3-thiazol-5-yl)acetamide used as the starting material was obtained as follows:

a) An analogous reaction to that described in example 49c, but starting with D-prolinol (0.54 ml, 5.40 mmol) yielded N-(2,3-difluorophenyl)-2-(2-((7-(2-((2R)-2-(hydroxymethyl)pyrrolidin-1-yl)ethoxy)-6-methoxyquinazolin-4-yl) amino)-1,3-thiazol-5-yl)acetamide (580 mg, 75% yield) as a pale yellow solid after drying in vacuo:

$^1$H-NMR (DMSO d$_6$): 10.21 (s, 1H), 9.45 (m, 1H), 8.80 (s, 1H), 7.92 (m, 1H), 7.58 (m, 1H), 7.45 (s, 1H), 7.28 (s, 1H), 7.11 (m, 2H), 4.46 (m, 2H), 3.94 (s, 2H), 3.89 (s, 3H), 3.83 (m, 2H), 3.72 (m, 2H), 3.60 (m, 2H), 3.24 (m, 2H), 1.99 (m, 2H), 1.78 (m, 1H), 1.65 (m, 2H);

MS (+ve ESI): 571 (M+H)$^+$

MS (−ve ESI): 569 (M−H)$^−$.

EXAMPLE 51

Preparation of Compound 51 in Table 2—2-(4-(2-((4-((5-(2-(2,3-difluorophenyl)amino)-2-oxoethyl)-1,3-thiazol-2-yl)amino)-6-methoxyquinazolin-7-yl) oxy)ethyl)piperazin-1-yl)ethyl dihydrogen phosphate An analogous reaction to that described in example 1, but starting with di(tert-butyl) 2-(4-(2-((4-((5-(2-(2,3-difluorophenyl)amino)-2-oxoethyl)-1,3-thiazol-2-yl)amino)-6-methoxyquinazolin-7-yl)oxy)ethyl)piperazin-1-yl)ethyl phosphate (919 mg, 1.16 mmol) yielded the title compound (881 mg, 96% yield):

$^1$H-NMR (DMSO d$_6$): 10.50 (s, 1H), 9.00 (s, 1H), 7.90 (s, 1H), 7.75 (m, 1H), 7.60 (s, 1H), 7.40 (s, 1H), 7.10-7.25 (m, 2H), 4.60-4.70 (m, 2H), 4.20-4.30 (m, 2H), 4.10 (s, 2H), 4.01 (s, 3H), 3.45-3.80 (m, 8H), 3.30-3.40 (m, 2H):

MS (+ve ESI): 680 (M+H)$^+$.

di(tert-butyl) 2-(4-(2-((4-((5-(2-(2,3-difluorophenyl)amino)-2-oxoethyl)-1,3-thiazol-2-yl)amino)-6-methoxyquinazolin-7-yl)oxy)ethyl)piperazin-1-yl)ethyl phosphate used as the starting material was obtained as follows:

a) An analogous reaction to that described in example 49c, but starting with N-(2-hydroxyethyl)piperazine (2.57 g, 19.8 mmol) yielded N-(2,3-difluorophenyl)-2-(2-((7-(2-(1-(4-(2-hydroxyethyl))piperazin-1-yl)ethoxy)-6-methoxyquinazolin-4-yl)amino)-1,3-thiazol-5-yl)acetamide (1.28 g, 54% yield):

$^1$H-NMR (DMSO d$_6$): 10.20 (s, 1H), 8.60 (s, 1H), 8.10 (s, 1H), 7.60-7.70 (m, 1H), 7.40 (s, 1H), 7.25 (s, 1H), 7.13 (m, 2H), 4.30 (br s, 1H), 4.20 (t, 2H), 3.98 (s, 2H), 3.95 (s, 3H), 3.40-3.50 (m, 2H), 2.75 (t, 2H) 2.30-2.50 (m, 10H):

MS (+ve ESI): 600 (M+H)$^+$

MS (−ve ESI): 598 (M−H)$^−$.

b) An analogous reaction to that described in example 1i, but starting with N-(2,3-difluorophenyl)-2-(2-((7-(2-(1-(4-(2-hydroxyethyl))piperazin-1-yl)ethoxy)-6-methoxyquinazolin-4-yl)amino)-1,3-thiazol-5-yl)acetamide (1.18 g, 1.97 mmol) yielded di(tert-butyl) 2-(4-(2-((4-((5-(2-(2,3-difluorophenyl)amino)-2-oxoethyl)-1,3-thiazol-2-yl)amino)-6-methoxyquinazolin-7-yl)oxy)ethyl)piperazin-1-yl)ethyl phosphate (919 mg, 59% yield):

$^1$H-NMR (DMSO d$_6$): 10.20 (s, 1H), 8.60 (s, 1H), 8.10 (s, 1H), 7.60-7.70 (m, 1H), 7.40 (s, 1H), 7.25 (s, 1H), 7.10-7.20 (m, 2H), 4.20 (t, 2H), 3.98 (s, 2H), 3.90 (s, 3H), 3.83 (m, 2H), 2.80 (t, 2H), 2.40-2.60 (m, 8H), 1.40 (s, 18H):

MS (+ve ESI): 792 (M+H)$^+$.

EXAMPLE 52

Preparation of Compound 52 in Table 2—2-(1-(2-((4-((5-(2-((3-fluorophenyl)amino)-2-oxoethyl)-1,3-thiazol-2-yl)amino)-6-methoxyquinazolin-7-yl)oxy) ethyl)piperidin-2-yl)ethyl dihydrogen phosphate An analogous reaction to that described in example 1i, but starting with N-(3-fluorophenyl)-2-(2-((7-(2-(2-(2-hydroxyethyl)piperidin-1-yl)ethoxy)-6-methoxyquinazolin-4-yl) amino)-1,3-thiazol-5-yl)acetamide (650 mg, 1.12 mmol) yielded di(tert-butyl) 2-(1-(2-((4-((5-(2-((3-fluorophenyl)amino)-2-oxoethyl)-1,3-thiazol-2-yl)amino)-6-methoxyquinazolin-7-yl)oxy)ethyl)piperidin-2-yl)ethyl phosphate which was not isolated. This material was not isolated but immediately subjected to an analogous reaction to that described in example 1 to yield the title compound (511 mg, 51% yield) as a pale yellow dihydrochloride salt:

¹H-NMR (DMSO-d₆): 10.80 (m, 2H), 9.06 (s, 1H), 7.90 (br s, 1H), 7.69 (m, 2H), 7.42 (s, 1H), 7.38 (m, 2H), 6.92 (m, 1H), 4.65 (m, 2H), 4.03 (s, 2H), 4.00 (s, 3H), 3.70 (m, 4H), 3.42 (m, 1H), 3.32 (m, 2H), 2.05 (m, 2H), 1.84 (m, 2H), 1.72 (m, 2H), 1.51 (m, 2H):

MS (+ve ESI): 661 (M+H)⁺.

N-(3-fluorophenyl)-2-(2-((7-(2-(2-(2-hydroxyethyl)piperidin-1-yl)ethoxy)-6-methoxyquinazolin-4-yl)amino)-1,3-thiazol-5-yl)acetamide used as the starting material was obtained as follows:

a) Water (1 ml) and trifluoroacetic acid (10 ml) were added to (2-((tert-butoxy-carbonyl)amino)-1,3-thiazol-5-yl)acetic acid (621 mg, 1.76 mol—for method see example 1n) and the reaction stirred at ambient temperature for 45 minutes. Water (10 ml) was added and the reaction stirred for a further 15 minutes before the solid (which had precipitated) was collected by suction filtration, washed with water (3×10 ml) and dried in vacuo to yield N-(3-fluorophenyl)-2-amino-1,3-thiazol-5-ylacetamide (402 mg, 91% yield):

¹H-NMR (DMSO d₆): 10.28 (br s, 1H), 7.58 (m, 1H), 7.30 (m, 2H), 6.88 (m, 1H), 6.75 (s, 1H), 6.72 (br s, 2H), 2.12 (s, 2H):

MS (+ve ESI): 252 (M+H)⁺

MS (−ve ESI): 250 (M−H)⁻.

b) A mixture of N-(3-fluorophenyl)-2-amino-1,3-thiazol-5-ylacetamide (9.99 g, 27.4 mmol) and N'-(5-(2-chloroethoxy)-2-cyano-4-methoxyphenyl)-N,N-dimethylimidoformamide (7.68 g, 27.4 mmol) in acetic acid (40 ml) was heated at reflux for 6 hours. The mixture was cooled and the solid product collected by suction filtration, washed with acetic acid and then diethyl ether. The solid was dissolved in dimethylacetamide (120 ml) and filtered. Aqueous sodium bicarbonate solution (500 ml) was added slowly to the filtrate and the solid product collected by suction filtration, washed with water and dried to yield N-(3-fluorophenyl)-2-(2-(7-(2-chloroethoxy)-6-methoxyquinazolin-4-yl-amino-1,3-thiazol-5-yl)acetamide (7.69 g, 58% yield) as a pale yellow solid:

¹H-NMR (DMSO d₆): 10.43 (br s, 1H), 8.55 (s, 1H), 8.02 (s, 1H), 7.63 (m, 1H), 7.33 (m, 3H), 7.17 (s, 1H), 6.89 (m, 1H), 4.42 (t, 2H), 4.05 (t, 2H), 3.95 (s, 3H), 3.82 (s, 2H);

MS (+ve ESI): 488 (M+H)⁺

MS (−ve ESI): 486 (M−H)⁻.

c) An analogous reaction to that described in example 1h, but starting with 2-(hydroxyethyl)piperidine (0.22 ml, 1.6 mmol) and N-(3-fluorophenyl)-2-(2-(7-(2-chloroethoxy)-6-methoxyquinazolin-4-yl-amino-1,3-thiazol-5-yl)acetamide (200 mg, 0.41 mmol) yielded N-(3-fluorophenyl)-2-(2-((7-(2-(2-(2-hydroxyethyl)piperidin-1-yl)ethoxy)-6-methoxyquinazolin-4-yl)amino)-1,3-thiazol-5-yl)acetamide (19 mg, 8% yield):

¹H-NMR (DMSO d₆): 11.99 (m, 1H), 10.45 (br s, 1H), 8.68 (s, 1H), 8.12 (br s, 1H), 7.63 (m, 1H), 7.38 (m, 3H), 7.30 (s, 1H), 6.90 (m, 1H), 4.24 (t, 2H), 3.99 (s, 3H), 3.91 (s, 2H), 3.48 (m, 2H), 3.07 (m, 1H), 2.89 (m, 2H), 2.55 (m, 2H), 1.80 (m, 1H), 1.55 (m, 5H), 1.31 (m, 2H):

MS (+ve ESI): 581 (M+H)⁺

MS (−ve ESI): 579 (M−H)⁻.

EXAMPLE 53

Preparation of Compound 53 in Table 2—2-(1-(2-((4-((5-(2-((3-fluorophenyl)amino)-2-oxoethyl)-1,3-thiazol-2-yl)amino)-6-methoxyquinazolin-7-yl)oxy)ethyl)piperidin-4-yl)ethyl dihydrogen phosphate An analogous reaction to that described in example 52, but starting with N-(3-fluorophenyl)-2-(2-((7-(2-(4-(2-hydroxyethyl)piperidin-1-yl)ethoxy)-6-methoxyquinazolin-4-yl)amino)-1,3-thiazol-5-yl)acetamide (1.10 g, 1.89 mmol) yielded the title compound (676 mg, 54% yield) as a pale yellow solid:

¹H-NMR (DMSO d₆): 11.05 (br s, 1H), 10.92 (s, 1H), 9.10 (s, 1H), 7.95 (br s, 1H), 7.79 (m, 2H), 7.50 (s, 1H), 7.42 (m, 2H), 6.95 (m, 1H), 4.75 (m, 2H), 4.10 (s, 2H), 4.05 (s, 3H), 3.95 (m, 2H), 3.70 (m, 4H), 3.18 (m, 2H), 1.95 (m, 2H), 1.75 (m, 1H), 1.63 (m, 4H):

³¹P-NMR (¹H) (DMSO-d₆): −0.01 (s, 1P):

MS (+ve ESI): 661 (M+H)⁺.

N-(3-fluorophenyl)-2-(2-((7-(2-(4-(2-hydroxyethyl)piperidin-1-yl)ethoxy)-6-methoxyquinazolin-4-yl)amino)-1,3-thiazol-5-yl)acetamide used as the starting material was obtained as follows:

a) An analogous reaction to that described in example 52a, but starting with 4-(2-hydroxyethyl)piperidine (0.22 ml, 1.6 mmol) yielded N-(3-fluorophenyl)-2-(2-((7-(2-(4-(2-hydroxyethyl)piperidin-1-yl)ethoxy)-6-methoxyquinazolin-4-yl)amino)-1,3-thiazol-5-yl)acetamide (52 mg, 22% yield):

¹H-NMR (DMSO d₆): 12.00 (m, 1H), 10.45 (br s, 1H), 8.68 (s, 1H), 8.12 (br s, 1H), 7.63 (m, 1H), 7.37 (m, 3H), 7.29 (s, 1H), 6.91 (m, 1H), 4.30 (m, 4H), 3.98 (s, 3H), 3.92 (s, 2H), 3.45 (q, 2H), 2.97 (m, 2H), 2.79 (m, 2H), 2.06 (m, 2H), 1.65 (m, 2H), 1.37 (m, 2H), 1.18 (m, 2H):

MS (+ve ESI): 581 (M+H)⁺

MS (−ve ESI): 579 (M−H)⁻.

EXAMPLE 54

Preparation of Compound 54 in Table 2—4-(ethyl(2-((4-((5-(2-((3-fluorophenyl)amino)-2-oxoethyl)-1,3-thiazol-2-yl)amino)-6-methoxyquinazolin-7-yl)oxy)ethyl)amino)butyl dihydrogen phosphate An analogous reaction to that described in example 52, but starting with 2-(2-((7-(2-(ethyl(4-hydroxybutyl)amino)ethoxy)-6-methoxyquinazolin-4-yl)amino)-1,3-thiazol-5-yl)-N-(3-fluorophenyl)acetamide (602 mg, 1.06 mmol) yielded the title compound (85 mg, 15% yield) as a pale yellow solid:

¹H-NMR (DMSO d₆): 10.65 (m, 2H), 8.97 (s, 1H), 7.85 (br s, 1H), 7.55 (m, 2H), 7.30 (m, 3H), 6.85 (m, 1H), 4.57 (m, 2H), 3.95 (s, 2H), 3.93 (s, 3H), 3.58 (m, 2H), 3.20 (m, 4H), 1.75 (m, 2H), 1.60 (m, 2H), 1.25 (t, 3H):

³¹P-NMR (¹H) (DMSO-d₆): −0.12 (s, 1P)

MS (+ve ESI): 649 (M+H)⁺.

2-(2-((7-(2-(ethyl(4-hydroxybutyl)amino)ethoxy)-6-methoxyquinazolin-4-yl)amino)-1,3-thiazol-5-yl)-N-(3-fluorophenyl)acetamide used as the starting material was obtained as follows:

a) An analogous reaction to that described in example 52a, but starting with 4-(ethylamino)-1-butanol (0.2 ml, 1.6 mmol) yielded 2-(2-((7-(2-(ethyl(4-hydroxybutyl)amino)ethoxy)-6-methoxyquinazolin-4-yl)amino)-1,3-thiazol-5-yl)-N-(3-fluorophenyl)acetamide (32 mg, 14% yield):

$^1$H-NMR (DMSO d$_6$): 11.96 (m, 1H), 10.45 (br s, 1H), 8.67 (s, 1H), 8.12 (br s, 1H), 7.62 (m, 1H), 7.38 (m, 3H), 7.28 (s, 1H), 6.91 (m, 1H), 4.26 (m, 2H), 3.98 (s, 3H), 3.90 (s, 2H), 3.42 (m, 2H), 2.95 (m, 2H), 2.64 (m, 4H), 1.48 (m, 4H), 1.03 (t, 3H):
MS (+ve ESI): 569 (M+H)$^+$
MS (−ve ESI): 567 (M−H)$^−$.

EXAMPLE 55

Preparation of Compound 55 in Table 2—2-(ethyl(2-((4-((5-(2-((3-fluorophenyl)amino)-2-oxoethyl)-1,3-thiazol-2-yl)amino)-6-methoxyquinazolin-7-yl)oxy) ethyl)amino)ethyl dihydrogen phosphate An analogous reaction to that described in example 52, but starting with 2-(2-((7-(2-(ethyl(2-hydroxyethyl)amino) ethoxy)-6-methoxyquinazolin-4-yl)amino)-1,3-thiazol-5-yl)-N-(3-fluorophenyl)acetamide (710 mg, 1.31 mmol) yielded the title compound (616 mg, 76% yield) as a pale yellow solid:
$^1$H-NMR (DMSO d$_6$): 10.90 (s, 1H), 8.99 (s, 1H), 7.86 (br s, 1H), 7.65 (d, 1H), 7.60 (s, 1H), 7.41 (m, 3H), 6.90 (m, 1H), 4.70 (m, 2H), 4.33 (m, 2H), 4.05 (s, 2H), 3.97 (s, 3H), 3.75 (m, 2H), 3.55 (m, 2H), 3.38 (q, 2H), 1.37 (t, 3H):
$^{31}$P-NMR ($^1$H) (DMSO d$_6$): −0.15 (s, 1P)
MS (+ve ESI): 621 (M+H)$^+$.

2-(2-((7-(2-(ethyl(2-hydroxyethyl)amino)ethoxy)-6-methoxyquinazolin-4-yl)amino)-1,3-thiazol-5-yl)-N-(3-fluorophenyl)acetamide used as the starting material was obtained as follows:
a) An analogous reaction to that described in example 52a, but starting with 2-(ethylamino)-1-ethanol (0.15 ml, 1.6 mmol) yielded 2-(2-((7-(2-(ethyl(2-hydroxyethyl)amino) ethoxy)-6-methoxyquinazolin-4-yl)amino)-1,3-thiazol-5-yl)-N-(3-fluorophenyl)acetamide (41 mg, 19% yield):
$^1$H-NMR (DMSO d$_6$): 11.98 (m, 1H), 10.45 (br s, 1H), 8.67 (s, 1H), 8.12 (br s, 1H), 7.62 (m, 1H), 7.37 (m, 3H), 7.27 (s, 1H), 6.91 (m, 1H), 4.29 (t, 1H), 4.22 (t, 2H), 3.97 (s, 3H), 3.90 (s, 2H), 3.48 (q, 2H), 2.94 (t, 2H), 2.65 (m, 4H), 1.01 (t, 3H):
MS (+ve ESI): 541 (M+H)$^+$
MS (−ve ESI): 539 (M−H)$^−$.

EXAMPLE 56

Preparation of Compound 56 in Table 3—(1-(3-((4-((5-(2-((3-fluorophenyl)amino)-2-oxoethyl)-1,3-thiazol-2-yl)amino)quinazolin-7-yl)oxy)propyl)piperidin-4-yl)methyl dihydrogen phosphate An analogous reaction to that described in example 1, but starting with di(tert-butyl) (1-(3-((4-((5-(2-((3-fluorophenyl) amino)-2-oxoethyl)-1,3-thiazol-2-yl)amino)quinazolin-7-yl)oxy)propyl)piperidin-4-yl)methyl phosphate (640 mg, 0.86 mmol) yielded the title compound (353 mg, 55% yield), as the dihydrochloride salt, as a pale yellow solid:
$^1$H-NMR (DMSO d$_6$): 10.87 (s, 1H), 10.58 (s, 1H), 9.04 (s, 1H), 8.42 (d, 1H), 7.65 (m, 2H), 736 (m, 4H), 6.91 (m, 1H), 4.28 (m, 2H), 4.05 (s, 2H), 3.72 (t, 2H), 3.55 (d, 2H), 3.23 (m, 3H), 2.95 (m, 2H), 2.33 (m, 2H), 1.85 (m, 2H), 1.61 (m, 2H):
$^{31}$P-NMR($^1$H) (DMSO d$_6$): 0.05 (1P):
MS (−ve ESI): 629 (M−H)$^−$
MS (+ve ESI): 631 (M+H)$^+$.

di(tert-butyl) (1-(3-((4-((5-(2-((3-fluorophenyl)amino)-2-oxoethyl)-1,3-thiazol-2-yl)amino)quinazolin-7-yl)oxy)propyl)piperidin-4-yl)methyl phosphate used as the starting material was obtained as follows:
a) 2-Amino-4-fluorobenzoic acid (15 g, 96.7 mmol) was dissolved in 2-methoxyethanol (97 ml) and formamidine acetate (20.13 g, 193.4 mmol) was added before the mixture was heated at reflux for 18 hours. The reaction was cooled, concentrated and the residue stirred in 0.01 N aqueous ammonium hydroxide solution (250 ml) for 1 hour. The suspension was filtered, washed with water and dried over phosphorus pentoxide to yield 7-fluoroquinazolin-4 (3H)-one as an off-white solid (10.35 g, 65% yield):
$^1$H-NMR (DMSO d$_6$): 12.32 (br s, 1H), 8.19 (dd, 1H), 8.14 (s, 1H), 7.45 (dd, 1H), 7.39 (m, 1H):
MS (+ve ESI): 165 (M+H)$^+$
MS (−ve ESI): 163 (M−H)$^−$.
b) Sodium hydride (14.6 g, 365 mmol) was added at 0° C. to a solution of 1,3-propanediol (27.8 g, 365.5 mmol) in dimethylformamide (70 ml). 7-Fluoroquinazolin-4(3H)-one (10 g, 60.9 mmol) was added portionwise and the reaction mixture heated at 60° C., then at 110° C. for 3 hours. The reaction was cooled to 0° C., quenched with water (280 ml) and acidified to pH 5.9. The resulting suspension was filtered, washed with water then diethyl ether and dried over phosphorus pentoxide to yield 7-(3-hydroxypropoxy) quinazolin-4(3H)-one as a white powder (12.41 g, 92% yield):
$^1$H-NMR (DMSO d$_6$): 11.90 (br s, 1H), 8.04 (s, 1H), 8.00 (d, 1H), 7.10 (m, 2H), 4.17 (t, 2H), 3.58 (t, 2H), 1.92 (m, 2H):
MS (+ve ESI): 221 (M+H)$^+$.
c) Dimethylformamide (1 ml) was added dropwise to a mixture of thionyl chloride (100 ml, 137 mmol) and 7-(3-hydroxypropoxy)quinazolin-4(3H)-one (10.5 g, 47.7 mmol) and the reaction mixture heated to 85° C. for 1 hour. The mixture was cooled to ambient temperature, diluted with toluene and evaporated to dryness. This was repeated until all thionyl chloride was removed. The residue was dissolved in dichloromethane and washed with a saturated sodium bicarbonate solution. The aqueous layer was extracted with dichloromethane. The organics were combined, dried (magnesium sulphate) and concentrated to leave a yellow solid. Trituration with diethyl ether removed a less soluble impurity and the ether filtrate was concentrated to yield 4-chloro-7-(3-chloropropoxy)quinazoline as an off-white solid (8.5 g, 70% yield):
$^1$H-NMR (DMSO d$_6$): 13.25 (br s, 1H), 8.34 (s, 1H), 8.06 (d, 1H), 7.17 (m, 2H), 4.21 (t, 2H), 3.83 (t, 2H), 2.23 (m, 2H):
MS (+ve ESI): 257, 259 (M+H)$^+$.
d) Sodium tert-butoxide (76.5 mg, 0.80 mmol) was added to a suspension of 2-(2-amino-1,3-thiazol-5-yl)-N-(3-fluorophenyl)acetamide (100 mg, 0.398 mmol) and 4-chloro-7-(3-chloropropoxy)quinazoline (102 mg, 0.398 mmol) in dioxan (1 ml) and the reaction heated at reflux for 7 hours. The reaction was cooled to ambient temperature and dioxan (1 ml) and water (8 ml) were added before the pH was adjusted to <8 by addition of a few drops of 1.0 N hydrochloric acid. Collection of the resultant solid by suction filtration followed by prolonged drying in vacuo yielded 2-(2-((7-(3-chloropropoxy)quinazolin-4-yl) amino)-1,3-thiazol-5-yl)-N-(3-fluorophenyl)acetamide (139 mg, 74% yield) as a brown powdery solid:
$^1$H-NMR (DMSO-d$_6$): 12.12 (br s, 1H), 10.47 (s, 1H), 8.73 (s, 1H), 8.63 (s, 1H), 7.63 (d, 1H), 7.18-7.44 (m, 5H), 6.91 (dd, 1H), 4.29 (t, 2H), 3.88 (s, 2H), 3.83 (t, 2H), 2.25 (m, 2H):
MS (−ve ESI): 470, 472 (M−H)$^−$
MS (+ve ESI): 472, 474 (M+H)$^+$.
e) An analogous reaction to that described in example 1h, but starting with 2-(2-((7-(3-chloropropoxy)quinazolin-4-yl)

amino)-1,3-thiazol-5-yl)-N-(3-fluorophenyl)acetamide (1.50 g, 3.18 mol) and piperidin-4-ylmethanol (1.28 g, 11.1 mmol) yielded N-(3-fluorophenyl)-2-(2-((7-(3-(4-hydroxymethyl)piperidin-1-yl)propoxy)quinazolin-4-yl) amino)-1,3-thiazol-5-yl)acetamide (580 mg, 33% yield) as an off-white solid:

$^1$H-NMR (DMSO d$_6$): 12.00 (br s, 1H), 10.47 (s, 1H), 8.71 (s, 1H), 8.60 (d, 1H), 7.62 (d, 1H), 7.14-7.46 (m, 5H), 6.86 (m, 1H), 4.37 (s, 1H), 4.20 (s, 2H), 3.89 (s, 2H), 3.29 (s, 2H), 2.95 (m, 2H), 1.80-2.13 (m, 5H), 1.66 (m, 2H), 1.37 (s, 1H), 1.17 (m, 2H):

MS (−ve ESI): 549 (M−H)$^-$

MS (+ve ESI): 551 (M+H)$^+$.

f) An analogous reaction to that described in example 1i, but starting with N-(3-fluorophenyl)-2-(2-((7-(3-(4-(hydroxymethyl)piperidin-1-yl)propoxy)quinazolin-4-yl) amino)-1,3-thiazol-5-yl)acetamide (518 mg, 0.94 mmol) yielded di(tert-butyl) (1-(3-((4-((5-(2-((3-fluorophenyl) amino)-2-oxoethyl)-1,3-thiazol-2-yl)amino)quinazolin-7-yl)oxy)propyl)piperidin-4-yl)methyl phosphate (651 mg, 93% yield) as an orange oil:

$^1$H-NMR (DMSO d$_6$): 12.11 (br s, 1H), 10.43 (s, 1H), 8.72 (s, 1H), 8.60 (d, 1H), 7.62 (d, 1H), 7.19-7.40 (m, 5H), 6.86 (dd, 1H), 4.20 (t, 2H), 3.90 (s, 2H), 3.70 (t, 2H), 3.16 (m, 1H), 2.90 (m, 2H), 2.47 (m, 2H), 1.90 (m, 2H), 1.50-1.68 (m, 4H), 1.40 (s, 18H), 1.24 (m, 2H):

$^{31}$P-NMR($^1$H) (DMSO d$_6$): −8.55 (1P):

MS (−ve ESI): 741 (M−H)$^-$

MS (+ve ESI): 743 (M+H)$^+$.

EXAMPLE 57

Preparation of Compound 57 in Table 4—2-{4-[({4-[(5-{2-[(3-fluorophenyl)amino]-2-oxoethyl}-1,3-thiazol-2-yl)amino]-6-methoxyquinazolin-7-yl}oxy) methyl]piperidin-1-yl}ethyl dihydrogen phosphate An analogous reaction to that described in example 1, but starting with di-tert-butyl 2-{4-[({4-[(5-{2-[(3-fluorophenyl) amino]-2-oxoethyl}-1,3-thiazol-2-yl)amino]-6-methoxyquinazolin-7-yl}oxy)methyl]piperidin-1-yl}ethyl phosphate (145 mg, 0.19 mmol) yielded the title compound (117 mg, 85% yield), as the dihydrochloride salt, as a pale yellow solid:

$^1$H-NMR (DMSO d$_6$): 10.70 (s, 1H), 10.50 (br s, 1H), 9.04 (s, 1H), 7.90 (s, 1H), 7.50-7.60 (m, 2H), 7.40 (s, 1H), 7.20-7.30 (m, 2H), 6.80-6.90 (m, 1H), 4.30-4.40 (m, 2H), 4.07 (m, 2H), 4.00 (s, 2H), 3.98 (s, 3H), 3.60-3.70 (m, 2H), 3.30-3.40 (m, 2H), 3.00-3.20 (m, 2H), 2.10-2.20 (m, 1H), 2.00 (d, 2H), 1.80-1.90 (m, 2H):

$^{31}$P-NMR($^1$H) (DMSO d$_6$): 0.30 (1P):

MS (+ve ESI): 647 (M+H)$^+$.

di-tert-butyl 2-{4-[({4-[(5-{2-[(3-fluorophenyl)amino]-2-oxoethyl}-1,3-thiazol-2-yl)amino]-6-methoxyquinazolin-7-yl}oxy)methyl]piperidin-1-yl}ethyl phosphate, used as the starting material, was obtained as follows:

a) A solution of di-tert-butyl dicarbonate (41.7 g, 0.19 mol) in ethyl acetate (75 ml) was added dropwise to a solution of ethyl 4-piperidinylcarboxylate (30 g, 0.19 mol) in ethyl acetate (150 ml) while maintaining the temperature in the range 0-5° C. The reaction was stirred at ambient temperature for 48 hours, poured onto water (300 ml) and the organic layer was separated and washed with i) water (200 ml), ii) 0.1N aqueous hydrochloric acid (200 ml), iii) saturated sodium hydrogen carbonate (200 ml) and iv) brine (200 ml). Evaporation and drying in vacuo yielded ethyl (1-tert-butyloxycarbonylpiperidin-4-yl)carboxylate (48 g, 98% yield) as a white solid:

$^1$H NMR (CDCl$_3$): 4.15 (q, 2H), 3.91-4.10 (s, 2H), 2.70-2.95 (t, 2H), 2.35-2.50 (m, 1H), 1.80-2.00 (d, 2H), 1.55-1.70 (m, 2H), 1.45 (s, 9H), 1.25 (t, 3H).

b) A solution of 1.0N lithium aluminium hydride in tetrahydrofuran (133 ml, 0.133 mol) was added dropwise to a solution of ethyl (1-tert-butyloxycarbonylpiperidin-4-yl) carboxylate (48 g, 0.19 mol) in dry tetrahydrofuran (180 ml) at 0° C. The reaction was stirred at 0° C. for 2 hours, water (30 ml) and 2.0N sodium hydroxide (10 ml) were added and the precipitate was filtered through diatomaceous earth and washed with ethyl acetate. The filtrate was washed with water and brine before being evaporated to yield 4-hydroxymethyl-1-tert-butyloxycarbonylpiperidine (36.3 g, 89% yield) as a white solid:

$^1$H NMR (CDCl$_3$): 4.10 (s, 2H), 3.40-3.60 (t, 2H), 2.60-2.80 (t, 2H), 1.60-1.80 (m, 2H), 1.35-1.55 (m, 10H), 1.05-1.20 (m, 2H):

MS (+ve EI): 215 (M+H)$^+$.

c) 1,4-Diazabicyclo[2.2.2]octane (42.4 g, 0.378 mol) was added to a solution of 4-hydroxymethyl-1-tert-butyloxycarbonylpiperidine (52.5 g, 0.244 mol) in tert-butyl methyl ether (525 ml) and the reaction stirred at ambient temperature for 15 minutes. The reaction was cooled to 5° C. and a solution of 4-toluenesulphonyl chloride (62.8 g, 0.33 mmol) in tert-butyl methyl ether (525 ml) was added dropwise over 2 hours while maintaining the temperature at 0° C. The reaction was stirred at ambient temperature for 1 hour, isohexane was added and the resultant precipitate was collected by suction filtration. Solvent evaporation in vacuo afforded a solid which was dissolved in diethyl ether (250 ml) and washed successively with 0.5 N aqueous hydrochloric acid (2×500 ml), water, saturated sodium hydrogen carbonate and brine. Solvent evaporation and drying in vacuo yielded 4-(4-methylphenylsulphonyloxymethyl)-1-tert-butyloxy-carbonylpiperidine (76.7 g, 85% yield) as a white solid:

$^1$H NMR (CDCl$_3$): 7.80 (d, 2H), 7.35 (d, 2H), 4.00-4.20 (s, 2H), 3.85 (d, 1H), 2.55-2.75 (m, 2H), 2.45 (s, 3H), 1.75-1.90 (m, 2H), 1.65 (d, 2H), 1.45 (s, 9H), 1.00-1.20 (m, 2H):

MS (+ve ESI): 392 (M+Na)$^+$.

d) N'-(2-cyano-5-hydroxy-4-methoxyphenyl)-N,N-dimethylimidoformamide (2.46 g, 7.42 mmol), tert-butyl 4-({[(4-methylphenyl)sulfonyl]oxy}methyl)piperidin-1-ylcarboxylate (3.00 g, 8.90 mmol) and caesium carbonate (6.00 g, 18.6 mmol) were combined in acetonitrile (150 ml) and the reaction heated at reflux for 18 hours. The solvents were removed in vacuo, the residue was stirred with saturated sodium hydrogen carbonate solution and then extracted with ethyl acetae (3×75 ml). Solvent evaporation in vacuo yielded tert-butyl 4-[(4-cyano-5-{[(1E)-(dimethylamino) methylene]amino}-2-methoxyphenoxy)methyl]piperidin-1-ylcarboxylate, as a brown oil, which was not characterised but taken up in acetic acid (15 ml) and heated at 145° C. for 4 hours with tert-butyl (5-{2-[(3-fluorophenyl) amino]-2-oxoethyl}-1,3-thiazol-2-yl)carbamate (2.60 g, 7.42 mmol). The reaction was cooled, concentrated in vacuo, taken up in methanol and neutralised by addition of excess saturated aqueous sodium hydrogen carbonate solution. The water was decanted off and the brown gum was taken up in methanol and purified by flash chromatography on silica gel, eluting with 10-20% methanol in dichloromethane (with 1% ammonia added). Solvent evalporation in vacuo followed by trituartion with deithyl ether and drying in vacuo yielded N-(3-fluorophenyl)-2-(2-{[6- methoxy-7-(piperidin-4-ylmethoxy)quinazolin-4-yl]amino}-1,3-thiazol-5-yl)acetamide (1.92 g, 49% yield) as an off-white solid:

¹H-NMR (DMSO d₆): 10.42 (s, 1H), 8.60 (s, 1H), 8.05 (s, 1H), 7.55-7.65 (m, 1H), 7.25-7.40 (m, 3H), 7.20 (s, 1H), 6.80-6.90 (m, 1H), 4.00 (d, 2H), 3.98 (s, 3H), 3.80 (s, 2H), 2.90-3.00 (m, 2H), 2.50-2.60 (m, 2H), 1.80-2.00 (m, 1H), 1.65-1.75 (m, 2H), 1.15-1.30 (m, 2H):

MS (−ve ESI): 521 (M−H)⁻
MS (+ve ESI): 523 (M+H)⁺.

e) Sodium tri(acetoxy)borohydride (814 mg), was added to a stirred solution of N-(3-fluorophenyl)-2-(2-{[6-methoxy-7-(piperidin-4-ylmethoxy)quinazolin-4-yl]amino}-1,3-thiazol-5-yl)acetamide (1.00 g, 1.92 mmol), {[tert-butyl(dimethyl)silyl]oxy}acetaldehyde (1.67 g, 9.58 mmol) and acetic acid (0.88 ml, 15.4 mmol) in a mixture of tetrahydrofuran (15 ml) and methanol (15 ml) and the reaction stirred for 18 hours at ambient temperature. The volatiles were removed in vacuo, the residue was basified by washing with saturated aquoeus sodium hydrogen carbonate solution and the aqueous layer was extracted with dichloromethane (3×50 ml). Purification by flash chromatography on silica gel, eluting with dichloromethane:methanol (90:10) to dichloromethane:methanol:7.0 N aqueous ammonia (19:80:1) yielded 2-{2-[(7-{[1-(2-{[tert-butyl(dimethyl)silyl]oxy}ethyl)piperidin-4-yl]methoxy}-6-methoxyquinazolin-4-yl)amino]-1,3-thiazol-5-yl}-N-(3-fluorophenyl)acetamide (302 mg, 23% yield) as a pale yellow solid:

¹H-NMR (DMSO d₆): 10.38 (s, 1H), 8.60 (s, 1H), 8.05 (br s, 1H), 7.58 (m, 1H), 7.35 (s, 1H), 7.20-7.30 (m, 2H), 7.15 (s, 1H), 6.80-6.90 (m, 1H), 3.98 (m, 2H), 3.90 (s, 3H), 3.80 (s, 2H), 3.60 (t, 2H), 2.80-2.90 (m, 2H), 2.37 (m, 2H), 1.90-2.10 (m, 2H), 1.65-1.80 (m, 3H), 1.20-1.40 (m, 2H), 0.80 (s, 9H), 0.10 (s, 6H):

MS (−ve ESI): 679 (M−H)⁻
MS (+ve ESI): 680 (M+H)⁺.

f) Tetrabutylammonium fluoride (3.75 ml of a 1.0 N solution in tetrahydrofuran, 3.75 mmol) was added to a stirred solution of 2-{2-[(7-{[1-(2-{[tert-butyl(dimethyl)silyl]oxy}-ethyl)piperidin-4-yl]methoxy}-6-methoxyquinazolin-4-yl)amino]-1,3-thiazol-5-yl}-N-(3-fluorophenyl)acetamide (511 mg, 0.75 mmol) in tetrahydrofuran (5 ml) and the reaction stirred for 3 hours at ambient temperature. The volatiles were removed in vacuo and the reaction was diluted by addition of dimethylsulphoxide (10.5 ml), acetonitrile (3 ml) and water (1.5 ml). The reaction was acidified with trifluoroacetic acid and the product purified by reverse phase HPLC. Concentration of the fraction sin vacuo, followed by treatment with solid sodium carbonate, caused precipitation of a yellow solid which was collected by suction filtration. Extended drying in vacuo yielded N-(3-fluorophenyl)-2-{2-[(7-{[1-(2-hydroxyethyl)piperidin-4-yl]methoxy}-6-methoxyquinazolin-4-yl)amino]-1,3-thiazol-5-yl}acetamide (318 mg, 75% yield) as a yellow solid:

¹H-NMR (DMSO d₆): 10.42 (s, 1H), 8.60 (s, 1H), 8.00 (s, 1H), 7.57 (m, 1H), 7.25-7.35 (m, 3H), 7.20 (s, 1H), 6.80-6.90 (m, 1H), 4.35 (br s, 1H), 4.00 (d, 2H), 3.95 (s, 3H), 3.80 (s, 2H), 3.40-3.50 (m, 2H), 2.80-2.90 (m, 2H), 2.40 (t, 2H), 1.90-2.00 (m, 2H), 1.70-1.80 (m, 3H), 1.20-1.30 (m, 2H):

MS (−ve ESI): 565 (M−H)⁻
MS (+ve ESI): 567 (M+H)⁺.

g) An analogous reaction to that described in example 1i, but starting with N-(3-fluorophenyl)-2-{2-[(7-{[1-(2-hydroxyethyl)piperidin-4-yl]methoxy}-6-methoxyquinazolin-4-yl)amino]-1,3-thiazol-5-yl}acetamide (290 mg, 0.51 mmol) yielded di-tert-butyl 2-{4-[({4-[(5-{2-[(3-fluorophenyl)amino]-2-oxoethyl}-1,3-thiazol-2-yl)amino]-6-methoxyquinazolin-7-yl}oxy)methyl]piperidin-1-yl}ethyl phosphate (145 mg, 37% yield) as a yellow solid:

¹H-NMR (DMSO d₆): 10.42 (s, 1H), 8.60 (s, 1H), 8.20 (s, 1H), 7.57 (m, 1H), 7.40 (s, 1H), 7.33 (m, 2H), 7.20 (s, 1H), 6.80-6.90 (m, 1H), 4.00 (d, 2H), 3.98 (s, 3H), 3.92 (m, 2H), 3.87 (s, 2H), 3.60-3.70 (m, 2H), 2.90-3.00 (m, 2H), 2.57 (m, 2H), 2.00-2.20 (m, 2H), 1.88 (m, 3H), 1.40 (s, 18H), 1.30-1.40 (m, 2H):

MS (+ve ESI): 759 (M+H)⁺.

The invention claimed is:

1. A compound selected from:

(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)methyl dihydrogen phosphate;

((2R)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-(4-(3-((4-((5-(2-((3-fluorophenyl)amino)-2-oxoethyl)-1,3-thiazol-2-yl)amino)-6-methoxy-quinazolin-7-yl)oxy)propyl)piperazin-1-yl)ethyl dihydrogen phosphate;

1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-3-yl dihydrogen phosphate;

1-(3-((4-((5-(2-((3-fluorophenyl)amino)-2-oxoethyl)-1,3-thiazol-2-yl)amino)-6-methoxyquinazolin-7-yl)oxy)propyl)piperidin-3-yl dihydrogen phosphate;

2-(ethyl(3-((4-((5-(2-((3-fluorophenyl)amino)-2-oxoethyl)-1,3-thiazol-2-yl)amino)-6-methoxyquinazolin-7-yl)oxy)propyl)amino)ethyl dihydrogen phosphate;

((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-(ethyl(((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)amino)ethyl dihydrogen phosphate;

1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl dihydrogen phosphate;

2-((((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)methyl)amino)ethyl dihydrogen phosphate;

2-((3-((4-((5-(2-((3-fluorophenyl)amino)-2-oxoethyl)-1,3-thiazol-2-yl)amino)-6-methoxyquinazolin-7-yl)oxy)propyl)amino)ethyl dihydrogen phosphate;

3-(ethyl(3-((4-((5-(2-((3-fluorophenyl)amino)-2-oxoethyl)-1,3-thiazol-2-yl)amino)-6-methoxyquinazolin-7-yl)oxy)propyl)amino)propyl dihydrogen phosphate;

2-((2-fluoroethyl)(3-((4-((5-(2-((3-fluorophenyl)amino)-2-oxoethyl)-1,3-thiazol-2-yl)amino)-6-methoxyquinazolin-7-yl)oxy)propyl)amino)ethyl dihydrogen phosphate;

2-(1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)ethyl dihydrogen phosphate;

2-((3-((4-((5-(2-((3-fluorophenyl)amino)-2-oxoethyl)-1,3-thiazol-2-yl)amino)-6-methoxyquinazolin-7-yl)oxy)propyl)(2-methoxyethyl)amino)ethyl dihydrogen phosphate;

2-((2S)-1-(3-((4-((5-(2-((3-fluorophenyl)amino)-2-oxoethyl)-1,3-thiazol-2-yl)amino)-6-methoxyquinazolin-7-yl)oxy)propyl)pyrrolidin-2-yl)ethyl dihydrogen phosphate;

2-((3-((4-((5-(2-((3-fluorophenyl)amino)-2-oxoethyl)-1,3-thiazol-2-yl)amino)-6-methoxyquinazolin-7-yl)oxy)propyl)amino)-2-methylpropyl dihydrogen phosphate;

((2R)-1-(3-((4-((5-(2-((3-chlorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-(1-(3-((4-((5-(2-((3-chlorophenyl)amino)-2-oxoethyl)-1,3-thiazol-2-yl)amino)-6-methoxyquinazolin-7-yl)oxy)propyl)piperidin-4-yl)ethyl dihydrogen phosphate;

2-(4-(3-((4-((5-(2-(3,5-difluorophenyl)amino)-2-oxoethyl)-1,3-thiazol-2-yl)amino)-6-methoxyquinazolin-7-yl)oxy)propyl)piperazin-1-yl)ethyl dihydrogen phosphate;

2-((3-((4-((5-(2-((3,5-difluorophenyl)amino)-2-oxoethyl)-1,3-thiazol-2-yl)amino)-6-methoxyquinazolin-7-yl)oxy)propyl)(methyl)amino)ethyl dihydrogen phosphate;

((2S)-1-(3-((4-((5-(2-((3,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

(1R)-2-((3-((4-((5-(2-((3,5-difluorophenyl)amino)-2-oxoethyl)-1,3-thiazol-2-yl)amino)-6-methoxyquinazolin-7-yl)oxy)propyl)amino)-1-methylethyl dihydrogen phosphate;

((2R)-1-(3-((4-((5-(2-((3,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2S)-1-(3-((4-((5-(2-((3,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

1-(3-((4-((5-(2-((3,4-difluorophenyl)amino)-2-oxoethyl)-1,3-thiazol-2-yl)amino)-6-methoxyquinazolin-7-yl)oxy)propyl)piperidin-4-ylmethyl dihydrogen phosphate;

(1-(3-((4-((5-(2-((2-fluorophenyl)amino)-2-oxoethyl)-1,3-thiazol-2yl)amino)-6-methoxyquinazolin-7-yl)oxy)propyl)piperidin-4-yl) methyl dihydrogen phosphate;

((2R)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2S)-1-(3-((4-((5-(2-((2-fluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-(ethyl(3-((4-((5-(2-((2-fluorophenyl)amino)-2-oxoethyl)-1,3-thiazol-2-yl)amino)-6-methoxyquinazolin-7-yl)oxy)propyl)amino)ethyl dihydrogen phosphate;

2-(1-(3-((4-((5-(2-((2-fluorophenyl)amino)-2-oxoethyl)-1,3-thiazol-2-yl)amino)-6-methoxyquinazolin-7-yl)oxy)propyl)piperidin-2-yl)ethyl dihydrogen phosphate;

((2R)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2S)-1-(3-((4-((5-(2-((2,3-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)(methyl)amino)ethyl dihydrogen phosphate;

2-(1-(3-((4-((5-(2-((2,3-difluorophenyl)amino)-2-oxoethyl)-1,3-thiazol-2-yl)amino)-6-methoxyquinazolin-7-yl)oxy)propyl)piperidin-2-yl)ethyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)(ethyl)amino)ethyl dihydrogen phosphate;

1-(3-((4-((5-(2-((2,3-difluorophenyl)amino)-2-oxoethyl)-1,3-thiazol-2-yl)amino)-6-methoxyquinazolin-7-yl)oxy)propyl)piperidin-4-ylmethyl dihydrogen phosphate;

2-(4-(3-((4-((5-(2-((2,3-difluorophenyl)amino)-2-oxoethyl)-1,3-thiazol-2-yl)amino)-6-methoxy-quinazolin-7-yl)oxy)propyl)piperazin-1-yl)ethyl dihydrogen phosphate;

3-((3-((4-((5-(2-((2,3-difluorophenyl)amino)-2-oxoethyl)-1,3-thiazol-2-yl)amino)-6-methoxyquinazolin-7-yl)oxy)propyl)amino)-3-methylbutyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)amino)-2-methylpropyl dihydrogen phosphate;

2-((3-((4-((5-(2-((2,3-difluorophenyl)amino)-2-oxoethyl)-1,3-thiazol-2-yl)amino)-6-methoxyquinazolin-7-yl)oxy)propyl)amino)ethyl dihydrogen phosphate;

((2R)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

((2S)-1-(3-((4-((5-(2-((2,5-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-((3-((4-((5-(2-((2,5-difluorophenyl)amino)-2-oxoethyl)-1,3-thiazol-2-yl)amino)-6-methoxyquinazolin-7-yl)oxy)propyl)(ethyl)amino)ethyl dihydrogen phosphate;

((2S)-1-(3-((4-((5-(2-((2,4-difluorophenyl)amino)-2-oxoethyl)-1,3-thiazol-2-yl)amino)-6-methoxyquinazolin-7-yl)oxy)propyl)pyrrolidin-2-yl)methyl dihydrogen phosphate;

2-(1-(3-((4-((5-(2-((2,4-difluorophenyl)amino)-2-oxoethyl)-1,3-thiazol-2-yl)amino)-6-methoxyquinazolin-7-yl)oxy)propyl)piperidin-2-yl)ethyl dihydrogen phosphate;

2-{cyclopropyl[3-({4-[(5-{2-[(3-fluorophenyl)amino]-2-oxoethyl}-1,3-thiazol-2-yl)amino]-6-methoxyquinazolin-7-yl}oxy)propyl]amino}ethyl dihydrogen phosphate;

2-{cyclopropyl[3-({4-[(5-{2-[(2,3-difluorophenyl)amino]-2-oxoethyl}-1,3-thiazol-2-yl)amino]-6-methoxyquinazolin-7-yl}oxy)propyl]amino}ethyl dihydrogen phosphate;

(1-(2-((4-((5-(2-((2,3-difluorophenyl)amino)-2-oxoethyl)-1,3-thiazol-2-yl)amino)-6-methoxyquinazolin-7-yl)oxy)ethyl)piperidin-4-yl)methyl dihydrogen phosphate;

((2R)-1-(2-((4-((5-(2-((2,3-difluorophenyl)amino)-2-oxoethyl)-1,3-thiazol-2-yl)amino)-6-methoxyquinazolin-7-yl)oxy)ethyl)pyrrolidin-2-yl)methyl dihydrogen phosphate;

2-(4-(2-((4-((5-(2-(2,3-difluorophenyl)amino)-2-oxoethyl)-1,3-thiazol-2-yl)amino)-6-methoxyquinazolin-7-yl)oxy)ethyl)piperazin-1-yl)ethyl dihydrogen phosphate;

2-(1-(2-((4-((5-(2-((3-fluorophenyl)amino)-2-oxoethyl)-1,3-thiazol-2-yl)amino)-6-methoxyquinazolin-7-yl)oxy)ethyl)piperidin-2-yl)ethyl dihydrogen phosphate;

2-(1-(2-((4-((5-(2-((3-fluorophenyl)amino)-2-oxoethyl)-1,3-thiazol-2-yl)amino)-6-methoxyquinazolin-7-yl)oxy)ethyl)piperidin-4-yl)ethyl dihydrogen phosphate;

4-(ethyl(2-((4-((5-(2-((3-fluorophenyl)amino)-2-oxoethyl)-1,3-thiazol-2-yl)amino)-6-methoxyquinazolin-7-yl)oxy)ethyl)amino)butyl dihydrogen phosphate;

2-(ethyl(2-((4-((5-(2-((3-fluorophenyl)amino)-2-oxoethyl)-1,3-thiazol-2-yl)amino)-6-methoxyquinazolin-7-yl)oxy)ethyl)amino)ethyl dihydrogen phosphate;

(1-(3-((4-((5-(2-((3-fluorophenyl)amino)-2-oxoethyl)-1,3-thiazol-2-yl)amino)quinazolin-7-yl)oxy)propyl)piperidin-4-yl)methyl dihydrogen phosphate; and 2-{4-[({4-[(5-{2-[(3-fluorophenyl)amino]-2-oxoethyl}-1,3-thiazol-2-yl)amino]-6-methoxyquinazolin-7-yl}oxy)methyl]piperidin-1-yl}ethyl dihydrogen phosphate;

or a pharmaceutically acceptable salt thereof.

2. A compound according to claim 1, wherein the compound is (1-(3-((4-((5-(2-((3-fluorophenyl)amino)-2-oxoethyl)-1,3-thiazol-2-yl)amino)-6-methoxyquinazolin-7-yl)oxy)propyl)piperidin-4-yl)methyl dihydrogen phosphate, or a pharmaceutically acceptable salt thereof.

3. A pharmaceutical composition comprising a compound according to claim 1 or a pharmaceutically acceptable salt thereof in association with a pharmaceutically acceptable diluent or carrier.

* * * * *